US012674001B2

(12) United States Patent
Satijn et al.

(10) Patent No.: US 12,674,001 B2
(45) Date of Patent: Jul. 7, 2026

(54) METHOD OF TREATING CANCER BY ADMINISTERING AN ANTIBODY WHICH BINDS TO 5T4

(71) Applicant: GENMAB A/S, Valby (DK)

(72) Inventors: David Satijn, Nieuwegein (NL); Esther C. W. Breij, Driebergen (NL); Bart E. C. G. De Goeij, Utrecht (NL); Patrick Engelberts, Amersfoort (NL); Kristel Kemper, Utrecht (NL); Edward N. Van Den Brink, Halfweg (NL); Rik Rademaker, Utrecht (NL); Dennis Verzijl, Amstelveen (NL); Sjeng Horbach, Oss (NL); Paul Parren, Odijk (NL); Reshma Abdulla Rangwala, Philadelphia, PA (US); Sri Ghatta, Princeton, NJ (US); Ruud Brakenhoff, Amsterdam (NL); Rieneke Van De Ven, Amsterdam (NL)

(73) Assignee: GENMAB A/S, Valby (DK)

( * ) Notice: Subject to any disclaimer, the term of this patent is extended or adjusted under 35 U.S.C. 154(b) by 1005 days.

(21) Appl. No.: 17/642,488

(22) PCT Filed: Sep. 11, 2020

(86) PCT No.: PCT/EP2020/075570
§ 371 (c)(1),
(2) Date: Mar. 11, 2022

(87) PCT Pub. No.: WO2021/048423
PCT Pub. Date: Mar. 18, 2021

(65) Prior Publication Data
US 2023/0257479 A1     Aug. 17, 2023

Related U.S. Application Data

(60) Provisional application No. 62/902,856, filed on Sep. 19, 2019, provisional application No. 62/899,636, filed on Sep. 12, 2019.

(51) Int. Cl.
| *C07K 16/30* | (2006.01) |
| *A61K 39/00* | (2006.01) |
| *A61P 1/00* | (2006.01) |
| *A61P 35/00* | (2006.01) |

(52) U.S. Cl.
CPC ............... *C07K 16/30* (2013.01); *A61P 1/00* (2018.01); *A61P 35/00* (2018.01); *A61K 2039/505* (2013.01); *C07K 2317/33* (2013.01); *C07K 2317/34* (2013.01); *C07K 2317/524* (2013.01); *C07K 2317/526* (2013.01); *C07K 2317/565* (2013.01); *C07K 2317/72* (2013.01); *C07K 2317/73* (2013.01); *C07K 2317/76* (2013.01); *C07K 2317/77* (2013.01); *C07K 2317/92* (2013.01)

(58) Field of Classification Search
CPC ............... C07K 16/30; C07K 16/2809; C07K 2317/33; C07K 2317/34; C07K 2317/524; C07K 2317/526; C07K 2317/565; C07K 2317/72; C07K 2317/73; C07K 2317/76; C07K 2317/77; C07K 2317/93; C07K 2317/31; A61P 1/00; A61P 35/00; A61K 2039/505
See application file for complete search history.

(56) References Cited

U.S. PATENT DOCUMENTS

| 5,747,035 | A | * | 5/1998 | Presta | ................ | C07K 16/2845 |
| | | | | | | 424/153.1 |
| 9,150,663 | B2 | | 10/2015 | Labrijn et al. | | |
| 9,212,230 | B2 | | 12/2015 | Schuurman et al. | | |
| 9,493,553 | B2 | * | 11/2016 | Kaluza | ............... | C07K 16/2881 |
| 10,344,050 | B2 | | 7/2019 | Gramer et al. | | |
| 10,407,501 | B2 | | 9/2019 | Van Den Brink et al. | | |
| 10,434,184 | B2 | | 10/2019 | Dengl et al. | | |
| 10,465,006 | B2 | | 11/2019 | Van Den Brink et al. | | |
| 10,590,206 | B2 | | 3/2020 | Labrijn et al. | | |
| 10,597,464 | B2 | | 3/2020 | Labrijn et al. | | |
| 10,906,991 | B2 | | 2/2021 | Schuurman et al. | | |
| 11,008,399 | B2 | | 5/2021 | Satijn et al. | | |
| 11,130,819 | B2 | | 9/2021 | Satijn et al. | | |
| 11,359,015 | B2 | | 6/2022 | Rademaker et al. | | |
| 11,485,796 | B2 | | 11/2022 | Labrijn et al. | | |
| 11,492,371 | B2 | | 11/2022 | Gramer et al. | | |
| 11,613,575 | B2 | | 3/2023 | Van Den Brink et al. | | |

(Continued)

FOREIGN PATENT DOCUMENTS

| WO | 1998/55607 A2 | 12/1998 |
| WO | 2001/036486 A2 | 5/2001 |

(Continued)

OTHER PUBLICATIONS

Ferrara F, et al. (Jan./Feb. 2015) mAbs 7(1):32-41. (http://dx.doi.org/10.4161/19420862.2015.989047).*

(Continued)

*Primary Examiner* — Robert S Landsman

(74) *Attorney, Agent, or Firm* — Nelson Mullins Riley & Scarborough LLP; Jane E. Remillard, Esq.; Christopher L. Frank

(57) ABSTRACT

The present invention relates to multispecific antibodies binding to 5T4 and CD3 for use in the treatment of cancer selected from the group consisting of esophageal cancer, Non-small Cell Lung Cancer (NSCLC) and Squamous Cell Carcinoma of the Head and Neck (SCCHN).

25 Claims, 55 Drawing Sheets

Specification includes a Sequence Listing.

(56) References Cited

U.S. PATENT DOCUMENTS

| 11,866,514 | B2 | 1/2024 | Labrijn et al. |
| 11,970,544 | B2 | 4/2024 | Satijn et al. |
| 12,415,859 | B2 | 9/2025 | Alfonso Martin et al. |
| 2006/0088522 | A1 | 4/2006 | Boghaert et al. |
| 2010/0105874 | A1 | 4/2010 | Schuurman et al. |
| 2013/0039913 | A1 | 2/2013 | Labrijn et al. |
| 2014/0303356 | A1 | 10/2014 | Gramer et al. |
| 2015/0337049 | A1 | 11/2015 | Labrijn et al. |
| 2016/0046727 | A1 | 2/2016 | Labrijn et al. |
| 2016/0159930 | A1 | 6/2016 | Schuurman et al. |
| 2016/0168247 | A1 | 6/2016 | Van Den Brink et al. |
| 2016/0333095 | A1 | 11/2016 | Van Den Brink et al. |
| 2017/0233497 | A1 | 8/2017 | Labrijn et al. |
| 2019/0284278 | A1 | 9/2019 | Rademaker et al. |
| 2020/0048304 | A1 | 2/2020 | Gramer et al. |
| 2020/0123255 | A1 | 4/2020 | Van Den Brink et al. |
| 2020/0199229 | A1 | 6/2020 | Van Den Brink et al. |
| 2020/0262932 | A1 | 8/2020 | Labrijn et al. |
| 2020/0277397 | A1 | 9/2020 | Satijn et al. |
| 2020/0332022 | A1 | 10/2020 | Labrijn et al. |
| 2021/0070877 | A1 | 3/2021 | Satijn et al. |
| 2021/0230296 | A1 | 7/2021 | Satijn et al. |
| 2022/0049013 | A1 | 2/2022 | Satijn et al. |
| 2022/0380464 | A1 | 12/2022 | Rademaker et al. |
| 2022/0389101 | A1 | 12/2022 | Rademaker et al. |
| 2023/0027394 | A1 | 1/2023 | Rademaker et al. |
| 2023/0227495 | A1 | 7/2023 | Gramer et al. |
| 2023/0322947 | A1 | 10/2023 | Labrijn et al. |
| 2023/0374131 | A1 | 11/2023 | Van Den Brink et al. |

FOREIGN PATENT DOCUMENTS

| WO | 01/77342 | A1 | 10/2001 |
| WO | 03038098 | A2 | 5/2003 |
| WO | 2006/031653 | A2 | 3/2006 |
| WO | 2007/106744 | A2 | 9/2007 |
| WO | 2008119353 | A1 | 10/2008 |
| WO | 2011048369 | A1 | 4/2011 |
| WO | 2011131746 | A2 | 10/2011 |
| WO | 2011147986 | A1 | 12/2011 |
| WO | 2012/131527 | A1 | 10/2012 |
| WO | 2013/041687 | A1 | 3/2013 |
| WO | 2013060867 | A2 | 5/2013 |
| WO | 2014108483 | A1 | 7/2014 |
| WO | 2014137931 | A1 | 9/2014 |
| WO | 2015001085 | A1 | 1/2015 |
| WO | 2015/104346 | A1 | 7/2015 |
| WO | 2015/155345 | A1 | 10/2015 |
| WO | 2016/022939 | A1 | 2/2016 |
| WO | 2016/097408 | A1 | 6/2016 |
| WO | 2017009442 | A1 | 1/2017 |
| WO | 2017/072207 | A1 | 5/2017 |
| WO | 2017/072208 | A1 | 5/2017 |
| WO | 2017/089447 | A1 | 6/2017 |
| WO | 2017/107973 | A1 | 6/2017 |
| WO | 2017/182672 | A1 | 10/2017 |
| WO | 2018/127175 | A1 | 7/2018 |
| WO | 2018/167486 | A1 | 9/2018 |
| WO | 2018/184558 | A1 | 10/2018 |
| WO | 2019/016402 | A1 | 1/2019 |
| WO | 2019/109047 | A1 | 6/2019 |
| WO | 2019/160904 | A1 | 8/2019 |
| WO | 2019/175198 | A2 | 9/2019 |

OTHER PUBLICATIONS

Lloyd C, et al. (2009) Protein Engineering, Design & Selection. 22(3): 159-168 (Published online Oct. 29, 2008 doi:10.1093/protein/gzn058).*

Edwards BM, et al. (2003) J. Mol. Biol. 334:103-118. (doi:10.1016/j.jmb.2003.09.054).*

Paul, WE (1993) Fundamental Immunology, 3rd ed. Raven Press, NY, Chap. 9, pp. 292-295.*

Rudikoff, S et al. (1982) Proc. Natl. Acad. Sci. USA, 79:1979-1983 (doi: 10.1073/pnas.79.6.1979).*

Colman, PM (1994) Research in Immunology, Elsevier, NY, 145(1):33-36.*

Bendig M. M. (1995) Methods: A Companion to Methods in Enzymology, 8:83-93.*

MacCallum et al. (Oct. 11, 1996) J. Mol. Biol., 262(5):732-745. (doi: 10.1006/jmbi.1996.0548).*

Casset et al (2003) Biochemical and Biophysical Research Communications, 307:198-205. (doi:10.1016/S0006-291X(03)01131-8).*

Chen et al. (1995) EMBO J., 14(12):2784-2794. (doi: 10.1002/j.1460-2075.1995.tb07278.x).*

Kerk SA, et al. (May 15, 2017) Clin Cancer Res. 23(10):2516-2527. (doi:10.1158/1078-0432.CCR-16-1834).*

Abdiche YN, et al. "Antibodies Targeting Closely Adjacent or Minimally Overlapping Epitopes Can Displace One Another," PLoS One, vol. 12(1): e0169535. doi:10.1371/journal.pone.0169535 (2017).

Abdiche, Y. et al., "Exploring blocking assays using Octet, ProteOn, and Biacore biosensors," Anal Biochem., vol. 386 (2): 172-180 (2009).

Carsberg, C. et al., "Metastasis-associated 5T4 antigen disrupts cell-cell contacts and induces cellular motility in epithelial cells," Int J Cancer, vol. 68: 84-92 (1996).

Clinical Trials Report NCT04424641: "A Study on the Safety of GEN1044 (DuoBody—CD3x5T4) in Patients With Malignant Solid Tumors," National Library of Medicine, Jul. 25, 2023, 13 pages.

Damelin, M. et al., "Delineation of a cellular hierarchy in lung cancer reveals an oncofetal antigen expressed on tumor-initiating cells," Cancer Res., vol. 71(12), 4236-4246 (2011).

Edwards, B. et al., "The Remarkable Flexibility of the Human Antibody Repertoire; Isolation of Over One Thousand Different Antibodies to a Single Protein, BLyS," J Mol Biol., vol. 334:103-118 (2003).

Eisen, T. et al., "Naptumomab estafenatox: targeted immunotherapy with a novel immunotoxin," Curr Oncol Rep., vol. 16:370 (2014).

Gershoni J. M et al., "Epitope mapping—The first step in developing epitope-based vaccines," Biodrugs, vol. 21 (3):145-156 (2007).

Gramer, M. et al., "Production of stable bispecific IgG1 by controlled Fab-arm exchange: scalability from bench to large-scale manufacturing by application of standard approaches," MAbs, vol. 5:962-973 (2013).

Huang, L. et al. "A 5T4 x CD3 Bispecific DART(R) Molecule with Extended Half-life for T-cell Immunotherapy of Cancers," Cancer Research, vol. 77, No. 13, Jul. 1, 2017, 1 page.

International Search Report and Written Opinion for PCT Application No. PCT/EP2020/075570 dated Dec. 10, 2020, 14 pages.

Ishiguro, T. et al. "An anti-glypican 3/CD3 bispecific T cell-redirecting antibody for treatment of solid tumors," Sci. Transl. Med. 2017 (9), eaal4219, pp. 1-13.

Kagermeier-Schenk, B. et al., "Waif1/5T4 inhibits Wnt/B-catenin signaling and activates noncanonical Wnt pathways by modifying LRP6 subcellular localization," Dev Cell, vol. 21:1129-1143 (2011).

Kemper, K. et al., "DuoBody(R)-CD3x5T4 shows potent preclinical anti-tumor activity in vitro and in vivo in a range of cancer indicators," abstract P783, p. 149, Journal of Immunotherapy of Cancer 2019, 7(Suppl 1):283.

Kerk, S. et al., "514 oncofetal antigen as a prognostic marker and target for treatment in head and neck squamous cell carcinoma," Journal of Clinical Oncology, vol. 34, No. 15, May 20, 2016, e17516, 3 pages.

Labrijn, A. et al., "Efficient generation of stable bispecific IgG1 by controlled Fab-arm exchange," PNAS, vol. 110(13): 5145-5150 (2013).

Marchalonis, J. et al., "The antibody repertoire in evolution: Chance, selection, and continuity," Dev & Comp Immunol., vol. 30:223-247 (2006).

Pirie-Shepherd, S. R., et al., "Detecting expression of 5T4 in CTCs and tumor samples from NSCLC patients," PLoS One 12(7): e0179561, Jul. 20, 2017; 26 pages.

(56) References Cited

OTHER PUBLICATIONS

Scurr, M. et al., "Effect of Modified Vaccinia Ankara-5T4 and Low-Dose Cyclophosphamide on Antitumor Immunity in Metastatic Colorectal Cancer: A Randomized Clinical Trial," JAMA Oncol., vol. 3:10 (2017).

Shapiro, G. et al., "First-in-human trial of an anti-5T4 antibody-monomethylauristatin conjugate, PF-06263507, in patients with advanced solid tumors," Invest New Drugs, vol. 35:315-323 (2017).

Shaw, D. et al., "Glycosylation and epitope mapping of the 5T4 glycoprotein oncofoetal antigen," Biochem. J., vol. 363: 137-45 (2002).

Shields, R. et al., "High resolution mapping of the binding site on human IgG1 for Fc gamma RI, Fc gamma RII, Fc gamma RIII, and FcRn and design of IgG1 variants with improved binding to the Fc gamma R," J. Biol. Chem., vol. 276(9):6591-6604 (2001).

Southall, P. J. et al., "Immunohistological distribution of 5T4 antigen in normal and malignant tissues," Br J Cancer, vol. 61: 89-95 (1990).

Stern, P. et al., "5T4 oncofoetal antigen: an attractive target for immune intervention in cancer," Cancer Immunol Immunother., vol. 66: 415-426 (2017).

Van Schouwenburg, P. et al., "Functional Analysis of the Anti-adalimumab Response Using Patient-derived Monoclonal Antibodies," J Biol Chem. vol. 289(50):34482-34488 (2014).

Zhao, Y. et al., "Structural insights into the inhibition of Wnt signaling by cancer antigen 5T4/Wnt-activated inhibitory factor 1," Structure, vol. 22:612-620 (2014).

* cited by examiner

□ IgG1-5T4-H8-FEAR
▦ IgG1-5T4-A3-F405L
▨ IgG1-5T4-207-FEAR
▨ IgG1-5T4-226-FEAR
▦ IgG1-5T4-A1-F405L
□ IgG1-b12

FIG. 4A

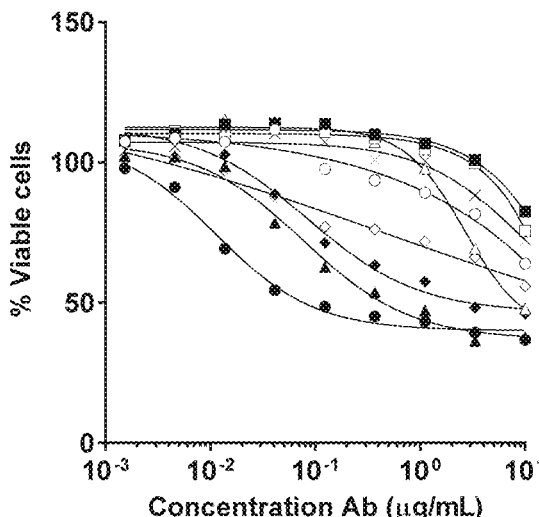

MDA-MB-468

- bsIgG1-5T4-H8-FEARxb12-vcDuo3
- bsIgG1-5T4-059-FEARxb12-vcDuo3
- bsIgG1-5T4-076-FEARxb12-vcDuo3
- bsIgG1-5T4-085-FEARxb12-vcDuo3
- bsIgG1-5T4-106-FEARxb12-vcDuo3
- bsIgG1-5T4-127-FEARxb12-vcDuo3
- bsIgG1-5T4-207-FEARxb12-vcDuo3
- bsIgG1-5T4-226-FEARxb12-vcDuo3
- IgG1-b12-vcDuo3

FIG. 4B

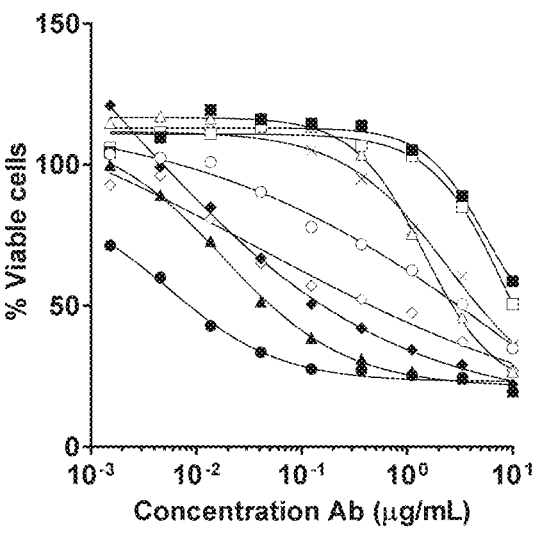

HCC1954

- bsIgG1-5T4-H8-FEARxb12-vcDuo3
- bsIgG1-5T4-059-FEARxb12-vcDuo3
- bsIgG1-5T4-076-FEARxb12-vcDuo3
- bsIgG1-5T4-085-FEARxb12-vcDuo3
- bsIgG1-5T4-106-FEARxb12-vcDuo3
- bsIgG1-5T4-127-FEARxb12-vcDuo3
- bsIgG1-5T4-207-FEARxb12-vcDuo3
- bsIgG1-5T4-226-FEARxb12-vcDuo3
- IgG1-b12-vcDuo3

FIG. 5(I)A
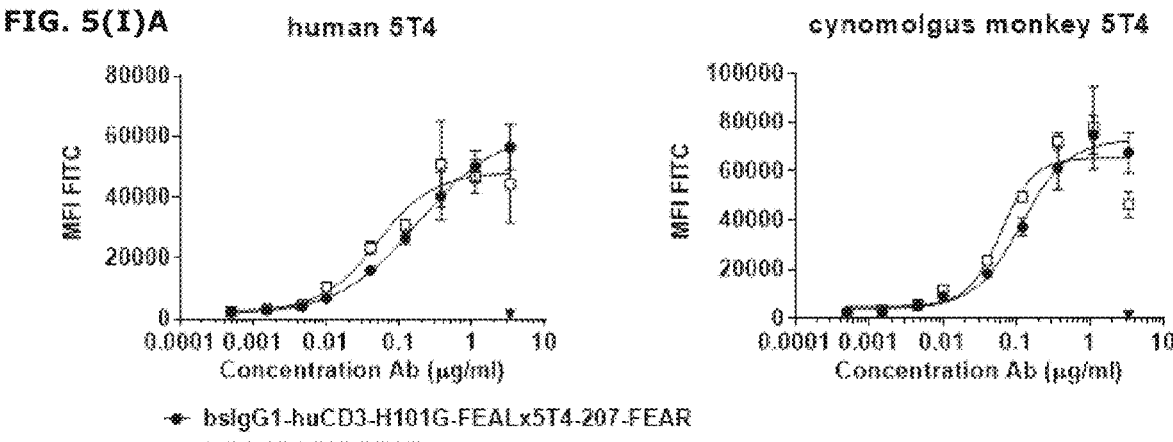
- ● bsIgG1-huCD3-H101G-FEALx5T4-207-FEAR
- ○ IgG1-5T4-207-FEAR
- ▼ IgG1-b12-K409R
FIG. 5(I)B
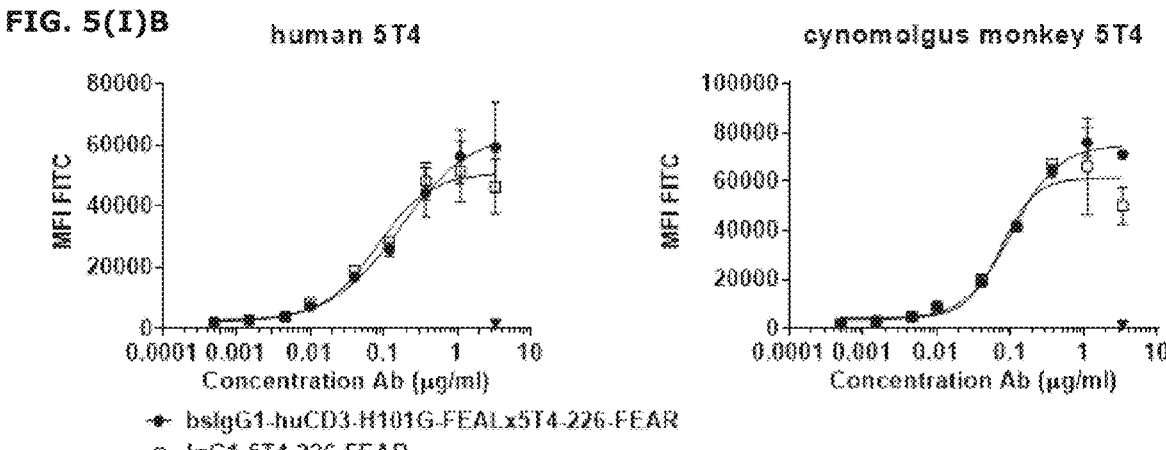
- ● bsIgG1-huCD3-H101G-FEALx5T4-226-FEAR
- ○ IgG1-5T4-226-FEAR
- ▼ IgG1-b12-K409R

FIG. 5(I)C
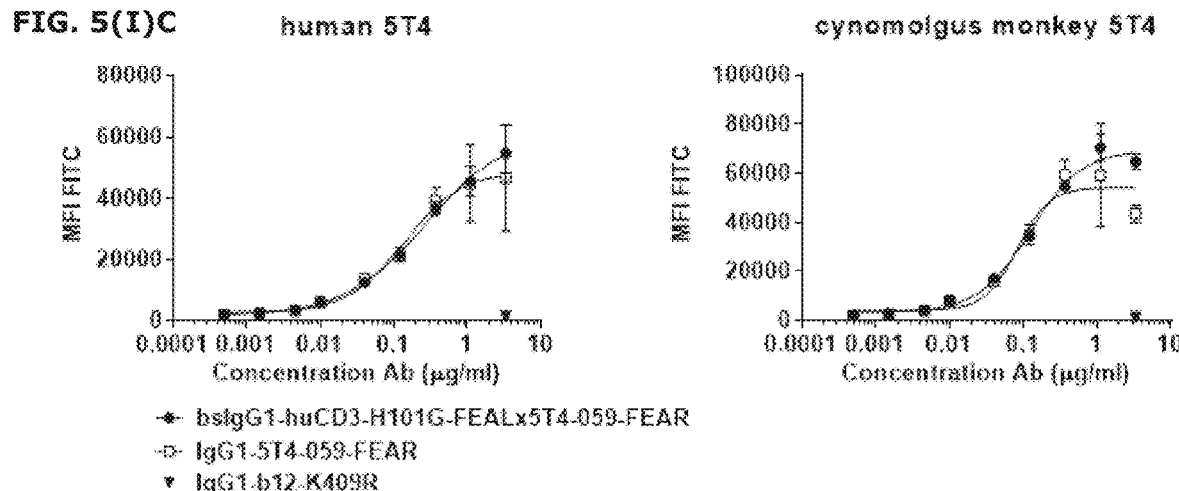
- bsIgG1-huCD3-H101G-FEALx5T4-059-FEAR
- IgG1-5T4-059-FEAR
- IgG1-b12-K409R
FIG. 5(I)D
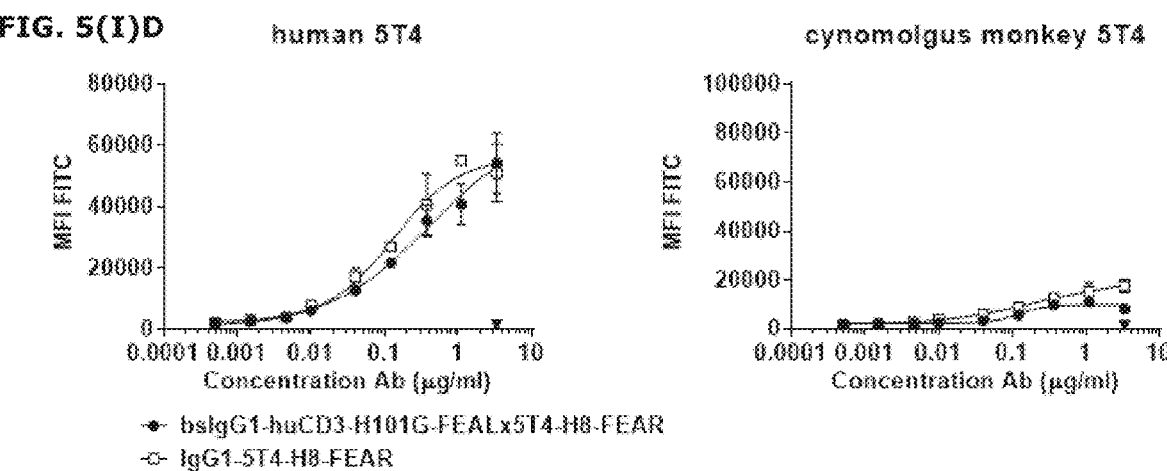
- bsIgG1-huCD3-H101G-FEALx5T4-H8-FEAR
- IgG1-5T4-H8-FEAR
- IgG1-b12-K409R

FIG. 5(II)A
human 5T4
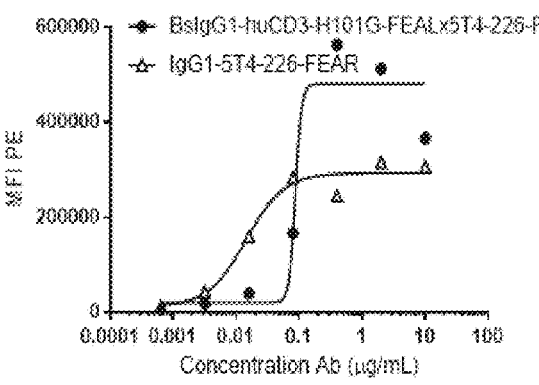
cynomolgus monkey 5T4
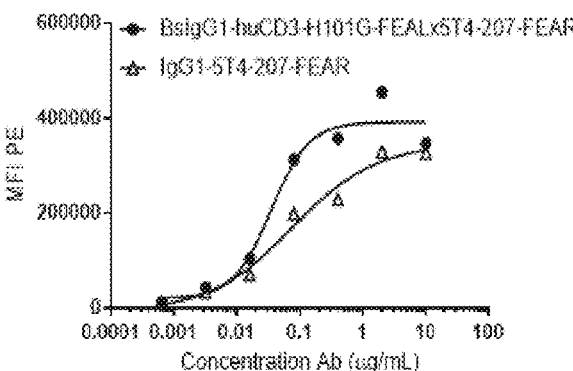
FIG. 5(II)B
human 5T4
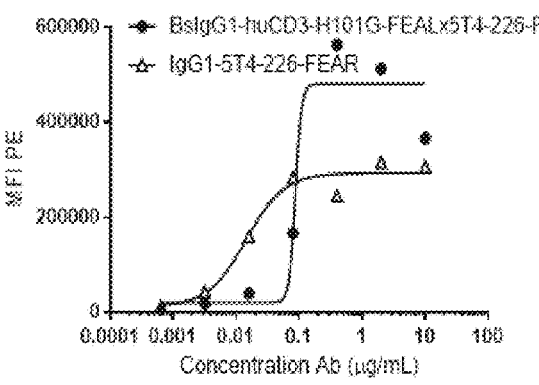
cynomolgus monkey 5T4
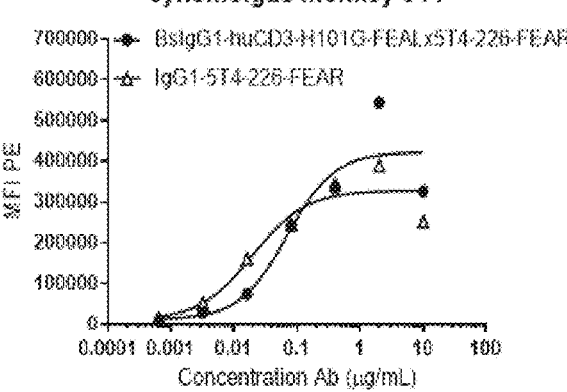
FIG. 5(II)C
human 5T4
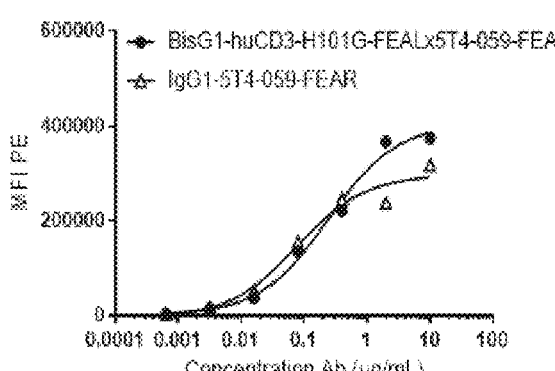
cynomolgus monkey 5T4
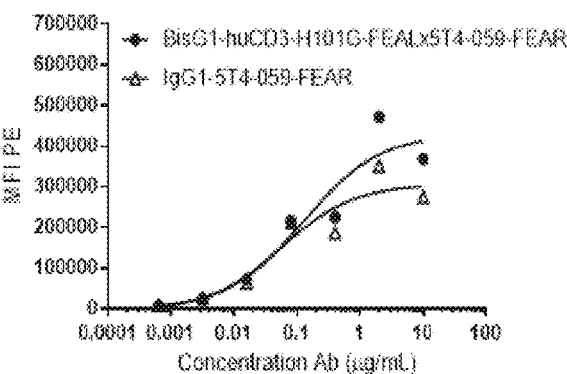

FIG. 5(II)D
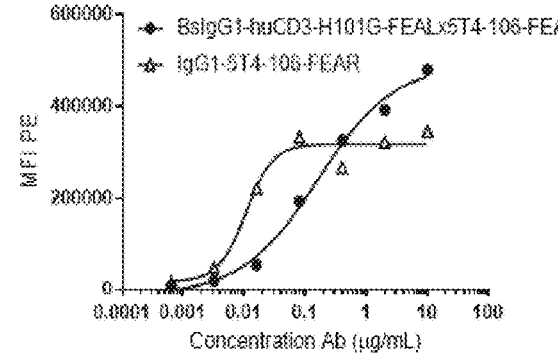
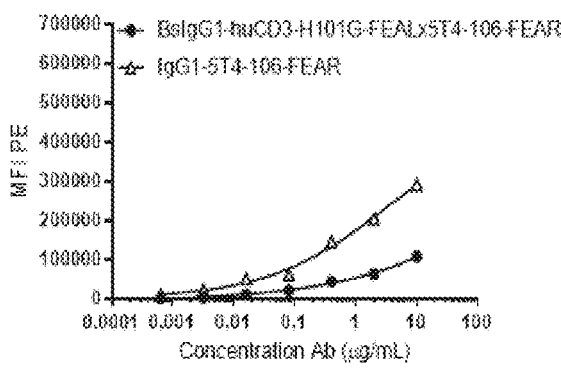
FIG. 5(II)E
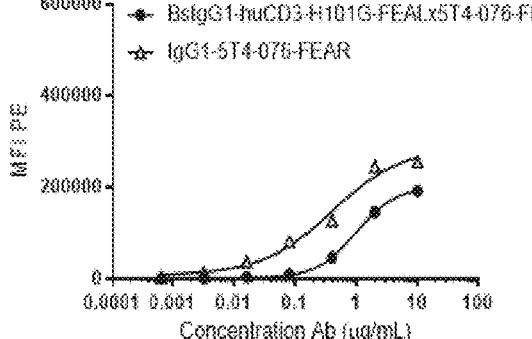
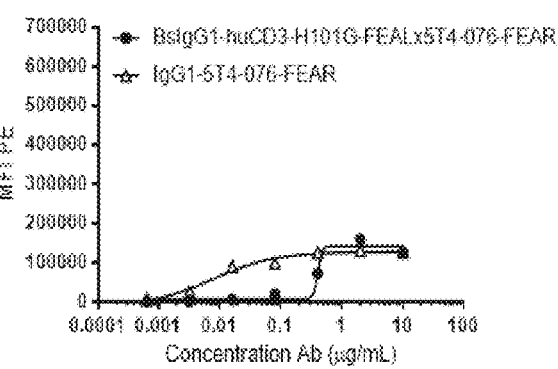

FIG. 5(II)F
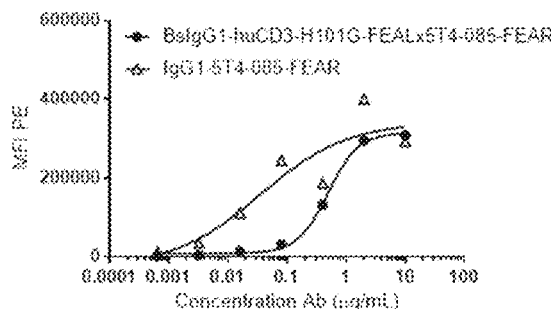
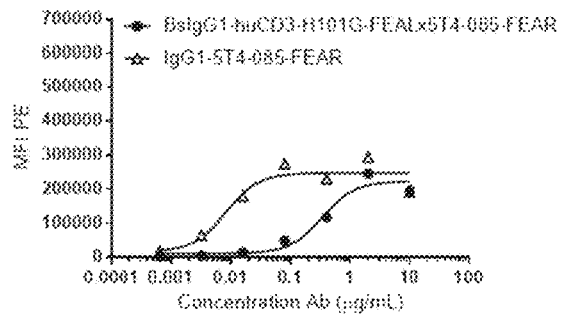
FIG. 5(II)G
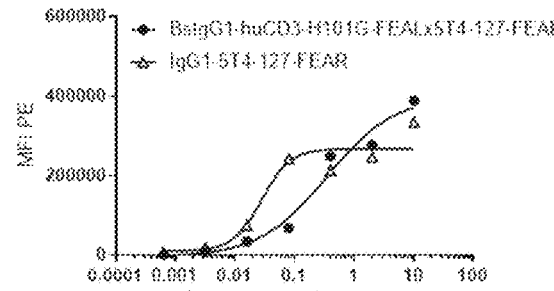
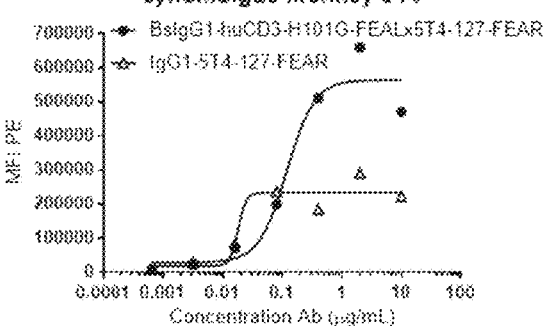
FIG. 5(II)H
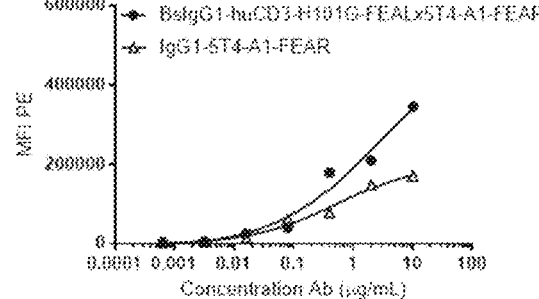
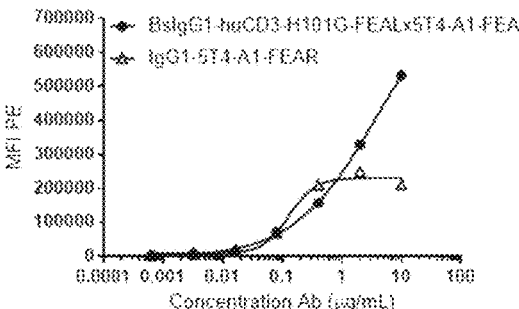

FIG. 5(II)I
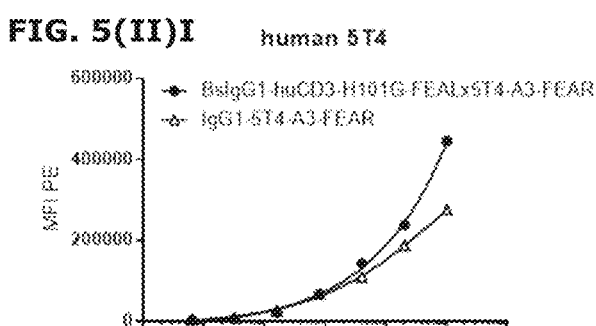
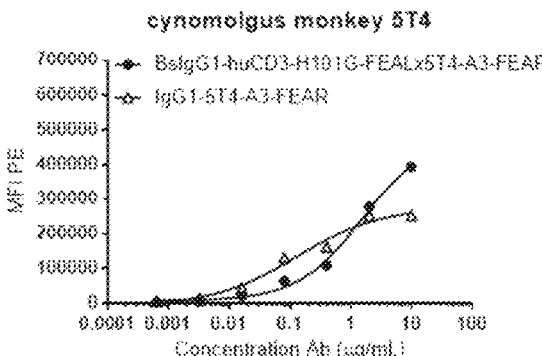

FIG. 6(I)A
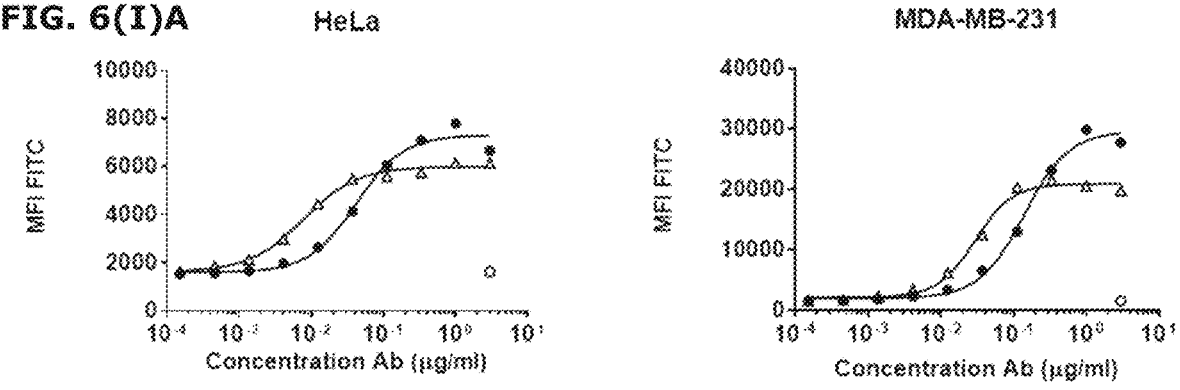
- ◆ bsIgG1-huCD3-H101G-FEALx5T4-207-FEAR
- △ IgG1-5T4-207-FEAR
- ○ IgG1-b12-K409R
FIG. 6(I)B
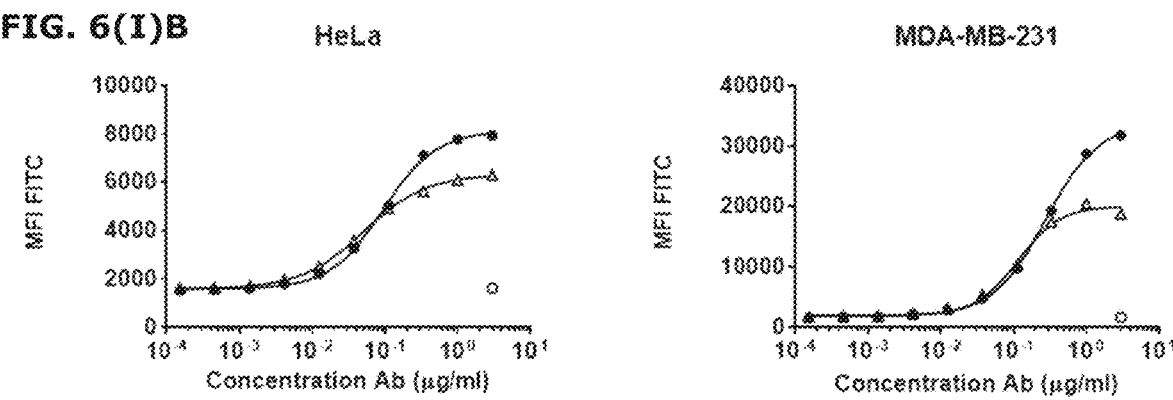
- ◆ bsIgG1-huCD3-H101G-FEALx5T4-059-FEAR
- △ IgG1-5T4-059-FEAR
- ○ IgG1-b12-K409R FIG. 6(I)C
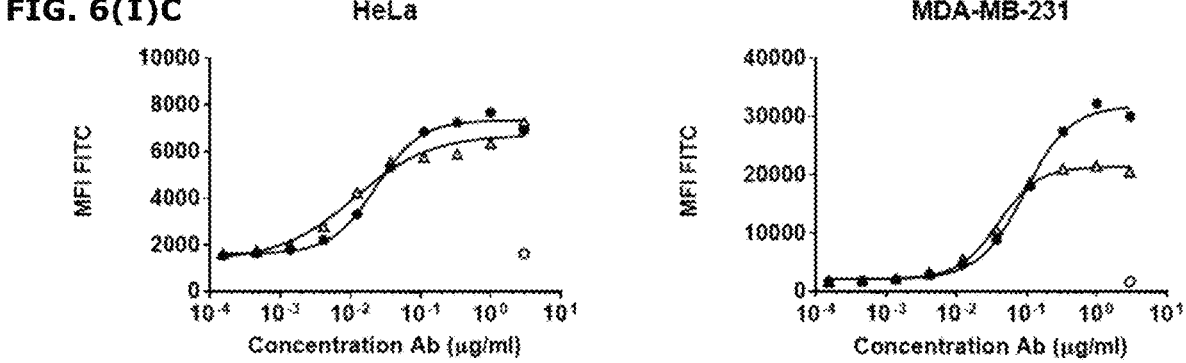

FIG. 6(II)A
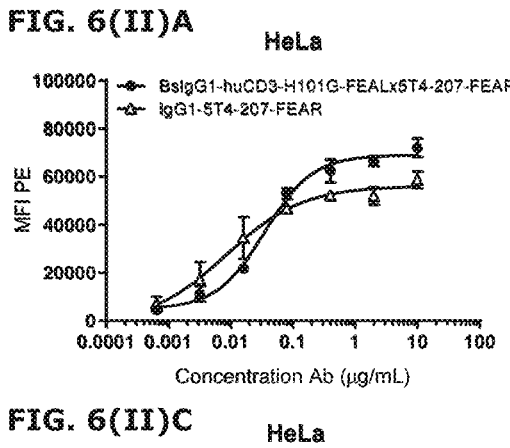
FIG. 6(II)B
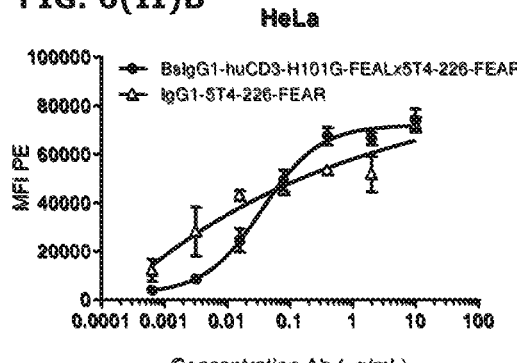
FIG. 6(II)C
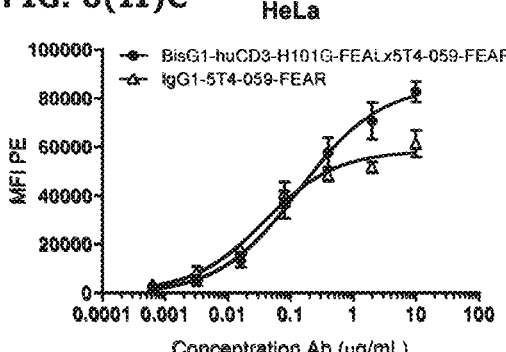
FIG. 6(II)D
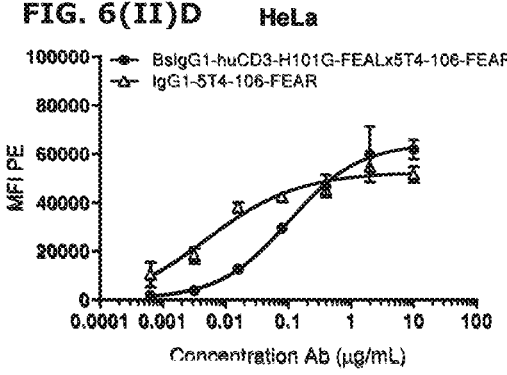
FIG. 6(II)E
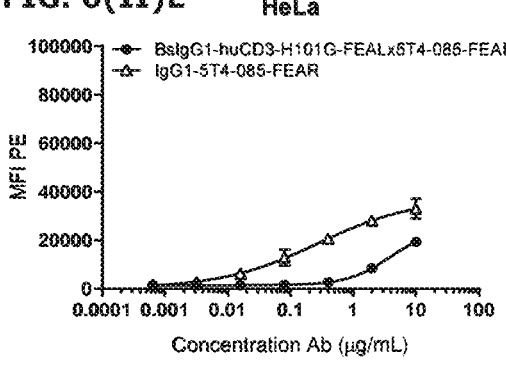
FIG. 6(II)F
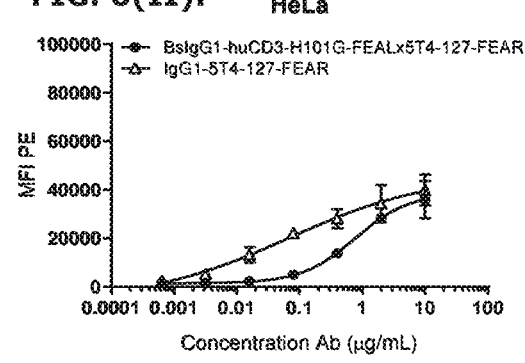
FIG. 6(II)G
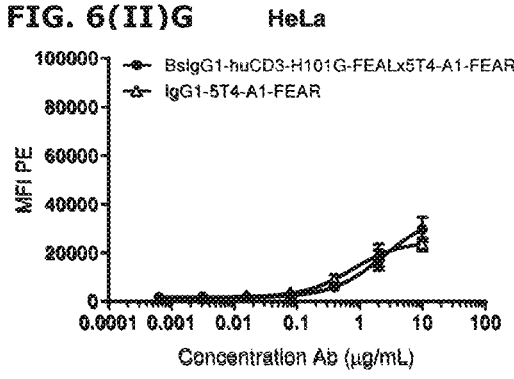
FIG. 6(II)H
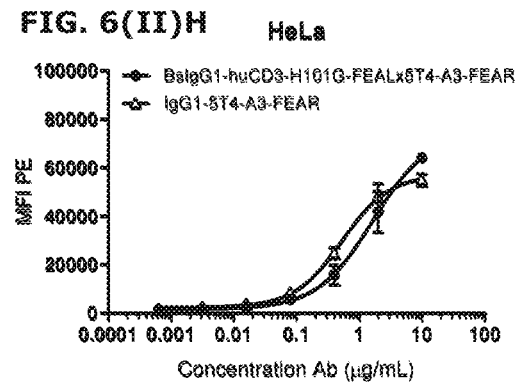

FIG. 6(III)A
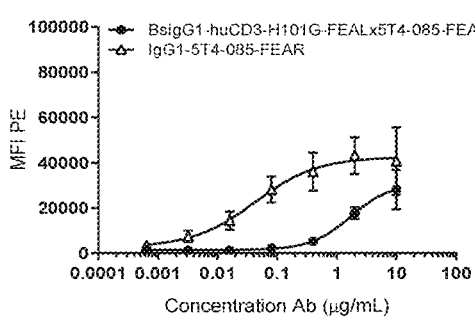
FIG. 6(III)B
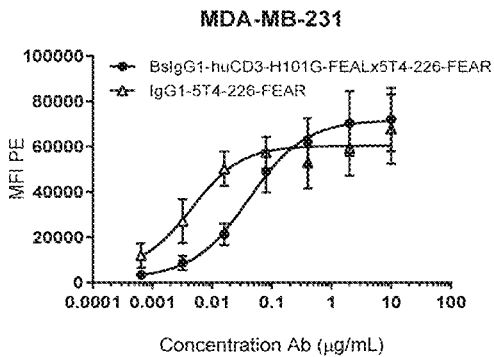
FIG. 6(III)C
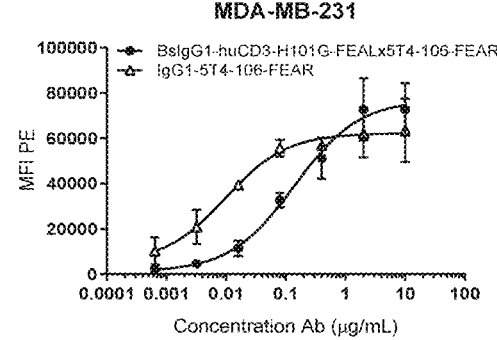
FIG. 6(III)D
FIG. 6(III)E
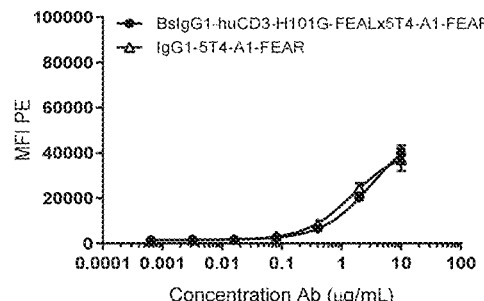
FIG. 6(III)F
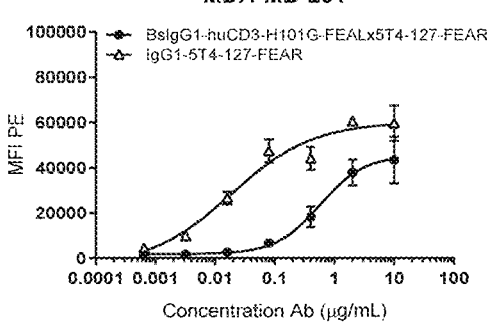
FIG. 6(III)G
FIG. 6(III)H
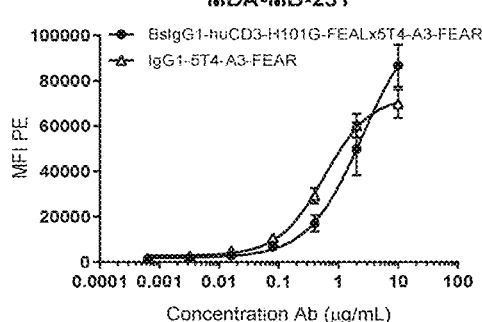

FIG. 7(I)A
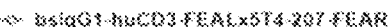
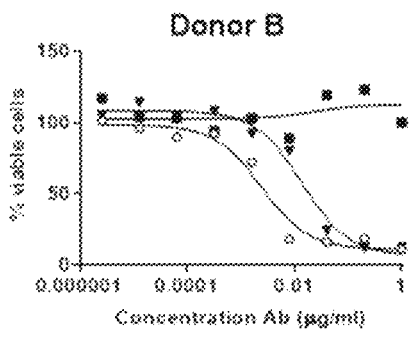
Donor A          Donor B
- bsIgG1-huCD3-FEALx5T4-207-FEAR
- bsIgG1-huCD3-H101G-FEALx5T4-207-FEAR
- IgG1-5T4-207-FEAR
FIG. 7(I)B
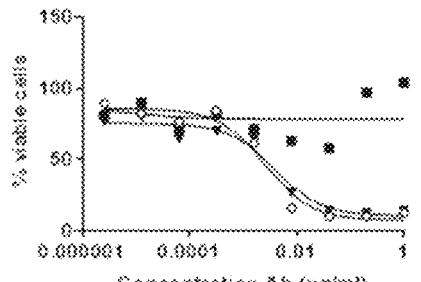
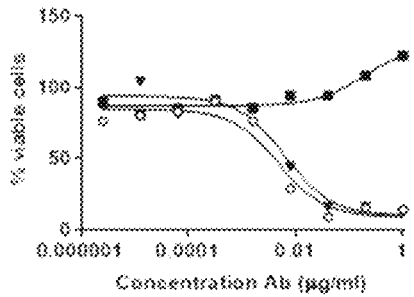
- bsIgG1-huCD3-FEALx5T4-226-FEAR
- bsIgG1-huCD3-H101G-FEALx5T4-226-FEAR
- IgG1-5T4-226-FEAR
FIG. 7(I)C
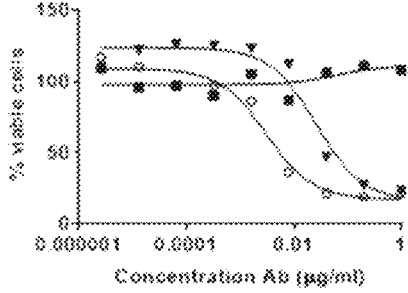
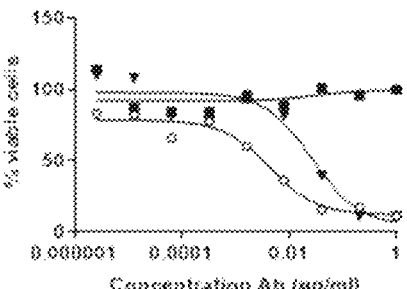
- bsIgG1-huCD3-FEALx5T4-059-FEAR
- bsIgG1-huCD3-H101G-FEALx5T4-059-FEAR
- IgG1-5T4-059-FEAR ■ bsIgG1-huCD3-FEALx5T4-207-FEAR □ bsIgG1-huCD3-H101G-FEALx5T4-207-FEAR ▨ bsIgG1-huCD3-FEALx5T4-226-FEAR ▨ bsIgG1-huCD3-H101G-FEALx5T4-226-FEAR ▨ bsIgG1-huCD3-FEALx5T4-059-FEAR ▨ bsIgG1-huCD3-H101G-FEALx5T4-059-FEAR

FIG. 8(I)A
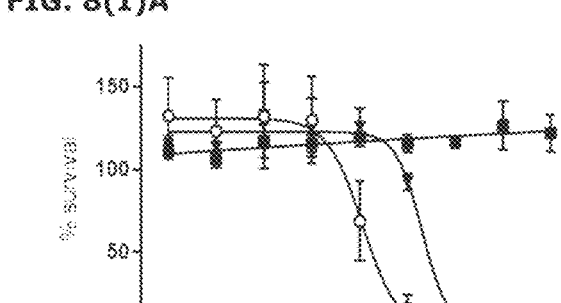
—○— BsigG1-huCD3-FEALxST4-207-FEAR
—✱— BsigG1-huCD3-H101G-FEALxST4-207-FEAR
—✦— IgG1-ST4-207-FEAR
FIG. 8(I)B
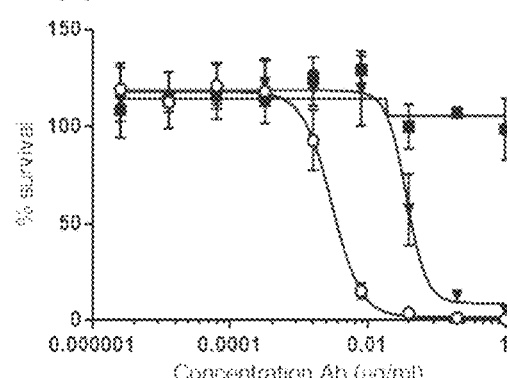
—○— BsigG1-huCD3-FEALxST4-226-FEAR
—✱— BsigG1-huCD3-H101G-FEALxST4-226-FEAR
—✦— IgG1-ST4-226-FEAR
FIG. 8(I)C
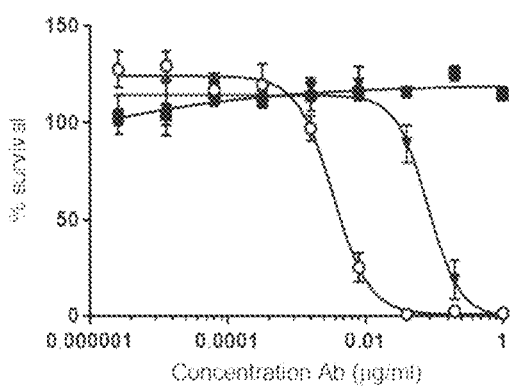
—○— BsigG1-huCD3-FEALxST4-059-FEAR
—✱— BsigG1-huCD3-H101G-FEALxST4-059-FEAR
—✦— IgG1-ST4-059-FEAR
FIG. 8(I)D
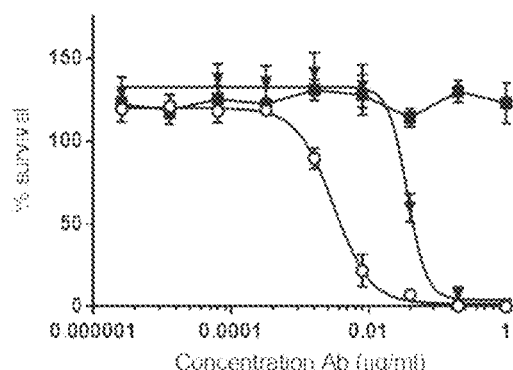
—○— BsigG1-huCD3-FEALxST4-105-FEAR
—✱— BsigG1-huCD3-H101G-FEALxST4-105-FEAR
—✦— IgG1-ST4-105-FEAR

FIG. 8(I)E
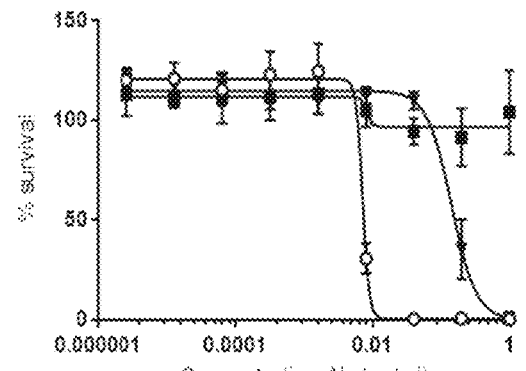
-○- BsIgG1-huCD3-FEALx5T4-A1-FEAR
-✳- BsIgG1-huCD3-H101G-FEALx5T4-A1-FEAR
-✻- IgG1-5T4-A1-FEAR
FIG. 8(I)F
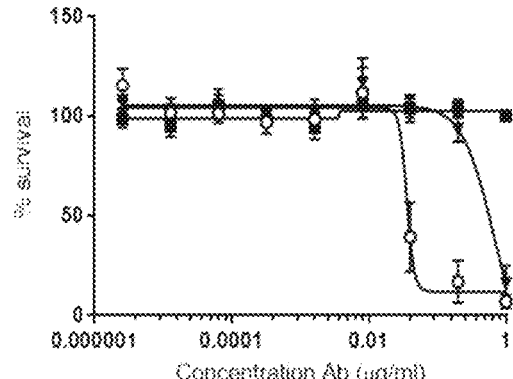
-○- BsIgG1-huCD3-FEALx5T4-A3-FEAR
-✳- BsIgG1-huCD3-H101G-FEALx5T4-A3-FEAR
-✻- IgG1-5T4-A3-FEAR

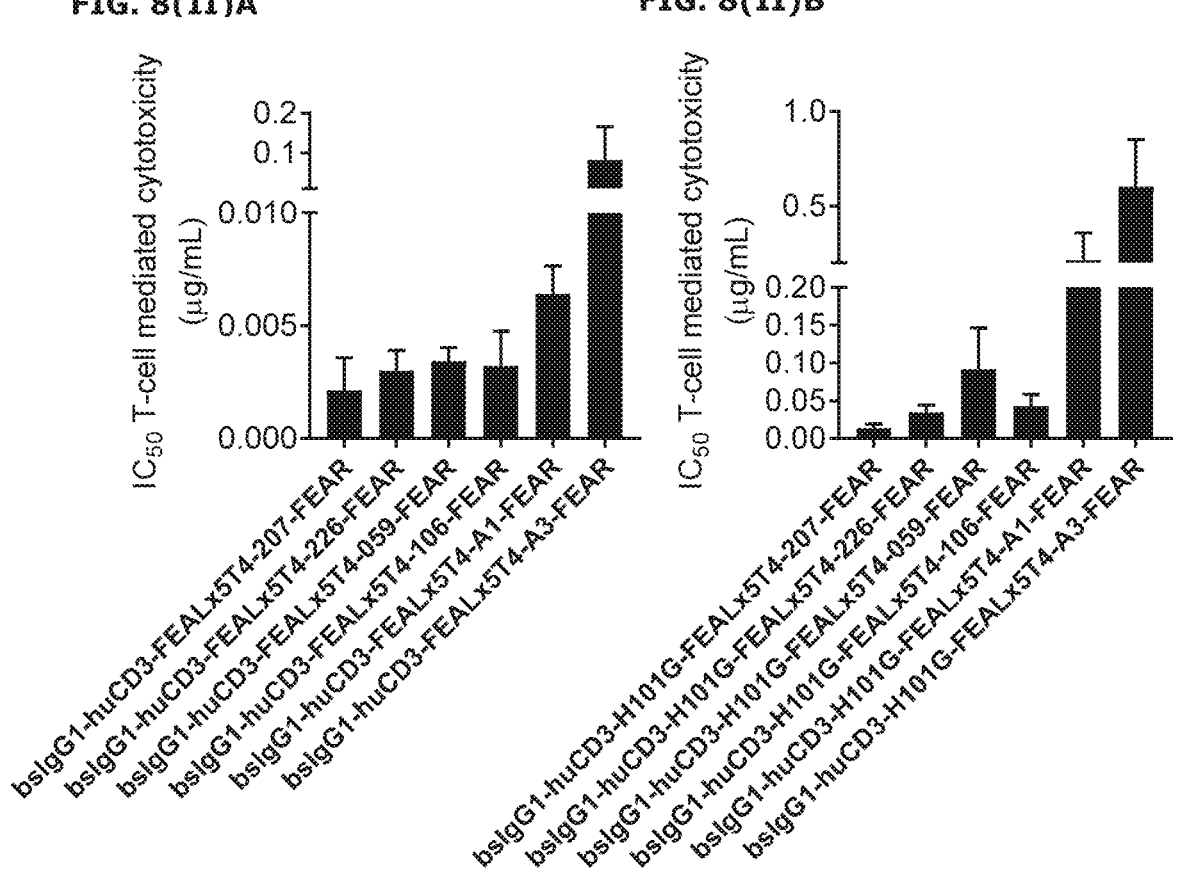
FIG. 8(II)A
FIG. 8(II)B

FIG. 9(I)A                 FIG. 9(I)B
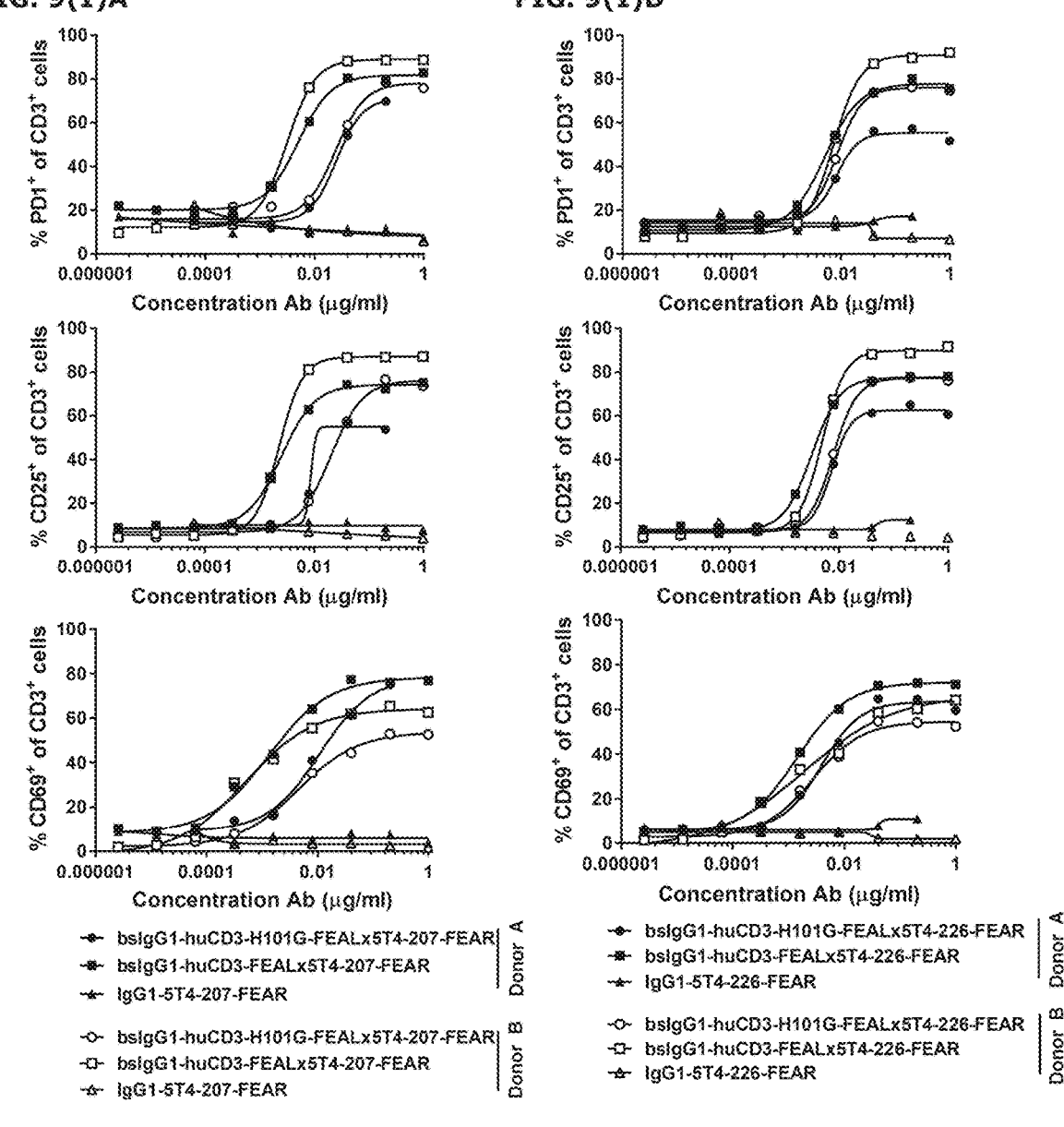

FIG. 9(I)C
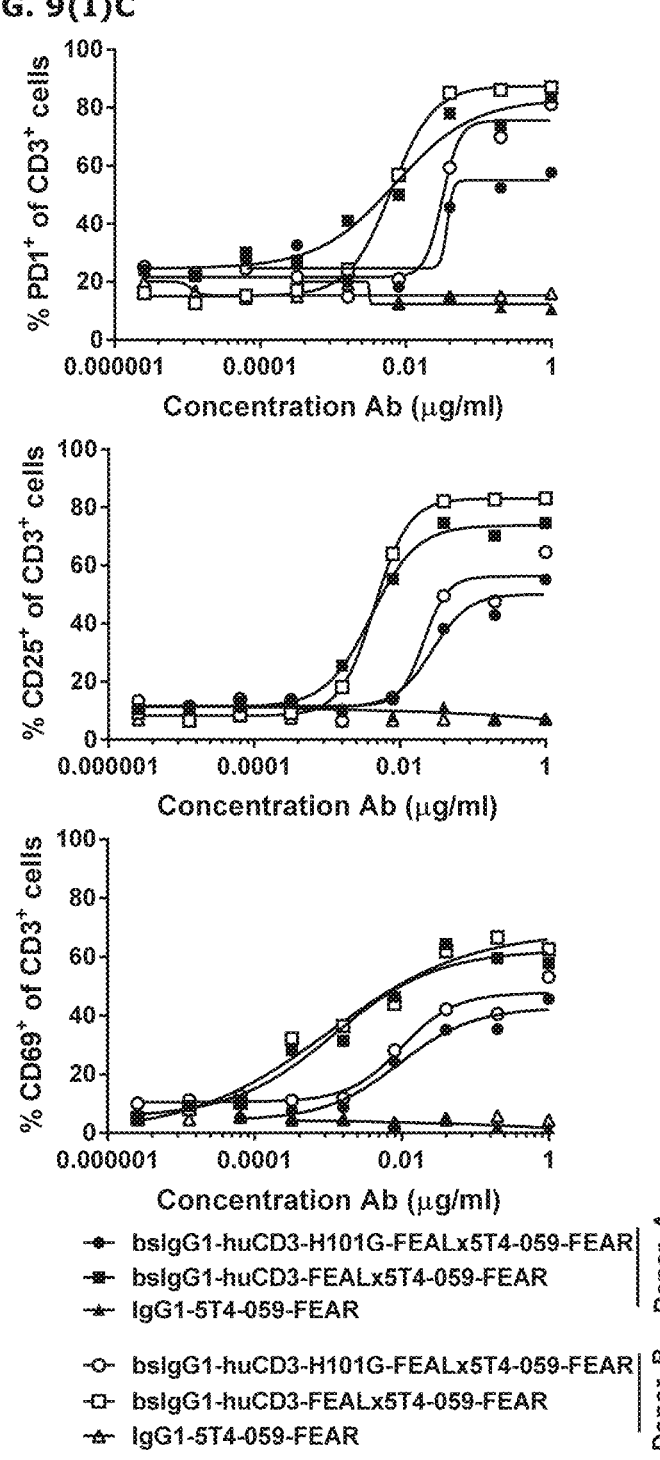

bsIgG1-huCD3-FEALx5T4-207-FEAR bsIgG1-huCD3-H101G-FEALx5T4-207-FEAR bsIgG1-huCD3-FEALx5T4-226-FEAR bsIgG1-huCD3-H101G-FEALx5T4-226-FEAR bsIgG1-huCD3-FEALx5T4-059-FEAR bsIgG1-huCD3-H101G-FEALx5T4-059-FEAR

FIG. 10(I)A

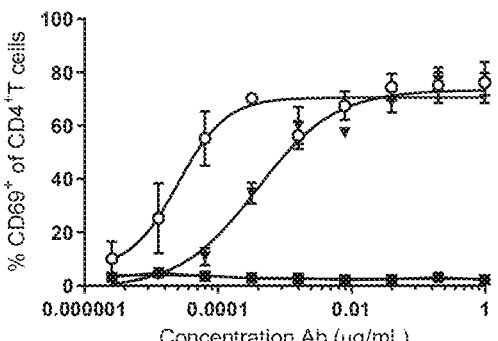

- BsIgG1-huCD3-FEALx5T4-207-FEAR
- BsIgG1-huCD3-H101G-FEALx5T4-207-FEAR
- IgG1-5T4-207-FEAR

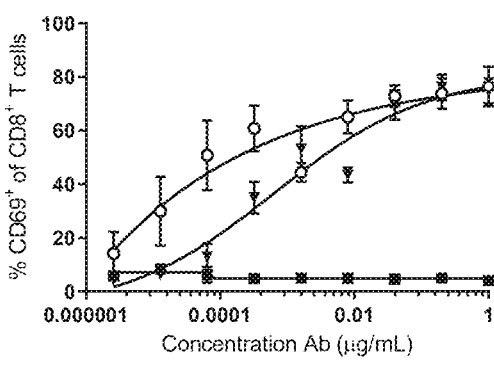

- BsIgG1-huCD3-FEALx5T4-207-FEAR
- BsIgG1-huCD3-H101G-FEALx5T4-207-FEAR
- IgG1-5T4-207-FEAR

FIG. 10(I)B

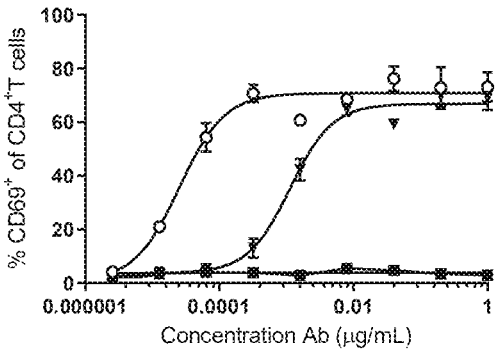

- BsIgG1-huCD3-FEALx5T4-226-FEAR
- BsIgG1-huCD3-H101G-FEALx5T4-226-FEAR
- IgG1-5T4-226-FEAR

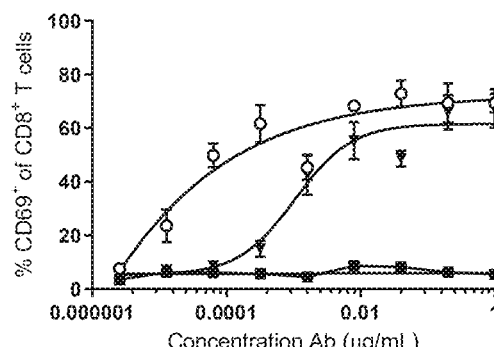

- BsIgG1-huCD3-FEALx5T4-226-FEAR
- BsIgG1-huCD3-H101G-FEALx5T4-226-FEAR
- IgG1-5T4-226-FEAR

FIG. 10(I)C

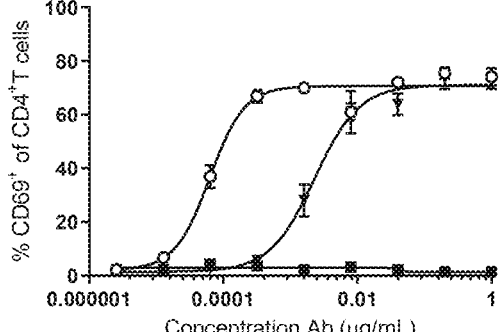

- BsIgG1-huCD3-FEALx5T4-059-FEAR
- BsIgG1-huCD3-H101G-FEALx5T4-059-FEAR
- IgG1-5T4-059-FEAR

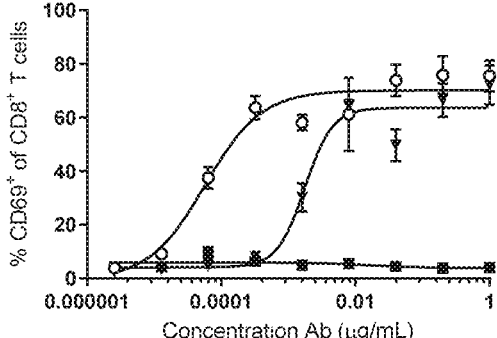

- BsIgG1-huCD3-FEALx5T4-059-FEAR
- BsIgG1-huCD3-H101G-FEALx5T4-059-FEAR
- IgG1-5T4-059-FEAR

FIG. 10(I)D

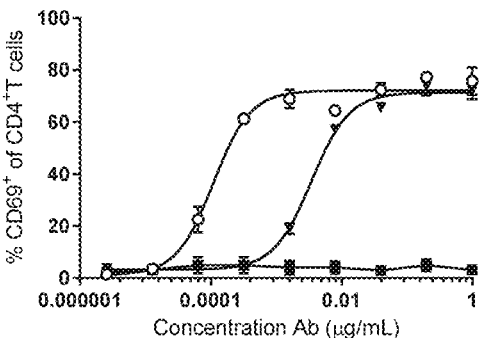

-○- BsIgG1-huCD3-FEALx5T4-106-FEAR
-▼- BsIgG1-huCD3-H101G-FEALx5T4-106-FEAR
-✳- IgG1-5T4-106-FEAR

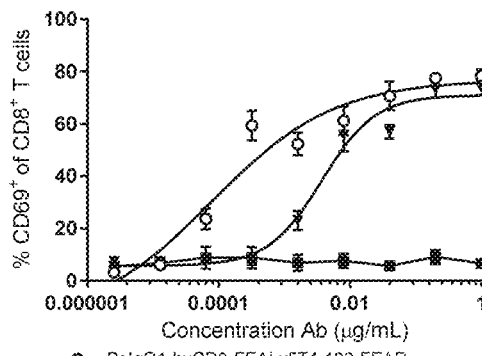

-○- BsIgG1-huCD3-FEALx5T4-106-FEAR
-▼- BsIgG1-huCD3-H101G-FEALx5T4-106-FEAR
-✳- IgG1-5T4-106-FEAR

FIG. 10(I)E

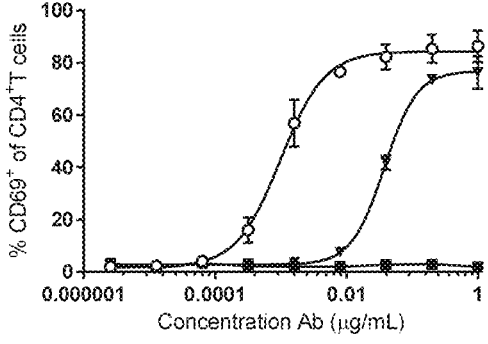

-○- BsIgG1-huCD3-FEALx5T4-A1-FEAR
-▼- BsIgG1-huCD3-H101G-FEALx5T4-A1-FEAR
-✳- IgG1-5T4-A1-FEAR

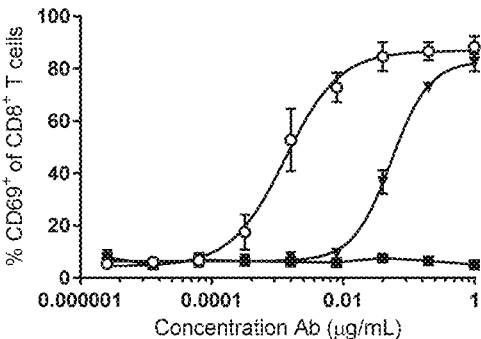

-○- BsIgG1-huCD3-FEALx5T4-A1-FEAR
-▼- BsIgG1-huCD3-H101G-FEALx5T4-A1-FEAR
-✳- IgG1-5T4-A1-FEAR

FIG. 10(I)F

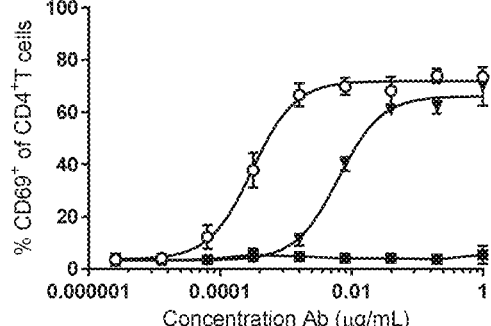

-○- BsIgG1-huCD3-FEALx5T4-A3-FEAR
-▼- BsIgG1-huCD3-H101G-FEALx5T4-A3-FEAR
-✳- IgG1-5T4-A3-FEAR

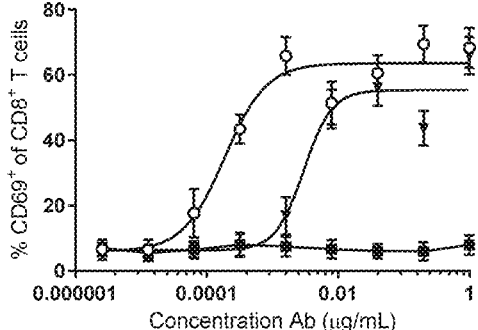

-○- BsIgG1-huCD3-FEALx5T4-A3-FEAR
-▼- BsIgG1-huCD3-H101G-FEALx5T4-A3-FEAR
-✳- IgG1-5T4-A3-FEAR

FIG. 10(II)A
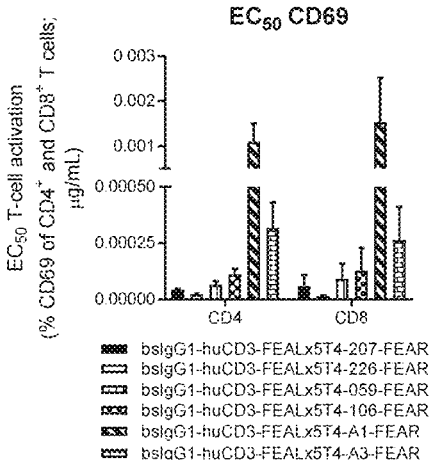
FIG. 10(II)B
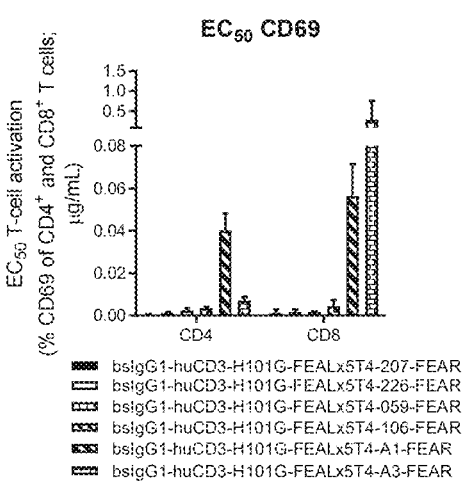
FIG. 10(II)C
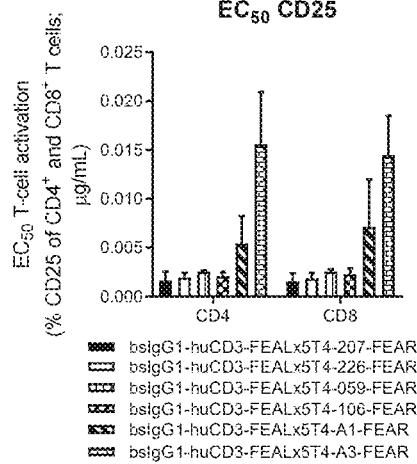
FIG. 10(II)D
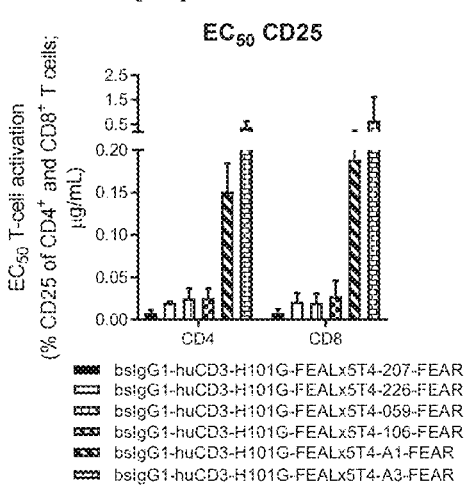
FIG. 10(II)E
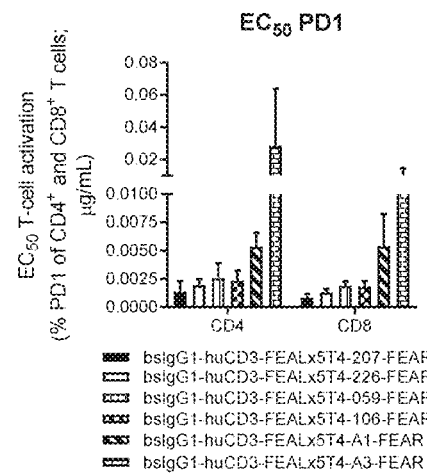
FIG. 10(II)F
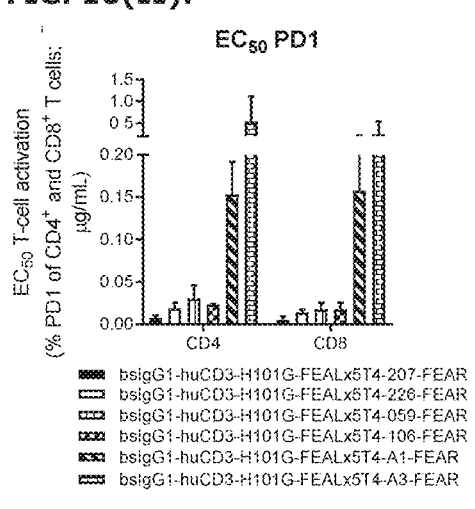

FIG. 11A

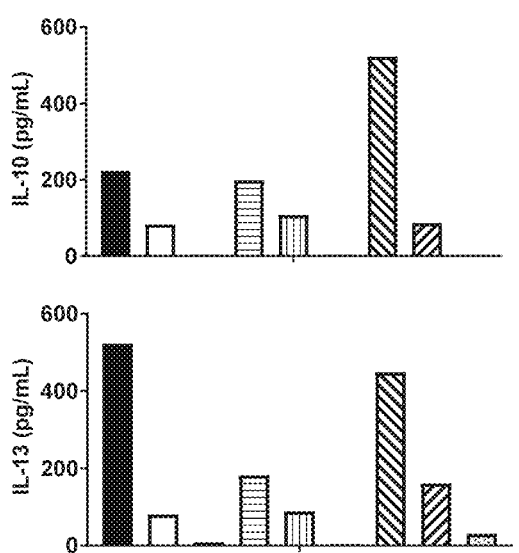

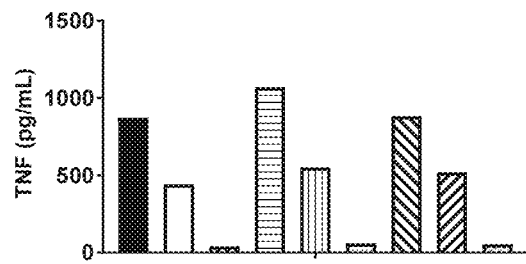

■ bsIgG1-huCD3-FEALx5T4-207-FEAR
□ bsIgG1-huCD3-H101G-FEALx5T4-207-FEAR
▨ IgG1-5T4-207-FEAR
▤ bsIgG1-huCD3-FEALx5T4-226-FEAR
▥ bsIgG1-huCD3-H101G-FEALx5T4-226-FEAR
▭ IgG1-5T4-226-FEAR
▧ bsIgG1-huCD3-FEALx5T4-059-FEAR
▨ bsIgG1-huCD3-H101G-FEALx5T4-059-FEAR
▤ IgG1-5T4-059-FEAR

FIG. 11B

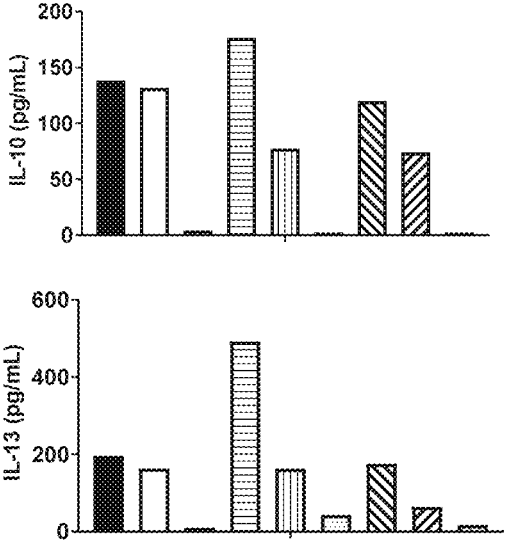

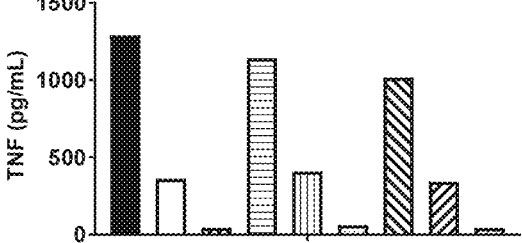

■ bsIgG1-huCD3-FEALx5T4-207-FEAR
□ bsIgG1-huCD3-H101G-FEALx5T4-207-FEAR
▨ IgG1-5T4-207-FEAR
▤ bsIgG1-huCD3-FEALx5T4-226-FEAR
▥ bsIgG1-huCD3-H101G-FEALx5T4-226-FEAR
▭ IgG1-5T4-226-FEAR
▧ bsIgG1-huCD3-FEALx5T4-059-FEAR
▨ bsIgG1-huCD3-H101G-FEALx5T4-059-FEAR
▤ IgG1-5T4-059-FEAR

FIG. 12A
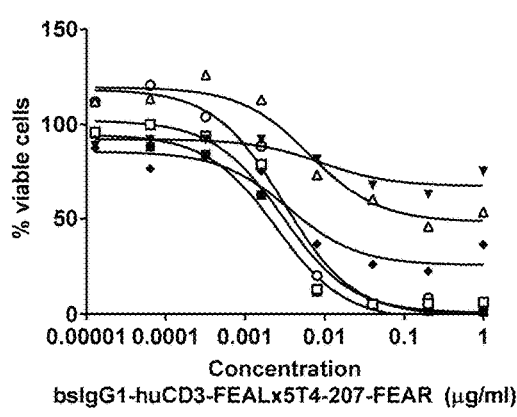
bsIgG1-huCD3-FEALx5T4-207-FEAR (μg/ml)
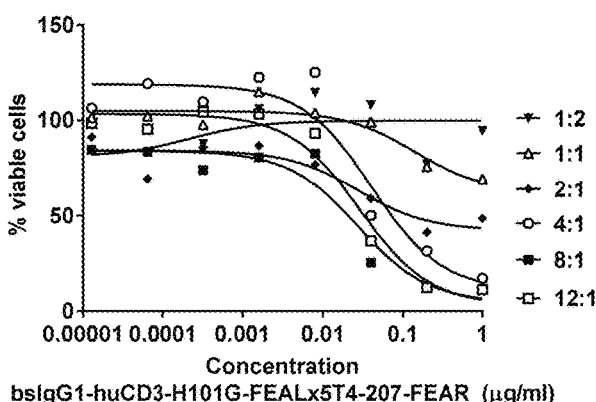
bsIgG1-huCD3-H101G-FEALx5T4-207-FEAR (μg/ml)
FIG. 12B
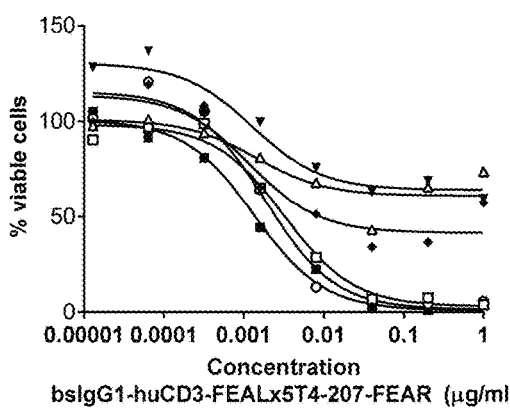
bsIgG1-huCD3-FEALx5T4-207-FEAR (μg/ml)
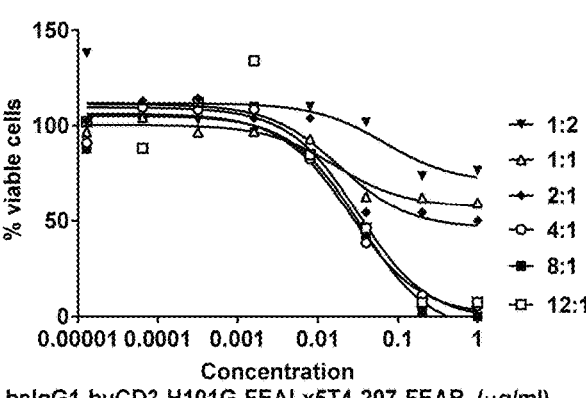
bsIgG1-huCD3-H101G-FEALx5T4-207-FEAR (μg/ml)

FIG. 13A
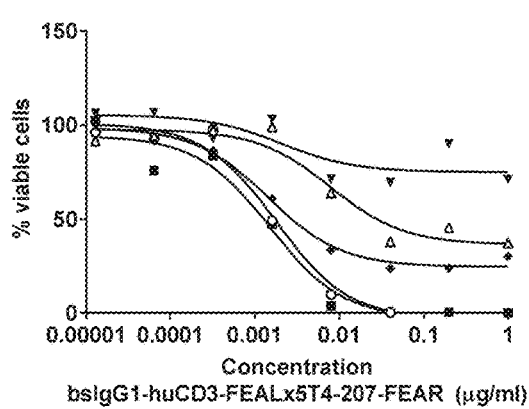
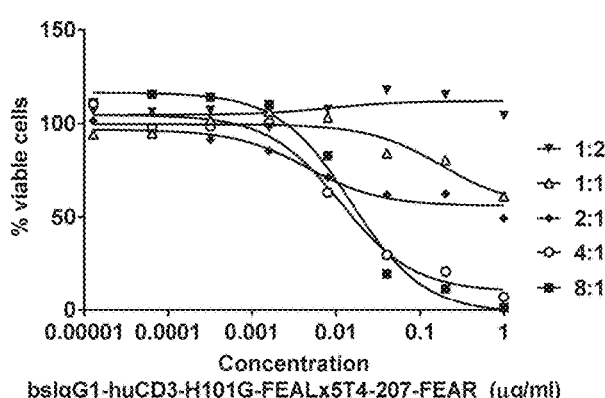
FIG. 13B
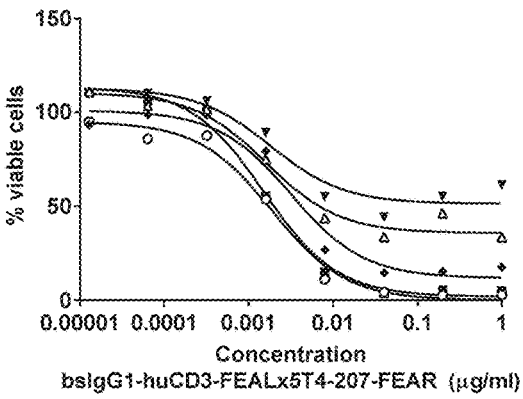
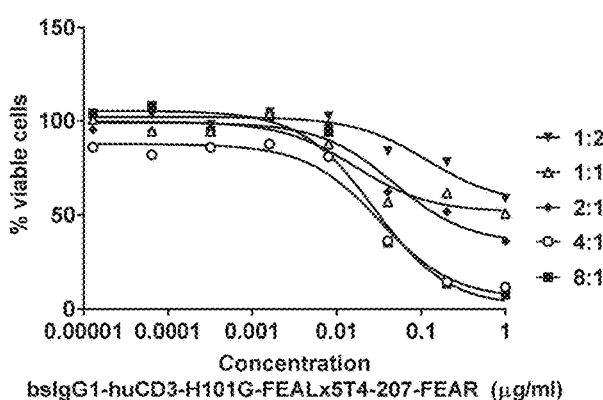

-○- PBS

-△- 0.5 mg/kg bsIgG1-huCD3-FEALx5T4-207-FEAR

-▲- 0.5 mg/kg bsIgG1-huCD3-H101G-FEALx5T4-207-FEAR

▽ Treatment bsIgG1-b12-FEALx5T4-059-FEAR-FITC bsIgG1-b12-FEALx5T4-207-FEAR-FITC

FIG. 16(I)A
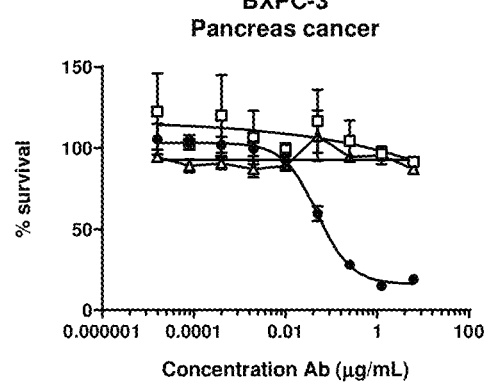
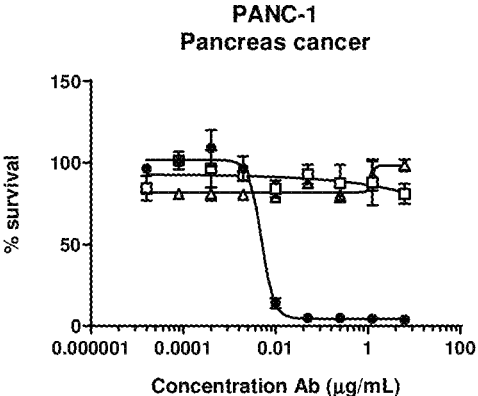
FIG. 16(I)B
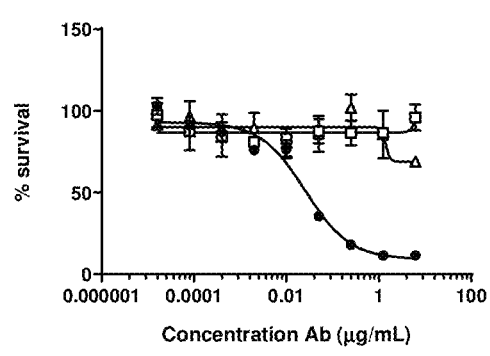
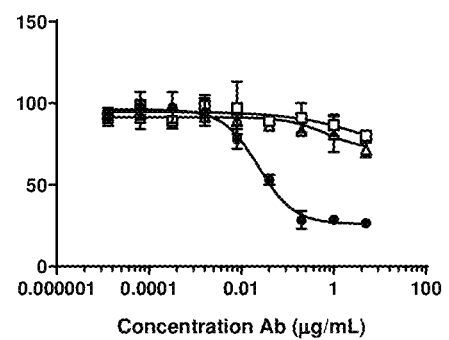
- ●— BsIgG1-huCD3-H101G-FEALx5T4-207-FEAR
- □— BsIgG1-b12-FEALx5T4-207-FEAR
- △— BsIgG1-huCD3-H101G-FEALxb12-FEAR

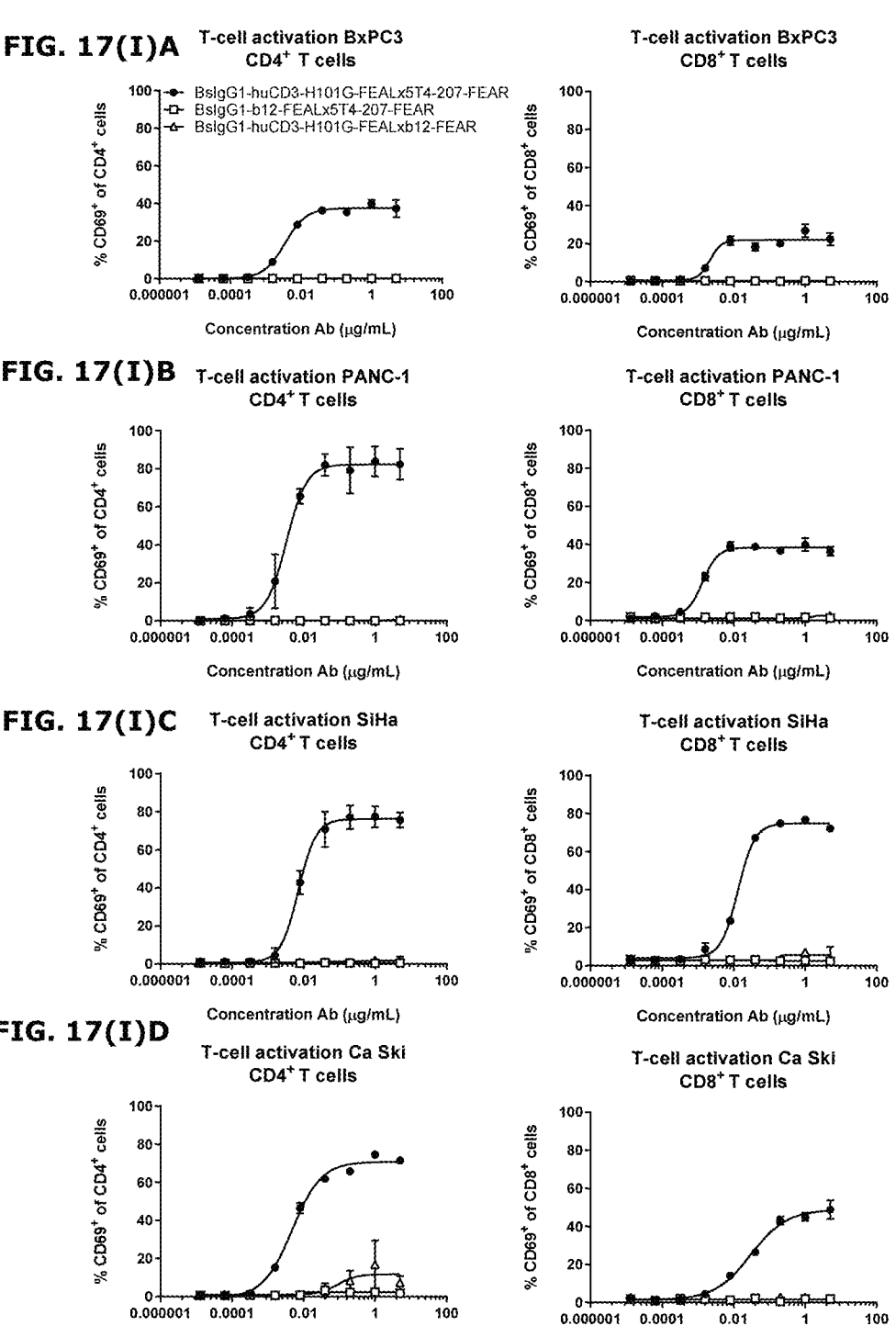
FIG. 17(I)A  T-cell activation BxPC3 CD4⁺ T cells
T-cell activation BxPC3 CD8⁺ T cells
FIG. 17(I)B  T-cell activation PANC-1 CD4⁺ T cells
T-cell activation PANC-1 CD8⁺ T cells
FIG. 17(I)C  T-cell activation SiHa CD4⁺ T cells
T-cell activation SiHa CD8⁺ T cells
FIG. 17(I)D  T-cell activation Ca Ski CD4⁺ T cells
T-cell activation Ca Ski CD8⁺ T cells FIG. 17(II)A
FIG. 17(II)B
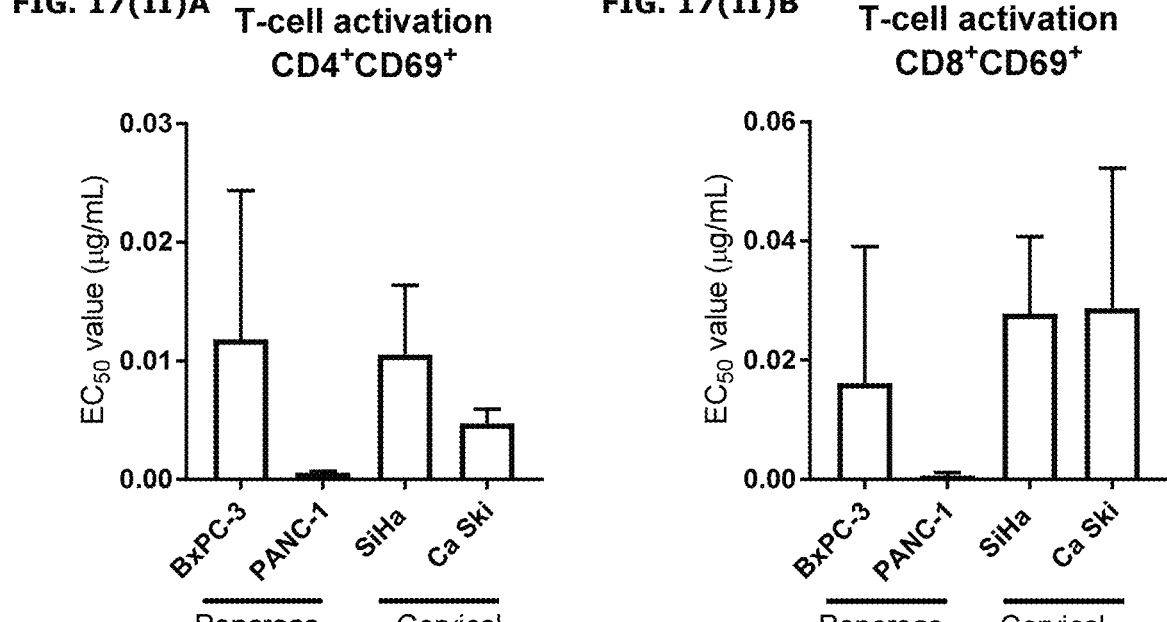

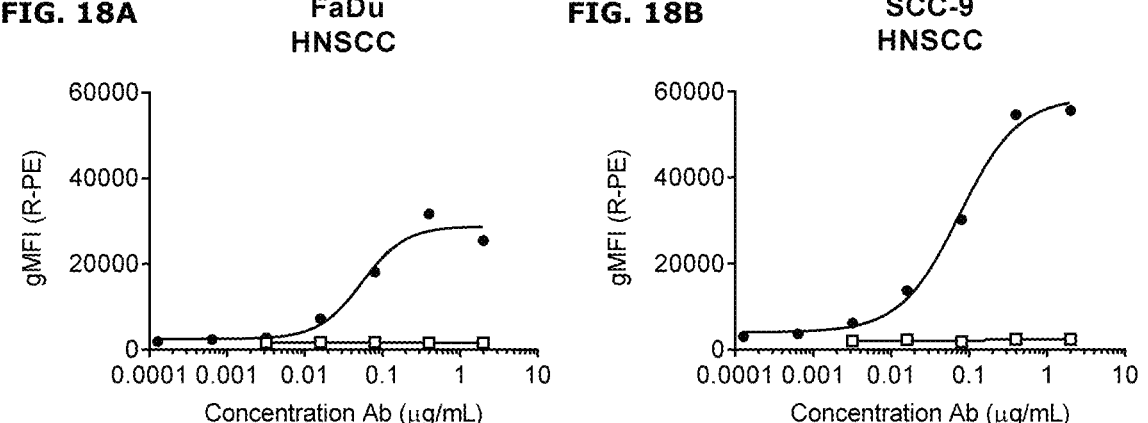
FIG. 18A     FaDu HNSCC       FIG. 18B     SCC-9 HNSCC
● bsIgG1-huCD3-H101G-FEALx5T4-207-FEAR
□ bsIgG1-huCD3-H101G-FEALxb12-FEAR

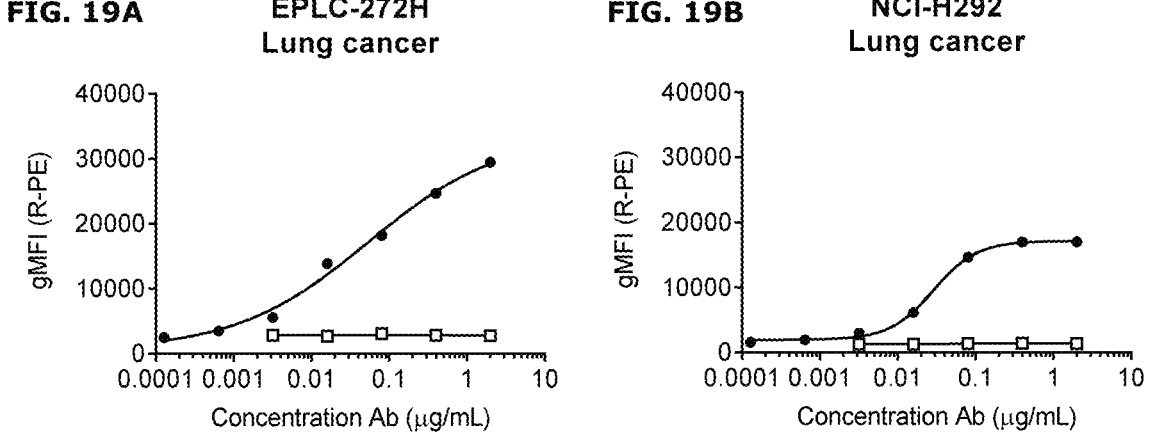
FIG. 19A     EPLC-272H Lung cancer
FIG. 19B     NCI-H292 Lung cancer
● bsIgG1-huCD3-H101G-FEALx5T4-207-FEAR
□ bsIgG1-huCD3-H101G-FEALxb12-FEAR

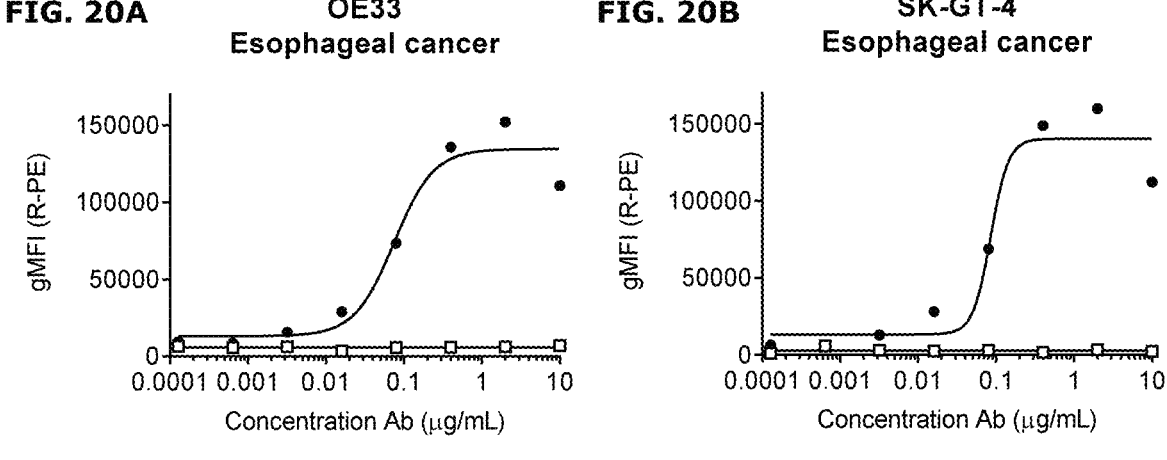
FIG. 20A OE33 Esophageal cancer
FIG. 20B SK-GT-4 Esophageal cancer
bsIgG1-huCD3-H101G-FEALx5T4-207-FEAR

FIG. 21A
SK-GT-4
Esophageal cancer
Percentage tumor cell viability vs Concentration Ab (μg/mL)
● bsIgG1-huCD3-H101G-FEALx5T4-207-FEAR
□ bsIgG1-huCD3-H101G-FEALxb12-FEAR
△ bsIgG1-b12-FEALx5T4-207-FEAR
FIG. 21B
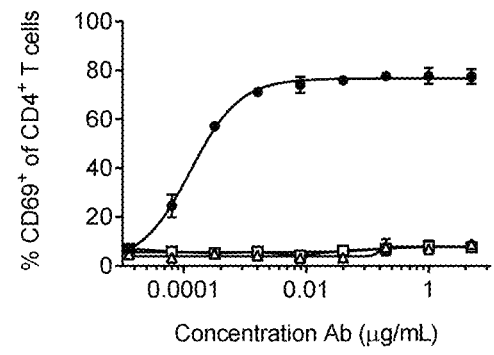
% CD69$^+$ of CD4$^+$ T cells vs Concentration Ab (μg/mL)
FIG. 21C
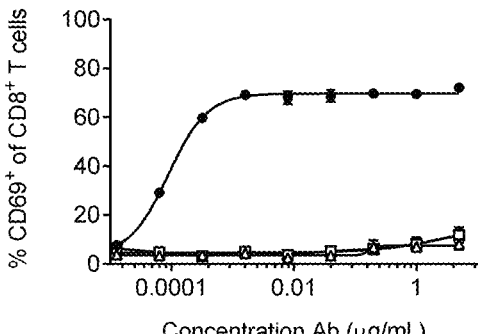
% CD69$^+$ of CD8$^+$ T cells vs Concentration Ab (μg/mL)

FIG. 24A EPLC-272H Lung cancer

FIG. 24D NCI-H292 Lung cancer

- ● bsIgG1-huCD3-H101G-FEALxST4-207-FEAR
- ○ bsIgG1-huCD3-H101G-FEALxb12-FEAR
- ☆ bsIgG1-b12-FEALxST4-207-FEAR

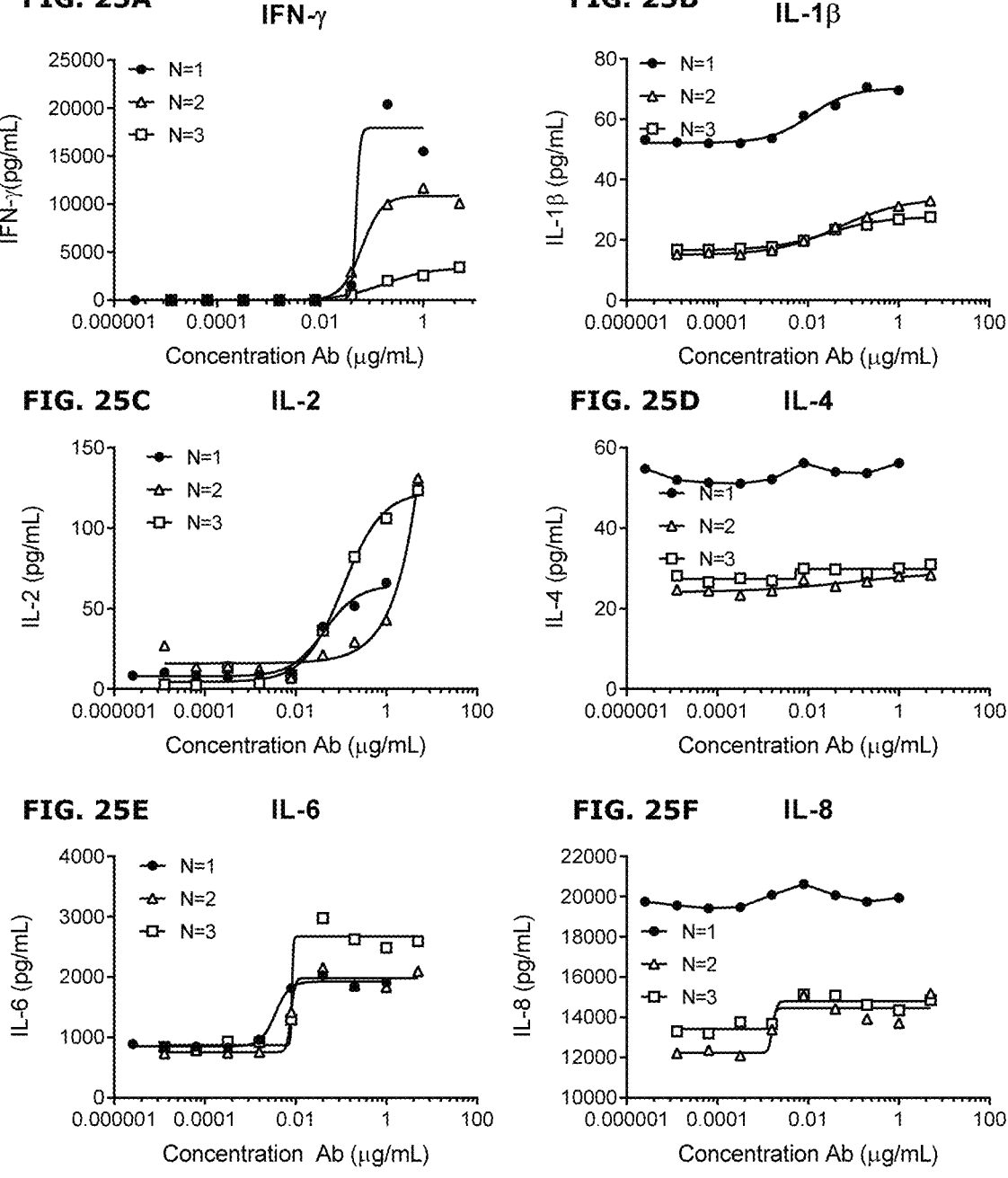
FIG. 25A   IFN-γ
FIG. 25B   IL-1β
FIG. 25C   IL-2
FIG. 25D   IL-4
FIG. 25E   IL-6
FIG. 25F   IL-8

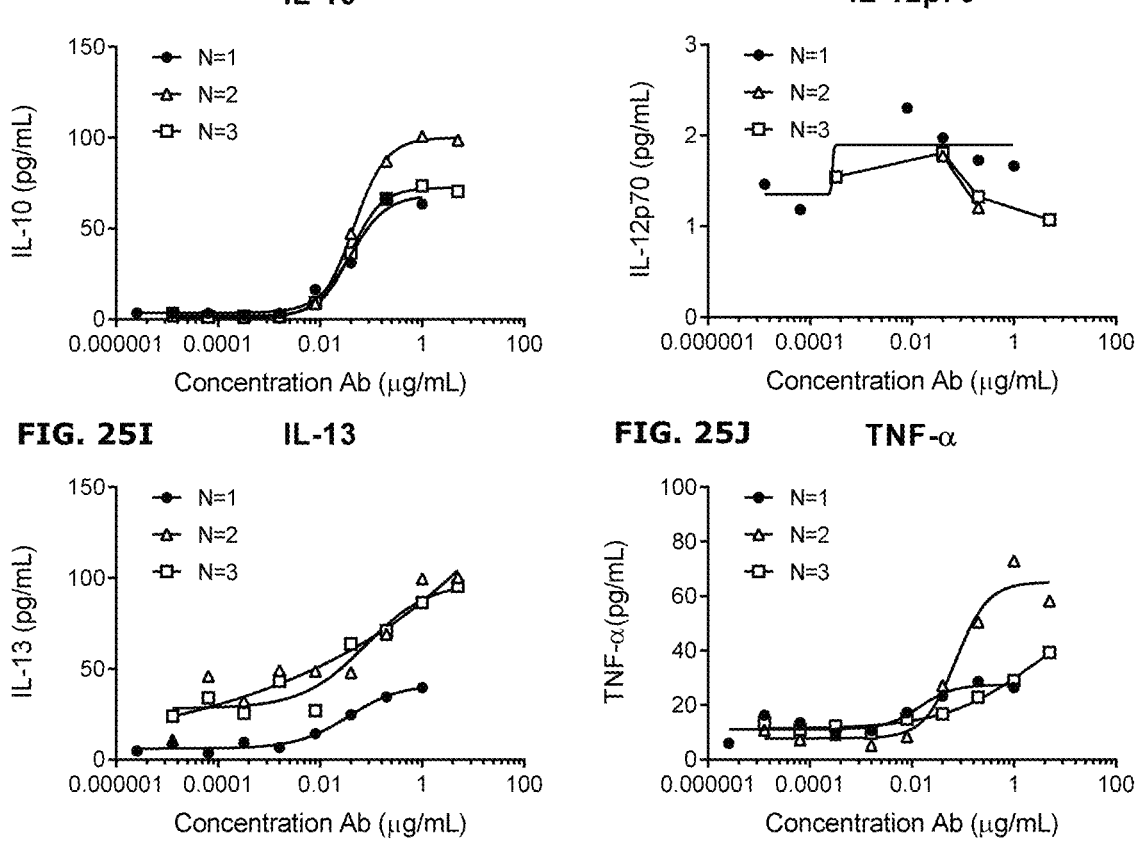
FIG. 25G    IL-10
FIG. 25H    IL-12p70
FIG. 25I    IL-13
FIG. 25J    TNF-α

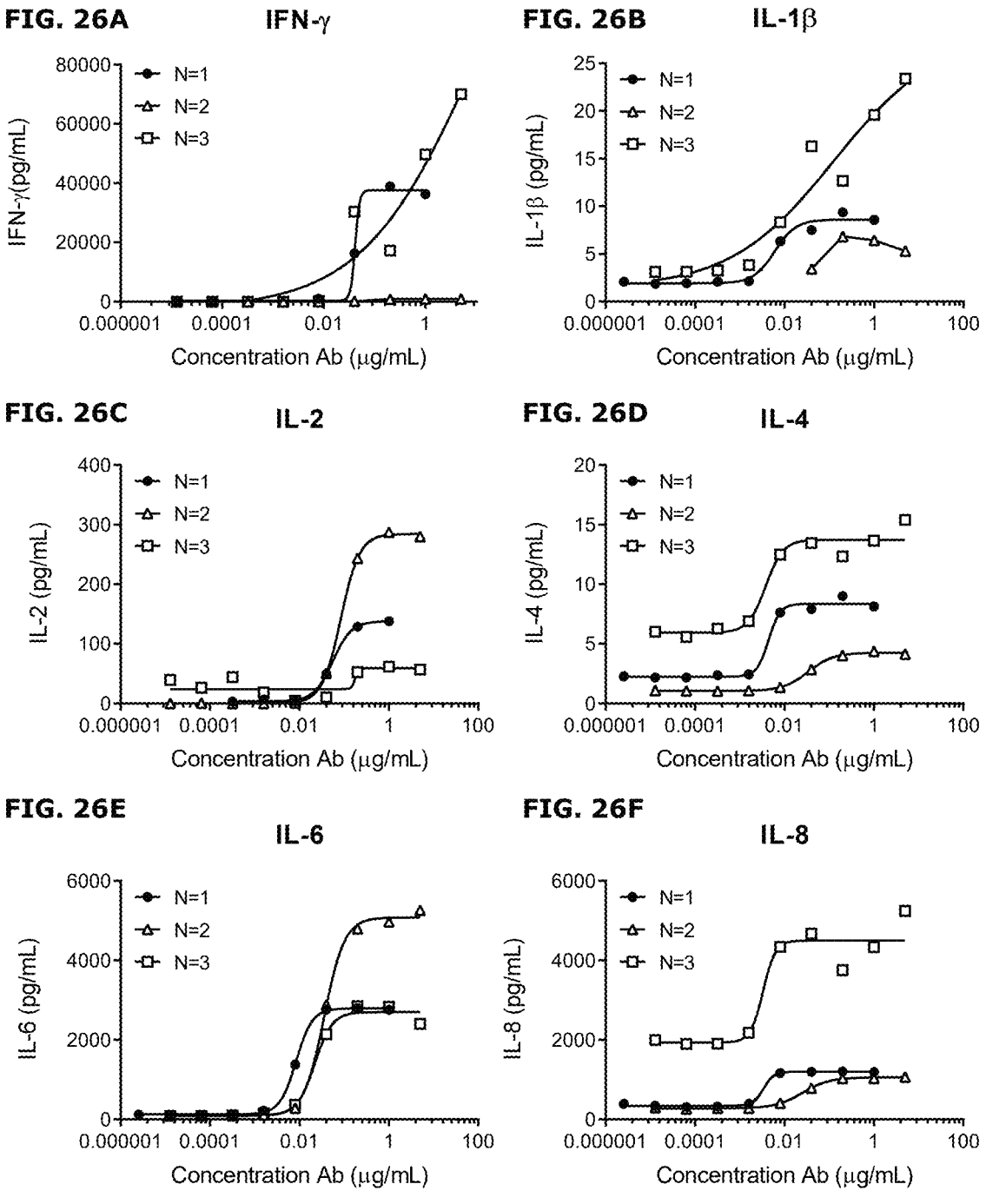

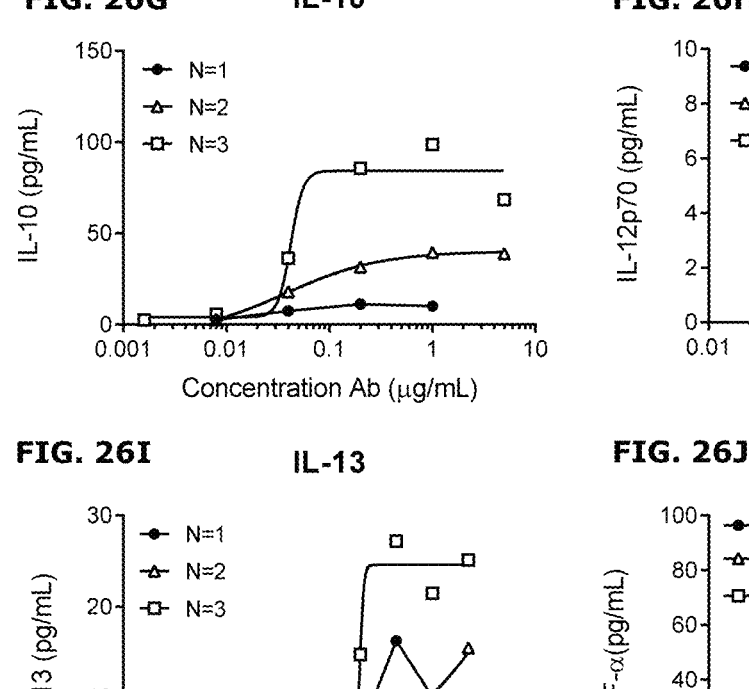
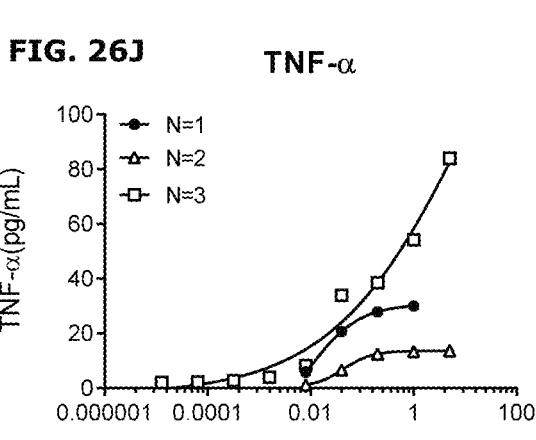

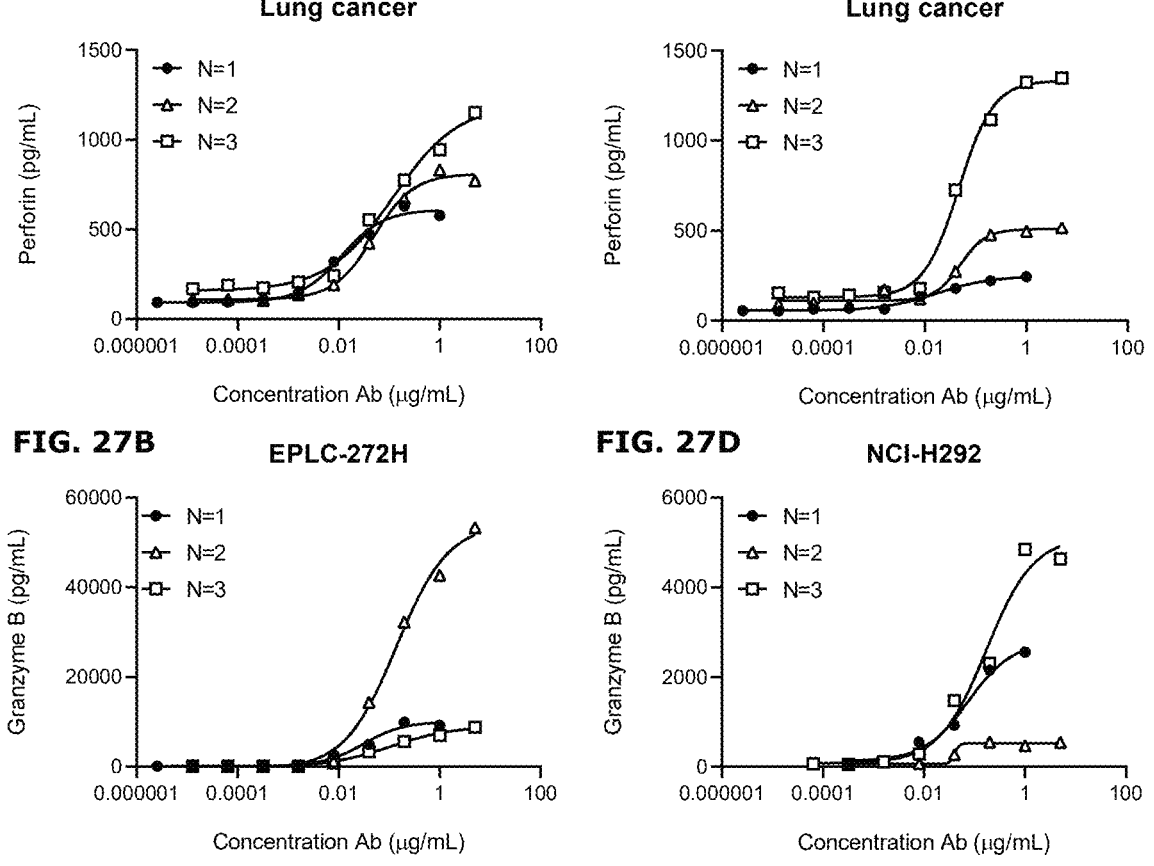
FIG. 27A EPLC-272H Lung cancer
FIG. 27C NCI-H292 Lung cancer
FIG. 27B EPLC-272H
FIG. 27D NCI-H292

FIG. 28A Fadu Head and neck cancer

FIG. 28D SCC-9 Head and neck cancer bsIgG1-huCD3-H101G-FEALx5T4-207-FEAR
bsIgG1-huCD3-H101G-FEALxb12-FEAR
bsIgG1-b12-FEALx5T4-207-FEAR

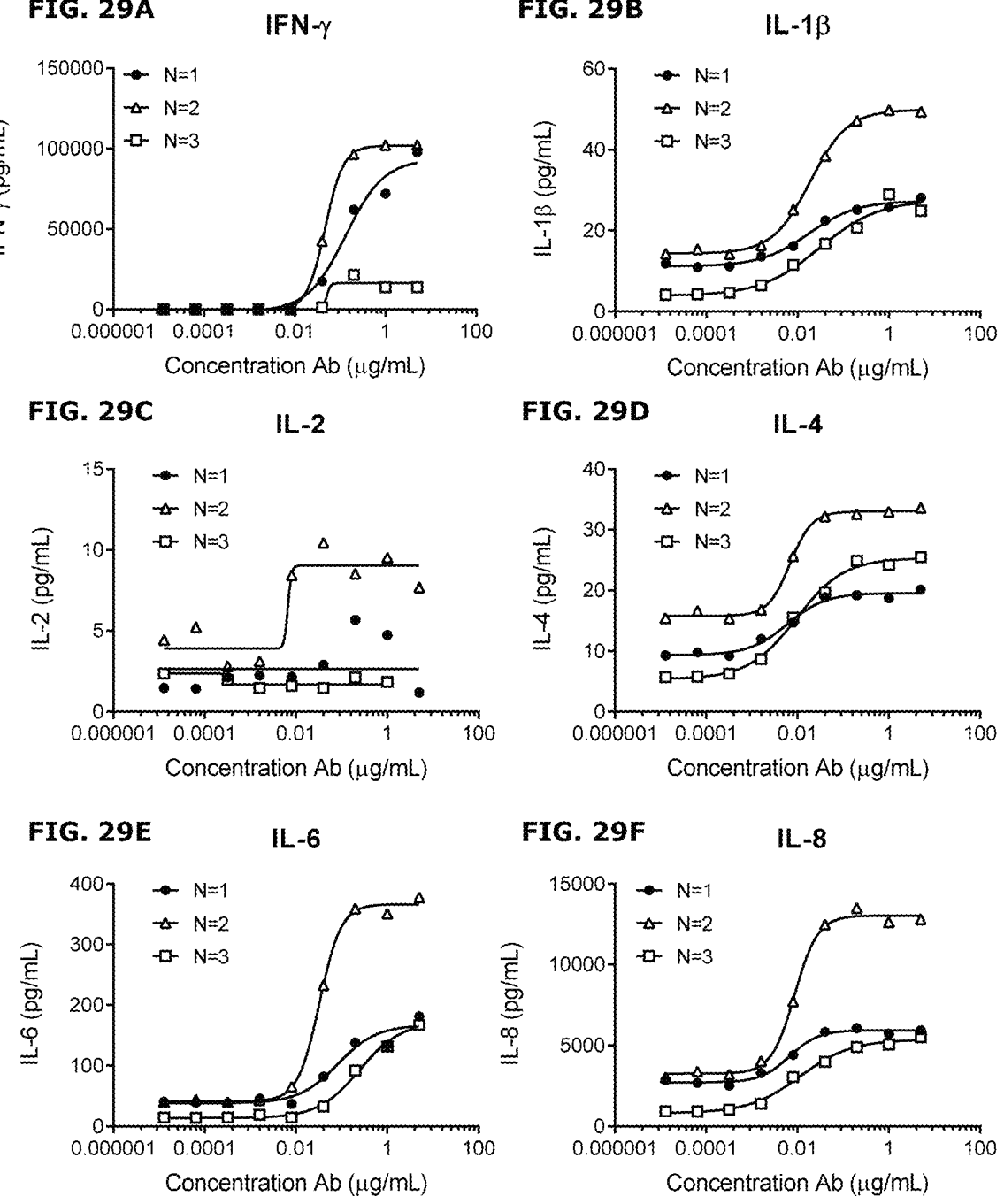

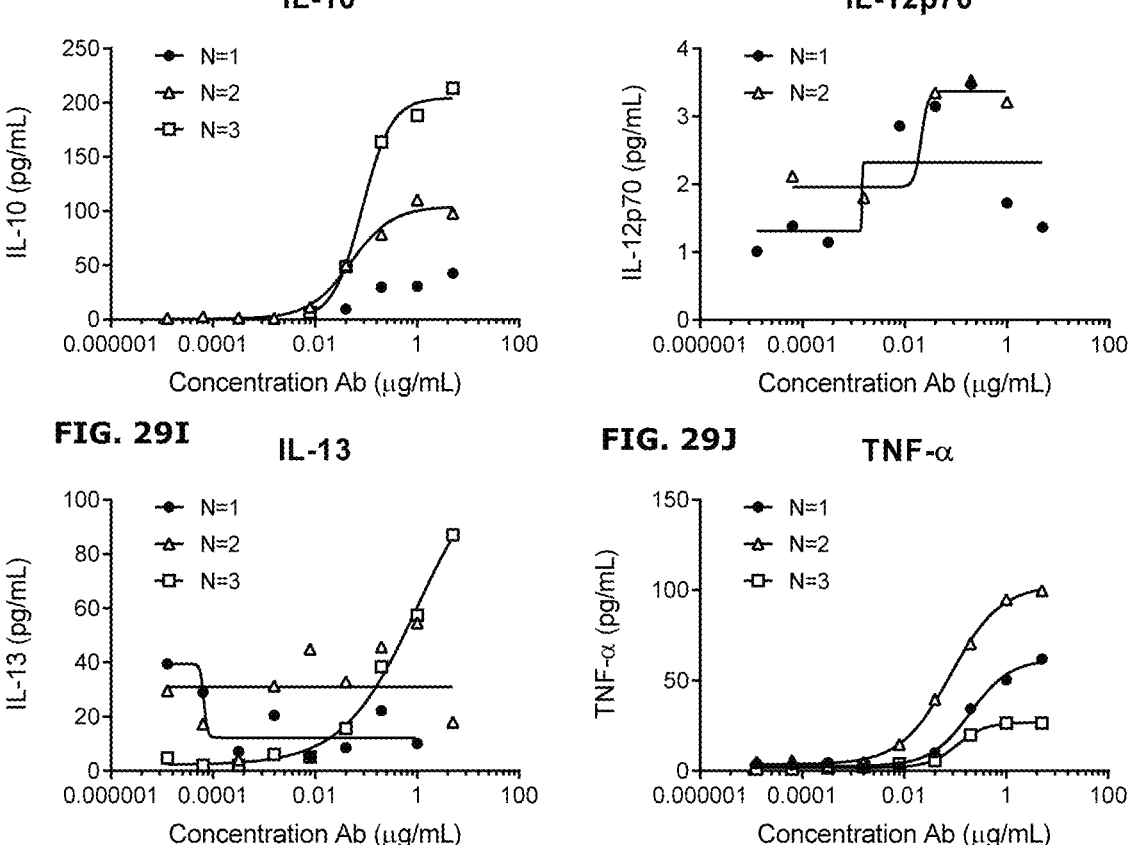
FIG. 29G    IL-10
FIG. 29H    IL-12p70
FIG. 29I    IL-13
FIG. 29J    TNF-α

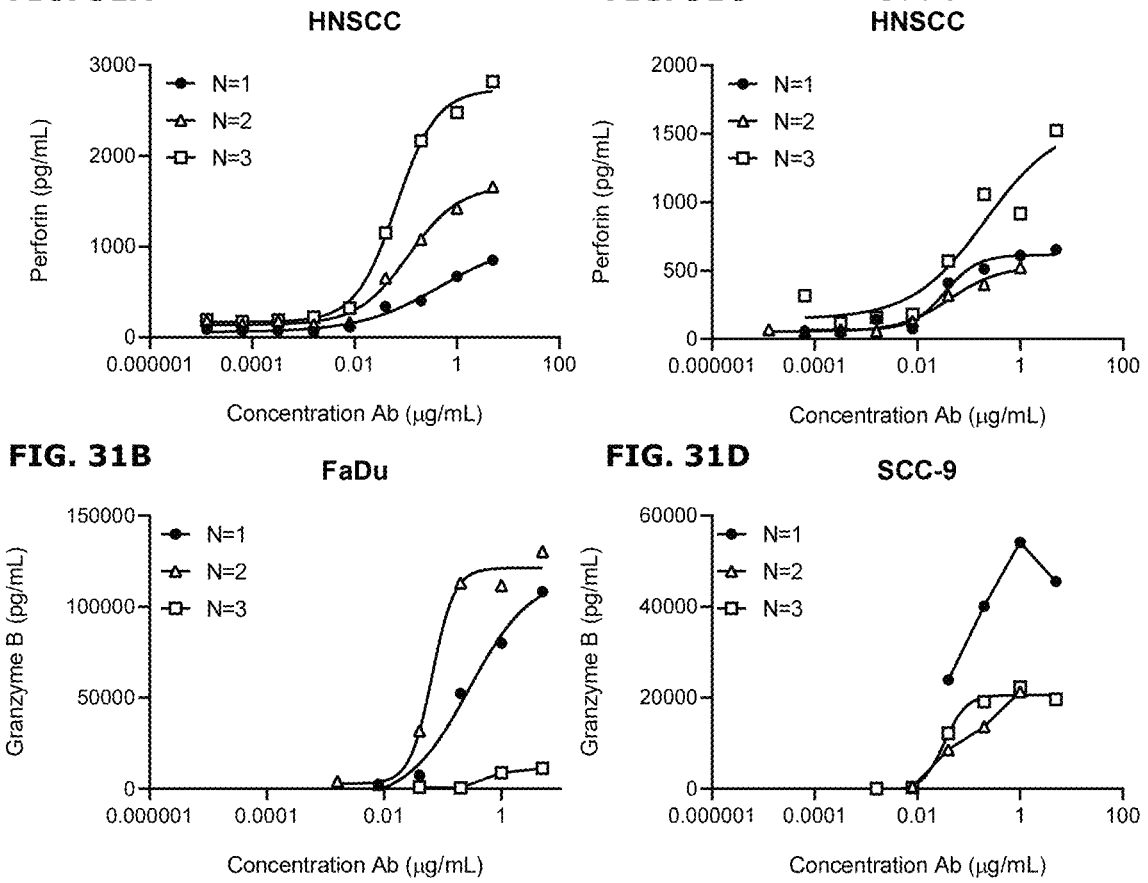
FIG. 31A      FaDu HNSCC
FIG. 31C      SCC-9 HNSCC
FIG. 31B      FaDu
FIG. 31D      SCC-9

| | | |
|---|---|---|
| ▲ bsIgG1-huCD3-H101G-FEALxb12-FEAR | E:T = 25:1 |
| ★ bsIgG1-b12-FEALx5T4-207-FEAR | E:T = 25:1 |
| ○ bsIgG1-huCD3-H101G-FEALx5T4-207-FEAR | E:T = 4:1 |
| △ bsIgG1-huCD3-H101G-FEALx5T4-207-FEAR | E:T = 10:1 |
| ▫ bsIgG1-huCD3-H101G-FEALx5T4-207-FEAR | E:T = 25:1 |

METHOD OF TREATING CANCER BY ADMINISTERING AN ANTIBODY WHICH BINDS TO 5T4

RELATED APPLICATIONS

This application is a 35 U.S.C. 371 national stage filing of International Application No. PCT/EP2020/075570, filed Sep. 11, 2020, which claims priority to U.S. Provisional Application No. 62/902,856, filed Sep. 19, 2019, U.S. Provisional Application No. 62/899,636, filed Sep. 12, 2019, the contents of the aforementioned applications are hereby incorporated by reference.

SEQUENCE LISTING

The instant application contains a Sequence Listing which has been submitted electronically in ASCII format and is hereby incorporated by reference in its entirety. Said ASCII copy, created on Mar. 11, 2022, is named Sequence_Listing_GMI_187US.txt and is 110888 bytes in size.

FIELD OF INVENTION

The present invention relates to the use of multispecific antibodies for use in the treatment of cancer selected from the group consisting of esophageal cancer, Non-small Cell Lung Cancer (NSCLC) and Squamous Cell Carcinoma of the Head and Neck (SCCHN).

BACKGROUND

5T4 (also known as trophoblast glycoprotein [TPBG] or Wnt-activated inhibitory factor 1 [WAIF1]) is a 72 kDa, single-pass transmembrane protein that contains 8 leucine-rich repeats (LRR) and 7 potential N-glycosylation sites (Zhao et al., 2014 Structure 22, 612-620).

5T4 expression is limited in normal adult tissues, except for placenta (Southall et al., 1990 Br J Cancer 61, 89-95). 5T4 is expressed in many human cancers, including renal, cervical, ovarian, lung, prostate and colon cancer (Stern and Harrop, 2017 Cancer Immunol Immunother 66, 415-426; Southall et al., 1990 Br J Cancer 61, 89-95). 5T4 expression in tumor cells drives tumor development by 1) facilitating epithelial-to-mesenchymal transition (Damelin et al., 2011 Cancer Res 71, 4236-4246; Carsberg et al., 1996 Int J Cancer 68, 84-92), and 2) inhibition of the canonical Wnt/beta-catenin signaling pathway and activation of the non-canonical Wnt pathway (Kagermeier-Schenk et al., 2011 Dev Cell 21, 1129-1143).

5T4-targeting antibodies and 5T4-targeting therapies have clinical activity in several cancers known to express 5T4 (including colorectal, lung and renal cancer). For example, naptumomab estafenatox is a recombinant fusion protein that consist of the 5T4-Fab moiety genetically fused to the engineered superantigen variant SEA/E-120. It is currently in clinical trials as an immunotherapy for non-small cell lung cancer (NSCLC), renal cell (RCC) and pancreatic cancer (see e.g. Eisen, et al., 2014 Curr Oncol Rep 16, 370). Furthermore, TroVax® is a modified vaccinia Ankara that expresses 5T4 constructs (MVA-5T4), which shows clinical benefit in colorectal, prostate and renal cancer (see e.g. Stern and Harrop, 2017 Cancer Immunol Immunother 66, 415-426; Scurr et al., 2017 JAMA Oncol 12, 10). Further anti-5T4 antibodies have been described in

WO2007106744, WO03038098, WO2011048369, WO2013041687, WO2017072207.

While significant progress has been made on eradication of cancer, there is still a need for further improvement of antibody-based cancer therapy.

SUMMARY OF INVENTION

It is an object of the present invention to provide a multispecific antibody, comprising an antigen binding region capable of binding to 5T4 and an antigen binding region capable of binding to CD3, for use in treatment of cancer selected from the group consisting of esophageal cancer, Non-small Cell Lung Cancer (NSCLC) and Squamous Cell Carcinoma of the Head and Neck (SCCHN).

In another aspect, the present invention relates to the use of a multispecific antibody comprising an antigen binding region capable of binding to 5T4 and an antigen binding region capable of binding to CD3 for the manufacture of a medicament for treatment of esophageal cancer.

Finally, an aspect of the invention provides a method of treating esophageal cancer, the method comprising administering a multispecific antibody comprising an antigen binding region capable of binding to 5T4 and an antigen binding region capable of binding to CD3, to a subject in need thereof.

BRIEF DESCRIPTION OF FIGURES

FIGS. 1A-1C. IgG1-5T4-A3-F405L showed no binding to the immobilized IgG1-5T4-A3-F405L-5T4ECDHis complex, indicating cross-block (self-block) with IgG1-5T4-A3-F405L. IgG1-5T4-H8-FEAR antibodies showed an increase in mass (indicating binding to the immobilized IgG1-5T4-A3-F405L-5T4ECDHis complex) and hence no cross-block with IgG1-5T4-A3-F405L. FIG. 1A. IgG1-5T4-059-FEAR, FIG. 1B. IgG1-5T4-207-FEAR and FIG. 1C. IgG1-5T4-226-FEAR all showed an initial increase in mass (indicating binding of the antibodies to the immobilized IgG1-5T4-A3-F405L-5T4ECDHis complex) followed by a rapid decrease in mass. This behavior of the antibodies is indicative of antibody displacement (Abdiche Y N, et al. (2017) Antibodies Targeting Closely Adjacent or Minimally Overlapping Epitopes Can Displace One Another. PLoS ONE 12(1): e0169535. doi:10.1371/journal.pone.0169535).

FIGS. 4A and 4B: Internalization capacity of monovalent 5T4 antibodies. Bispecific, toxin-conjugated antibodies that recognize 5T4 with one Fab-arm while recognizing an irrelevant antigen (HIV-1 gp120, which is not expressed on tumor cells) with the second Fab-arm, were generated by controlled Fab-arm exchange of unconjugated 5T4 antibodies with (HIV-1 gp120-specific) IgG1-b12 antibodies that had been conjugated with one Duostatin-3 molecule per antibody. MDA-MB-468 (FIG. 4A) and HCC1954 (FIG. 4B) cells were incubated with increasing concentrations of antibodies, as indicated. Cell viability was measured after 5 days. Data are presented as mean percentage viable cells of three replicate experiments. As negative control, monospecific, bivalent IgG1-b12 conjugated with Duostatin-3 (IgG1-b12-vcDuo3) was included.

FIGS. 5(I)A-5(I)D: Binding of CD3x5T4 bispecific antibodies to full length human and cynomolgus monkey 5T4 transfected into HEK-293 cells. Binding of monovalent and bivalent 5T4 antibodies was analysed using HEK-293 cells transiently transfected with full length human (left panels) or cynomolgus monkey 5T4 (right panels). Cells were incubated with increasing concentrations of antibodies, as indicated. After secondary labelling with FITC conjugated goat-anti-human IgG F(ab')2, binding was analysed by flow cytometry. As negative control antibody, IgG1-b12-K409R (3 μg/mL) was included. Data are presented as mean fluorescence intensity (MFI) values of two technical replicates±SD. FIG. 5(I)A. Binding of bsIgG1-huCD3-H101G-FEALx5T4-207-FEAR and IgG1-5T4-207-FEAR. FIG. 5(I)B. Binding of bsIgG1-huCD3-H101G-FEALx5T4-226-FEAR and IgG1-5T4-226-FEAR. FIG. 5(I)C. Binding of bsIgG1-huCD3-H101G-FEALx5T4-059-FEAR and IgG1-5T4-059-FEAR. FIG. 5(I)D. Binding of bsIgG1-huCD3-H101G-FEALx5T4-H8-FEAR and IgG1-5T4-H8-FEAR.

FIGS. 5(II)A-5(II)I: Binding of bispecific CD3x5T4 antibodies to cynomolgus monkey and human 5T4 transfected into HEK-293 cells. Mono- and bivalent binding of 5T4 antibodies was analysed using HEK-293 cells transiently transfected with human 5T4 (left panels) or with cynomolgus monkey 5T4 (right panels). Cells were incubated with increasing concentrations of antibodies, as indicated. After secondary labelling with phycoerythrin (PE)-conjugated goat-anti-human IgG F(ab')2, binding was analysed by flow cytometry. FIG. 5(II)A. Binding of bsIgG1-huCD3-H101G-FEALx5T4-207-FEAR and IgG1-5T4-207-FEAR; FIG. 5(II)B. Binding of bsIgG1-huCD3-H101G-FEALx5T4-226-FEAR and IgG1-5T4-226-FEAR; FIG. 5(II)C. Binding of bsIgG1-huCD3-H101G-FEALx5T4-059-FEAR and IgG1-5T4-059-FEAR; FIG. 5(II)D. Binding of bsIgG1-huCD3-H101G-FEALx5T4-106-FEAR and IgG1-5T4-106-FEAR; FIG. 5(II)E. Binding of bsIgG1-huCD3-H101G-FEALx5T4-076-FEAR and IgG1-5T4-076-FEAR; FIG. 5(II)F. Binding of bsIgG1-huCD3-H101G-FEALx5T4-085-

FEAR and IgG1-5T4-085-FEAR; FIG. 5(II)G. Binding of bsIgG1-huCD3-H101G-FEALx5T4-127-FEAR and IgG1-5T4-127-FEAR; FIG. 5(II)H. Binding of bsIgG1-huCD3-H101G-FEALx5T4-A1-FEAR and IgG1-5T4-A1-FEAR; FIG. 5(II)I. Binding of bsIgG1-huCD3-H101G-FEALx5T4-A3-FEAR and IgG1-5T4-A3-FEAR.

FIGS. 6(I)A-6(I)C: Binding of CD3x5T4 bispecific and 5T4 monospecific antibodies to 5T4-positive human tumor cells. Mono- and bivalent binding of 5T4 antibodies to HeLa cells (left panels) or MDA-MB-231 cells (right panels) was determined by flow cytometry. Cells were incubated with increasing concentrations of antibodies. After secondary labelling with FITC-conjugated goat-anti-human IgG F(ab')2, the MFI was determined by flow cytometry. FIG. 6(I)A. Binding of bsIgG1-huCD3-H101G-FEALx5T4-207-FEAR and IgG1-5T4-207-FEAR antibodies to HeLa cells (left panel) or MDA-MB-231 cells (right panel). FIG. 6(I)B. Binding of bsIgG1-huCD3-H101G-FEALx5T4-059-FEAR and IgG1-5T4-059-FEAR antibodies to HeLa cells (left panel) or MDA-MB-231 cells (right panel). FIG. 6(I)C. Binding of bsIgG1-huCD3-H101G-FEALx5T4-226-FEAR and IgG1-5T4-226-FEAR antibodies to HeLa cells (left panel) or MDA-MB-231 cells (right panel). IgG1-b12-K409R (3 μg/mL) was included as negative control (open circles).

FIGS. 6(II)A-6(II)H: Binding of CD3x5T4 bispecific and 5T4 monospecific antibodies to HeLa cells. Mono- and bivalent binding of 5T4 antibodies to HeLa cells was determined by flow cytometry. Cells were incubated with increasing concentrations of antibodies. After secondary labelling with Phycoerythrin (PE)-conjugated goat-anti-human IgG F(ab')2, the mean fluorescence intensity (MFI) was determined by flow cytometry. FIG. 6(II)A. Binding of bsIgG1-huCD3-H101G-FEALx5T4-207-FEAR and IgG1-5T4-207-FEAR; FIG. 6(II)B. Binding of bsIgG1-huCD3-H101G-FEALx5T4-226-FEAR and IgG1-5T4-226-FEAR; FIG. 6(II)C. Binding of bsIgG1-huCD3-H101G-FEALx5T4-059-FEAR and IgG1-5T4-059-FEAR; FIG. 6(II)D. Binding of bsIgG1-huCD3-H101G-FEALx5T4-106-FEAR and IgG1-5T4-106-FEAR; FIG. 6(II)E. Binding of bsIgG1-huCD3-H101G-FEALx5T4-085-FEAR and IgG1-5T4-085-FEAR; FIG. 6(II)F. Binding of bsIgG1-huCD3-H101G-FEALx5T4-127-FEAR and IgG1-5T4-127-FEAR; FIG. 6(II)G. Binding of bsIgG1-huCD3-H101G-FEALx5T4-A1-FEAR and IgG1-5T4-A1-FEAR; FIG. 6(II)H. Binding of bsIgG1-huCD3-H101G-FEALx5T4-A3-FEAR and IgG1-5T4-A3-FEAR FIGS. 6(III)A-6(III)H: Binding of CD3x5T4 bispecific and 5T4 monospecific antibodies to MDA-MB-231 cells. Mono- and bivalent binding of 5T4 antibodies to MDA-MB-231 cells was determined by flow cytometry. Cells were incubated with increasing concentrations of antibodies. After secondary labelling with PE-conjugated goat-anti-human IgG F(ab')2, the mean fluorescence intensity (MFI) was determined by flow cytometry. FIG. 6(III)A. Binding of bsIgG1-huCD3-H101G-FEALx5T4-207-FEAR and IgG1-5T4-207-FEAR; FIG. 6(III)B. Binding of bsIgG1-huCD3-H101G-FEALx5T4-226-FEAR and IgG1-5T4-226-FEAR; FIG. 6(III)C. Binding of bsIgG1-huCD3-H101G-FEALx5T4-059-FEAR and IgG1-5T4-059-FEAR; FIG. 6(III)D. Binding of bsIgG1-huCD3-H101G-FEALx5T4-106-FEAR and IgG1-5T4-106-FEAR; FIG. 6(III)E. Binding of bsIgG1-huCD3-H101G-FEALx5T4-085-FEAR and IgG1-5T4-085-FEAR; FIG. 6(III)F. Binding of bsIgG1-huCD3-H101G-FEALx5T4-127-FEAR and IgG1-5T4-127-FEAR; FIG. 6(III)G. Binding of bsIgG1-huCD3-H101G-FEALx5T4-A1-FEAR and IgG1-5T4-A1-FEAR; FIG.

6(III)H. Binding of bsIgG1-huCD3-H101G-FEALx5T4-A3-FEAR and IgG1-5T4-A3-FEAR.

FIGS. 7(I)A-7(I)C: Induction of cytotoxicity in vitro by CD3x5T4 bispecific antibodies in MDA-MB-231 cells using Purified T cells as effector cells. MDA-MB-231 cells were incubated with increasing concentrations of CD3x5T4 bispecific antibodies or monospecific, bivalent 5T4 antibodies and isolated T cells as effector cells in an Effector:Target cell (E:T) ratio of 8:1. Purified T cells obtained from two different donors were used for this experiment, donor A (left panels) and donor B (right panels). Cytotoxicity was determined by measuring the percentage of viable MDA-MB-231 cells after 72 hrs of incubation (% viable cells=[absorbance sample−absorbance staurosporine-treated target cells]/[absorbance untreated target cells−absorbance staurosporine-treated target cells]×100). FIG. 7(I)A. Cytotoxicity induced in the presence of bsIgG1-huCD3-FEALx5T4-207-FEAR, bsIgG1-huCD3-H101G-FEALx5T4-207-FEAR and IgG1-5T4-207-FEAR; FIG. 7(I)B. Cytotoxicity induced in the presence of bsIgG1-huCD3-FEALx5T4-226-FEAR, bsIgG1-huCD3-H101G-FEALx5T4-226-FEAR and IgG1-5T4-226-FEAR; FIG. 7(I)C. Cytotoxicity induced in the presence of bsIgG1-huCD3-FEALx5T4-059-FEAR, bsIgG1-huCD3-H101G-FEALx5T4-059-FEAR and IgG1-5T4-059-FEAR.

Figure 7:
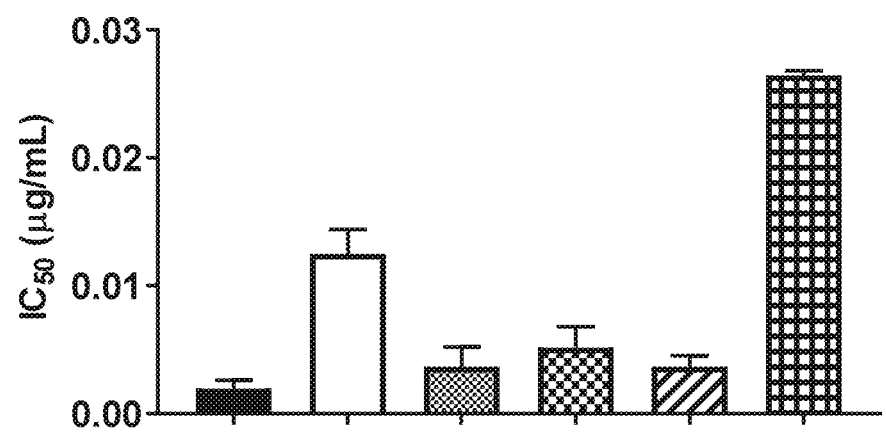

FIG. 7(II): IC50 values of cytotoxicity induced in vitro by CD3x5T4 bispecific antibodies in MDA-MB-231 cells using purified T cells as effector cells. IC50 values of the T-cell mediated cytotoxicity induced by bsIgG1-huCD3-FEALx5T4-207-FEAR, bsIgG1-huCD3-H101G-FEALx5T4-207-FEAR, bsIgG1-huCD3-FEALx5T4-226-FEAR, bsIgG1-huCD3-H101G-FEALx5T4-226-FEAR, bsIgG1-huCD3-FEALx5T4-059-FEAR or bsIgG1-huCD3-H101G-FEALx5T4-059-FEAR in MDA-MB-231 cells were analyzed using GraphPad Prism V7.02 software. Data are presented as mean IC50 values of two different donors±SD.

FIGS. 8(I)A-8(I)F: Induction of cytotoxicity by CD3x5T4 bispecific antibodies in MDA-MB-231 cells using T cells as effector cells in vitro. MDA-MB-231 cells were incubated with increasing concentrations of CD3x5T4 bispecific antibodies or 5T4 homodimers and isolated T cells as effector cells in an E:T ratio of 8:1. Three different donors were used for this experiment. Data shown are mean % survival±standard error of the mean (SEM) of three donors tested. FIG. 8(I)A. T-cell-mediated cytotoxicity (decrease in survival) induced in the presence of bsIgG1-huCD3-FEALx5T4-207-FEAR, bsIgG1-huCD3-H101G-FEALx5T4-207-FEAR and IgG1-5T4-207-FEAR; FIG. 8(I)B. T-cell-mediated cytotoxicity induced in the presence of bsIgG1-huCD3-FEALx5T4-226-FEAR, bsIgG1-huCD3-H101G-FEALx5T4-226-FEAR and IgG1-5T4-226-FEAR; FIG. 8(I)C. T-cell-mediated cytotoxicity induced in the presence of bsIgG1-huCD3-FEALx5T4-059-FEAR, bsIgG1-huCD3-H101G-FEALx5T4-059-FEAR and IgG1-5T4-059-FEAR; FIG. 8(I)D. T-cell-mediated cytotoxicity induced in the presence of bsIgG1-huCD3-FEALx5T4-106-FEAR, bsIgG1-huCD3-H101G-FEALx5T4-106-FEAR and IgG1-5T4-106-FEAR; FIG. 8(I)E. T-cell-mediated cytotoxicity induced in the presence of bsIgG1-huCD3-FEALx5T4-A1-FEAR, bsIgG1-huCD3-H101G-FEALx5T4-A1-FEAR and IgG1-5T4-A1-FEAR; FIG. 8(I)F. T-cell-mediated cytotoxicity induced in the presence of bsIgG1-huCD3-FEALx5T4-A3-FEAR, bsIgG1-huCD3-H101G-FEALx5T4-A3-FEAR and IgG1-5T4-A3-FEAR.

FIGS. 8(II)A and 8(II)B: IC50 values of cytotoxicity induced by CD3x5T4 bispecific antibodies in MDA-MB- 231 cells using T cells as effector cells in vitro. IC50 values of the T-cell-mediated cytotoxicity induced CD3x5T4 bispecific antibodies in MDA-MB-231 cells were analyzed using GraphPad Prism V7.02 software. Data are presented as mean IC50 values of three different donors±SD. FIG. 8(II)A. IC50 values of the T-cell-mediated cytotoxicity induced by bsIgG1-huCD3-FEALx5T4-207-FEAR, bsIgG1-huCD3-FEALx5T4-226-FEAR, bsIgG1-huCD3-FEALx5T4-059-FEAR, bsIgG1-huCD3-FEALx5T4-106-FEAR, bsIgG1-huCD3-FEALx5T4-A1-FEAR and bsIgG1-huCD3-FEALx5T4-A3-FEAR; FIG. 8(II)B. IC50 values of the T-cell-mediated cytotoxicity induced by bsIgG1-huCD3-H101G-FEALx5T4-207-FEAR, bsIgG1-huCD3-H101G-FEALx5T4-226-FEAR, bsIgG1-huCD3-H101G-FEALx5T4-059-FEAR, bsIgG1-huCD3-H101G-FEALx5T4-106-FEAR, bsIgG1-huCD3-H101G-FEALx5T4-A1-FEAR and bsIgG1-huCD3-H101G-FEALx5T4-A3-FEAR.

FIGS. 9(I)A-9(I)C: In vitro T-cell activation by CD3x5T4 bispecific antibodies in the presence of MDA-MB-231 cells. MDA-MB-231 cells were incubated with increasing concentrations of CD3x5T4 bispecific antibodies and monospecific, bivalent 5T4 antibodies, as indicated, and isolated T cells as effector cells in an E:T ratio of 8:1. The expression of three T cell activation markers (PD1 [upper panels], CD25 [middle panels] and CD69 [lower panels]) was analyzed by flow cytometry. Two different donors were used for this experiment, donor A (closed symbols) and donor B (open symbols). FIG. 9(I)A. T-cell activation induced in the presence of bsIgG1-huCD3-FEALx5T4-207-FEAR, bsIgG1-huCD3-H101G-FEALx5T4-207-FEAR and IgG1-5T4-207-FEAR; FIG. 9(I)B. T-cell activation induced in the presence of bsIgG1-huCD3-FEALx5T4-226-FEAR, bsIgG1-huCD3-H101G-FEALx5T4-226-FEAR and IgG1-5T4-226-FEAR; FIG. 9(I)C. T-cell activation induced in the presence of bsIgG1-huCD3-FEALx5T4-059-FEAR, bsIgG1-huCD3-H101G-FEALx5T4-059-FEAR and IgG1-5T4-059-FEAR.

Figure 9:
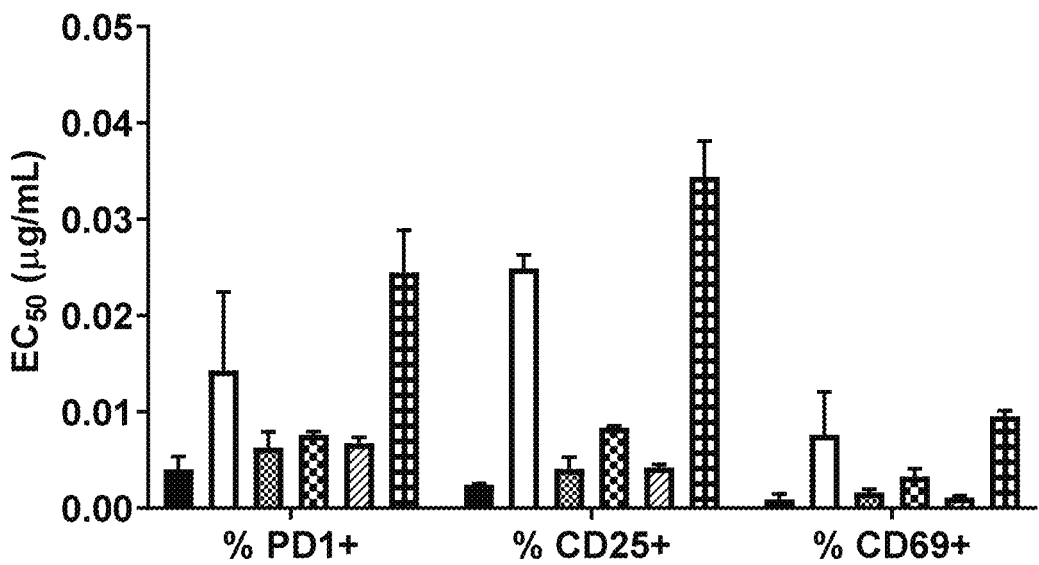

FIG. 9(II): EC50 values of in vitro T-cell activation by CD3x5T4 bispecific antibodies in the presence of MDA-MB-231 cells. EC50 values of in vitro T-cell activation markers (PD1, CD25 and CD69) induced by bsIgG1-huCD3-FEALx5T4-207-FEAR, bsIgG1-huCD3-H101G-FEALx5T4-207-FEAR, bsIgG1-huCD3-FEALx5T4-226-FEAR, bsIgG1-huCD3-H101G-FEALx5T4-226-FEAR, bsIgG1-huCD3-FEALx5T4-059-FEAR or bsIgG1-huCD3-H101G-FEALx5T4-059-FEAR in the presence of MDA-MB-231 cells were analyzed using GraphPad Prism V7.02 software. Data are presented as mean of two different donors±SD.

FIGS. 10(I)A-10(I)F: In vitro T-cell activation by CD3x5T4 bispecific antibodies in the presence of MDA-MB-231 cells. MDA-MB-231 cells were incubated with increasing concentrations of CD3x5T4 bispecific antibodies and 5T4 homodimers and isolated T cells as effector cells in an E:T ratio of 8:1. T-cell activation was measured by an increase in % CD69+ cells within the CD4+(left panels) and CD8+(right panels) T cell populations. Three different donors were used for this experiment; data shown are mean % CD69 upregulation±SEM of three donors tested. FIG. 10(I)A. T-cell activation induced in the presence of bsIgG1-huCD3-FEALx5T4-207-FEAR, bsIgG1-huCD3-H101G-FEALx5T4-207-FEAR and IgG1-5T4-207-FEAR; FIG. 10(I)B. T-cell activation induced in the presence of bsIgG1-huCD3-FEALx5T4-226-FEAR, bsIgG1-huCD3-H101G-FEALx5T4-226-FEAR and IgG1-5T4-226-FEAR; FIG. 10(I)C. T-cell activation induced in the presence of bsIgG1- huCD3-FEALx5T4-059-FEAR, bsIgG1-huCD3-H101G-FEALx5T4-059-FEAR and IgG1-5T4-059-FEAR; FIG. 10(I)D. T-cell activation induced in the presence of bsIgG1-huCD3-FEALx5T4-106-FEAR, bsIgG1-huCD3-H101G-FEALx5T4-106-FEAR and IgG1-5T4-106-FEAR; FIG. 10(I)E. T-cell activation induced in the presence of bsIgG1-huCD3-FEALx5T4-A1-FEAR, bsIgG1-huCD3-H101G-FEALx5T4-A1-FEAR and IgG1-5T4-A1-FEAR; FIG. 10(I)F. T-cell activation induced in the presence of bsIgG1-huCD3-FEALx5T4-A3-FEAR, bsIgG1-huCD3-H101G-FEALx5T4-A3-FEAR and IgG1-5T4-A3-FEAR.

FIGS. 10(II)A-10(II)F: $EC_{50}$ values of in vitro T-cell activation by CD3x5T4 bispecific antibodies in the presence of MDA-MB-231 cells. $EC_{50}$ values of T-cell activation markers (increase in % of CD69+[FIGS. 10(II)A and 10(II)B], CD25+[FIGS. 10(II)C and 10(II)D] and PD1+[FIGS. 10(II)E and 10(II)F], CD25 and CD69 cells within the CD4+ and CD8+ T cell populations) induced in vitro by CD3x5T4 bispecific antibodies in the presence of MDA-MB-231 cells were analyzed using GraphPad Prism V7.02 software. Data are presented as mean of three different donors±SD. FIG. 10(II)A. $EC_{50}$ values of the CD69 upregulation induced by bsIgG1-huCD3-FEALx5T4-207-FEAR, bsIgG1-huCD3-FEALx5T4-226-FEAR, bsIgG1-huCD3-FEALx5T4-059-FEAR, bsIgG1-huCD3-FEALx5T4-106-FEAR, bsIgG1-huCD3-FEALx5T4-A1-FEAR and bsIgG1-huCD3-FEALx5T4-A3-FEAR; FIG. 10(II)B. $EC_{50}$ values of the CD69 upregulation induced by bsIgG1-huCD3-H101G-FEALx5T4-207-FEAR, bsIgG1-huCD3-H101G-FEALx5T4-226-FEAR, bsIgG1-huCD3-H101G-FEALx5T4-059-FEAR, bsIgG1-huCD3-H101G-FEALx5T4-106-FEAR, bsIgG1-huCD3-H101G-FEALx5T4-A1-FEAR and bsIgG1-huCD3-H101G-FEALx5T4-A3-FEAR. FIG. 10(II)C. $EC_{50}$ values of the CD25 upregulation induced by bsIgG1-huCD3-FEALx5T4-207-FEAR, bsIgG1-huCD3-FEALx5T4-226-FEAR, bsIgG1-huCD3-FEALx5T4-059-FEAR, bsIgG1-huCD3-FEALx5T4-106-FEAR, bsIgG1-huCD3-FEALx5T4-A1-FEAR and bsIgG1-huCD3-FEALx5T4-A3-FEAR; FIG. 10(II)D. $EC_{50}$ values of the CD25 upregulation induced by bsIgG1-huCD3-H101G-FEALx5T4-207-FEAR, bsIgG1-huCD3-H101G-FEALx5T4-226-FEAR, bsIgG1-huCD3-H101G-FEALx5T4-059-FEAR, bsIgG1-huCD3-H101G-FEALx5T4-106-FEAR, bsIgG1-huCD3-H101G-FEALx5T4-A1-FEAR and bsIgG1-huCD3-H101G-FEALx5T4-A3-FEAR. FIG. 10(II)E. $EC_{50}$ values of the PD1 upregulation induced by bsIgG1-huCD3-FEALx5T4-207-FEAR, bsIgG1-huCD3-FEALx5T4-226-FEAR, bsIgG1-huCD3-FEALx5T4-059-FEAR, bsIgG1-huCD3-FEALx5T4-106-FEAR, bsIgG1-huCD3-FEALx5T4-A1-FEAR and bsIgG1-huCD3-FEALx5T4-A3-FEAR; FIG. 10(II)F. $EC_{50}$ values of the PD1 upregulation induced by bsIgG1-huCD3-H101G-FEALx5T4-207-FEAR, bsIgG1-huCD3-H101G-FEALx5T4-226-FEAR, bsIgG1-huCD3-H101G-FEALx5T4-059-FEAR, bsIgG1-huCD3-H101G-FEALx5T4-106-FEAR, bsIgG1-huCD3-H101G-FEALx5T4-A1-FEAR and bsIgG1-huCD3-H101G-FEALx5T4-A3-FEAR.

FIGS. 11A and 11B: T cell cytokine release induced by CD3x5T4 bispecific antibodies in the presence of 5T4-positive tumor cells. MDA-MB-231 cells were incubated with 0.2 µg/mL CD3x5T4 bispecific antibodies (bsIgG1-huCD3-FEALx5T4-207-FEAR, bsIgG1-huCD3-H101G-FEALx5T4-207-FEAR, bsIgG1-huCD3-FEALx5T4-226-FEAR, bsIgG1-huCD3-H101G-FEALx5T4-226-FEAR, bsIgG1-huCD3-FEALx5T4-059-FEAR or bsIgG1-huCD3-H101G-FEALx5T4-059-FEAR) and 5T4 monospecific anti-bodies (IgG1-5T4-207-FEAR, IgG1-5T4-226-FEAR or IgG1-5T4-059-FEAR) and isolated T cells as effector cells in an E:T ratio of 8:1. Release of cytokines was analyzed by U-PLEX assay. FIG. 11A. Concentration of IL-10, IL-13 and TNF in the supernatant of T cell (derived from donor A)-tumor cell co-cultures, after 72 h of incubation with CD3x5T4 bispecific antibodies or 5T4 monospecific anti-bodies. FIG. 11B. Concentration of IL-10, IL-13 and TNF in the supernatant of T cell (derived from donor B)-tumor cell co-cultures, after 72 h of incubation with CD3x5T4 bispe-cific antibodies or 5T4 monospecific antibodies.

FIGS. 12A and 12B: Induction of cytotoxicity in vitro by CD3x5T4 bispecific antibodies in SK-OV-3 cells using PBMCs as effector cells at varying E:T ratios. SK-OV-3 cells were incubated with increasing concentrations of bsIgG1-huCD3-FEALx5T4-207-FEAR (left panels) or bsIgG1-huCD3-H101G-FEALx5T4-207-FEAR (right pan-els) and PBMCs as effector cells in an E:T ratio of 1:2, 1:1, 2:1, 4:1, 8:1 and 12:1. Cytotoxicity was determined by measuring the percentage of viable SK-OV-3 cells after 72 h of incubation (% viable cells=[absorbance sample–absor-bance staurosporine-treated target cells]/[absorbance untreated target cells–absorbance staurosporine-treated tar-get cells]×100). PBMCs from two different donors were used for this experiment: FIG. 12A. donor C and FIG. 12B. donor D.

FIGS. 13A and 13B: Induction of cytotoxicity in SK-OV-3 cells in vitro by CD3x5T4 bispecific antibodies using T cells as effector cells at varying E:T ratios. SK-OV-3 cells were incubated with increasing concentrations of bsIgG1-huCD3-FEALx5T4-207-FEAR (left panels) or bsIgG1-huCD3-H101G-FEALx5T4-207-FEAR (right panels) and isolated T cells as effector cells in an E:T ratio of 1:2, 1:1, 2:1, 4:1 and 8:1. The efficiency of cytotoxicity was deter-mined by measuring the percentage of viable SK-OV-3 cells after 72 h of incubation (% viable cells=[absorbance sample–absorbance staurosporine-treated target cells]/[ab-sorbance untreated target cells–absorbance staurosporine-treated target cells]×100). T cells from two different donors were used for this experiment: FIG. 13A. donor E and FIG. 13B. donor F.

Figure 14A:
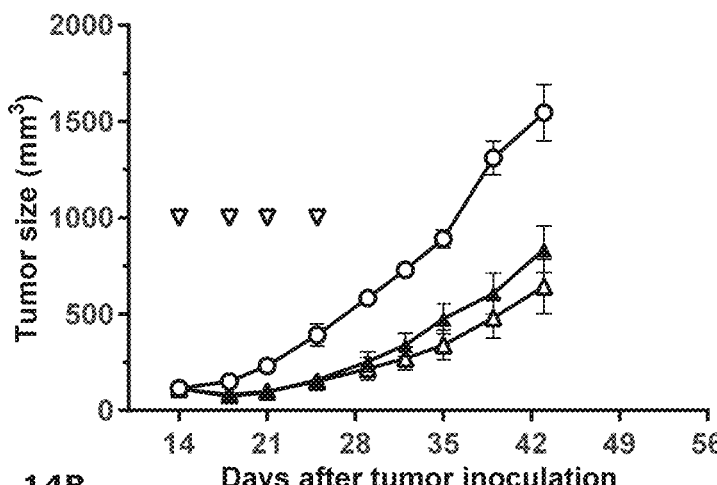
Figure 14B:
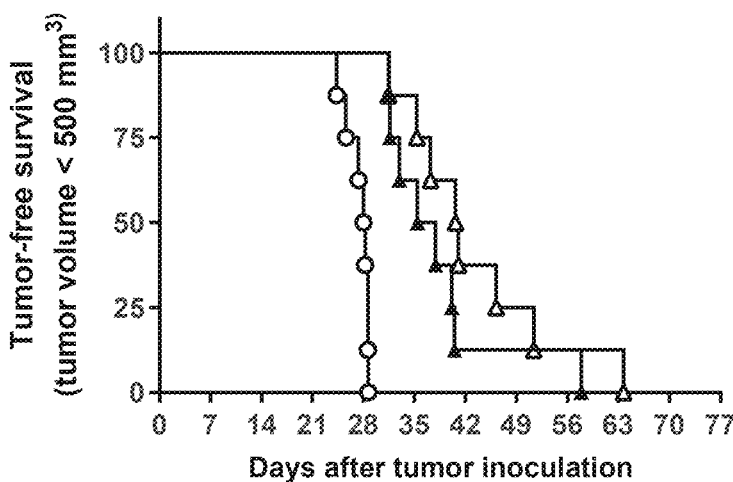
Figures 15A, 15B:
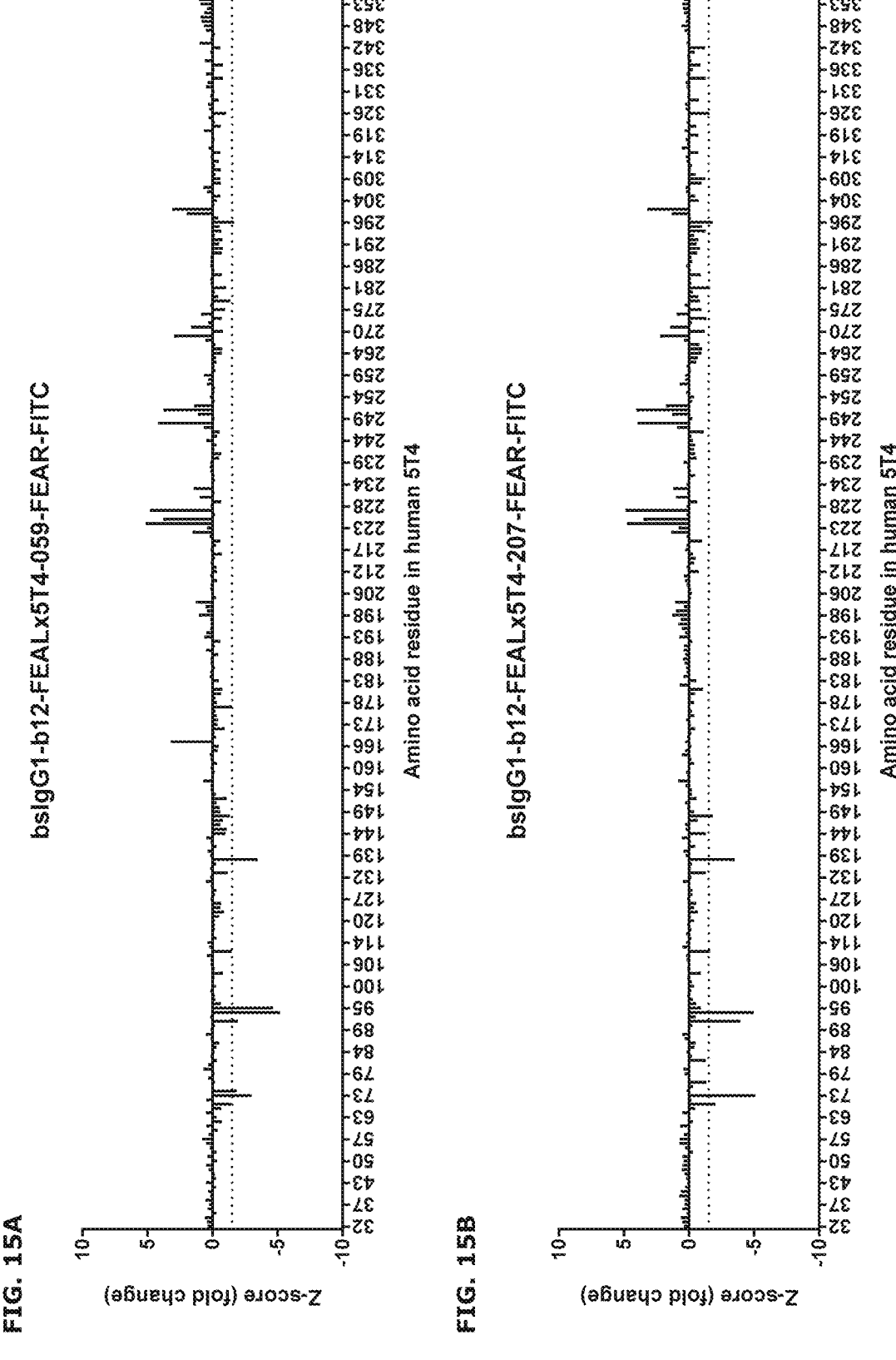
Figures 15C, 15D:
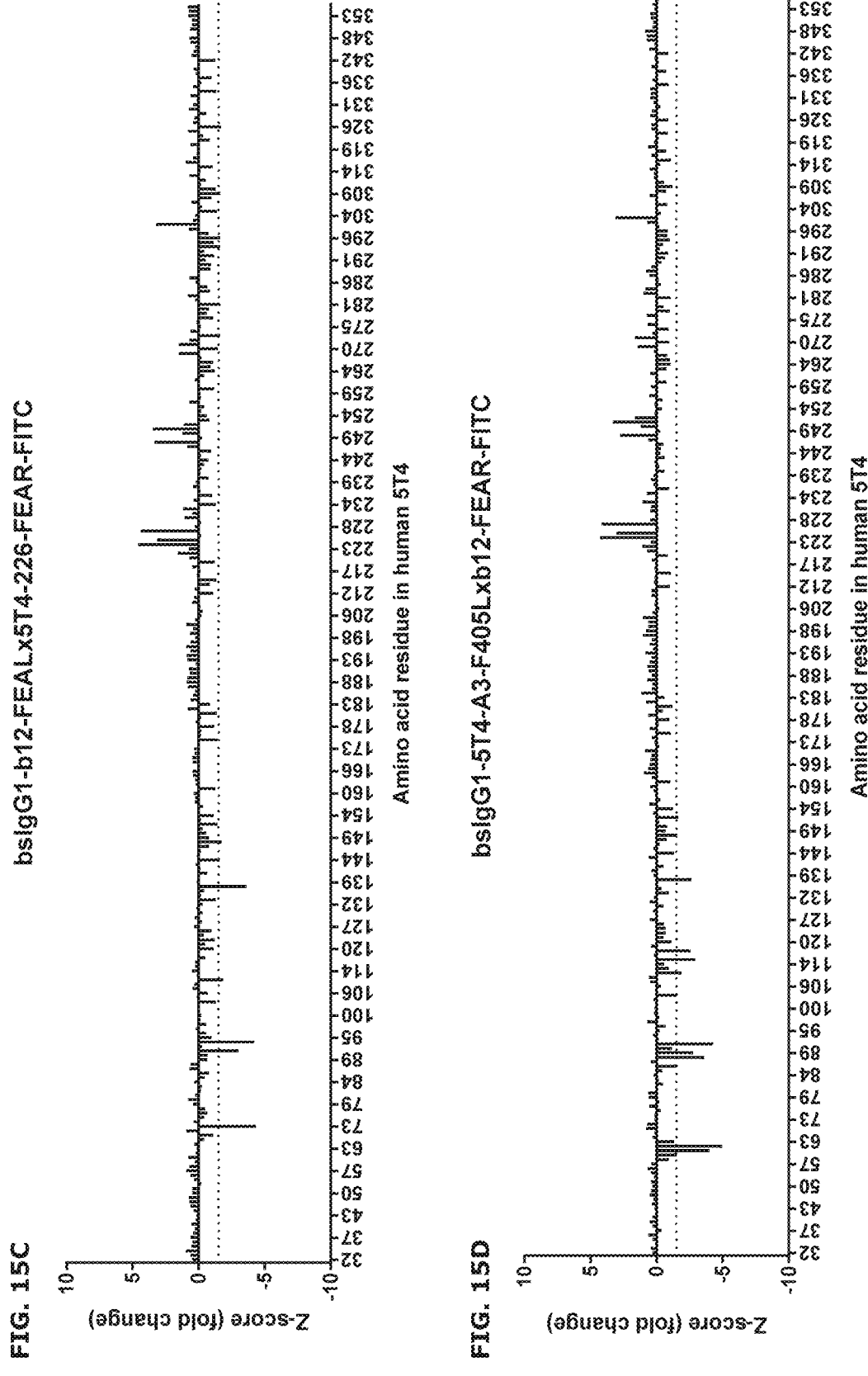

FIGS. 14A and 14B. Anti-tumor activity of CD3x5T4 bispecific antibodies in a MDA-MB-231 xenograft model in NSG-HIS mice. FIG. 14A. Average tumor size in the MDA-MB-231 xenograft model in NSG-HIS mice after treatment with PBS (vehicle control), 0.5 mg/kg bsIgG1-huCD3-FEALx5T4-207-FEAR or 0.5 mg/kg bsIgG1-huCD3-H101G-FEALx5T4-207-FEAR. Tumor size was assessed by caliper measurement. Error bars indicate SEM. FIG. 14B. Percentage of NSG-HIS mice injected with MDA-MB-231 cells with a tumor size <500 mm$^3$ after treatment with PBS, bsIgG1-huCD3-FEALx5T4-207-FEAR or bsIgG1-huCD3-H101G-FEALx5T4-207-FEAR.

FIGS. 15A-15D: Binding of directly FITC-labeled 5T4-specific antibodies to human 5T4 variants with single ala-nine mutations at positions 32 to 355 of human 5T4 ECD, as determined by flow cytometry. Binding was expressed as Z-score (fold change), as a measure for change in binding compared to a non-cross blocking 5T4-specific control anti-body (bsIgG1-5T4-A1-F405Lxb12-FEAR-FITC) used for normalization. The number on the x-axis refers to the amino acid positions in human 5T4 (SEQ ID: 1). Residues where the Z-score in binding was lower than −1.5 (indicated by the dotted line) were considered 'loss of binding mutants'. Residues with a positive Z-score in binding are loss of binding residues for the non-cross blocking 5T4 specific control antibody (bsIgG1-5T4-A1-67F-F405Lxb12-FEAR- FITC). Residues on aa position 38, 45, 49, 51, 54, 62, 64, 66, 68, 71, 72, 77, 91, 104, 108, 110, 112, 118, 121, 122, 135, 137, 155, 161, 167, 171, 201, 202, 205, 208, 218, 231, 269, 279, 298, 300, 303, 323, 324, 340 and 344 were not evaluated, as these positions contained either endogenous alanines or cysteines. Data shown are Z-scores for binding of (FIG. 15A) bsIgG1-b12-FEALx5T4-059-FEAR-FITC, (FIG. 15B) bsIgG1-b12-FEALx5T4-207-FEAR-FITC, (FIG. 15C) bsIgG1-b12-FEALx5T4-226-FEAR-FITC, and (FIG. 15D) bsIgG1-5T4-A3-F405Lxb12-FEAR-FITC. Buried residues with a Z-score just below −1.5 that were predicted to be spatially separated from the majority of surface-exposed loss of binding residues were excluded (for bIgG1-b12-FEALx5T4-207-FEAR-FITC: L281 [Z-score: −1.57] and P326 [Z-score: −1.54]; and for bsIgG1-b12-FEALx5T4-226-FEAR-FITC: L273 [Z-score: −1.58], L281 [Z-score: −1.65], N294 [Z-score: −1.57], L309 [Z-score: −1.63] and P326 [Z-score: −1.67]).

Figure 16:
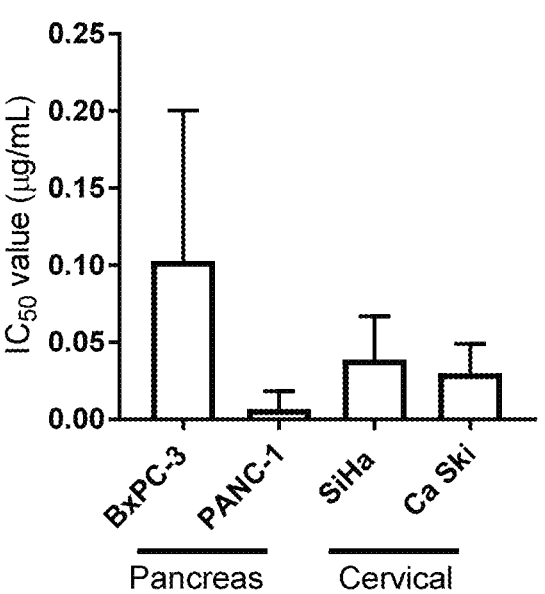

FIGS. 16(1)A and 16(1)B: Induction of cytotoxicity in vitro by CD3x5T4 bispecific antibodies in tumor cells of different indications using T cells as effector cells. Tumor cells were incubated with increasing concentrations of bsIgG1-huCD3-H101G-FEALx5T4-207-FEAR or control antibodies (bsIgG1-huCD3-H101G-FEALxb12-FEAR, bsIgG1-b12-FEALx5T4-207-FEAR) and isolated T cells as effector cells in an E:T ratio of 4:1. Cytotoxicity (decrease in survival) was determined by measuring the percentage of viable tumor cells after 72 h of incubation. Data shown are mean % survival±SEM of duplicate wells from one representative donor out of at least three donors tested. FIG. 16(I)A. Cytotoxicity (decrease in survival) induced in pancreas cancer cell lines; FIG. 16(I)B. Cytotoxicity (decrease in survival) induced in cervical cancer cell lines.

FIG. 16(II): IC50 values of cytotoxicity induced in vitro by CD3x5T4 bispecific antibodies in tumor cell lines of different indications using T cells as effector cells. IC50 values of the T-cell-mediated cytotoxicity induced by bsIgG1-huCD3-H101G-FEALx5T4-207-FEAR in tumor cells of the indicated indications were analyzed using GraphPad Prism V7.02 software. Data are presented as mean IC50 values of at least three different donors (see Table 10)±SD.

FIGS. 17(I)A-17(I)D: In vitro T-cell activation by CD3x5T4 bispecific antibodies in the presence of tumor cells of different indications. Tumor cells were incubated with increasing concentrations of bsIgG1-huCD3-H101G-FEALx5T4-207-FEAR or control antibodies (bsIgG1-huCD3-H101G-FEALxb12-FEAR, bsIgG1-b12-FEALx5T4-207-FEAR and isolated T cells as effector cells in an E:T ratio of 4:1 for 72 h. T-cell activation was measured by the upregulation of CD69 (% of CD69+ cells) within CD4+(left panels) and CD8+(right panels) T-cell populations. Data shown are mean % CD69+ cells±SD of duplicate wells from one representative donor out of at least three donors tested. FIG. 17(I)A. T-cell activation induced by CD3x5T4 bispecific antibodies in the presence of pancreas cancer cell line BxPc-3; FIG. 17(I)B. T-cell activation induced by CD3x5T4 bispecific antibodies in the presence of pancreas cancer cell line PANC-1; FIG. 17(I)C. T-cell activation induced by CD3x5T4 bispecific antibodies in the presence of cervical cancer cell line SiHa; FIG. 17(I)D. T-cell activation induced by CD3x5T4 bispecific antibodies in the presence of cervical cancer cell line Ca Ski.

FIGS. 17(II)A and 17(II)B: EC50 values of in vitro T-cell activation by CD3x5T4 bispecific antibodies in with the presence of tumor cell lines of different indications. EC50 values of the T-cell activation (% of CD69+ cells within CD4$^+$ and CD8$^+$ T-cell populations) induced by bsIgG1-huCD3-H101G-FEALx5T4-207-FEAR in co-culture with tumor cell lines of the different indications were analyzed using GraphPad Prism V7.02 software. Data are presented as mean EC50 values of at least three different donors (see Table 10)±SD. FIG. 17(II)A. EC50 values of CD4+ T-cell activation induced by bsIgG1-huCD3-H101G-FEALx5T4-207-FEAR in the presence of the indicated tumor cell lines; FIG. 17(II)B. EC50 values of CD8+ T-cell activation induced by bsIgG1-huCD3-H101G-FEALx5T4-207-FEAR in the presence of the indicated tumor cell lines.

FIGS. 18A and 18B: Binding of a CD3x5T4 bispecific antibody to FaDu and SCC-9 squamous head and neck tumor cells. Monovalent binding of CD3x5T4 bispecific antibody bsIgG1-huCD3-H101G-FEALx5T4-207-FEAR or control antibody bsIgG1-huCD3-H101G-FEALxb12-FEAR to FaDu cells or SCC-9 cells was determined by flow cytometry. Cells were incubated with increasing concentrations of antibodies. After secondary labelling with R-PE-conjugated goat-anti-human IgG F(ab')2, the geomean fluorescence intensity (gMFI) was determined by flow cytometry. FIG. 18A. Binding of bsIgG1-huCD3-H101G-FEALx5T4-207-FEAR and bsIgG1-huCD3-H101G-FEALxb12-FEAR antibodies to FaDu cells. FIG. 18B. Binding of bsIgG1-huCD3-H101G-FEALx5T4-207-FEAR and bsIgG1-huCD3-H101G-FEALxb12-FEAR antibodies to SCC-9 cells.

FIGS. 19A and 19B: Binding of a CD3x5T4 bispecific antibody to EPLC-272H and NCI-H292 squamous NSCLC tumor cells. Monovalent binding of CD3x5T4 bispecific antibody bsIgG1-huCD3-H101G-FEALx5T4-207-FEAR or control antibody bsIgG1-huCD3-H101G-FEALxb12-FEAR to EPLC-272H cells or NCI-H292 cells was determined by flow cytometry. Cells were incubated with increasing concentrations of antibodies. After secondary labelling with R-PE-conjugated goat-anti-human IgG F(ab')2, the gMFI was determined by flow cytometry. FIG. 19A. Binding of bsIgG1-huCD3-H101G-FEALx5T4-207-FEAR and bsIgG1-huCD3-H101G-FEALxb12-FEAR antibodies to EPLC-272H cells. FIG. 19B. Binding of bsIgG1-huCD3-H101G-FEALx5T4-207-FEAR and bsIgG1-huCD3-H101G-FEALxb12-FEAR antibodies to NCI-H292 cells.

FIGS. 20A and 20B: Binding of a CD3x5T4 bispecific antibody to OE33 and SK-GT-4 esophageal tumor cells. Monovalent binding of CD3x5T4 bispecific antibody bsIgG1-huCD3-H101G-FEALx5T4-207-FEAR or control antibody bsIgG1-huCD3-H101G-FEALxb12-FEAR to OE33 cells or SK-GT-4 cells was determined by flow cytometry. Cells were incubated with increasing concentrations of antibodies. After secondary labelling with R-PE-conjugated goat-anti-human IgG F(ab')2, the gMFI was determined by flow cytometry. FIG. 20A. Binding of bsIgG1-huCD3-H101G-FEALx5T4-207-FEAR and bsIgG1-huCD3-H101G-FEALxb12-FEAR antibodies to OE33 cells. FIG. 20B. Binding of bsIgG1-huCD3-H101G-FEALx5T4-207-FEAR and bsIgG1-huCD3-H101G-FEALxb12-FEAR antibodies to SK-GT-4 cells.

FIGS. 21A-21C: Induction of cytotoxicity and T-cell activation in vitro by CD3x5T4 bispecific antibodies in SK-GT-4 esophageal tumor cells using T cells as effector cells. SK-GT-4 esophageal tumor cells were incubated with increasing concentrations of bsIgG1-huCD3-H101G-FEALx5T4-207-FEAR or control antibodies (bsIgG1-huCD3-H101G-FEALxb12-FEAR, bsIgG1-b12-FEALx5T4-207-FEAR) and isolated T cells as effector cells (E:T ratio=4:1) for 72 h. T-cell mediated cytotoxicity (FIG. 21A) was measured as percentage viability of the tumor cells. T-cell activation was measured by the percentage of CD4+(FIG. 21B) of CD8+(FIG. 21C) T cells that have upregulated CD69. Data shown are mean percentages±SD of duplicate wells from one representative donor out of three donors tested.

Figure 22A:
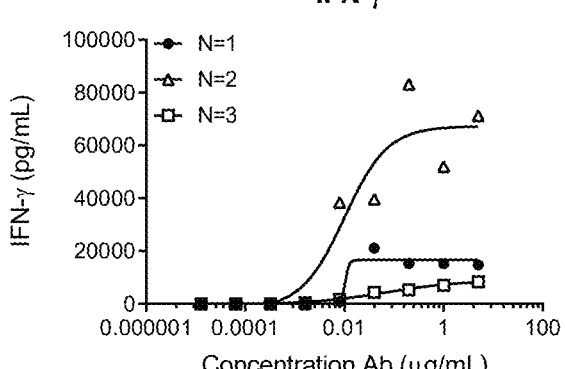
Figure 22B:
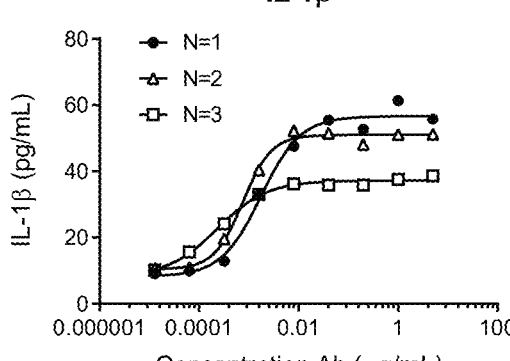
Figure 22C:
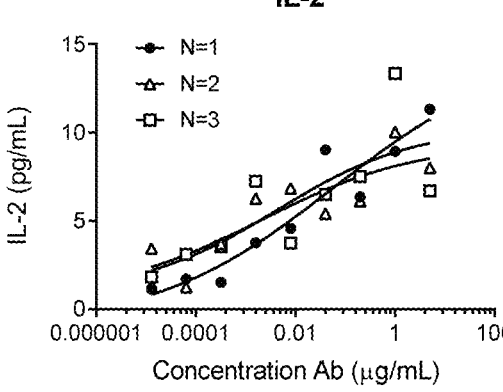
Figure 22D:
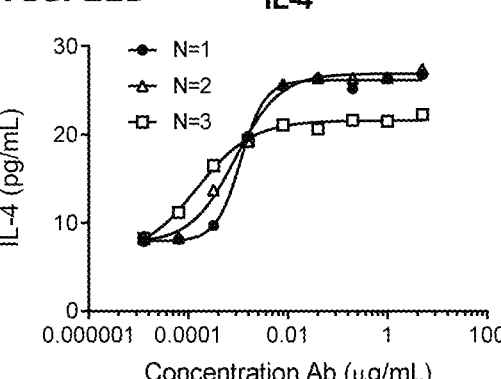
Figure 22E:
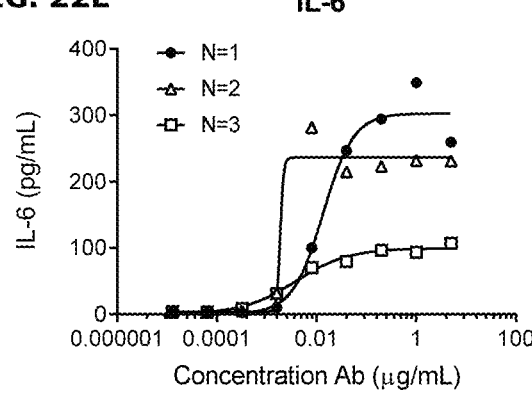
Figure 22F:
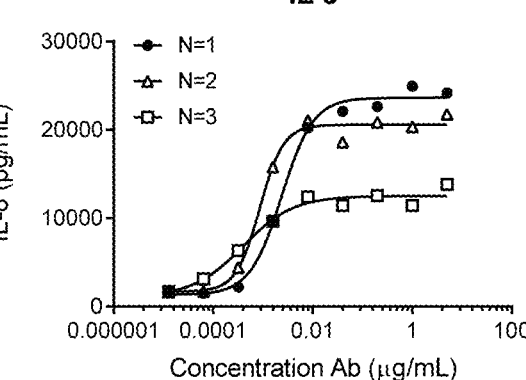
Figures 22G, 22H, 22I, 22J:
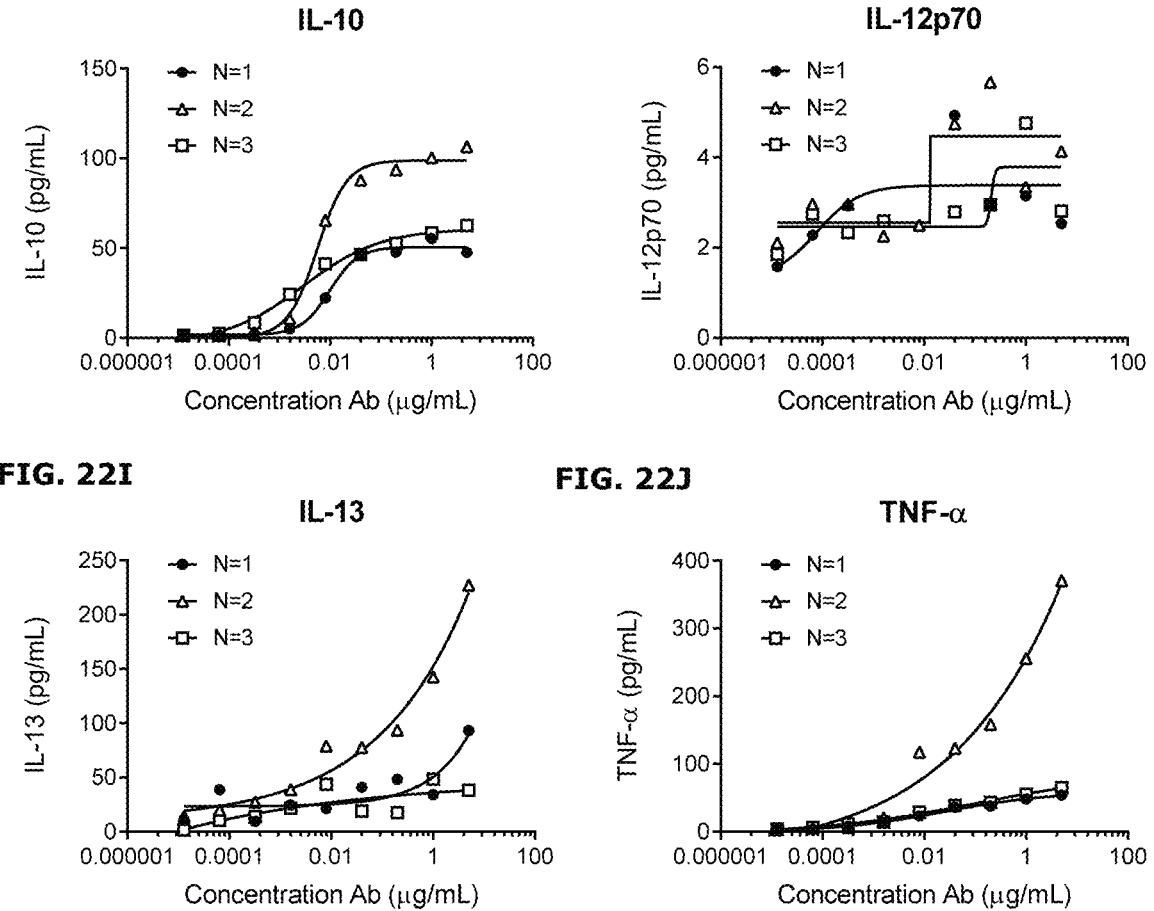

FIGS. 22A-22J: Induction of cytokine production in vitro by a CD3x5T4 bispecific antibody in SK-GT-4 esophageal tumor cells using T cells as effector cells. SK-GT-4 esophageal tumor cells expressing 5T4 were incubated with isolated T cells (E:T ratio=4:1) of three different donors and increasing concentrations of bsIgG1-huCD3-H101G-FEALx5T4-207-FEAR for 72 h. Cytokines in the supernatant were measured by a multiplex U-plex assay. No data is shown when the sample was below the detection limit of the assay. FIG. 22A. IFN-γ; FIG. 22B. IL-1β; FIG. 22C. IL-2; FIG. 22D. IL-4; FIG. 22E. IL-6; FIG. 22F. IL-8; FIG. 22G. IL-10; FIG. 22H. IL-12p70; FIG. 22I. IL-13; FIG. 22J. TNF-α.

Figures 23A, 23B:
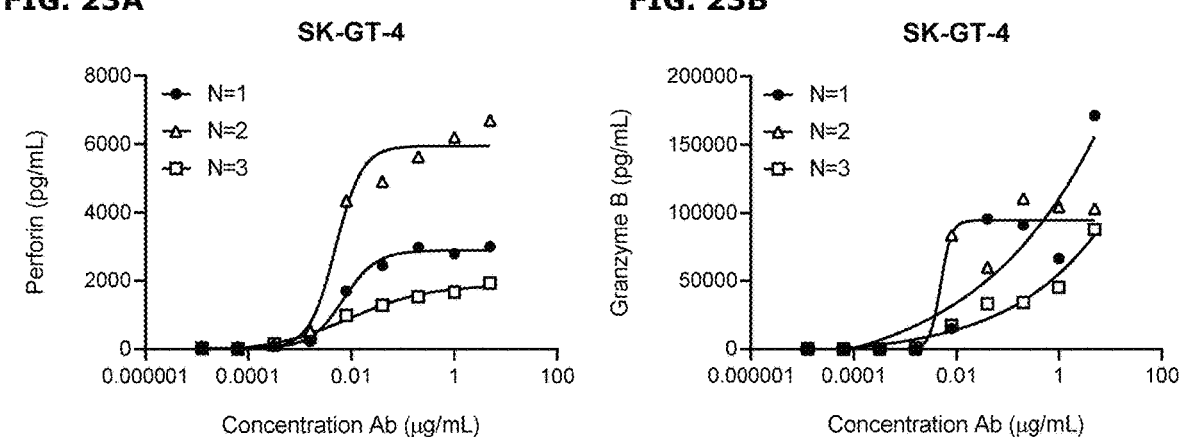

FIGS. 23A and 23B: Induction of granzyme B and Perforin release in vitro by a CD3x5T4 bispecific antibody in SK-GT-4 esophageal tumor cells using T cells as effector cells. SK-GT-4 esophageal tumor cells were incubated with isolated T cells (E:T ratio=4:1) of three different donors and increasing concentrations of bsIgG1-huCD3-H101G-FEALx5T4-207-FEAR for 72 h. Perforin and granzyme B released in the supernatant were measured by ELISA. FIG. 23A. Perforin release induced by incubating T cells with bsIgG1-huCD3-H101G-FEALx5T4-207-FEAR and SK-GT-4 cells FIG. 23B. Granzyme B release induced by incubating T cells with bsIgG1-huCD3-H101G-FEALx5T4-207-FEAR and SK-GT-4 cells.

Figures 24B, 24C, 24E, 24F:
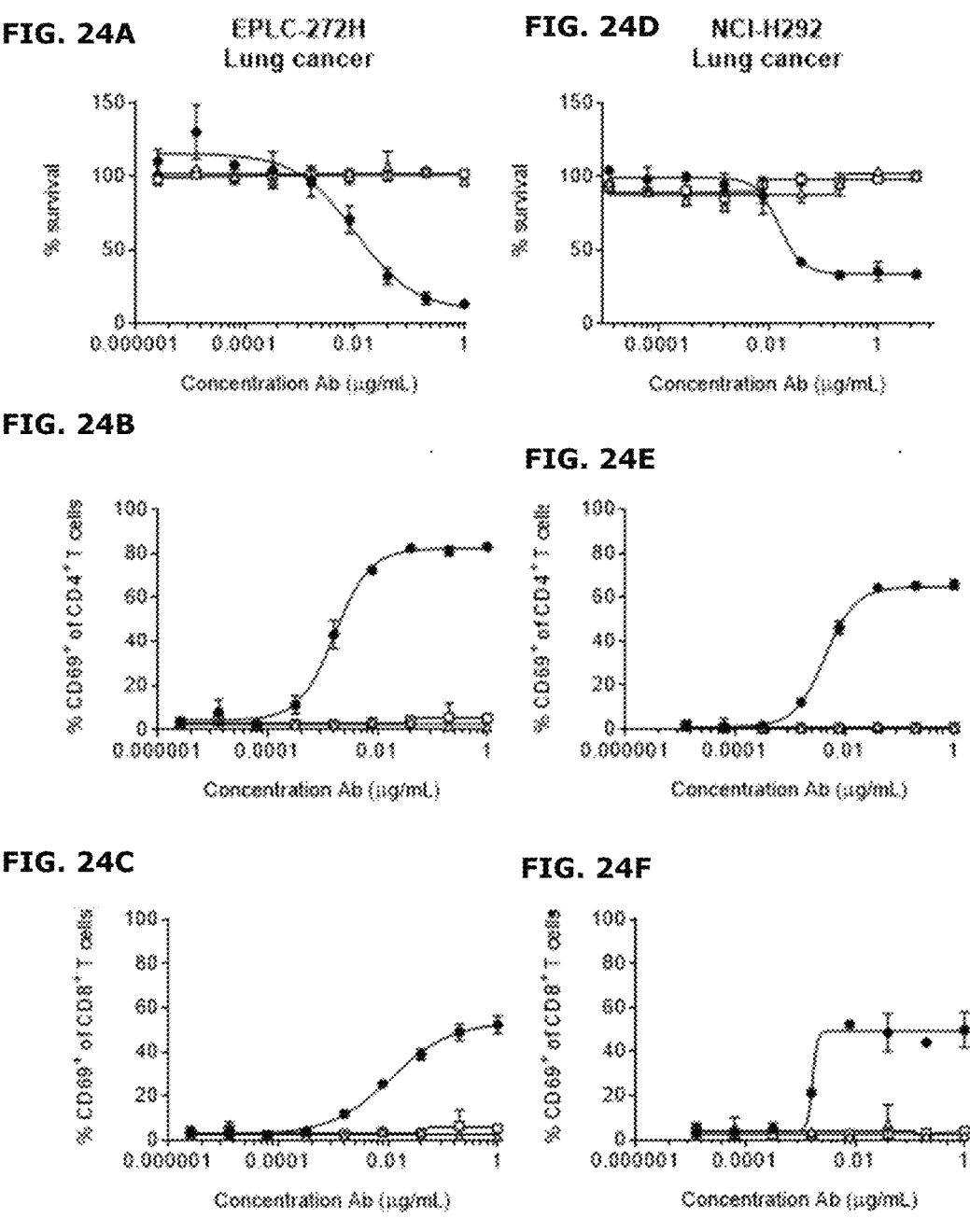

FIGS. 24A-24F: Induction of cytotoxicity and T-cell activation in vitro by CD3x5T4 bispecific antibodies in EPLC-272H and NCI-H292 squamous NSCL using T cells as effector cells. EPLC-272H and NCI-H292 squamous NSCL tumor cells were incubated with increasing concentrations of bsIgG1-huCD3-H101G-FEALx5T4-207-FEAR or control antibodies (bsIgG1-huCD3-H101G-FEALxb12-FEAR, bsIgG1-b12-FEALx5T4-207-FEAR) and isolated T cells as effector cells (E:T ratio=4:1) for 72 h. FIGS. 24A-24C. T-cell mediated cytotoxicity of EPLC-272H cells (FIG. 24A) and CD4+(FIG. 24B) and CD8+(FIG. 24C) T-cell activation in the presence of EPLC-272H cells. FIGS. 24D-24F. T-cell mediated cytotoxicity of NCI-H292 cells (FIG. 24D) and CD4+(FIG. 24E) and CD8+(FIG. 24F) T-cell activation in the presence of NCI-H292 cells. Data shown are mean percentages±SD of duplicate wells from one representative donor of at least three donors tested.

FIGS. 25A-25J: Induction of cytokine production in vitro by a CD3x5T4 bispecific antibody in EPLC-272H squamous NSCL tumor cells using T cells as effector cells. EPLC-272H squamous NSCL tumor cells expressing 5T4 were incubated with isolated T cells (E:T ratio=4:1) of three different donors and increasing concentrations of bsIgG1-huCD3-H101G-FEALx5T4-207-FEAR for 72 h. Cytokines in the supernatant were measured by a multiplex U-plex assay. No data is shown when the sample was below the detection limit of the assay. FIG. 25A. IFN-γ; FIG. 25B. IL-1β; FIG. 25C. IL-2; FIG. 25D. IL-4; FIG. 25E. IL-6; FIG. 25F. IL-8; FIG. 25G. IL-10; FIG. 25H. IL-12p70; FIG. 25I. IL-13; FIG. 25J. TNF-α.

FIGS. 26A-26J: Induction of cytokine production in vitro by a CD3x5T4 bispecific antibody in NCI-H292 NSCL tumor cells using T cells as effector cells. NCI-H292 squamous NSCL tumor cells expressing 5T4 were incubated with isolated T cells (E:T ratio=4:1) of three different donors and increasing concentrations of bsIgG1-huCD3-H101G-

FEALx5T4-207-FEAR for 72 h. Cytokines in the supernatant were measured by a multiplex U-plex assay. No data is shown when the sample was below the detection limit of the assay. FIG. 26A. IFN-γ; FIG. 26B. IL-1β; FIG. 26C. IL-2; FIG. 26D. IL-4; FIG. 26E. IL-6; FIG. 26F. IL-8; FIG. 26G. IL-10; FIG. 26H. IL-12p70; FIG. 26I. IL-13; FIG. 26J. TNF-α.

FIGS. 27A-27D: Induction of granzyme B and Perforin release in vitro by a CD3x5T4 bispecific antibody in EPLC-272H and NCI-H292 squamous NSCL tumor cells using T cells as effector cells. EPLC-272H and NCI-H292 squamous NSCL tumor cells were incubated with isolated T cells (E:T ratio=4:1) of three different donors and increasing concentrations of bsIgG1-huCD3-H101G-FEALx5T4-207-FEAR for 72 h. Perforin and granzyme B released in the supernatant were measured by ELISA. FIG. 27A. Perforin release induced by incubating T cells with bsIgG1-huCD3-H101G-FEALx5T4-207-FEAR and EPLC-272H cells FIG. 27B. Granzyme B release induced by incubating T cells with bsIgG1-huCD3-H101G-FEALx5T4-207-FEAR and EPLC-272H cells. FIG. 27C. Perforin release induced by incubating T cells with bsIgG1-huCD3-H101G-FEALx5T4-207-FEAR and NCI-H292 cells FIG. 27D. Granzyme B release induced by incubating T cells with bsIgG1-huCD3-H101G-FEALx5T4-207-FEAR and NCI-H292 cells.

Figures 28B, 28C, 28E, 28F:
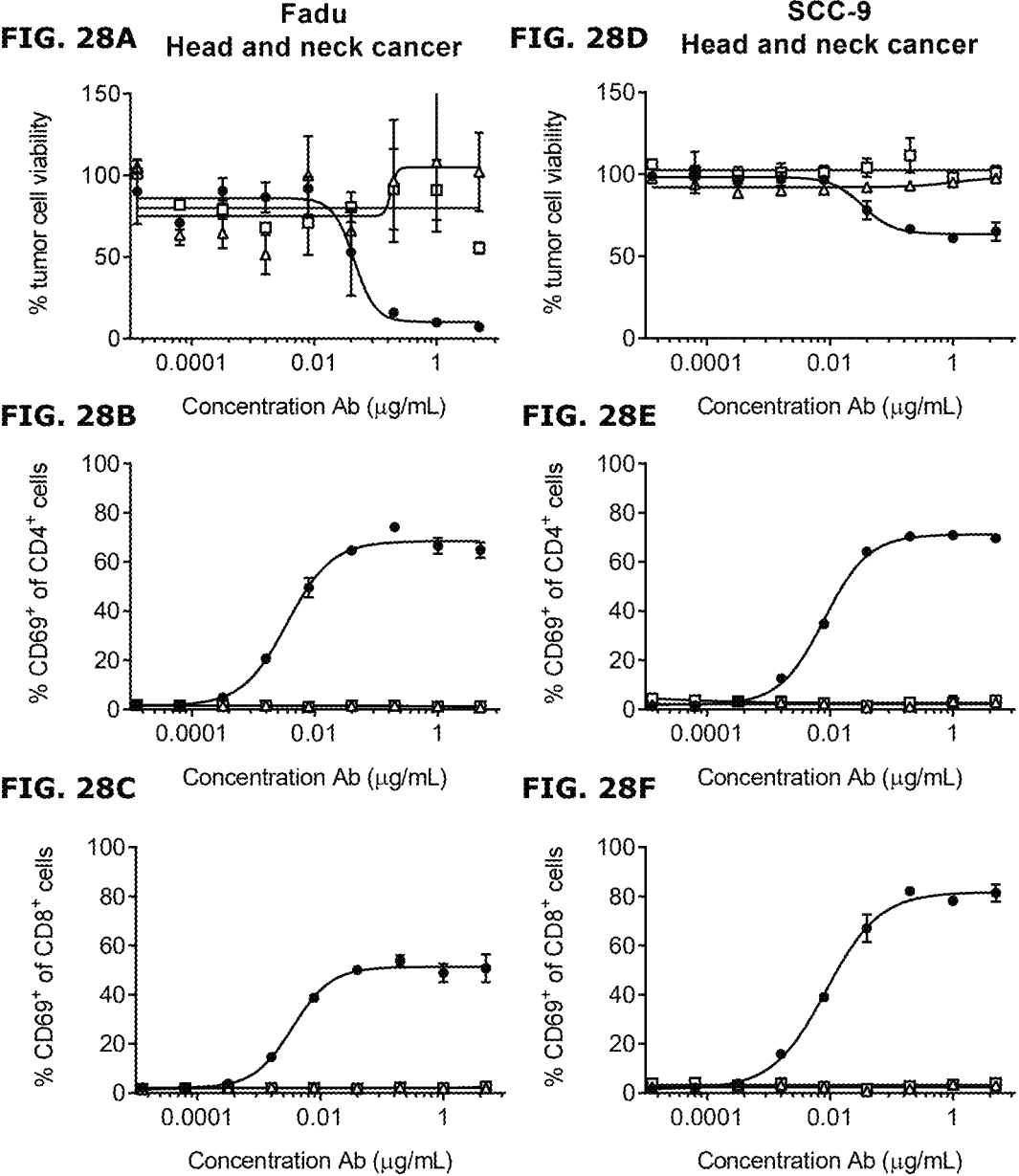

FIGS. 28A-28F: Induction of cytotoxicity and T-cell activation in vitro by CD3x5T4 bispecific antibodies in FaDu and SCC-9 squamous head and neck tumor cells using T cells as effector cells. Fa Du and SCC-9 squamous head and neck tumor cells were incubated with increasing concentrations of bsIgG1-huCD3-H101G-FEALx5T4-207-FEAR or control antibodies (bsIgG1-huCD3-H101G-FE-ALxb12-FEAR, bsIgG1-b12-FEALx5T4-207-FEAR) and isolated T cells as effector cells (E:T ratio=4:1) for 72 h. FIGS. 28A-28C. T-cell mediated cytotoxicity of Fadu cells (FIG. 28A) and CD4+ (FIG. 28B) and CD8+ (FIG. 28C) T-cell activation in the presence of Fadu cells. FIGS. 28D-28F. T-cell mediated cytotoxicity of SCC-9 cells (FIG. 28D) and CD4+ (FIG. 28E) and CD8+ (FIG. 28F) T-cell activation in the presence of SCC-9 cells. Data shown are mean percentages±SD of duplicate wells from one representative donor out of at least three donors tested.

FIGS. 29A-29J: Induction of cytokine production in vitro by a CD3x5T4 bispecific antibody in FaDu squamous head and neck tumor cells using T cells as effector cells. FaDu squamous head and neck tumor cells expressing 5T4 were incubated with isolated T cells (E:T ratio=4:1) of three different donors and increasing concentrations of bsIgG1-huCD3-H101G-FEALx5T4-207-FEAR for 72 h. Cytokines in the supernatant were measured by a multiplex U-plex assay. No data is shown when the sample was below the detection limit of the assay. FIG. 29A. IFN-γ; FIG. 29B. IL-1β; FIG. 29C. IL-2; FIG. 29D. IL-4; FIG. 29E. IL-6; FIG. 29F. IL-8; FIG. 29G. IL-10; FIG. 29H. IL-12p70; FIG. 29I. IL-13; FIG. 29J. TNF-α.

FIGS. 30A-30J: Induction of cytokine production in vitro by a CD3x5T4 bispecific antibody in SCC-9 squamous head and neck tumor cells using T cells as effector cells. SCC-9 squamous head and neck tumor cells expressing 5T4 were incubated with isolated T cells (E:T ratio=4:1) of three different donors and increasing concentrations of bsIgG1-huCD3-H101G-FEALx5T4-207-FEAR for 72 h.

Figures 30A, 30B, 30C, 30D, 30E, 30F:
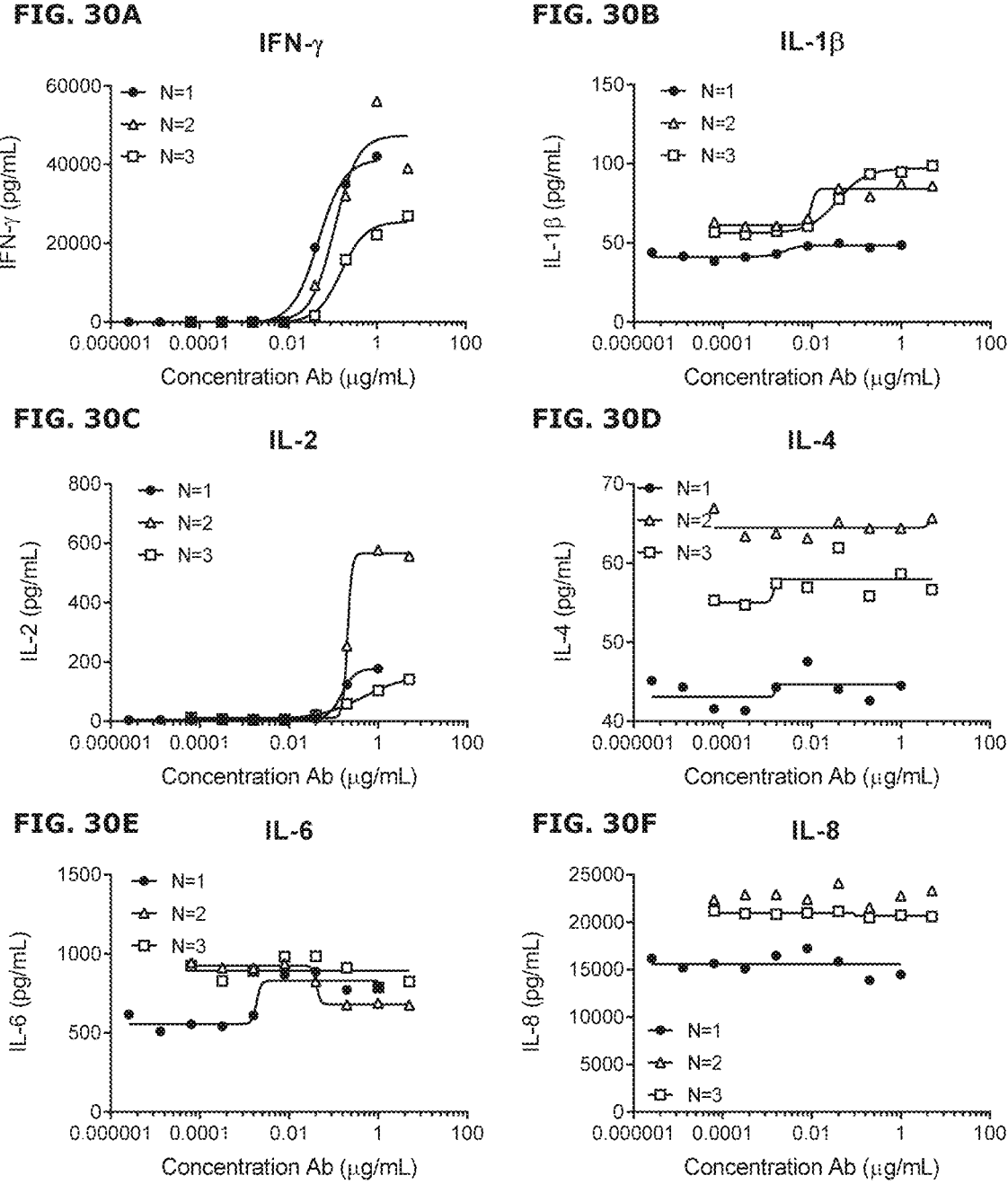

Cytokines in the supernatant were measured by a multiplex U-plex assay. No data is shown when the sample was below the detection limit of the assay. FIG. 30A. IFN-γ; FIG. 30B. IL-1β; FIG. 30C. IL-2; FIG. 30D. IL-4; FIG. 30E.

US 12,674,001 B2

13

Figures 30G, 30H, 30I, 30J:
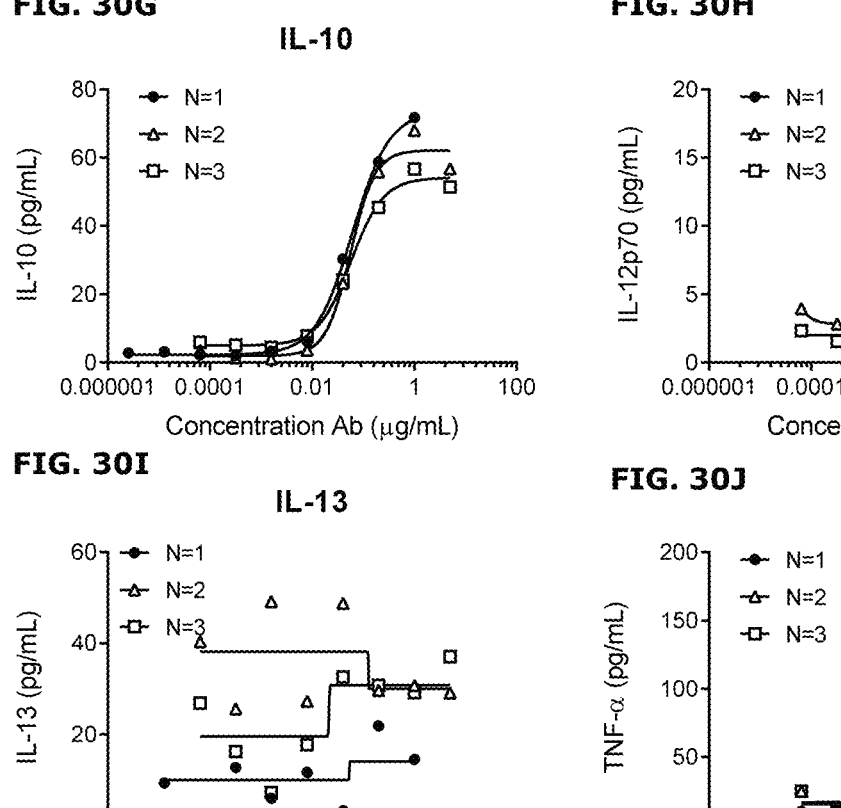
Figure 32A:
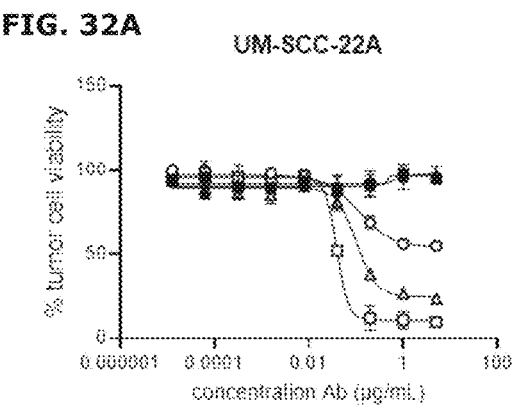
Figure 32B:
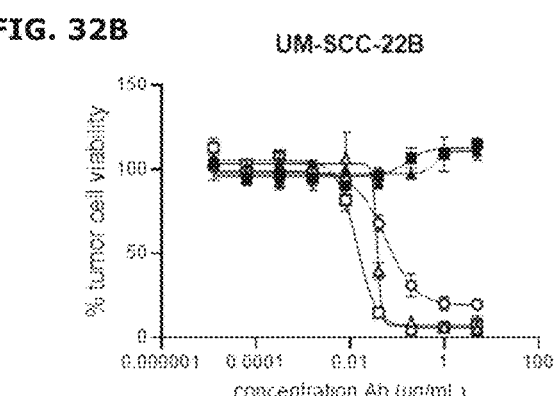
Figure 32C:
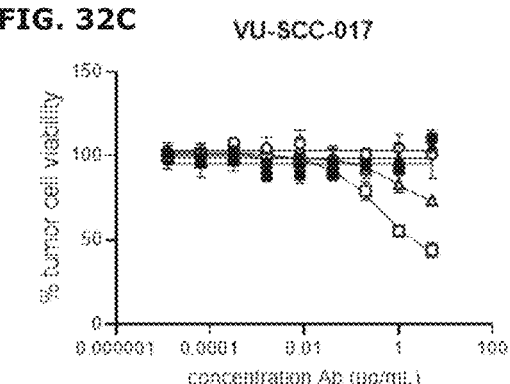
Figure 32D:
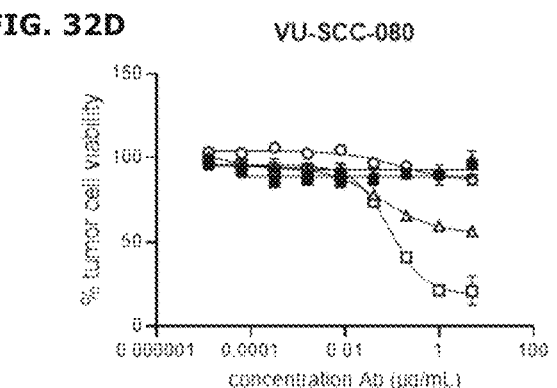
Figure 32E:
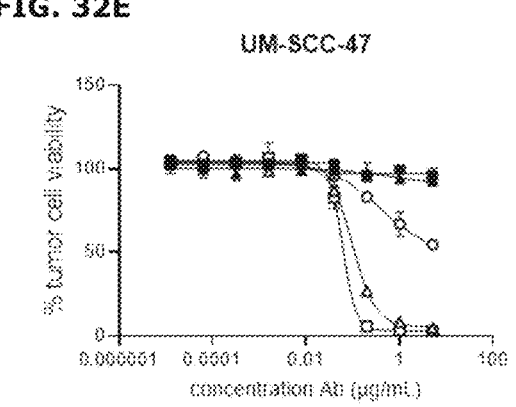
Figure 32F:
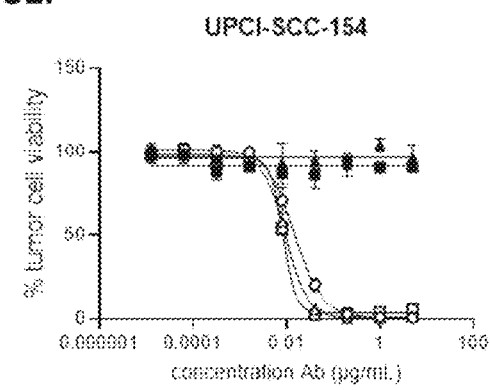

IL-6; FIG. 30F. IL-8; FIG. 30G. IL-10; FIG. 30H. IL-12p70; FIG. 30I. IL-13; FIG. 30J. TNF-α.

FIGS. 31A-31D: Induction of granzyme B and Perforin release in vitro by a CD3x5T4 bispecific antibody in FaDu and SCC-9 squamous head and neck tumor cells using T cells as effector cells. FaDu and SCC-9 squamous head and neck tumor cells were incubated with isolated T cells (E:T ratio=4:1) of three different donors and increasing concentrations of bsIgG1-huCD3-H101G-FEALx5T4-207-FEAR for 72 h. Perforin and granzyme B released in the supernatant were measured by ELISA. FIG. 31A. Perforin release induced by incubating T cells with bsIgG1-huCD3-H101G-FEALx5T4-207-FEAR and FaDu cells FIG. 31B. Granzyme B release induced by incubating T cells with bsIgG1-huCD3-H101G-FEALx5T4-207-FEAR and FaDu cells. FIG. 31C. Perforin release induced by incubating T cells with bsIgG1-huCD3-H101G-FEALx5T4-207-FEAR and SCC-9 cells FIG. 31D. Granzyme B release induced by incubating T cells with bsIgG1-huCD3-H101G-FEALx5T4-207-FEAR and SCC-9 cells.

FIGS. 32A-32F: Induction of cytotoxicity in vitro by CD3x5T4 bispecific antibodies in HPV-negative and HPV-positive SCCHN cells at increasing E:T ratios. HPV-negative and HPV-positive SCCHN cancer cells were incubated with increasing concentrations of bsIgG1-huCD3-H101G-FEALx5T4-207-FEAR or control antibodies (bsIgG1-huCD3-H101G-FEALxb12-FEAR, bsIgG1-b12-FEALx5T4-207-FEAR) and purified T cells as effector cells (E:T ratio=4:1, 10:1 or 25:1) for 72 h. FIGS. 32A-32F. T-cell mediated cytotoxicity in the HPV-negative UM-SCC-22A (FIG. 32A), UM-SCC-22B (FIG. 32B), VU-SCC-017 (FIG. 32C), VU-SCC-080 (FIG. 32D), and the HPV-positive UM-SCC-47 (FIG. 32E) and UPCI-SCC-154 (FIG. 32F) SCCHN cell lines. Data shown are mean percentages±SD of duplicate wells from one representative donor out of at least two donors tested.

DETAILED DESCRIPTION

Definitions

The term "antibody" (Ab) in the context of the present invention refers to an immunoglobulin molecule, a fragment of an immunoglobulin molecule, or a derivative of either thereof, which has the ability to specifically bind to an antigen under typical physiological conditions with a half-life of significant periods of time, such as at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen and/or time sufficient for the antibody to recruit an effector activity). The variable regions of the heavy and light chains of the immunoglobulin molecule contain a binding domain that interacts with an antigen. The term "antibody-binding region", as used herein, refers to the region which interacts with the antigen and comprises both the VH and the VL regions. The term antibody when used herein comprises not only monospecific antibodies, but also multispecific antibodies which comprise multiple, such as two or more, e.g. three or more, different antigen-binding regions. The constant regions of the antibodies (Abs) may mediate the binding of the immunoglobulin to host tissues or factors, including various cells of the immune system (such as effector cells) and components of the complement system such as C1q, the first component in the classical pathway of complement activation. As indicated above, the term antibody herein, unless otherwise stated or clearly contradicted by context, includes fragments of an antibody that are antigen-binding fragments, i.e., retain the ability to specifically bind to the antigen. It has been shown that the antigen-binding function of an antibody may be performed by fragments of a full-length antibody. Examples of antigen-binding fragments encompassed within the term "antibody" include (i) a Fab' or Fab fragment, a monovalent fragment consisting of the VL, VH, CL and CH1 domains, or a monovalent antibody as described in WO2007059782 (Genmab); (ii) F(ab')2 fragments, bivalent fragments comprising two Fab fragments linked by a disulfide bridge at the hinge region; (iii) a Fd fragment consisting essentially of the VH and CH1 domains; (iv) a Fv fragment consisting essentially of the VL and VH domains of a single arm of an antibody, (v) a dAb fragment (Ward et al., Nature 341, 544 546 (1989)), which consists essentially of a VH domain and also called domain antibodies (Holt et al; Trends Biotechnol. 2003 November; 21(11):484-90); (vi) camelid or nanobodies (Revets et al; Expert Opin Biol Ther. 2005 January; 5(1):111-24) and (vii) an isolated complementarity determining region (CDR). Furthermore, although the two domains of the Fv fragment, VL and VH, are coded for by separate genes, they may be joined, using recombinant methods, by a synthetic linker that enables them to be made as a single protein chain in which the VL and VH regions pair to form monovalent molecules (known as single chain antibodies or single chain Fv (scFv), see for instance Bird et al., Science 242, 423 426 (1988) and Huston et al., PNAS USA 85, 5879 5883 (1988)). Such single chain antibodies are encompassed within the term antibody unless otherwise noted or clearly indicated by context. Although such fragments are generally included within the meaning of antibody, they collectively and each independently are unique features of the present invention, exhibiting different biological properties and utility. These and other useful antibody fragments in the context of the present invention, as well as bispecific formats of such fragments, are discussed further herein. It also should be understood that the term antibody, unless specified otherwise, also includes polyclonal antibodies, monoclonal antibodies (mAbs), antibody-like polypeptides, chimeric antibodies and humanized antibodies, and antibody fragments retaining the ability to specifically bind to the antigen (antigen-binding fragments) provided by any known technique, such as enzymatic cleavage, peptide synthesis, and recombinant techniques. An antibody as provided herein can possess any isotype. An antibody can be produced in and collected from different in vitro or ex vivo expression or production systems, for example from recombinantly modified host cells, from hybridomas or systems that use cellular extracts supporting in vitro transcription and/or translation of nucleic acid sequences encoding the antibody. It is to be understood that a multitude of different antibodies, the antibodies being as defined in the context of the present invention, is one that can be provided by producing each antibody separately in a production system as mentioned above and thereafter mixing the antibodies, or by producing several antibodies in the same production system.

The term "immunoglobulin" refers to a class of structurally related glycoproteins consisting of two pairs of polypeptide chains, one pair of light (L) low molecular weight chains and one pair of heavy (H) chains, all four interconnected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as VH or $V_H$) and a heavy chain constant region (abbreviated herein as CH or $C_H$). The heavy chain constant region typically is comprised of three domains, CH1, CH2, and CH3. The hinge region is the region between the CH1 and CH2 domains of the heavy chain and is highly flexible. Disulphide bonds in the hinge region are part of the interactions between two heavy chains in an IgG molecule. Each light chain typically is comprised of a light chain variable region (abbreviated herein as VL or $V_L$) and a light chain constant region (abbreviated herein as CL or $C_L$). The light chain constant region typically is comprised of one domain, CL. The VH and VL regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901-917 (1987)). Unless otherwise stated or contradicted by context, CDR sequences herein are identified according to IMGT rules (Brochet X., Nucl Acids Res. 2008; 36: W503-508 and Lefranc M P., Nucleic Acids Research 1999; 27:209-212; see also internet http address http://www.imgt.org/). Unless otherwise stated or contradicted by context, reference to amino acid positions in the constant regions in the present invention is according to the EU-numbering (Edelman et al., Proc Natl Acad Sci USA. 1969 May; 63(1):78-85; Kabat et al., Sequences of Proteins of Immunological Interest, Fifth Edition. 1991 NIH Publication No. 91-3242). For example, SEQ ID NO: 15 herein sets forth amino acids positions 118-447 according to EU numbering, of the IgG1 heavy chain constant region.

The term "amino acid corresponding to position . . . " as used herein refers to an amino acid position number in a human IgG1 heavy chain. Corresponding amino acid positions in other immunoglobulins may be found by alignment with human IgG1. Thus, an amino acid or segment in one sequence that "corresponds to" an amino acid or segment in another sequence is one that aligns with the other amino acid or segment using a standard sequence alignment program such as ALIGN, ClustalW or similar, typically at default settings and has at least 50%, at least 80%, at least 90%, or at least 95% identity to a human IgG1 heavy chain. It is considered well-known in the art how to align a sequence or segment in a sequence and thereby determine the corresponding position in a sequence to an amino acid position according to the present invention.

The term "immunoglobulin heavy chain" or "heavy chain of an immunoglobulin" as used herein is intended to refer to one of the heavy chains of an immunoglobulin. A heavy chain is typically comprised of a heavy chain variable region (abbreviated herein as VH) and a heavy chain constant region (abbreviated herein as CH) which defines the isotype of the immunoglobulin. The heavy chain constant region typically is comprised of three domains, CH1, CH2, and CH3. The term "immunoglobulin" as used herein is intended to refer to a class of structurally related glycoproteins consisting of two pairs of polypeptide chains, one pair of light (L) low molecular weight chains and one pair of heavy (H) chains, all four potentially inter-connected by disulfide bonds. The structure of immunoglobulins has been well characterized (see for instance Fundamental Immunology Ch. 7 (Paul, W., ed., 2nd ed. Raven Press, N.Y. (1989)). Within the structure of the immunoglobulin, the two heavy chains are inter-connected via disulfide bonds in the so-called "hinge region". Equally to the heavy chains, each light chain is typically comprised of several regions; a light chain variable region (abbreviated herein as VL) and a light chain constant region. The light chain constant region typically is comprised of one domain, CL. Furthermore, the VH and VL regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4. CDR sequences are defined according to IMGT (see Lefranc M P. et al., Nucleic Acids Research, 27, 209-212, 1999] and Brochet X. Nucl. Acids Res. 36, W503-508 (2008)).

When used herein, the terms "half molecule", "Fab-arm" and "arm" refer to one heavy chain-light chain pair. When a bispecific antibody is described to comprise a half-molecule antibody "derived from" a first antibody, and a half-molecule antibody "derived from" a second antibody, the term "derived from" indicates that the bispecific antibody was generated by recombining, by any known method, said half-molecules from each of said first and second antibodies into the resulting bispecific antibody. In this context, "recombining" is not intended to be limited by any particular method of recombining and thus includes all of the methods for producing bispecific antibodies described herein below, including for example recombining by half-molecule exchange, as well as recombining at nucleic acid level and/or through co-expression of two half-molecules in the same cells.

The term "antigen-binding region" or "binding region" as used herein, refers to a region of an antibody which is capable of binding to the antigen. The antigen can be any molecule, such as a polypeptide, e.g. present on a cell, bacterium, or virion. The terms "antigen" and "target" may, unless contradicted by the context, be used interchangeably in the context of the present invention. The terms "antigen-binding region" and "antigen-binding site" may, unless contradicted by the context, be used interchangeably in the context of the present invention.

The term "blocks binding" or "blocking the binding of an antibody" or "cross-blocking binding" or "cross-blocks binding" refers to the situation where one antibody bound to a specific antigen prevents binding of the second antibody to the same antigen and vice versa. In the absence of the other antibody, each antibody has the ability to bind to the antigen as determined by a significant binding response, whereas one of the antibodies lacks a binding response when the other antibody is present. The ability of one antibody to block the binding of another antibody may be determined by biolayer interferometry in a classical sandwich epitope binning assay format, for instance as described in Example 3 in the present application and by Abdiche et al. (Abdiche Y N, Malashock D S, Pinkerton A, Pons J. Exploring blocking assays using Octet, ProteOn, and Biacore biosensors. Anal Biochem. 2009; 386(2): 172-180). Briefly, in a sandwich epitope binning assay, an antibody in solution is tested for binding to its specific antigen that is first captured via an immobilized antibody. In the context of the present invention, one antibody does not block the binding of another antibody if it is capable of "displacing" the other antibody, according to the definition of "displacement" below. The terms "blocks binding" and "blocking the binding of an antibody" and "cross-blocking binding" and "cross-blocks binding" may, unless contradicted by the context, be used interchangeably in the context of the present invention. Preferably, the ability of one antibody to block the binding of another antibody is determined using full-length antibodies.

The term "displacement" or "ability to displace" or "displacing" refers to the situation wherein two antibodies perturb one another's binding to an antigen by kinetically altering one another's binding to their specific antigen via the formation of a transient trimolecular complex, which rapidly collapses by retaining one antibody to the antigen and displacing the other. Antibody displacement is defined in Abdiche et al., 2017 (Abdiche Y N, Yeung A Y, Ni I, Stone D, Miles A, Morishige W, et al. (2017) Antibodies Targeting Closely Adjacent or Minimally Overlapping Epitopes Can Displace One Another. PLoS ONE 12(1): e0169535. doi: 10.1371/journal.pone.0169535). Antibody displacement may be determined by biolayer interferometry using real-time label-free biosensors in a classical sandwich assay format as described in Abdiche et al. 2017 and Example 4 in the present application. Preferably, antibody displacement is determined using antibodies which are in the IgG format.

The term "binding" as used herein refers to the binding of an antibody to a predetermined antigen or target, typically with a binding affinity corresponding to a $K_D$ Of $1E^{-6}$ M or less, e.g. $5E^{-7}$ M or less, $1E^{-7}$ M or less, such as $5E^{-8}$ M or less, such as $1E^{-8}$ M or less, such as $5E^{-9}$ M or less, or such as $1E^{-9}$ M or less, when determined by biolayer interferometry using the antibody as the ligand and the antigen as the analyte and binds to the predetermined antigen with an affinity corresponding to a $K_D$ that is at least ten-fold lower, such as at least 100-fold lower, for instance at least 1,000-fold lower, such as at least 10,000-fold lower, for instance at least 100,000-fold lower than its affinity for binding to a non-specific antigen (e.g., BSA, casein) other than the predetermined antigen or a closely-related antigen.

The term "$K_D$" (M), as used herein, refers to the dissociation equilibrium constant of a particular antibody-antigen interaction, and is obtained by dividing $k_d$ by $k_a$.

The term "$k_d$" (sec$^{-1}$), as used herein, refers to the dissociation rate constant of a particular antibody-antigen interaction. Said value is also referred to as the $k_{off}$ value or off-rate.

The term "$k_a$" (M$^{-1}$×sec$^{-1}$), as used herein, refers to the association rate constant of a particular antibody-antigen interaction. Said value is also referred to as the $k_{on}$ value or on-rate.

The term "5T4" as used herein, refers to the protein entitled 5T4, which is also referred to as trophoblast glycoprotein, 5T4 oncofetal antigen, 5T4 oncofetal trophoblast glycoprotein, TPBG, WAIF1 and M6P1. It is 72-80 kDa transmembrane protein with an extensively N-linked glycosylated core. In humans (*Homo sapiens*), the 5T4 protein has the amino acid sequence shown in SEQ ID NO: 1 (Human Trophoblast glycoprotein: Uniprot accession no. Q13641). In the amino acid sequence shown in SEQ ID NO: 1, amino acid residues 1-31 are a signal peptide, and amino acid residues 32-420 are the mature polypeptide. In cynomolgus monkey (*Macaca fascicularis*), the 5T4 protein has the amino acid sequence shown in SEQ ID NO: 2 (Uniprot accession no. Q4R8Y9). In the amino acid sequence shown in SEQ ID NO: 2, amino acid residues 1-34 are a signal peptide, and amino acid residues 35-420 are the mature polypeptide. In chicken (*Gallus gallus*), the 5T4 protein has the amino acid sequence shown in SEQ ID NO: 3 (Uniprot accession no. R4GM46). In the sequence shown in SEQ ID NO: 3, amino acid residues 1-27 are a signal peptide, and amino acid residues 28-379 are the mature polypeptide.

The term "CD3" as used herein, refers to the human Cluster of Differentiation 3 protein which is part of the T-cell co-receptor protein complex and is composed of four distinct chains. CD3 is also found in other species, and thus, the term "CD3" is not limited to human CD3 unless contradicted by context. In mammals, the complex contains a CD3γ (gamma) chain (human CD3γ chain UniProtKB/Swiss-Prot No P09693, or cynomolgus monkey CD3γ UniProtKB/Swiss-Prot No Q95LI7), a CD3δ (delta) chain (human CD3δ UniProtKB/Swiss-Prot No P04234, or cynomolgus monkey CD3δ UniProtKB/Swiss-Prot No Q95LI8), two CD3ε (epsilon) chains (human CD3ε UniProtKB/Swiss-Prot No P07766; amino acid residues 1-22 is a signal peptide and amino acid residues 23-207 is the mature CD3ε polypeptide, which is identified herein as SEQ ID NO: 4; cynomolgus monkey CD3ε UniProtKB/Swiss-Prot No Q95LI5; or rhesus monkey CD3ε UniProtKB/Swiss-Prot No G7NCB9), and a CD3ζ-chain (zeta) chain (human CD3ζ UniProtKB/Swiss-Prot No P20963, cynomolgus monkey CD3ζ UniProtKB/Swiss-Prot No Q09TK0). These chains associate with a molecule known as the T-cell receptor (TCR) and generate an activation signal in T lymphocytes. The TCR and CD3 molecules together comprise the TCR complex.

The term "antibody binding region" refers to a region of the antigen, which comprises the epitope to which the antibody binds. An antibody binding region may be determined by epitope binning using biolayer interferometry, by alanine scan, or by shuffle assays (using antigen constructs in which regions of the antigen are exchanged with that of another species and determining whether the antibody still binds to the antigen or not). The amino acids within the antibody binding region that are involved in the interaction with the antibody may be determined by hydrogen/deuterium exchange mass spectrometry and by crystallography of the antibody bound to its antigen.

The term "epitope" means an antigenic determinant which is specifically bound by an antibody. Epitopes usually consist of surface groupings of molecules such as amino acids, sugar side chains or a combination thereof and usually have specific three dimensional structural characteristics, as well as specific charge characteristics. Conformational and non-conformational epitopes are distinguished in that the binding to the former but not the latter is lost in the presence of denaturing solvents. The epitope may comprise amino acid residues which are directly involved in the binding, and other amino acid residues, which are not directly involved in the binding, such as amino acid residues which are effectively blocked or covered by the antibody when it is bound to the antigen (in other words, the amino acid residue is within or closely adjacent to the footprint of the specific antibody).

The terms "monoclonal antibody", "monoclonal Ab", "monoclonal antibody composition", "mAb", or the like, as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human monoclonal antibodies may be produced by a hybridoma which includes a B cell obtained from a transgenic or transchromosomal non-human animal, such as a transgenic mouse, having a genome comprising a human heavy chain transgene and a light chain transgene, fused to an immortalized cell. Monoclonal antibodies may also be produced from recombinantly modified host cells, or systems that use cellular extracts supporting in vitro transcription and/or translation of nucleic acid sequences encoding the antibody.

The term "isotype" as used herein refers to the immunoglobulin class (for instance IgG1, IgG2, IgG3, IgG4, IgD, IgA, IgE, or IgM) or any allotypes thereof, such as IgG1m (za) and IgG1m(f)) that is encoded by heavy chain constant region genes. Further, each heavy chain isotype can be combined with either a kappa (κ) or lambda (λ) light chain.

The term "full-length antibody" when used herein, refers to an antibody (e.g., a parent or variant antibody) comprising one or two pairs of heavy and light chains, each containing all heavy and light chain constant and variable domains that are normally found in a heavy chain-light chain pair of a wild-type antibody of that isotype. In a full length variant antibody, the heavy and light chain constant and variable domains may in particular contain amino acid substitutions that improve the functional properties of the antibody when compared to the full length parent or wild type antibody. A full-length antibody according to the present invention may be produced by a method comprising the steps of (i) cloning the CDR sequences into a suitable vector comprising complete heavy chain sequences and complete light chain sequence, and (ii) expressing the complete heavy and light chain sequences in suitable expression systems. It is within the knowledge of the skilled person to produce a full-length antibody when starting out from either CDR sequences or full variable region sequences. Thus, the skilled person would know how to generate a full-length antibody according to the present invention.

The term "human antibody", as used herein, is intended to include antibodies having variable and framework regions derived from human germline immunoglobulin sequences and a human immunoglobulin constant domain. The human antibodies of the invention may include amino acid residues not encoded by human germline immunoglobulin sequences (e.g., mutations, insertions or deletions introduced by random or site-specific mutagenesis in vitro or by somatic mutation in vivo). However, the term "human antibody", as used herein, is not intended to include antibodies in which CDR sequences derived from the germline of another non-human species, such as a mouse, have been grafted onto human framework sequences.

The term "humanized antibody" as used herein, refers to a genetically engineered non-human antibody, which contains human antibody constant domains and non-human variable domains modified to contain a high level of sequence homology to human variable domains. This can be achieved by grafting of the six non-human antibody complementarity-determining regions (CDRs), which together form the antigen binding site, onto a homologous human acceptor framework region (FR) (see WO92/22653 and EP0629240). In order to fully reconstitute the binding affinity and specificity of the parental antibody, the substitution of framework residues from the parental antibody (i.e. the non-human antibody) into the human framework regions (back-mutations) may be required. Structural homology modeling may help to identify the amino acid residues in the framework regions that are important for the binding properties of the antibody. Thus, a humanized antibody may comprise non-human CDR sequences, primarily human framework regions optionally comprising one or more amino acid back-mutations to the non-human amino acid sequence, and fully human constant regions. Optionally, additional amino acid modifications, which are not necessarily back-mutations, may be applied to obtain a humanized antibody with preferred characteristics, such as affinity and biochemical properties.

The term "Fc region" as used herein, refers to a region comprising, in the direction from the N- to C-terminal end of the antibody, at least a hinge region, a CH2 region and a CH3 region. An Fc region of the antibody may mediate the binding of the immunoglobulin to host tissues or factors, including various cells of the immune system (such as effector cells) and components of the complement system.

The term "hinge region" as used herein refers to the hinge region of an immunoglobulin heavy chain. Thus, for example the hinge region of a human IgG1 antibody corresponds to amino acids 216-230 according to the Eu numbering as set forth in Kabat Kabat, E. A. et al., Sequences of proteins of immunological interest. 5th Edition—US Department of Health and Human Services, NIH publication No. 91-3242, pp 662,680,689 (1991). However, the hinge region may also be any of the other subtypes as described herein.

The term "CH1 region" or "CH1 domain" as used herein refers to the CH1 region of an immunoglobulin heavy chain. Thus, for example the CH1 region of a human IgG1 antibody corresponds to amino acids 118-215 according to the Eu numbering as set forth in Kabat (ibid). However, the CH1 region may also be any of the other subtypes as described herein.

The term "CH2 region" or "CH2 domain" as used herein refers to the CH2 region of an immunoglobulin heavy chain. Thus, for example the CH2 region of a human IgG1 antibody corresponds to amino acids 231-340 according to the Eu numbering as set forth in Kabat (ibid). However, the CH2 region may also be any of the other subtypes as described herein.

The term "CH3 region" or "CH3 domain" as used herein refers to the CH3 region of an immunoglobulin heavy chain. Thus for example the CH3 region of a human IgG1 antibody corresponds to amino acids 341-447 according to the Eu numbering as set forth in Kabat (ibid). However, the CH3 region may also be any of the other subtypes as described herein.

The term "Fc-mediated effector functions," as used herein, is intended to refer to functions that are a consequence of binding a polypeptide or antibody to its target or antigen on a cell membrane wherein the Fc-mediated effector function is attributable to the Fc region of the polypeptide or antibody. Examples of Fc-mediated effector functions include (i) C1q binding, (ii) complement activation, (iii) complement-dependent cytotoxicity (CDC), (iv) antibody-dependent cell-mediated cytotoxity (ADCC), (v) Fc-gamma receptor (FcgR)-binding, (vi) antibody-dependent, FcγR-mediated antigen crosslinking, (vii) antibody-dependent cellular phagocytosis (ADCP), (viii) complement-dependent cellular cytotoxicity (CDCC), (ix) complement-enhanced cytotoxicity, (x) binding to complement receptor of an opsonized antibody mediated by the antibody, (xi) opsonisation, and (xii) a combination of any of (i) to (xi).

The term "inertness", "inert" or "non-activating" as used herein, refers to an Fc region which is at least not able to bind any FcγR, induce Fc-mediated cross-linking of FcγRs, or induce FcγR-mediated cross-linking of target antigens via two Fc regions of individual antibodies, or is not able to bind C1q. The inertness of an Fc region of an antibody, may be tested using the antibody in a monospecific or bispecific format.

The term "full-length" when used in the context of an antibody indicates that the antibody is not a fragment, but contains all of the domains of the particular isotype normally found for that isotype in nature, e.g. the VH, CH1, CH2, CH3, hinge, VL and CL domains for an IgG1 antibody.

The term "monovalent antibody", in the context of the present invention, refers to an antibody molecule that can interact with a specific epitope on an antigen, with only one antigen binding domain (e.g. one Fab arm). In the context of a bispecific antibody, "monovalent antibody binding" refers to the binding of the bispecific antibody to one specific epitope on an antigen with only one antigen binding domain (e.g. one Fab arm).

The term "monospecific antibody" in the context of the present invention, refers to an antibody that has binding specificity to one epitope only. The antibody may be a monospecific, monovalent antibody (i.e. carrying only one antigen binding region) or a monospecific, bivalent antibody (i.e. an antibody with two identical antigen binding regions).

The term "bispecific antibody" refers to an antibody having two non-identical antigen binding domains, e.g. two non-identical Fab-arms or two Fab-arms with non-identical CDR regions. In the context of this invention, bispecific antibodies have specificity for at least two different epitopes. Such epitopes may be on the same or different antigens or targets. If the epitopes are on different antigens, such antigens may be on the same cell or different cells, cell types or structures, such as extracellular matrix or vesicles and soluble protein. A bispecific antibody may thus be capable of crosslinking multiple antigens, e.g. two different cells.

The term "bivalent antibody" refers to an antibody that has two antigen binding regions., which bind to epitopes on one or two targets or antigens or binds to one or two epitopes on the same antigen. Hence, a bivalent antibody may be a monospecific, bivalent antibody or a bispecific, bivalent antibody.

The term "amino acid" and "amino acid residue" may herein be used interchangeably, and are not to be understood limiting. Amino acids are organic compounds containing amine (~NH$_2$) and carboxyl (—COOH) functional groups, along with a side chain (R group) specific to each amino acid. In the context of the present invention, amino acids may be classified based on structure and chemical characteristics. Thus, classes of amino acids may be reflected in one or both of the following tables:

| Main classification based on structure and general chemical characterization of R group | |
| --- | --- |
| Class | Amino acid |
| Acidic Residues | D and E |
| Basic Residues | K, R, and H |
| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y, and W |

| Alternative Physical and Functional Classifications of Amino Acid Residues | |
| --- | --- |
| Class | Amino acid |
| Hydroxyl group containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |
| Very small residues | A, G, and S |
| Residues involved in turn formation | A, C, D, E, G, H, K, N, Q, R, S, P, and T |
| Flexible residues | Q, T, K, S, G, P, D, E, and R |

Substitution of one amino acid for another may be classified as a conservative or non-conservative substitution. In the context of the invention, a "conservative substitution" is a substitution of one amino acid with another amino acid having similar structural and/or chemical characteristics, such substitution of one amino acid residue for another amino acid residue of the same class as defined in any of the two tables above: for example, leucine may be substituted with isoleucine as they are both aliphatic, branched hydrophobes. Similarly, aspartic acid may be substituted with glutamic acid since they are both small, negatively charged residues.

In the context of the present invention, a substitution in an antibody is indicated as:

Original amino acid—position—substituted amino acid;

Referring to the well-recognized nomenclature for amino acids, the three letter code, or one letter code, is used, including the codes "Xaa" or "X" to indicate any amino acid residue. Thus, Xaa or X may typically represent any of the 20 naturally occurring amino acids. The term "naturally occurring" as used herein refers to any one of the following amino acid residues; glycine, alanine, valine, leucine, isoleucine, serine, threonine, lysine, arginine, histidine, aspartic acid, asparagine, glutamic acid, glutamine, proline, tryptophan, phenylalanine, tyrosine, methionine, and cysteine. Accordingly, the notation "K409R" or "Lys409Arg" means, that the antibody comprises a substitution of Lysine with Arginine in amino acid position 409.

Substitution of an amino acid at a given position to any other amino acid is referred to as:

Original amino acid—position; or e.g. "K409"

For a modification where the original amino acid(s) and/or substituted amino acid(s) may comprise more than one, but not all amino acid(s), the more than one amino acid may be separated by "," or "/". E.g. the substitution of Lysine with Arginine, Alanine, or Phenylalanine in position 409 is:

"Lys409Arg,Ala,Phe" or "Lys409Arg/Ala/Phe" or "K409R,A,F" or "K409R/A/F" or "K409 to R, A, or F".

Such designation may be used interchangeably in the context of the invention but have the same meaning and purpose.

Furthermore, the term "a substitution" embraces a substitution into any one or the other nineteen natural amino acids, or into other amino acids, such as non-natural amino acids. For example, a substitution of amino acid K in position 409 includes each of the following substitutions: 409A, 409C, 409D, 409E, 409F, 409G, 409H, 409I, 409L, 409M, 409N, 409Q, 409R, 409S, 409T, 409V, 409W, 409P, and 409Y. This is, by the way, equivalent to the designation 409X, wherein the X designates any amino acid other than the original amino acid. These substitutions may also be designated K409A, K409C, etc. or K409A,C, etc. or K409A/C/etc. The same applies by analogy to each and every position mentioned herein, to specifically include herein any one of such substitutions.

The antibody according to the invention may also comprise a deletion of an amino acid residue. Such deletion may be denoted "del", and includes, e.g., writing as K409del. Thus, in such embodiments, the Lysine in position 409 has been deleted from the amino acid sequence.

The term "host cell", as used herein, is intended to refer to a cell into which an expression vector has been introduced. It should be understood that such terms are intended to refer not only to the particular subject cell, but also to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, transfectomas, such as CHO cells, HEK-293 cells, Expi293F cells, PER.C6 cells, NS0 cells, and lymphocytic cells, and prokaryotic cells such as *E. coli* and other eukaryotic hosts such as plant cells and fungi.

The term "transfectoma", as used herein, includes recombinant eukaryotic host cells expressing the antibody or a target antigen, such as CHO cells, PER.C6 cells, NS0 cells, HEK-293 cells, Expi293F cells, plant cells, or fungi, including yeast cells.

For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

$$\text{(Identical Residues} \times 100)/\text{(Length of Alignment} - \text{Total Number of Gaps in Alignment).}$$

The retention of similar residues may also or alternatively be measured by a similarity score, as determined by use of a BLAST program (e.g., BLAST 2.2.8 available through the NCBI using standard settings BLOSUM62, Open Gap=11 and Extended Gap=1). Suitable variants typically exhibit at least about 45%, such as at least about 55%, at least about 65%, at least about 75%, at least about 85%, at least about 90%, at least about 95%, or more (e.g., about 99%) similarity to the parent sequence.

The term "internalized" or "internalization" as used herein, refers to a biological process in which molecules such as the antibody according to the present invention, are engulfed by the cell membrane and drawn into the interior of the cell. Internalization may also be referred to as "endocytosis".

In a first aspect, the present invention provide a multispecific antibody, comprising an antigen binding region capable of binding to 5T4 and an antigen binding region capable of binding to CD3, for use in treatment of cancer selected from the group consisting of esophageal cancer, Non-small Cell Lung Cancer (NSCLC) and Squamous Cell Carcinoma of the Head and Neck (SCCHN).

The multispecific antibody may in particular be for use in treatment of esophageal cancer.

The esophageal cancer may be an adenocarcinoma, such as an adenocarcinoma of the esophagus.

In other embodiments of the invention, the esophageal cancer is a squamous cell carcinoma, such as a squamous cell carcinoma of the esophagus.

In further embodiments, the esophageal cancer is an adenosquamous carcinoma.

Also, the esophageal cancer may be a Siewert type I adenocarcinoma of the esophagogastric junction (EGJ).

The multispecific antibody may in particular be for use as set forth above, wherein the esophageal cancer is advanced, locally advanced or metastatic.

The multispecific antibody may be for use as specified above, wherein the treatment of esophageal cancer is provided to a subject that has received at least one prior line of systemic treatment for advanced disease.

The treatment of esophageal cancer as defined herein may be provided to a subject that has progressed on or after at least one prior line of systemic treatment for advanced disease; e.g. a platinum-based regimen (chemotherapy including a platinum agent) such as tubulin inhibition in combination with platin and 5-fluorouracil (5-FU) or irinotecan.

The esophageal cancer may in particular be a HER2/neu positive cancer.

The multispecific antibody may be for use, wherein the treatment of esophageal cancer is provided to a subject, that has received prior treatment with HER2/neu targeted therapy.

The HER2/neu targeted therapy may comprise treatment with Trastuzumab or Pertuzumab.

The multispecific antibody may be for use in treatment of Non-small Cell Lung Cancer The Non-small Cell Lung Cancer may be an adenocarcinoma (ACC).

Alternatively, the Non-small Cell Lung Cancer may be a squamous cell carcinoma (SCC)].

In further embodiments, the Non-small Cell Lung Cancer is an adenosquamous carcinoma.

The Non-small Cell Lung Cancer is a locally advanced, advanced or metastatic cancer.

The treatment of Non-small Cell Lung Cancer wherein the the antibody is used according to the invention may be provided to a subject who has received at least one prior line of systemic treatment for locally advanced, advanced or metastatic disease.

The multispecific antibody may be administered to a subject that has experienced progression of the Non-small Cell Lung Cancer on or after prior systemic treatment for locally advanced or metastatic disease.

The multispecific antibody may in particular be administered to a subject that has received prior therapy selected from the group consisting of therapy with a platinum-based regimen (chemotherapy including a platinum agent; e.g. tubulin inhibition in combination with platin and 5-fluorouracil (5-FU) or irinotecan), therapy with a tyrosine kinase inhibitor and therapy with anti PD-1/PD-L1 treatment, such as therapy with one or more PD-1 and/or PD-L1 inhibitors. An example of prior treatment is Pembrolizumab, which has been approved as monotherapy for tumors with substantial expression of PD-L1 and has further been approved in combination therapy irrespective of or not depending on PD-L1 expression.

The tyrosine kinase inhibitor may be selected from the group consisting of an inhibitor of Anaplastic lymphoma kinase (ALK; ALK tyrosine kinase), an inhibitor of proto-oncogene tyrosine-protein kinase ROS1, and an inhibitor of the epidermal growth factor receptor (EGFR).

The multispecific antibody may also be for use in treatment of Squamous Cell Carcinoma of the Head and Neck (SCCHN).

The multispecific antibody may be for use in treatment of SCCHN, which is human papillomavirus (HPV) positive SCCHN or HPV-associated SCCHN/SCCHN associated with HPV infection.

Alternatively, the multispecific antibody may be for use in treatment of SCCHN, which is human papillomavirus (HPV) negative SCCHN/SCCHN that is not associated with HPV infection.

In particular, the treatment may be for squamous cell carcinoma of the oral cavity.

The anti-EGFR therapy/the EGFR inhibitor may be selected from the group consisting of erlotinib, osimertinib, gefintinib, olmutinib, nazartinib, avitinib, cetuximab and panitumumab.

The therapy with a platinum-based regimen may comprise therapy with cisplatin or carboplatin in combination with 5FU and cetuximab or therapy with Pembrolizumab in combination with cisplatin or carboplatin and cetuximab.

In particular, the treatment may be provided to a subject that has measurable disease according to the Response Evaluation Criteria In Solid Tumors; version 1.1 (RECIST Criteria v1.1). The RECIST Criteria are set forth in the table below.

| Definition of Response (RECIST Criteria v1.1) | | |
|---|---|---|
| | Category | Criteria |
| Based on target lesions | Complete Response (CR) | Disappearance of all target lesions. Any pathological lymph nodes must have reduction in short axis to <10 mm. |
| | Partial Response (PR) | >30% decrease in the sum of the LD of target lesions, taking as reference the baseline sum LD. |
| | Stable Disease (SD) | Neither sufficient shrinkage to qualify for PR nor sufficient increase to qualify for PD, taking as reference the smallest sum of LDs since the treatment started. |
| | Progressive Disease (PD) | >20% increase in the sum of the LDs of target lesions, taking as reference the smallest sum of the LDs recorded since the treatment started or the appearance of one or more new lesions. |
| Based on non-target lesions | CR | Disappearance of all non-target lesions and normalization of tumor marker level. All lymph nodes must be non-pathological in size (<10 mm short axis). |
| | SD | Persistence of one or more non-target lesion(s) or/and maintenance of tumor marker level above the normal limits. |
| | PD | Appearance of one or more new lesions and/or unequivocal progression of existing non-target lesions. |

Further, the treatment is for squamous cell carcinoma of the oropharynx.

Also, the treatment may be for squamous cell carcinoma of the paranasal sinuses.

In some embodiments, the treatment is for squamous cell carcinoma of the nasal cavity.

The treatment may in particular be for squamous cell carcinoma of the hypopharynx.

Also, the treatment may be for squamous cell carcinoma of the larynx.

For treatment of Squamous Cell Carcinoma of the Head and Neck the multispecific antibody may be administered to a subject that has received prior therapy selected from the group consisting of therapy with a platinum-based regimen (chemotherapy including a platinum agent), therapy with anti PD-1/PD-L1, such as therapy with one or more PD-1 and/or PD-L1 inhibitors, and anti-EGFR therapy; e.g. therapy with an EGFR inhibitor.

The platinum-based regimen (chemotherapy including a platinum agent) may comprise cisplatin or carboplatin.

The subject to which the treatment is provided or offered may have received prior therapy comprising treatment with 5-fluorouracil (5-FU).

The anti PD-1/PD-L1 PD-1 and/or the one or more PD-1 and/or PD-L1 inhibitors may be selected from the group consisting of nivolumab, genolimzumab, atezolizumab, durvalumab, avelumab, pembrolizumab, genolimzumab, nivolumab, cemiplimab and tislelizumab.

Further, the treatment may be provided to a subject that has an Eastern Cooperative Oncology Group (ECOG) score of 0-1.

The said subject, that is being treated or to whom treatment is offered is a human.

In the multispecific antibody for use according to the invention, the antigen binding region, capable of binding to 5T4 may be able to block, or may be an antigen binding region of an antibody which is able t block, binding to 5T4 of an antibody comprising a variable heavy chain (VH) region comprising the sequence set forth in SEQ ID NO: 5, and a variable light chain (VL) region comprising the sequence set forth in SEQ ID NO: 9 [059].

The antigen binding region capable of binding to 5T4 may be able to block, or may be an antigen binding region of an antibody which is able to block, binding to 5T4 of an antibody selected from the group consisting of:

a) an antibody comprising a variable heavy chain (VH) region comprising the sequence set forth in SEQ ID NO: 40 and a variable light chain (VL) region comprising the sequence set forth in SEQ ID NO: 44 [207], b) an antibody comprising a variable heavy chain (VH) region comprising the sequence set forth in SEQ ID NO: 47 and a variable light chain (VL) region comprising the sequence set forth in SEQ ID NO: 51 [226]; and c) an antibody comprising a variable heavy chain (VH) region comprising the sequence set forth in SEQ ID NO: 5 and a variable light chain (VL) region comprising the sequence set forth in SEQ ID NO: 9 [059].

The antigen binding region, capable of binding to 5T4 may be able to block binding, or may be from an antibody which is able to block binding, to 5T4 of an antibody selected from the group consisting of:

a) an antibody comprising a variable heavy chain (VH) region comprising the sequence set forth in SEQ ID NO: 40 and a variable light chain (VL) region comprising the sequence set forth in SEQ ID NO: 44 [207]; and b) an antibody comprising a variable heavy chain (VH) region comprising the sequence set forth in SEQ ID NO: 47 and a variable light chain (VL) region comprising the sequence set forth in SEQ ID NO: 51 [226].

The binding region which is able to bind to 5T4 may be able to bind to human 5T4, cynomolgus monkey and/or chicken 5T4, with a binding affinity that corresponds to a $K_D$ value 1E−7 M or less, such as 5E−8 M or less, 1E−8 M or less, 5E−9 M or less or such as 1E−9 M or less such as with a binding affinity corresponding to a $K_D$ value which is within the range of 1E−7 to 5E−10 M, such as within the range of 1E−7 to 1E−9 M, such as 5E−8 to 5E−10 M, 5E−8 to 1E−9 M, such as 1E−8 to 1E−9 M or such as 1E−8 to 5E−9 M. This may in particular be the case when binding is determined of a monospecific, bivalent parent antibody comprising the biding region that ais able to bind 5T4. Binding is preferably determined using biolayer interferometry methodology In the context of the multispecific antibody for use according to the invention, 5T4 is human (*Homo sapiens*) 5T4, such the mature polypeptide sequence of SEQ ID NO: 1.

In the context of the multispecific antibody for use according to the invention, 5T4 may also be cynomolgus monkey (*Macaca fascicularis*) 5T4, such as the mature polypeptide sequence of SEQ ID NO: 2.

In the context of the multispecific antibody for use according to the invention, 5T4 may also be chicken (*Gallus gallus*) 5T4, such as the mature polypeptide sequence of SEQ ID NO: 3.

In some embodiments, 5T4 is human 5T4 such as the mature polypeptide of SEQ ID NO: 1 and cynomolgous monkey 5T4, such as the mature polypeptide of SEQ ID NO: 2.

In other embodiments, 5T4 is human 5T4, such as the mature polypeptide sequence of SEQ ID NO: 1, cynomolgous monkey 5T4, such as the mature polypeptide sequence of SEQ ID NO: 2 and chicken 5T4 such as the mature polypeptide sequence of SEQ ID NO: 3.

The multispecific antibody for use according to the invention may bind an epitope or antibody binding region or binding site on 5T4, said antibody binding region, binding site or epitope being recognized by any one of the antibodies selected from the group consisting of:

a) an antibody comprising a VH region comprising the sequence set forth in SEQ ID NO: 5 and a VL region comprising the sequence set forth in SEQ ID NO: 9 [059], b) an antibody comprising a VH region comprising the sequence set forth in SEQ ID NO: 12 and a VL region comprising the sequence set forth in SEQ ID NO: 16 [076], c) an antibody comprising a VH region comprising the sequence set forth in SEQ ID NO: 19 and a VL region comprising the sequence set forth in SEQ ID NO: 23 [085],

d) an antibody comprising a VH region comprising the sequence set forth in SEQ ID NO: 26 and a VL region comprising the sequence set forth in SEQ ID NO: 30 [106], e) an antibody comprising a VH region comprising the sequence set forth in SEQ ID NO: 33 and a VL region comprising the sequence set forth in SEQ ID NO: 37 [127], f) an antibody comprising a VH region comprising the sequence set forth in SEQ ID NO: 40 and a VL region comprising the sequence set forth in SEQ ID NO: 44 [207]; and g) an antibody comprising a VH region comprising the sequence set forth in SEQ ID NO: 47 and a VL region comprising the sequence set forth in SEQ ID NO: 51 [226].

In the context of the present invention, cross-block, or the ability of an antibody as defined herein to block binding of another antibody to 5T4 may be determined by the fluorescence-activated cell sorting (FACS) assay, such as in an assay performed as described in Example 5.

Cross-block, or the ability of an antibody as defined in any of the preceding claims to block binding of another antibody to 5T4, may be determined as the ability of an unconjugated antibody to block binding of a conjugated antibody, and is optionally determined in a procedure comprising the steps of:

i) Providing a set of samples, each sample comprising a mixture of human ovary adenocarcinoma SK-OV-3 cells, an antibody which binds to 5T4 and is conjugated to fluorescein isothiocyanate (FITC) and an excess of unconjugated antibody targeting 5T4, ii) Incubating the samples for 30 minutes at 4° C., and thereafter subjecting the samples to centrifugation, iii) Removing the supernatant from each sample and resuspending the cells in buffer and determining mean fluorescence intensity (MFI) of the FITC using a flow cytometer; and iv) Calculating the percentage of binding as following:

The difference in MFI between cells incubated with a mixture of FITC-conjugated antibodies and unconjugated antibodies and cells incubated without FITC-conjugated or unconjugated antibodies, multiplied by 100, and subsequently divided by the difference in MFI between cells incubated with a mixture of FITC-conjugated antibodies and IgG-b12 antibodies and cells incubated without FITC-conjugated or unconjugated antibodies.

The ability of said antibody to block binding of another antibody to 5T4 or to displace another antibody bound to 5T4ECDHis (mature protein of SEQ ID NO: 99), may be determined using biolayer interferometry, such as in an assay as described in Example 3.

The antigen binding region capable of binding to 5T4 may be able to bind to an epitope or antibody binding region on human 5T4 comprising the amino acid residues R73, Y92 and R94; the numbering of each amino acid residue referring to its position in SEQ ID NO: 1.

The antigen binding region capable of binding to 5T4 may be able to bind to an epitope or antibody binding region on human 5T4 comprising the amino acid residues S69, R73, Y92 and R94; the numbering of each amino acid residue referring to its position in SEQ ID NO: 1.

The antigen binding region capable of binding to 5T4 may be able to bind to an epitope or antibody binding region on human 5T4 comprising the amino acid residues R73, T74, Y92, R94 and N95; the numbering of each amino acid residue referring to its position in SEQ ID NO: 1.

The amino acid residues mentioned above may be directly involved in the binding of the antibody to 5T4.

One or more of the following additional amino acid residues of 5T4 may also be involved binding of the antigen binding region capable of binding to 5T4, such as indirectly involved in binding, e.g. by impacting protein folding and/or positioning of one or more amino acid residues directly involved in binding of the antigen binding region: L89, F111, L117, F138, L144, D148, N152; the numbering of each amino acid residue referring to its position in SEQ ID NO: 1.

In some embodiments, the antigen binding region, capable of binding to 5T4 is able to bind to an epitope or antibody binding region on human 5T4 within which amino acid residues R73, Y92 and R94 are directly involved in binding the antibody, and wherein one or more of amino acid residues F111, F138, L144 and D148 are indirectly involved in said binding; the numbering of each amino acid residue referring to its position in SEQ ID NO: 1.

The antigen binding region, capable of binding to 5T4 may be able to bind to an epitope or antibody binding region on human 5T4 within which amino acid residues S69, R73, Y92 and R94 are directly involved in binding the antibody, and wherein one or more of amino acid residues F111, F138, and D148 are indirectly involved in said binding; the numbering of each amino acid residue referring to its position in SEQ ID NO: 1.

The antigen binding region, capable of binding to 5T4 may be able to bind to an epitope or antibody binding region on human 5T4 within which amino acid residues R73, T74, Y92, R94 and N95 are directly involved in binding the antibody, and wherein amino acid residue F138 is indirectly involved in said binding; the numbering of each amino acid residue referring to its position in SEQ ID NO: 1.

The amino acid residues comprised by said epitope or antibody binding region and optionally the one or more additional amino acid residues may be identified by alanine scanning of human 5T4 having the amino acid sequence set forth in SEQ ID NO: 1 or the mature polypeptide sequence of SEQ ID NO: 1.

The said alanine scanning is preferably performed as set forth or essentially as set forth in Example 16 herein.

In particular, the alanine scanning is performed by a procedure comprising the steps of:

i) Expressing mutant human 5T4 polypeptides in which all amino acid residues in the extracellular domain of human 5T4 (corresponding to amino acid residues 32-355 of SEQ ID NO: 1), except cysteines and alanines, are individually substituted with alanine, and wild type 5T4 polypeptides (amino acid residues 32-355 of SEQ ID NO: 1) individually in human embryonic kidney cells, e.g. HEK 293 cells, such that for each mutant or wild type 5T4 a sample comprising 70-90.000 cells, such as 80.000 cells is provided, ii) Incubating the cells in each sample with 20 µL of said antibody conjugated to fluorescein isothiocyanate (FITC)-conjugated antibody (3 µg/mL; in FACS buffer) for 40 minutes at room temperature, and subsequently washing each sample twice in 150-180 µL FACS buffer (phosphate-buffered saline+0.1% [w/v] BSA+0.02% [w/v] sodium azide) and resuspending the cells in each sample in 30 µL FACS buffer, iii) Determining, for each sample, the average amount of antibody bound per cell as the geometric mean of the fluorescence intensity (gMFI) for the viable, single cell population in said sample and normalizing the data for each test antibody against the binding intensity of a non-cross blocking 5T4-specific control antibody using the equation:

$$\text{Normalized } gMFI_{aa\,position} = \text{Log}_{10}\left(\frac{gMFI_{Test\,Ab}}{gMFI_{Control\,Ab}}\right)$$

wherein 'aa position' refers to the position that was mutated into an alanine, wherein the Z-score is calculated to express loss or gain of binding of the antibody, according to the calculation:

$$Z-\text{score(fold change)} = \frac{\text{Normalized } gMFI_{aa\,position} - \mu}{\sigma}$$

wherein $\mu$ and $\sigma$ are the mean and standard deviation, respectively, of the Normalized gMFI calculated from all mutants, wherein data is excluded from the analysis if the gMFI of the control antibody for a particular 5T4 mutant is lower than the mean $gMFI_{Control\,Ab} - 2.5 \times SD$ of the mean $gMFI_{Control\,Ab}$ (from all mutants); and optionally wherein data is excluded from the analysis if a residue binds with a Z-score just below −1.5 (e.g. between −1.5 and −1.8, such as between −1.5 and −1.7 or such as between −1.5 and −1.6) and that residue is predicted to be buried and spatially separated from the majority of residues, which are predicted to be surface-exposed and for which loss of binding or reduced binding is determined.

The non-cross blocking 5T4-specific control antibody used in step iv) may be a bispecific antibody comprising an antigen-binding region, which comprises a VH sequence as set forth in SEQ ID NO: 83 and a VL sequence as set forth in SEQ ID NO: 84 [A1]; and an antigen binding region, which comprises a VH sequence as set forth in SEQ ID NO: 97 and a VL sequence as set forth in SEQ ID NO: 98 [B12].

The antigen binding region capable of binding to 5T4 may bind to 5T4 such that there is loss of binding or binding is reduced if any one or more of the amino acid residues R73, Y92 and R94 is/are substituted with alanine; the numbering of each amino acid residue referring to its position in SEQ ID NO: 1.

Further, the antigen binding region, capable of binding to 5T4 may bind to 5T4 such that there is loss of binding or binding is reduced if any one or more of the amino acid residues S69, R73, Y92 and R94 is/are substituted with alanine; the numbering of each amino acid residue referring to its position in SEQ ID NO: 1.

In other embodiments, the antigen binding region, capable of binding to 5T4 may bind to 5T4 such that there is loss of binding or binding is reduced if any one or more of the amino acid residues R73, T74, Y92, R94 and N95 is/are substituted with alanine; the numbering of each amino acid residue referring to its position in SEQ ID NO: 1

The antigen binding region capable of binding to 5T4 may bind to 5T4 such that there is loss of binding or binding is reduced if any one or more of the amino acid residues: L89, F111, L117, F138, L144, D148, N152 is/are substituted with alanine; the numbering of each amino acid residue referring to its position in SEQ ID NO: 1.

The antigen binding region, capable of binding to 5T4 may bind to 5T4 such that there is loss of binding or binding is reduced if any one or more of the amino acid residues R73, Y92, R94, F111, F138, L144 and D148 is/are substituted with alanine; the numbering of each amino acid residue referring to its position in SEQ ID NO: 1.

The antigen binding region capable of binding to 5T4 may bind to 5T4 such that there is loss of binding or binding is reduced if any one or more of the amino acid residues S69, R73, Y92, R94, F111, F138, and D148 is/are substituted with alanine; the numbering of each amino acid residue referring to its position in SEQ ID NO: 1.

Also, in some embodiments, the said antibody binds to 5T4 such that there is loss of binding or binding is reduced if any one or more of the amino acid residues R73, T74, Y92, R94, N95 and F138 is/are substituted with alanine; the numbering of each amino acid residue referring to its position in SEQ ID NO: 1.

The effect of the alanine substitution may be determined by alanine scanning of a polypeptide comprising amino acid residues 32-355 of SEQ ID NO: 1.

The effect of the alanine substitution may be determined by a procedure as set forth or essentially as set forth in Example 16 herein.

In the present context, loss of binding may be defined as a Z-score in binding being lower than 1.5; the Z-score optionally being calculated as set forth or essentially as set forth in Example 16 herein.

The effect of alanine substitution may for example be determined by a procedure comprising the steps of:

i) Expressing mutant human 5T4 polypeptides in which all amino acid residues in the extracellular domain of human 5T4 (corresponding to amino acid residues 32-355 of SEQ ID NO: 1), except cysteines and alanines, are individually substituted with alanine, and wild type 5T4 polypeptides individually in human embryonic kidney cells, e.g. HEK 293 cells, such that for each mutant or wild type 5T4 a sample comprising 70-90.000 cells, such as 80.000 cells is provided, ii) Incubating the cells in each sample with 20 µL of said antibody conjugated to fluorescein isothiocyanate (FITC)-conjugated antibody (3 µg/mL; in FACS buffer) for 40 minutes at room temperature, and subsequently washing each sample twice in 150-180 µL FACS buffer (phosphate-buffered saline+0.1% [w/v] BSA+0.02% [w/v] sodium azide) and resuspending the cells in each sample in 30 µL FACS buffer, iii) Determining, for each sample, the average amount of antibody bound per cell as the geometric mean of the fluorescence intensity (gMFI) for the viable, single cell population in said sample and normalizing the data for each test antibody against the binding intensity of a non-cross blocking 5T4-specific control antibody using the equation:

$$\text{Normalized } gMFI_{aa\,position} = \text{Log}_{10}\left(\frac{gMFI_{Test\,Ab}}{gMFI_{Control\,Ab}}\right)$$

wherein 'aa position' refers to the position that was mutated into an alanine, wherein the Z-score is calculated to express loss or gain of binding of the antibody, according to the calculation:

$$Z-\text{score(fold change)} = \frac{\text{Normalized } gMFI_{aa\,position} - \mu}{\sigma}$$

wherein $\mu$ and $\sigma$ are the mean and standard deviation, respectively, of the Normalized gMFI calculated from all mutants, wherein data is excluded from the analysis if the gMFI of the control antibody for a particular 5T4 mutant is lower than the mean $gMFI_{Control\,Ab}-2.5\times SD$ of the mean $gMFI_{Control\,Ab}$ (from all mutants); and optionally wherein data is excluded from the analysis if a residue binds with a Z-score just below −1.5 (e.g. between −1.5 and −1.8, such as between −1.5 and −1.7 or such as between −1.5 and −1.6) and that residue is predicted to be buried and spatially separated from the majority of residues, which are predicted to be surface-exposed and for which loss of binding or reduced binding is determined.

A suitable antibody for use as non-cross blocking 5T4-specific control antibody in step iii) may be a bispecific antibody comprising an antigen-binding region, which comprises a VH sequence as set forth in SEQ ID NO: 83 and a VL sequence as set forth in SEQ ID NO: 84 [A1]; and an antigen binding region, which comprising a VH sequence as set forth in SEQ ID NO: 97 and a VL sequence as set forth in SEQ ID NO: 98 [B12].

The antigen-binding region capable of binding to 5T4 comprised by the multispecific antibody, may comprise a heavy chain variable region (VH) selected from the group consisting of:

a) a heavy chain variable region (VH) comprising the CDR1, CDR2, and CDR3 sequences of SEQ ID NOs.: 6, 7 and 8 [059], b) a heavy chain variable region (VH) comprising the CDR1, CDR2, and CDR3 sequences of SEQ ID NOs.: 13, 14 and 15 [076], c) a heavy chain variable region (VH) comprising the CDR1, CDR2, and CDR3 sequences of SEQ ID NOs.: 20, 21 and 22 [085], d) a heavy chain variable region (VH) comprising the CDR1, CDR2, and CDR3 sequences of SEQ ID NOs.: 27, 28 and 29 [106], e) a heavy chain variable region (VH) comprising the CDR1, CDR2, and CDR3 sequences of SEQ ID NOs.: 34, 35 and 36 [127], f) a heavy chain variable region (VH) comprising the CDR1, CDR2, and CDR3 sequences of SEQ ID NOs.: 41, 42 and 43 [207], g) a heavy chain variable region (VH) comprising the CDR1, CDR2, and CDR3 sequences of SEQ ID NOs.: 48, 49 and 50 [226], and h) a heavy chain variable region (VH) comprising CDR1, CDR2 and CDR3 sequences, said CDR1, CDR2 and CDR3 sequences comprising in total, at the most 1, 2, 3, 4, 5, 6, 7, 8, 9 or at the most 10 amino acid substitutions, when compared to the CDR1, CDR2 and CDR3 sequences defined in any one of a) to g).

The antigen-binding region capable of binding to 5T4 may comprise a heavy chain variable region (VH) selected from the group consisting of:

a) a heavy chain variable region (VH) comprising the CDR1, CDR2, and CDR3 sequences of SEQ ID NOs.: 6, 7 and 8 [059], b) a heavy chain variable region (VH) comprising the CDR1, CDR2, and CDR3 sequences of SEQ ID NOs.: 41, 42 and 43 [207], c) a heavy chain variable region (VH) comprising the CDR1, CDR2, and CDR3 sequences of SEQ ID NOs.: 48, 49 and 50 [226]; and d) a heavy chain variable region (VH) comprising CDR1, CDR2 and CDR3 sequences, said CDR1, CDR2 and CDR3 sequences comprising in total, at the most 1, 2, 3, 4, 5, 6, 7, 8, 9 or at the most 10 amino acid substitutions, when compared to the CDR1, CDR2 and CDR3 sequences defined in any one of a) to c).

The antigen-binding region capable of binding to 5T4 may comprise a heavy chain variable region (VH) comprising CDR1, CDR2, and CDR3 sequences of SEQ ID NOs.: 6, 7 and 8 [059].

The antigen-binding region capable of binding to 5T4 may comprise a heavy chain variable region (VH) selected from the group consisting of: a heavy chain variable region (VH) comprising CDR1, CDR2, and CDR3 sequences of SEQ ID NOs.: 41, 42 and 43 [207].

The antigen-binding region capable of binding to 5T4 may comprise a heavy chain variable region (VH) selected from the group consisting of: a heavy chain variable region (VH) comprising CDR1, CDR2, and CDR3 sequences of SEQ ID NOs.: 48, 49 and 50 [226].

The antigen-binding region capable of binding to 5T4 may comprise a heavy chain variable region (VH) and a light chain variable region (VL) selected from the group consisting of:

a) a heavy chain variable region (VH) comprising the CDR1, CDR2, and CDR3 sequences of SEQ ID NOs.: 6, 7 and 8, respectively, and a light chain variable region (VL) comprising the CDR1, CDR2, and CDR3 sequences of SEQ ID NO: 10, AAS and SEQ ID NO: 11, respectively [059], b) a heavy chain variable region (VH) comprising the CDR1, CDR2, and CDR3 sequences of SEQ ID NOs.: 13, 14 and 15, respectively; and a light chain variable region (VL) comprising the CDR1, CDR2, and CDR3 sequences of SEQ ID NO: 17, DAS and SEQ ID NO:18, respectively [076], c) a heavy chain variable region (VH) comprising the CDR1, CDR2, and CDR3 sequences of SEQ ID NOs.: 20, 21 and 22, respectively; and a light chain variable region (VL) comprising the CDR1, CDR2, and CDR3 sequences of SEQ ID NO: 24, DAS and SEQ ID NO: 25, respectively [085], d) a heavy chain variable region (VH) comprising the CDR1, CDR2, and CDR3 sequences of SEQ ID NOs.: 27, 28 and 29, respectively; and a light chain variable region (VL) comprising the CDR1, CDR2, and CDR3 sequences of SEQ ID NO: 31, DVS and SEQ ID NO: 32, respectively [106], e) a heavy chain variable region (VH) comprising the CDR1, CDR2, and CDR3 sequences of SEQ ID NOs.: 34, 35 and 36, respectively; and a light chain variable region (VL) comprising the CDR1, CDR2, and CDR3 sequences of SEQ ID NO: 38, DAS and SEQ ID NO: 39, respectively [127], f) a heavy chain variable region (VH) comprising the CDR1, CDR2, and CDR3 sequences of SEQ ID NOs.: 41, 42 and 43, respectively, and a light chain variable region (VL) comprising the CDR1, CDR2, and CDR3 sequences of SEQ ID NO: 45, DAS and SEQ ID NO: 46, respectively [207], g) a heavy chain variable region (VH) comprising the CDR1, CDR2, and CDR3 sequences of SEQ ID NOs.: 48, 49 and 50, respectively, and a light chain variable region (VL) comprising the CDR1, CDR2, and CDR3 sequences of SEQ ID NO: 52, DAS and SEQ ID NO: 53, respectively [226]; and h) a heavy chain variable region (VH) and a light chain variable region (VL) region, each region comprising CDR1, CDR2 and CDR3 sequences, said CDR1, CDR2 and CDR3 sequences comprising in total, at the most 1, 2, 3, 4, 5, 6, 7, 8, 9 or at the most 10 amino acid substitutions, when compared to the CDR1, CDR2 and CDR3 sequences defined in any one of a) to g).

The six complementarity-determining regions (CDRs) of the antigen binding region capable of binding to 5T4 may comprise, in total, at the most 1, 2, 3, 4, 5, 6, 7, 8, 9 or at the most 10 amino acid substitutions, when compared to i) the CDR sequences of SEQ ID NOs: 6, 7, 8, 10, AAS and SEQ ID NO: 11 [059], ii) the CDR sequences of SEQ ID NOs.: 41, 42, 43, 45, DAS and SEQ ID NO: 46 [207]; or iii) the CDR sequences of SEQ ID NOs.: 48, 49, 50, 52, DAS and SEQ ID NO: 53 [226].

In particular, 1, such as 2, 3, 4, 5, 6, 7, 8, 9 or 10, of the said amino acid substitutions may be conservative amino acid substitution(s).

The antigen-binding region capable of binding to 5T4 may comprise a heavy chain variable region in which the complementarity-determining region 3 (CDR3) comprises six consecutive amino acid residues of the sequence set forth in SEQ ID NO: 102 (YYGMDV); the six consecutive amino acid residues optionally being the most C-terminal amino acid residues within the CDR3 [059, 207, 226].

The antigen-binding region capable of binding to 5T4 may comprises a heavy chain variable region (VH) comprising the CDR1 sequence of SEQ ID NO: 41 (GGSFSGYY), the CDR2 sequence of SEQ ID NO: 103 (IDHSX$_1$ST), and the CDR3 sequence of SEQ ID NO: 104 (AX$_2$WFGELX$_3$X$_4$YYYGMDV), and a light chain variable region (VL) comprising the CDR1 sequence of SEQ ID NO: 105 (QSVSSX$_5$), the CDR2 sequence DAS, and the CDR3 sequence of SEQ ID NO: 46 (QQRSNWPLT), and wherein X$_1$ is G or E, X$_2$ is A or G, X$_3$ is W or Y, X$_4$ is D or H and X$_5$ is Y or F [207, 226].

The antigen-binding region capable of binding to 5T4 may comprises a heavy chain variable region (VH) comprising the CDR1, CDR2, and CDR3 sequences of SEQ ID NOs.: 6, 7, and 8, respectively, and a light chain variable region (VL) comprising the CDR1, CDR2, and CDR3 sequences of SEQ ID NO: 10, AAS and SEQ ID NO: 11, respectively [059].

The antigen-binding region capable of binding to 5T4 may comprise a heavy chain variable region (VH) comprising the CDR1, CDR2, and CDR3 sequences of SEQ ID NOs.: 41, 42 and 43, respectively, and a light chain variable region (VL) comprising the CDR1, CDR2, and CDR3 sequences of SEQ ID NO: 45, DAS and SEQ ID NO: 46, respectively [207].

The antigen-binding region capable of binding to 5T4 may comprise a heavy chain variable region (VH) comprising the CDR1, CDR2, and CDR3 sequences of SEQ ID NOs.: 48, 49 and 50, respectively, and a light chain variable region (VL) comprising the CDR1, CDR2, and CDR3 sequences of SEQ ID NO: 52, DAS and 53, respectively [226].

The antigen-binding region capable of binding to 5T4 may comprise a heavy chain variable region (VH) selected from the group consisting of:

a) a heavy chain variable region (VH) comprising the sequence of SEQ ID NO: 5 or a sequence having at least 90%, at least 95%, at least 97%, or at least 99% amino acid sequence identity to the sequence of SEQ ID NO: 5 [059], b) a heavy chain variable region (VH) comprising the sequence of SEQ ID NO: 12 or a sequence having at least 90%, at least 95%, at least 97%, or at least 99% amino acid sequence identity to the sequence of SEQ ID NO: 12 [076], c) a heavy chain variable region (VH) comprising the sequence of SEQ ID NO: 19 or a sequence having at least 90%, at least 95%, at least 97%, or at least 99% amino acid sequence identity to the sequence of SEQ ID NO: 19 [085], d) a heavy chain variable region (VH) comprising the sequence of SEQ ID NO: 26 or a sequence having at least 90%, at least 95%, at least 97%, or at least 99% amino acid sequence identity to the sequence of SEQ ID NO: 26 [106], e) a heavy chain variable region (VH) comprising the sequence of SEQ ID NO: 33 or a sequence having at least 90%, at least 95%, at least 97%, or at least 99% amino acid sequence identity to the sequence of SEQ ID NO: 33 [127], f) a heavy chain variable region (VH) comprising the sequence of SEQ ID NO: 40 or a sequence having at least 90%, at least 95%, at least 97%, or at least 99% amino acid sequence identity to the sequence of SEQ ID NO: 40 [207]; and g) a heavy chain variable region (VH) comprising the sequence of SEQ ID NO: 47 or a sequence having at least 90%, at least 95%, at least 97%, or at least 99% amino acid sequence identity to the sequence of SEQ ID NO: 47 [226].

The antigen-binding region capable of binding to 5T4 may comprise a heavy chain variable region (VH) comprising the sequence of SEQ ID NO: 5 or a sequence having at least 90%, at least 95%, at least 97%, or at least 99% amino acid sequence identity to the sequence of SEQ ID NO: 5 [059].

The antigen-binding region capable of binding to 5T4 may comprise a heavy chain variable region (VH) comprising the sequence of SEQ ID NO: 40 or a sequence having at least 90%, at least 95%, at least 97%, or at least 99% amino acid sequence identity to the sequence of SEQ ID NO: 40 [207].

The antigen-binding region capable of binding to 5T4 may comprise a heavy chain variable region (VH) comprising the sequence of SEQ ID NO: 47 or a sequence having at least 90%, at least 95%, at least 97%, or at least 99% amino acid sequence identity to the sequence of SEQ ID NO: 47 [226].

In the multispecific antibody for use according to the invention, the antigen-binding region capable of binding to 5T4 may comprise a heavy chain variable region (VH) and a light chain variable region (VL) selected from the group consisting of:

a) a heavy chain variable region (VH) comprising the sequence of SEQ ID NO: 5 or a sequence having at least 90%, at least 95%, at least 97%, or at least 99% amino acid sequence identity to the sequence of SEQ ID NO: 5, and a light chain variable region (VL) comprising the sequence of SEQ ID NO: 9 or a sequence having at least 90%, at least 95%, at least 97%, or at least 99% amino acid sequence identity to the sequence of SEQ ID NO: 9 [059], b) a heavy chain variable region (VH) comprising the sequence of SEQ ID NO: 12 or a sequence having at least 90%, at least 95%, at least 97%, or at least 99% amino acid sequence identity to the sequence of SEQ ID NO: 12, and a light chain variable region (VL) comprising the sequence of SEQ ID NO: 16 or a sequence having at least 90%, at least 95%, at least 97%, or at least 99% amino acid sequence identity to the sequence of SEQ ID NO: 16 [076], c) a heavy chain variable region (VH) comprising the sequence of SEQ ID NO: 19 or a sequence having at least 90%, at least 95%, at least 97%, or at least 99% amino acid sequence identity to the sequence of SEQ ID NO: 19, and a light chain variable region (VL) comprising the sequence of SEQ ID NO: 23 or a sequence having at least 90%, at least 95%, at least 97%, or at least 99% amino acid sequence identity to the sequence of SEQ ID NO: 23 [085], d) a heavy chain variable region (VH) comprising the sequence of SEQ ID NO: 26 or a sequence having at least 90%, at least 95%, at least 97%, or at least 99% amino acid sequence identity to the sequence of SEQ ID NO: 26, and a light chain variable region (VL) comprising the sequence of SEQ ID NO: 30 or a sequence having at least 90%, at least 95%, at least 97%, or at least 99% amino acid sequence identity to the sequence of SEQ ID NO: 30 [106], e) a heavy chain variable region (VH) comprising the sequence of SEQ ID NO: 33 or a sequence having at least 90%, at least 95%, at least 97%, or at least 99% amino acid sequence identity to the sequence of SEQ ID NO: 33, and a light chain variable region (VL) comprising the sequence of SEQ ID NO: 37 or a sequence having at least 90%, at least 95%, at least 97%, or at least 99% amino acid sequence identity to the sequence of SEQ ID NO: 37 [127], f) a heavy chain variable region (VH) comprising the sequence of SEQ ID NO: 40 or a sequence having at least 90%, at least 95%, at least 97%, or at least 99% amino acid sequence identity to the sequence of SEQ ID NO: 40, and a light chain variable region (VL) comprising the sequence of SEQ ID NO: 44 or a sequence having at least 90%, at least 95%, at least 97%, or at least 99% amino acid sequence identity to the sequence of SEQ ID NO: 44 [207], g) a heavy chain variable region (VH) comprising the sequence of SEQ ID NO: 47 or a sequence having at least 90%, at least 95%, at least 97%, or at least 99% amino acid sequence identity to the sequence of SEQ ID NO: 47, and a light chain variable region (VL) comprising the sequence of SEQ ID NO: 51 or a sequence having at least 90%, at least 95%, at least 97%, or at least 99% amino acid sequence identity to the sequence of SEQ ID NO: 51 [226].

In the multispecific antibody for use according to the invention, the said antigen-binding region capable of binding to 5T4 may comprise a heavy chain variable region (VH) and a light chain variable region (VL) selected from the group consisting of:

a) a heavy chain variable region (VH) comprising the sequence of SEQ ID NO: 5, and a light chain variable region (VL) comprising the sequence of SEQ ID NO: 9 [059], b) a heavy chain variable region (VH) comprising the sequence of SEQ ID NO: 12, and a light chain variable region (VL) comprising the sequence of SEQ ID NO: 16 [076], c) a heavy chain variable region (VH) comprising the sequence of SEQ ID NO: 19, and a light chain variable region (VL) comprising the sequence of SEQ ID NO: 23 [085], d) a heavy chain variable region (VH) comprising the sequence of SEQ ID NO: 26, and a light chain variable region (VL) comprising the sequence of SEQ ID NO: 30 [106], e) a heavy chain variable region (VH) comprising the sequence of SEQ ID NO: 33, and a light chain variable region (VL) comprising the sequence of SEQ ID NO: 37 [127], f) a heavy chain variable region (VH) comprising the sequence of SEQ ID NO: 40, and a light chain variable region (VL) comprising the sequence of SEQ ID NO: 44 [207]; and g) a heavy chain variable region (VH) comprising the sequence of SEQ ID NO: 47, and a light chain variable region (VL) comprising the sequence of SEQ ID NO: 51 [226].

In the multispecific antibody for use according to any one of the preceding claims, wherein the antigen binding region, capable of binding to CD3 is able to bind to human CD3ε (epsilon), such as human CD3ε (epsilon) as specified in SEQ ID NO: 4.

The antigen-binding region capable of binding to CD3 may comprise a heavy chain variable region (VH) comprising the CDR1, CDR2, and CDR3 sequences of SEQ ID NOs.: 54, 55 and 56, respectively;

and, optionally a light chain variable region (VL) comprising comprising the CDR1, CDR2, and CDR3 sequences of SEQ ID NO: 58, GTN and 59, respectively.

In the multispecific antibody for use according to the invention, the antigen binding region that binds to CD3 may comprise a heavy chain variable region (VH) comprising the sequence of SEQ ID NO: 57, or a sequence having at least 90%, at least 95%, at least 97%, or at least 99% amino acid sequence identity to the sequence of SEQ ID NO: 57 [wildtype anti-CD3—VH full length sequence];

and, optionally a light chain variable region (VL) comprising the sequence of SEQ ID NO: 60 or a sequence having at least 90%, at least 95%, at least 97%, or at least 99% amino acid sequence identity to the sequence of SEQ ID NO: 60, [wild type anti-CD3—VL full length sequence].

In currently preferred embodiments, the antibody has a lower human CD3ε binding affinity than an antibody having an antigen-binding region comprising a VH sequence as set forth in SEQ ID NO: 57, and a VL sequence as set forth in SEQ ID NO: 60, preferably wherein said affinity is at least 5-fold lower, such as at least 10-fold lower, e.g. at least 20-fold lower, at least 30 fold lower, at least 40 fold lower, at least 45 fold lower or such as at least 50-fold lower.

The antigen binding region that binds to CD3, may bind with an equilibrium dissociation constant $K_D$ within the range of 200-1000 nM, such as within the range of 300-1000 nM, within the range of 400-1000 nM, within the range of 500-1000 nM, within the range of 300-900 nM within the range of 400-900 nM, within the range of 400-700 nM, within the range of 500-900 nM, within the range of 500-800 nM, within the range of 500-700 nM, within the range of 600-1000 nM, within the range of 600-900 nM, within the range of 600-800 nM, or such as within the range of 600-700 nM.

Alternatively, the antigen binding region that binds to CD3, may bind with an equilibrium dissociation constant $K_D$ within the range of 1-100 nM, such as within the range of 5-100 nM, within the range of 10-100 nM, within the range of 1-80 nM, within the range of 1-60 nM within the range of 1-40 nM, within the range of 1-20 nM, within the range of 5-80 nM, within the range of 5-60 nM, within the range of 5-40 nM, within the range of 5-20 nM, within the range of 10-80 nM, within the range of 10-60 nM, within the range of 10-40 nM, or such as within the range of 10-20 nM.

The CDR1, CDR2 and CDR3 of the heavy chain variable (VH) region of the antigen binding region that binds to CD3 may comprise, in total, at the most 1, 2, 3, 4 or 5 amino acid substitutions, when compared to the CDR1, CDR2 and CDR3 of the sequence set forth in SEQ ID NO: 57.

The amino acid sequences of the CDR1, CDR2 and CDR3 of the heavy chain variable (VH) region of the antigen binding region that binds to CD3 may have at least 95% sequence identity, such as at least 96% sequence identity, at least 97% sequence identity, at least 98% sequence identity or at least 99% sequence identity to the amino acid sequences of the CDR1, CDR2 and CDR3 of the wild type heavy chain variable (VH) region, sequence identity being calculated based on an aligning an amino acid sequence consisting of the sequences of the CDR1, CDR2 and CDR3 of the heavy chain variable (VH) region of the antigen binding region that binds to CD with an amino acid sequence comprising the sequences of the CDR1, CDR2 and CDR3 of the wild type heavy chain variable (VH) region.

The antigen binding region that binds to CD3 may comprise a mutation selected from the group consisting of: T31M, T31P, N57E, H101G, H101N, G105P, S110A, S110G, Y114M, Y114R, Y114V.

The multispecific antibody for use according to the invention may be a bispecific antibody which is devoid of, or has reduced Fc-mediated effector function (i.e. an "inert" antibody), and which:

a) is capable of mediating concentration-dependent cytotoxicity of SK-OV-3 cells, when using purified PBMCs or T cells as effector cells e.g. when assayed as described in Example 14 herein, b) is capable of mediating concentration-dependent cytotoxicity of MDA-MB-231 cells, when using purified T cells as effector cells e.g. when assayed as described in Example 13 herein, c) is capable of activating T cells in vitro in the presence of MDA-MB-231 tumor cells; e.g. when assayed as described in Example 13 herein, d) is capable of activating T-cells in vitro in the presence of BxPC-3, PANC-1, Ca Ski and/or SiHa tumor cells; e.g. when assayed as described in Example 17 herein, e) is capable of inducing cytotoxicity of BxPC-3, PANC-1, Ca Ski and/or SiHa tumor cells when using purified T cells as effector cells e.g. when assayed as described in Example 17 herein; and/or f) shows anti-tumor activity, such as delayed tumor out-growth, in a humanized immune hematopoietic stem cell reconstitution mouse xenograft model, such as NOD.Cg-Prkdc$^{scid}$ Il2rg$^{tm1Wjl}$/SzJ inoculated with human MDA-MB-231 tumor cells; e.g. when deter-mined as described in Example 15.

The ability of the antibody to mediate concentration-dependent cytotoxicity of SK-OV-3 cells may be determined in an in vitro cytotoxicity assay comprising the steps of:

i) isolating peripheral blood mononuclear cells (PBMCs) or T cells from healthy human donor buffy coats, ii) providing a first set of samples, wherein each sample comprises PBMCs and human ovary adenocarcinoma SK-OV-3 cells, and wherein the ratios PBMCs:SK-OV-3 cells in said samples are 1:2, 1:1, 2:1, 4:1, 8:1, and 12:1; and a second set of samples, wherein each sample com-prises T cells and human ovary adenocarcinoma SK-OV-3 cells and wherein the ratios of T cells:SK-OV-3 cells in said samples are 1:2, 1:1, 2:1, 4:1 and 8:1 iii) adding the antibody to each set of samples at concen-trations ranging from 0.0128 ng/mL to 1000 ng/mL and incubating the samples for 72 hours at 37° C.; and then iv) assessing the viability of the SK-OV-3 cells using Resazurin (7-Hydroxy-3H-phenoxazin-3-one 10-ox-ide).

The ability of the multispecific antibody to activate T cells in vitro in the presence of MDA-MB-231 tumor cells may be determined in an assay comprising the steps of:

i) Isolating T cells from healthy human donor buffy coats, ii) Providing a set of samples, wherein each sample comprises T-cells and human breast adenocarcinoma MDA-MB-231 cells and wherein the ratio of T-cells: MDA-MB-231 cells in said samples is 8:1, iii) adding the antibody to the set of samples at concen-trations ranging from 0.0128 ng/mL to 1000 ng/mL and incubating the samples for 72 hours at 37° C., iv) staining the T-cells with fluorescent-labeled antibodies against T-cell activation markers, such as CD69-APC, CD25-PE-Cy7 and CD279/PD1-BV604 antibodies, by incubation with said antibodies for 30 minutes at 4° C.; and v) analyzing the samples by flow cytometry.

The ability of the multispecific antibody to activate T cells in vitro in the presence of BxPC-3, PANC-1, Ca Ski and/or SiHa tumor cells may be determined in an procedure com-prising the steps of:

i) Providing T cells isolated from healthy human donor buffy coats, ii) Providing a set of samples, wherein each sample comprises said T cells and BxPC-3, PANC-1, Ca Ski or SiHa tumor cells and wherein the ratio of T cells:tumor cells in said samples is 4:1, iii) adding the antibody to the set of samples at concen-trations ranging from 0.0128 ng/mL to 5000 ng/mL (such as 5-fold dilutions) and incubating the samples for 72 hours at 37° C., iv) collecting from each sample 110 µL supernatant con-taining T cells and staining the T cells with fluorescent-labeled antibodies against T-cell markers, such as CD3-eFluor450, CD4-APC-eFluor780, DC8-AF700, and with antibodies against T-cell markers, such as 69-APC, CD25-PE-Cy7 and CD279/PD1-BV604 anti-bodies, by incubation with said antibodies for 30 min-utes at 4° C.; and v) analyzing the samples by flow cytometry.

The ability of the multispecific antibody to induce cyto-toxicity of BxPC-3, PANC-1, Ca Ski and/or SiHa tumor cells may be determined in a procedure comprising the steps of i) Providing T cells isolated from healthy human donor buffy coats, ii) Providing a set of test samples and control samples, wherein each sample comprises said T-cells and BxPC-3, PANC-1, Ca Ski or SiHa tumor cells which have been allowed to adhere to the bottom of a 96-well tissue culture plate and wherein the ratio of T-cells:tumor cells in said samples is 4:1, iii) adding the antibody to the set of test samples at concentrations ranging from 0.0128 ng/mL to 5000 ng/mL (such as 5-fold dilutions), while the control samples remain untreated or are incubated with 5 µM staurosporin, and incubating all samples for 72 hours at 37° C., iv) Incubating the adherent cells in 10% (w/w) 7-hydroxy-3H-phenoxazin-3-one 10-oxide (Resazurin) in RPMI-1640 medium supplemented with 10% (w/w) donor bovine serum with iron and penicillin/streptomycin at 37° C. for 4 hours, v) Measuring the absorbance of the cells; setting the absorbance of the cells incubated with staurosporin as 0% viability and the untreated cells as 100% viability and calculating the percentage viable cells as $$\times 100\% \text{ viable cells} =$$

$$\left( \frac{[\text{absorbance sample} - \text{absorbance staurosporine treated cells}]}{[\text{absorbance untreated cells} - \text{absorbance staurosporine treated cells}]} \right)$$

The antigen-binding region capable of binding to CD3 may comprise:

a) a heavy chain variable region (VH) comprising CDR1, CDR2, and CDR3 having the sequences as set forth in SEQ ID NOs: 61, 55, and 56 [VH CDR1-T31P+Wild type VH CDRs 2,3], respectively, and a light chain variable region (VL) comprising CDR1, CDR2, and CDR3 having the sequences as set forth in SEQ ID NO: 58, the sequence GTN, and the sequence as set forth in SEQ ID NO: 59, respectively [Wild type VL CDRs 1,2,3], or b) a heavy chain variable region (VH) comprising CDR1, CDR2, and CDR3 having the sequences as set forth in SEQ ID NOs: 63, 55, and 56 [VH CDR1-T31M+Wild type VH CDRs 2,3], respectively, and a light chain variable region (VL) comprising CDR1, CDR2, and CDR3 having the sequences as set forth in SEQ ID NO: 58, the sequence GTN, and the sequence as set forth in SEQ ID NO: 59, respectively [Wild type VL CDRs 1,2,3], respectively, or c) a heavy chain variable region (VH) comprising CDR1, CDR2, and CDR3 having the sequences as set forth in SEQ ID NOs: 54, 65, and 56 [VH CDR-N57E+Wild type VH CDRs 1,3], respectively, and a light chain variable region (VL) comprising CDR1, CDR2, and CDR3 having the sequences as set forth in SEQ ID NO: 58, the sequence GTN, and the sequence as set forth in SEQ ID NO: 59, respectively [Wild type VL CDRs 1,2,3], respectively, or d) a heavy chain variable region (VH) comprising CDR1, CDR2, and CDR3 having the sequences as set forth in SEQ ID NOs: 54, 55, and 67 [Wild type VH CDRs 1,2+VH CDR3-H101G], respectively, and a light chain variable region (VL) comprising CDR1, CDR2, and CDR3 having the sequences as set forth in SEQ ID NO: 58, the sequence GTN, and the sequence as set forth in SEQ ID NO: 59, respectively [Wild type VL CDRs 1,2,3], respectively.

e) a heavy chain variable region (VH) comprising CDR1, CDR2, and CDR3 having the sequences as set forth in SEQ ID NOs: 54, 55, and 69 [Wild type VH CDRs 1,2+VH CDR3-H101N], respectively, and a light chain variable region (VL) comprising CDR1, CDR2, and CDR3 having the sequences as set forth in SEQ ID NO: 58, the sequence GTN, and the sequence as set forth in SEQ ID NO: 59, respectively [Wild type VL CDRs 1,2,3], respectively;

f) a heavy chain variable region (VH) comprising CDR1, CDR2, and CDR3 having the sequences as set forth in SEQ ID NOs: 54, 55, and 71 [Wild type VH CDRs 1,2+VH CDR3-G105P], respectively, and a light chain variable region (VL) comprising CDR1, CDR2, and CDR3 having the sequences as set forth in SEQ ID NO: 58, the sequence GTN, and the sequence as set forth in SEQ ID NO: 59, respectively [Wild type VL CDRs 1,2,3], respectively;

g) a heavy chain variable region (VH) comprising CDR1, CDR2, and CDR3 having the sequences as set forth in SEQ ID NOs: 54, 55, and 73 [Wild type VH CDRs 1,2+VH CDR3-S110A], respectively, and a light chain variable region (VL) comprising CDR1, CDR2, and CDR3 having the sequences as set forth in SEQ ID NO: 58, the sequence GTN, and the sequence as set forth in SEQ ID NO: 59, respectively [Wild type VL CDRs 1,2,3], respectively, or h) a heavy chain variable region (VH) comprising CDR1, CDR2, and CDR3 having the sequences as set forth in SEQ ID NOs: 54, 55, and 75 [Wild type VH CDRs 1,2+VH CDR3-S110G], respectively, and a light chain variable region (VL) comprising CDR1, CDR2, and CDR3 having the sequences as set forth in SEQ ID NO: 58, the sequence GTN, and the sequence as set forth in SEQ ID NO: 59, respectively [Wild type VL CDRs 1,2,3], respectively, i) a heavy chain variable region (VH) comprising CDR1, CDR2, and CDR3 having the sequences as set forth in SEQ ID NOs: 54, 55, and 77 [Wild type VH CDRs 1,2+VH CDR3-Y114V], respectively, and a light chain variable region (VL) comprising CDR1, CDR2, and CDR3 having the sequences as set forth in SEQ ID NO: 58, the sequence GTN, and the sequence as set forth in SEQ ID NO: 59, respectively [Wild type VL CDRs 1,2,3], respectively, or j) a heavy chain variable region (VH) comprising CDR1, CDR2, and CDR3 having the sequences as set forth in SEQ ID NOs: 54, 55, and 79 [Wild type VH CDRs 1,2+VH CDR3-Y114M], respectively, and a light chain variable region (VL) comprising CDR1, CDR2, and CDR3 having the sequences as set forth in SEQ ID NO: 58, the sequence GTN, and the sequence as set forth in SEQ ID NO: 59, respectively [Wild type VL CDRs 1,2,3], respectively, or k) a heavy chain variable region (VH) comprising CDR1, CDR2, and CDR3 having the sequences as set forth in SEQ ID NOs: 54, 55, and 81 [Wild type VH CDRs 1,2+VH CDR3-Y114R], respectively, and a light chain variable region (VL) comprising CDR1, CDR2, and CDR3 having the sequences as set forth in SEQ ID NO:

58, the sequence GTN, and the sequence as set forth in SEQ ID NO: 59, respectively [Wild type VL CDRs 1,2,3], respectively.

The antigen-binding region capable of binding to CD3 may in particular comprise a heavy chain variable region (VH) comprising CDR1, CDR2, and CDR3 having the sequences as set forth in SEQ ID NOs: 54, 55, and 67, respectively, and a light chain variable region (VL) comprising CDR1, CDR2, and CDR3 having the sequences as set forth in SEQ ID NO: 58, the sequence GTN, and the sequence as set forth in SEQ ID NO: 59, respectively.

In particular, the multispecific antibody may be an antibody, wherein the antigen-binding region capable of binding to 5T4 comprises a heavy chain variable region (VH) comprising CDR1, CDR2, and CDR3 sequences of SEQ ID NOs.: 6, 7 and 8, respectively, and a light chain variable region (VL) comprising the CDR1, CDR2, and CDR3 sequences of SEQ ID NO: 10, AAS and SEQ ID NO: 11, respectively [059];

and the antigen-binding region capable of binding to CD3 comprises a heavy chain variable region (VH) comprising CDR1, CDR2, and CDR3 having the sequences as set forth in SEQ ID NOs: 54, 55, and 67, respectively, and a light chain variable region (VL) comprising CDR1, CDR2, and CDR3 having the sequences as set forth in SEQ ID NO: 58, the sequence GTN, and the sequence as set forth in SEQ ID NO: 59, respectively.

The multispecific antibody may be an antibody, wherein the antigen-binding region capable of binding to 5T4 comprises a heavy chain variable region (VH) comprising the CDR1, CDR2, and CDR3 sequences of SEQ ID NOs.: 41, 42 and 43, respectively, and a light chain variable region (VL) comprising the CDR1, CDR2, and CDR3 sequences of SEQ ID NO: 45, DAS and 46, respectively [207];

and the antigen-binding region capable of binding to CD3 comprises a heavy chain variable region (VH) comprising CDR1, CDR2, and CDR3 having the sequences as set forth in SEQ ID NOs: 54, 55, and 67, respectively, and a light chain variable region (VL) comprising CDR1, CDR2, and CDR3 having the sequences as set forth in SEQ ID NO: 58, the sequence GTN, and the sequence as set forth in SEQ ID NO: 59, respectively, respectively.

The multispecific antibody may be an antibody, wherein the antigen-binding region capable of binding to 5T4 comprises a heavy chain variable region (VH) comprising the CDR1, CDR2, and CDR3 sequences of SEQ ID NOs.: 48, 49 and 50, respectively, and a light chain variable region (VL) comprising the CDR1, CDR2, and CDR3 sequences of SEQ ID NO: 52, DAS and 53, respectively [226];

and the antigen-binding region capable of binding to CD3 comprises a heavy chain variable region (VH) comprising CDR1, CDR2, and CDR3 having the sequences as set forth in SEQ ID NOs: 54, 55, and 67 [Wild type VH CDRs 1,2+VH CDR3-H101G], respectively, and a light chain variable region (VL) comprising CDR1, CDR2, and CDR3 having the sequences as set forth in SEQ ID NO: 58, the sequence GTN, and the sequence as set forth in SEQ ID NO: 59, respectively [Wild type VL CDRs 1,2,3], respectively.

Also, the multispecific antibody may be an antibody, wherein the antigen-binding region capable of binding to human CD3 comprises a VH sequence and a VL sequence selected from the group consisting of:

a) a VH sequence as set forth in SEQ ID NO: 62 [VH T31P full length sequence] and a VL sequence as set forth in SEQ ID NO: 60 [Wild type full length sequence], b) a VH sequence as set forth in SEQ ID NO: 64 [VH T31M full length sequence] and a VL sequence as set forth in SEQ ID NO: 60, c) a VH sequence as set forth in SEQ ID NO: 66 [VH N57E full length sequence] and a VL sequence as set forth in SEQ ID NO: 60, d) a VH sequence as set forth in SEQ ID NO: 68 [VH H101G full length sequence] and a VL sequence as set forth in SEQ ID NO: 60, e) a VH sequence as set forth in SEQ ID NO: 70 [VH H101N full length sequence] and a VL sequence as set forth in SEQ ID NO: 60, f) a VH sequence as set forth in SEQ ID NO: 72 [VH G105P full length sequence] and a VL sequence as set forth in SEQ ID NO: 60, g) a VH sequence as set forth in SEQ ID NO: 74 [VH S110A full length sequence] and a VL sequence as set forth in SEQ ID NO: 60, h) a VH sequence as set forth in SEQ ID NO: 76 [VH S110G full length sequence] and a VL sequence as set forth in SEQ ID NO: 60, i) a VH sequence as set forth in SEQ ID NO: 78 [VH Y114V full length sequence] and a VL sequence as set forth in SEQ ID NO: 60, j) a VH sequence as set forth in SEQ ID NO: 80 [VH Y114M full length sequence] and a VL sequence as set forth in SEQ ID NO: 60; and k) a VH sequence as set forth in SEQ ID NO: 82 [VH Y114R full length sequence] and a VL sequence as set forth in SEQ ID NO: 60.

The antigen-binding region capable of binding to human CD3 may comprise a VH sequence as set forth in SEQ ID NO: 68 [VH H101G full length sequence] and a VL sequence as set forth in SEQ ID NO: 60.

The multispecific antibody may be an antibody, wherein the antigen-binding region capable of binding to 5T4 comprises a heavy chain variable region (VH) comprising the sequence of SEQ ID NO: 5 or a sequence having at least 90%, at least 95%, at least 97%, or at least 99% amino acid sequence identity to the sequence of SEQ ID NO: 5 [059—VH full length sequence]; and the antigen-binding region capable of binding to human CD3 comprises a VH sequence as set forth in SEQ ID NO: 68 [VH H101G full length sequence] and a VL sequence as set forth in SEQ ID NO: 60.

The multispecific antibody may be an antibody, wherein the antigen-binding region capable of binding to 5T4 comprises a heavy chain variable region (VH) comprising the sequence of SEQ ID NO: 40 or a sequence having at least 90%, at least 95%, at least 97%, or at least 99% amino acid sequence identity to the sequence of SEQ ID NO: 40 [207—VH full length sequence]; and the antigen-binding region capable of binding to human CD3 comprises a VH sequence as set forth in SEQ ID NO: 68 [VH H101G full length sequence] and a VL sequence as set forth in SEQ ID NO: 60.

The multispecific antibody may be an antibody, wherein the antigen-binding region capable of binding to 5T4 comprises a heavy chain variable region (VH) comprising the sequence of SEQ ID NO: 47 or a sequence having at least 90%, at least 95%, at least 97%, or at least 99% amino acid sequence identity to the sequence of SEQ ID NO: 47 [226—VH full length sequence]; and the antigen-binding region capable of binding to human CD3 comprises a VH sequence as set forth in SEQ ID NO: 68 [VH H101G full length sequence] and a VL sequence as set forth in SEQ ID NO: 60.

The multispecific antibody may be an antibody, wherein the antigen-binding region capable of binding to 5T4 comprises a heavy chain variable region (VH) comprising the sequence of SEQ ID NO: 5 or a sequence having at least 90%, at least 95%, at least 97%, or at least 99% amino acid sequence identity to the sequence of SEQ ID NO: 5, and a heavy chain light region (VL) comprising the sequence of SEQ ID NO: 9 or a sequence having at least 90%, at least 95%, at least 97%, or at least 99% amino acid sequence identity to the sequence of SEQ ID NO: 9 [059]; and the antigen-binding region capable of binding to human CD3 comprises a VH sequence as set forth in SEQ ID NO: 68 [VH H101G full length sequence] and a VL sequence as set forth in SEQ ID NO: 60.

The multispecific antibody may be an antibody, wherein the antigen-binding region capable of binding to 5T4 comprises a heavy chain variable region (VH) comprising the sequence of SEQ ID NO: 40 or a sequence having at least 90%, at least 95%, at least 97%, or at least 99% amino acid sequence identity to the sequence of SEQ ID NO: 40, and a heavy chain light region (VL) comprising the sequence of SEQ ID NO: 44 or a sequence having at least 90%, at least 95%, at least 97%, or at least 99% amino acid sequence identity to the sequence of SEQ ID NO: 44 [207—VH+VL full length sequences]; and the antigen-binding region capable of binding to human CD3 comprises a VH sequence as set forth in SEQ ID NO: 68 [VH H101G full length sequence] and a VL sequence as set forth in SEQ ID NO: 60.

The multispecific antibody may be an antibody, wherein the antigen-binding region capable of binding to 5T4 comprises a heavy chain variable region (VH) comprising the sequence of SEQ ID NO: 47 or a sequence having at least 90%, at least 95%, at least 97%, or at least 99% amino acid sequence identity to the sequence of SEQ ID NO: 47, and a heavy chain light region (VL) comprising the sequence of SEQ ID NO: 51 or a sequence having at least 90%, at least 95%, at least 97%, or at least 99% amino acid sequence identity to the sequence of SEQ ID NO: 51 [226—VH+VL full length sequences]; and the antigen-binding region capable of binding to human CD3 comprises a VH sequence as set forth in SEQ ID NO: 68 [VH H101G full length sequence] and a VL sequence as set forth in SEQ ID NO: 60.

In the multispecific antibody for use according to the invention each antigen-binding region may comprise a heavy chain variable region (VH) and a light chain variable region (VL), and wherein said variable regions each comprise three CDR sequences, CDR1, CDR2 and CDR3, respectively, and four framework sequences, FR1, FR2, FR3 and FR4, respectively.

The multispecific antibody may comprise two heavy chain constant regions (CH), and two light chain constant regions (CL).

The multispecific antibody may comprise a first and a second heavy chain, each of said first and second heavy chain comprising at least a hinge region, a CH2 and CH3 region, wherein in said first heavy chain at least one of the amino acids in the positions corresponding to positions selected from the group consisting of T366, L368, K370, D399, F405, Y407 and K409 in a human IgG1 heavy chain has been substituted, and in said second heavy chain at least one of the amino acids in the positions corresponding to a position selected from the group consisting of T366, L368, K370, D399, F405, Y407, and K409 in a human IgG1 heavy chain has been substituted, wherein said substitutions of said first and said second heavy chains are not in the same positions, and wherein the amino acid positions are numbered according to EU numbering.

In the multispecific antibody for use according to the invention, the amino acid in the position corresponding to K409 in a human IgG1 heavy chain may be R in said first heavy chain, and the amino acid in the position corresponding to F405 in a human IgG1 heavy chain may be L in said second heavy chain, or vice versa.

The multispecific antibody may comprise a first and a second heavy chain, wherein in both the first and the second heavy chain, the amino acid residues at the positions corresponding to positions L234 and L235 in a human IgG1 heavy chain according to EU numbering are F and E, respectively.

The multispecific antibody for use according to the invention may comprise a first and a second heavy chain, and wherein in both the first and the second heavy chain, the amino acid residue at the position corresponding to position D265 in a human IgG1 heavy chain according to EU numbering is A.

The multispecific antibody may comprise a first and a second heavy chain and the constant region of said first or second heavy chain comprises or consists essentially of an amino acid sequence selected from the group consisting of
a) the sequence set forth in SEQ ID NO: 89,
b) a subsequence of the sequence in a), such as a subsequence wherein 1, 2, 3, 4, 5, 6, 7, 8, 9 or 10 consecutive amino acids has/have deleted, starting from the N-terminus or C-terminus of the sequence defined in a); and
c) a sequence having at the most 5 substitutions, such as at the most 4 substitutions, at the most 3, at the most 2 or at the most 1 substitutions compared to the amino acid sequence defined in a) or b).
The multispecific antibody may be an antibody, wherein
a) the antigen-binding region(s) capable of binding to 5T4 is/are humanized, and/or
b) the antigen-binding region capable of binding to CD3, if present, is humanized.
The multispecific antibody may be an antibody, wherein
a) the antigen-binding region(s) capable of binding to 5T4 is/are human, and/or
b) the antigen-binding region capable of binding to CD3, if present, is human.
The multispecific antibody may be an antibody, wherein
a) the antigen-binding region(s) capable of binding to 5T4 is/are chimeric, and/or
b) the antigen-binding region capable of binding to CD3, if present, is chimeric.

The multispecific antibody antibody may comprise a first heavy chain and a second heavy chain and the first heavy chain, and the second heavy chain may be modified so that the antibody induces Fc-mediated effector function to a lesser extent relative to an identical non-modified antibody.

The multispecific may comprise a first heavy chain and light chain comprising an antigen-binding region capable of binding to 5T4, such as the antigen binding region defined above, and a second heavy chain and light chain comprising an antigen-binding region capable of binding CD3, such as the antigen binding region defined above.

The multispecific antibody may comprise a kappa (κ) light chain.

The multispecific antibody may comprise a lambda (λ) light chain.

The multispecific antibody may comprise a lambda (λ) light chain and a kappa (κ) light chain; e.g. an antibody with a heavy chain and a lambda light chain which comprise the binding region capable of binding to CD3, and a heavy chain and a kappa light chain which comprise the binding region capable of binding to 5T4.

The kappa (κ) light chain may comprise an amino acid sequence selected from the group consisting of
a) the sequence set forth in SEQ ID NO: 95,
b) a subsequence of the sequence in a), such as a subsequence wherein 1, 2, 3, 4, 5, 6, 7, 8, 9 or 10 consecutive amino acids has/have deleted, starting from the N-terminus or C-terminus of the sequence defined in a); and
c) a sequence having at the most 5 substitutions, such as at the most 4 substitutions, at the most 3, at the most 2 or at the most 1 substitution compared to the amino acid sequence defined in a) or b).
The lambda (λ) light chain comprises an amino acid sequence selected from the group consisting of
a) the sequence set forth in SEQ ID NO: 96,
b) a subsequence of the sequence in a), such as a subsequence wherein 1, 2, 3, 4, 5, 6, 7, 8, 9 or 10 consecutive amino acids has/have deleted, starting from the N-terminus or C-terminus of the sequence defined in a); and
c) a sequence having at the most 5 substitutions, such as at the most 4 substitutions, at the most 3, at the most 2 or at the most 1 substitution compared to the amino acid sequence defined in a) or b).
The multispecific antibody may comprise, consists of or may essentially consist of
A first heavy chain comprising the amino acid sequence set forth in SEQ ID NO:108, or an amino acid sequence having at the most 10 substitutions, such as at the most 9, 8, 7, 6, 5, 4, 3, 2 or at the most 1 substitution compared to the amino acid sequence set forth in SEQ ID NO: 108;
A first light chain comprising the amino acid sequence set forth in SEQ ID NO: 109 or an amino acid sequence having at the most 10 substitutions, such as at the most 9, 8, 7, 6, 5, 4, 3, 2 or at the most 1 substitution compared to the amino acid sequence set forth in SEQ ID NO: 109;
A second heavy chain comprising the amino acid sequence set forth in SEQ ID NO: 106, or an amino acid sequence having at the most 10 substitutions, such as at the most 9, 8, 7, 6, 5, 4, 3, 2 or at the most 1 substitution compared to the amino acid sequence set forth in SEQ ID NO: 106;
A second light chains comprising the amino acid sequence set forth in SEQ ID NO: 107, or an amino acid sequence having at the most 10 substitutions, such as at the most 9, 8, 7, 6, 5, 4, 3, 2 or at the most 1 substitution compared to the amino acid sequence set forth in SEQ ID NO: 107.

The multispecific antibody may comprise, consist of or may essentially consists of A first heavy chain comprising the amino acid sequence set forth in SEQ ID NO: 111;

A first light chain comprising the amino acid sequence set forth in SEQ ID NO: 109;

A second heavy chain comprising the amino acid sequence set forth in SEQ ID NO: 110;

A second light chain comprising the amino acid sequence SEQ ID NO: 107.

It is well within the capacity of the skilled person to produce the multispecific antibody in a suitable expression system, including a choice of expression vector(s) and host cell. Suitable host cells include CHO, CHO-S, HEK, HEK293, HEK-293F, Expi293F, PER.C6 or NS0 cells, and lymphocytic cells. It is currently preferred that the multispecific antibody is produced in Chinese hamster ovary (CHO) cells. The heavy and light chains of the multispecific antibody may be expressed in the same host cell culture or may be produced separately in different host cell cultures.

The multispecific antibody may be obtained or may be obtainable by a method comprising expressing said first and second heavy chains and said first and second light chains in CHO cells, such as in one or more cultures of CHO cells.

The method may comprise isolating said said first and second heavy chains and said first and second light chains or comprises isolating said multispecific antibody from the CHO cells, such as from the one or more cultures of CHO cells.

The multispecific antibody for use according to any one of the preceding claims, which is a bispecific antibody.

When used in the context of the present invention, the multispecific antibody may be in a pharmaceutical composition.

The pharmaceutical composition may further comprise a pharmaceutically acceptable carrier excipient and/or diluent. The pharmaceutical compositions may be formulated with the carrier, excipient and/or diluent as well as any other components suitable of pharmaceutical compositions, including known adjuvants, in accordance with conventional techniques such as those disclosed in Remington: The Science and Practice of Pharmacy, 19th Edition, Gennaro, Ed., Mack Publishing Co., Easton, PA, 1995. The pharmaceutically acceptable carriers or diluents as well as any known adjuvants and excipients should be suitable for the antibody or antibody conjugate of the present invention and the chosen mode of administration. Suitability for carriers and other components of pharmaceutical compositions is determined based on the lack of significant negative impact on the desired biological properties of the chosen compound or pharmaceutical composition of the present invention (e.g., less than a substantial impact [10% or less relative inhibition, 5% or less relative inhibition, etc.] upon antigen binding).

The pharmaceutical composition may include diluents, fillers, salts, buffers, detergents (e. g., a nonionic detergent, such as Tween-20 or Tween-80), stabilizers (e.g., sugars or protein-free amino acids), preservatives, tissue fixatives, solubilizers, and/or other materials suitable for inclusion in a pharmaceutical composition.

The actual dosage levels of the active ingredients in the pharmaceutical compositions may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

Pharmaceutically acceptable carriers include any and all suitable solvents, dispersion media, coatings, antibacterial and antifungal agents, isotonicity agents, antioxidants and absorption-delaying agents, and the like that are physiologically compatible with a compound of the present invention.

Examples of suitable aqueous and non-aqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well known in the pharmaceutical arts.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated.

Pharmaceutical compositions of the present invention may also comprise pharmaceutically acceptable antioxidants for instance (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Pharmaceutical compositions of the present invention may also comprise isotonicity agents, such as sugars, polyalcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The compounds of the present invention may be prepared with carriers that will protect the compound against rapid release, such as a controlled release formulation, including implants, transdermal patches, and micro-encapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, poly-ortho esters, and polylactic acid alone or with a wax, or other materials well known in the art. Methods for the preparation of such formulations are generally known to those skilled in the art, see e.g. Sustained and Controlled Release Drug Delivery Systems, J. R. Robinson, ed., Marcel Dekker, Inc., New York, 1978.

In one embodiment, the compounds of the present invention may be formulated to ensure proper distribution in vivo. Pharmaceutically acceptable carriers for parenteral administration include sterile aqueous solutions or dispersions and sterile powders for the extemporaneous preparation of sterile injectable solutions or dispersion. The use of such media and agents for pharmaceutically active substances is known in the art. Except in so far as any conventional media or agent is incompatible with the active compound, use thereof in the pharmaceutical compositions of the present invention is contemplated. Other active or therapeutic compounds may also be incorporated into the compositions.

Pharmaceutical compositions for injection must typically be sterile and stable under the conditions of manufacture and storage. The composition may be formulated as a solution, micro-emulsion, liposome, or other ordered structure suitable to high drug concentration. The carrier may be an aqueous or a non-aqueous solvent or dispersion medium containing for instance water, ethanol, polyols (such as glycerol, propylene glycol, polyethylene glycol, and the like), and suitable mixtures thereof, vegetable oils, such as olive oil, and injectable organic esters, such as ethyl oleate. The proper fluidity may be maintained, for example, by the use of a coating such as lecithin, by the maintenance of the required particle size in the case of dispersion and by the use of surfactants. In many cases, it will be preferable to include isotonic agents, for example, sugars, polyalcohols such as glycerol, mannitol, sorbitol, or sodium chloride in the composition. Prolonged absorption of the injectable compositions may be brought about by including in the composition an agent that delays absorption, for example, monostearate salts and gelatin. Sterile injectable solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Sterile injectable solutions may be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, examples of methods of preparation are vacuum-drying and freeze-drying (lyophilization) that yield a powder of the active ingredient plus any additional desired ingredient from a previously sterile-filtered solution thereof.

The pharmaceutical composition of the present invention may contain one antibody, bispecific antibody or antibody-drug conjugate (ADC) of the present invention, a combination of an antibody, a bispecific antibody or ADC according to the invention with another therapeutic compound, or a combination of compounds of the present invention.

While the multispecific antibody disclosed herein may in principle be administered by any suitable route and mode it is currently preferred that the antibody is administered by intravenous infusion or injection. Also, the frequency of administration may be varied according to need; however it is currently preferred that the multispecific antibody is administered using intravenous infusion once every three weeks, such as on day 1 of each 3-week (21-day) treatment cycle. Alternatively, the multispecific antibody may be administered as a weekly dose (Q1W).

A further aspect of the invention provides the use of a multispecific antibody as defined above for the manufacture of a medicament for treatment of esophageal cancer.

Finally, an aspect of the invention provides a method of treating esophageal cancer, the method comprising administering a multispecific antibody and/or a pharmaceutical composition as defined above, to a subject in need thereof.

Sequences

| SEQ ID NO: | Name | Domain | Sequence |
|---|---|---|---|
| 1 | Human 5T4 | ORF | MPGGCSRGPAAGDGRLRLARLALVLLGWVSSSSPTSS ASSFSSSAPFLASAVSAQPPLPDQCPALCECSEAARTVK CVNRNLTEVPTDLPAYVRNLFLTGNQLAVLPAGAFARR PPLAELAALNLSGSRLDEVRAGAFEHLPSLRQLDLSHNP LADLSPFAFSGSNASVSAPSPLVELILNHIVPPEDERQNR SFEGMVVAALLAGRALQGLRRLELASNHFLYLPRDVLA QLPSLRHLDLSNNSLVSLTYVSFRNLTHLESLHLEDNALK VLHNGTLAELQGLPHIRVFLDNNPWVCDCHMADMVT WLKETEVVQGKDRLTCAYPEKMRNRVLLELNSADLDC DPILPPSLQTSYVFLGIVLALIGAIFLLVLYLNRKGIKKWM HNIRDACRDHMEGYHYRYEINADPRLTNLSSNSDV |
| 2 | Cynomolgus monkey 5T4 | ORF | MPGGCSRGPAAGDGRLRLARLALVLLGWVSSSSTSSA SSSSSSAPFLASAASAQPPLPDQCPALCECSEAARTVKC VNRNLTEVPTDLPLYVRNLFLTGNQLAVLPAGAFARRP PLAELAALNLSGSRLDEVRGGAFEHLPSLRQLDLSHNPL AYLSPFAFSGSNASISAPSPLVELILNHIVPPDDKRONRS FEGMVAAALVAGRALQGLHLLELASNHFLYLPRDVLAQ LPSLRYLDLSNNSLVSLTYVSFRNLTHLESLHLEDNALKV LHNGTLAELQGLPHVRVFLDNNPWVCDCHMADMVT WLKQTGVVQGKDRLTCAFPEKMRNRVLLELNSADLDC DPILPPSLQTSYVFLGIVLALIGAIFLLVLYLNRKGIKKWM HNIRDACRDHMEGYHYRYEINADPRLTNLSSNSDV |

-continued

| SEQ ID NO: | Name | Domain | Sequence |
|---|---|---|---|
| 3 | Chicken 5T4 | ORF | MPGREAERRGALCLGLLLHALLGCGSAQPPAACPAPCE CSEAAKTVKCVNKNLTEVPPDLPPYVRNLFITGNRLGRL PAGALSAPRLAELGSLNLSGNHLRAVEAGALAALPALR QLDLGGNPLAELSPLAFGRASPLEELALRGALREQGALL GLADLLQAGALRNLSRLELADNGLLLLLPTGMLGALPAL RHLDLSNNSLVGLRNVSFQGLVRLQSLNLSDNSLGVLR NGTLAQWRGLPALRRISLSHNTWVCDCAIEDMVAWL KESDQVEGKEALSCAFPEKMAGRALLKLNTSELNCSAP VDVPSQLQTSYVFLGIVLALIGAIFLLVLYLNRKGIKKWM HNIRDACRDHMEGYHYRYEINADPRLTNLSSNSDV |
| 4 | Mature Human CD3ε (epsilon) | Mature protein | QDGNEEMGGITQTPYKVSISGTTVILTCPQYPGSEILW QHNDKNIGGDEDDKNIGSDEDHLSLKEFSELEQSGYYV CYPRGSKPEDANFYLYLRARVCENCMEMDVMSVATIV IVDICITGGLLLLVYYWSKNRKAKAKPVTRGAGAGGRQ RGQNKERPPPVPNPDYEPIRKGQRDLYSGLNQRRI |
| 5 | HC_5T4-059 | VH | QVQLVESGGGVVQPGRSLRLSCAVSGFTFSSYDMNW VRQAPGKGLEWVTFISYDGSNKYNADSVKGRFTISRDN SKNTLYLQMNSLRAEDTAVYYCARDSYSRSWYGDYYG MDVWGQGTTVTVSS |
| 6 | HC_5T4-059 | VH_CDR1 | GFTFSSYD |
| 7 | HC_5T4-059 | VH_CDR2 | ISYDGSNK |
| 8 | HC_5T4-059 | VH_CDR3 | ARDSYSRSWYGDYYGMDV |
| 9 | LC_5T4-059 | VL | DIQMTQSPSSLSASVGDRVTITCRASQGISSWLAWYQ QKPEKAPKSLIYAASSLQSGVPSRFSGSGSGTDFTLTISSL QPEDFATYYCQQYNSYPLTFGGGTKVEIK |
| 10 | LC_5T4-059 | VL_CDR1 | QGISSW |
|  | LC_5T4-059 | VL_CDR2 | AAS |
| 11 | LC_5T4-059 | VL_CDR3 | QQYNSYPLT |
| 12 | HC_5T4-076 | VH | QVQLVQSGAEVKKPGASVKVSCKASGYTFTSYGISWVR QAPGQGLEWMGWISAYNGNTNYAQKLQGRVTMTT DTSTRTAYMELRSLRSDDTAVYYCARDPGYFDWLYGD YWGQGTLVTVSS |
| 13 | HC_5T4-076 | VH_CDR1 | GYTFTSYG |
| 14 | HC_5T4-076 | VH_CDR2 | ISAYNGNT |
| 15 | HC_5T4-076 | VH_CDR3 | ARDPGYFDWLYGDY |
| 16 | LC_5T4-076 | VL | AIQLTQSPSSLSASVGDRVTITCRASQGISSALAWYQQK PGKAPKLLIYDASSLESGVPSRFSGSGSGTDFTLTISSLQP EDFATYYCQQFNSYPRTFGQGTKVEIK |
| 17 | LC_5T4-076 | VL_CDR1 | QGISSA |
|  | LC_5T4-076 | VL_CDR2 | DAS |
| 18 | LC_5T4-076 | VL_CDR3 | QQFNSYPRT |
| 19 | HC_5T4-085 | VH | EVQLLESGGGLVQPGGSLRLSCAASGFTFSSYAMSWV RQAPGKGLEWVSAISGSGGSTYNADSVKGRFTIFRDNS KNTLYLHMNSLRAEDTAVYYCARDPGYNNVEYLDHW GQGTLVTVSS |
| 20 | HC_5T4-085 | VH_CDR1 | GFTFSSYA |
| 21 | HC_5T4-085 | VH_CDR2 | ISGSGGST |
| 22 | HC_5T4-085 | VH_CDR3 | ARDPGYNNVEYLDH |
| 23 | LC_5T4-085 | VL | AIQLTQSPSSLSASVGDRVTITCRASQGISSALAWYQQK PGKAPKLLIYDASSLESGVPSRFSGSGSGTDFTLTISSLQP EDFATYYCQQFNSYPLTFGGGTKVEIK |

-continued

| SEQ ID NO: | Name | Domain | Sequence |
|---|---|---|---|
| 24 | LC_5T4-085 | VL_CDR1 | QGISSA |
| | LC_5T4-085 | VL_CDR2 | DAS |
| 25 | LC_5T4-085 | VL_CDR3 | QQFNSYPLT |
| 26 | HC_5T4-106 | VH | EVQLVQSGAEVKKPGESLKISCKGSGYRFTSYWIGWVR QMPGKGLEWMGIIYPGDSDARYSPSFQGQVTISADKSI STAYLQWSSLKASDTGMYYCARSVLFDYWGQGTLVTV SS |
| 27 | HC_5T4-106 | VH_CDR1 | GYRFTSYW |
| 28 | HC_5T4-106 | VH_CDR2 | IYPGDSDA |
| 29 | HC_5T4-106 | VH_CDR3 | ARSVLFDY |
| 30 | LC_5T4-106 | VL | AIQLTQSPSSLSASVGDRVTITCRASQGISSALAWYQQK PGKAPKLLIYDVSNLESGVPSRFSGSGSGTDFTLTISSLQ PEDFATYYCQQFNSYPHTFGQGTKLEIK |
| 31 | LC_5T4-106 | VL_CDR1 | QGISSA |
| | LC_5T4-106 | VL_CDR2 | DVS |
| 32 | LC_5T4-106 | VL_CDR3 | QQFNSYPHT |
| 33 | HC_5T4-127 | VH | EVQLLESRGGLVQPGGSLRLSCAASGFTFSSYAMSWVR QAPGKGLEWVSTISGSGGSTYYADSVKGRFTISRDNSK KTLYLQMNSLRAEDTAVYYCAKDWGSGSYPAEYFQH WGQGTLVTVSS |
| 34 | HC_5T4-127 | VH_CDR1 | GFTFSSYA |
| 35 | HC_5T4-127 | VH_CDR2 | ISGSGGST |
| 36 | HC_5T4-127 | VH_CDR3 | AKDWGSGSYPAEYFQH |
| 37 | LC_5T4-127 | VL | EIVLTQSPATLSLSPGERATLSCRASQSVSSYLAWYQQK PGQAPRLLIYDASNRATGIPARFSGSGSGTDFTLTISSLE PEDFAVYYCQQRSNWLMYTFGQGTKLEIK |
| 38 | LC_5T4-127 | VL_CDR1 | QSVSSY |
| | LC_5T4-127 | VL_CDR2 | DAS |
| 39 | LC_5T4-127 | VL_CDR3 | QQRSNWLMYT |
| 40 | HC_5T4-207 | VH | QVQLQQWGAGLLKPSETLSLTCAVYGGSFSGYYWTWI RQPPGKGLEWIGEIDHSESTNYNPSLKSRVTISVDTSKN QFSLKLSSVTAADTAVYYCAGWFGELYHYYYGMDVW GQGTTVTVSS |
| 41 | HC_5T4-207 | VH_CDR1 | GGSFSGYY |
| 42 | HC_5T4-207 | VH_CDR2 | IDHSEST |
| 43 | HC_5T4-207 | VH_CDR3 | AGWFGELYHYYYGMDV |
| 44 | LC_5T4-207 | VL | EIVLTQSPATLSLSPGERATLSCRASQSVSSYLAWYQQK PGQAPRLLIYDASNRATGIPARFSGSGSGTDFTLTISSLE PEDFAVYYCQQRSNWPLTFGGGTKVEIK |
| 45 | LC_5T4-207 | VL_CDR1 | QSVSSY |
| | LC_5T4-207 | VL_CDR2 | DAS |
| 46 | LC_5T4-207 | VL_CDR3 | QQRSNWPLT |
| 47 | HC_5T4-226 | VH | QVQLQQWGAGLLKPSETLSLTCAVYGGSFSGYYWSWI RQPPGKGLEWIGEIDHSGSTNYNPSLKSRVTISVDTSKN QFSLKLSSVTAADTAVYYCAAWFGELWDYYYGMDVW GQGTTVTVSS |
| 48 | HC_5T4-226 | VH_CDR1 | GGSFSGYY |

-continued

| SEQ ID NO: | Name | Domain | Sequence |
|---|---|---|---|
| 49 | HC_5T4-226 | VH_CDR2 | IDHSGST |
| 50 | HC_5T4-226 | VH_CDR3 | AAWFGELWDYYYGMDV |
| 51 | LC_5T4-226 | VL | EIVLTQSPATLSLSPGERATLSCRASQSVSSFLAWYQQK<br>PGQAPRLLIYDASNRATGIPARFSGSGSGTDFTLTISSLE<br>PEDFAVYYCQQRSNWPLTFGQGTRLEIK |
| 52 | LC_5T4-226 | VL_CDR1 | QSVSSF |
|  | LC_5T4-226 | VL_CDR2 | DAS |
| 53 | LC_5T4-226 | VL_CDR3 | QQRSNWPLT |
| 54 | VH_huCD3-H1L1_CDR1 | VH_CDR1 | GFTFNTYA |
| 55 | VH_huCD3-H1L1_CDR2 | VH_CDR2 | IRSKYNNYAT |
| 56 | VH_huCD3-H1L1_CDR3 | VH_CDR3 | VRHGNFGNSYVSWFAY |
| 57 | VH_huCD3-H1L1 | VH | EVKLVESGGGLVQPGGSLRLSCAASGFTFNTYAMNWV<br>RQAPGKGLEWVARIRSKYNNYATYYADSVKDRFTISRD<br>DSKSSLYLQMNNLKTEDTAMYYCVRHGNFGNSYVSW<br>FAYWGQGTLVTVSS |
| 58 | VL_huCD3-H1L1_CDR1 | VL_CDR1 | TGAVTTSNY |
|  | VL_huCD3-H1L1_CDR2 | VL_CDR2 | GTN |
| 59 | VL_huCD3-H1L1_CDR3 | VL_CDR3 | ALWYSNLWV |
| 60 | VL_huCD3-H1L1 | VL | QAVVTQEPSFSVSPGGTVTLTCRSSTGAVTTSNYANW<br>VQQTPGQAFRGLIGGTNKRAPGVPARFSGSLIGDKAAL<br>TITGAQADDESIYFCALWYSNLWVFGGGTKLTVL |
| 61 | VH CDR1-T31P HC_T31P CDR1 | VH_CDR1 | GFTFNPYA |
| 62 | VH T31P full length sequence HC_T31P | VH | EVKLVESGGGLVQPGGSLRLSCAASGFTFNPYAMNWV<br>RQAPGKGLEWVARIRSKYNNYATYYADSVKDRFTISRD<br>DSKSSLYLQMNNLKTEDTAMYYCVRHGNFGNSYVSW<br>FAYWGQGTLVTVSS |
| 63 | VH CDR1-T31M HC_T31M CDR1 | VH_CDR1 | GFTFNMYA |
| 64 | VH T31M full length sequence HC_T31M | VH | EVKLVESGGGLVQPGGSLRLSCAASGFTFNMYAMNW<br>VRQAPGKGLEWVARIRSKYNNYATYYADSVKDRFTISR<br>DDSKSSLYLQMNNLKTEDTAMYYCVRHGNFGNSYVS<br>WFAYWGQGTLVTVSS |
| 65 | VH CDR2-N57E HC_N57E CDR2 | VH_CDR2 | IRSKYNEYAT |
| 66 | VH N57E full length sequence HC_N57E | VH | EVKLVESGGGLVQPGGSLRLSCAASGFTFNTYAMNWV<br>RQAPGKGLEWVARIRSKYNEYATYYADSVKDRFTISRD<br>DSKSSLYLQMNNLKTEDTAMYYCVRHGNFGNSYVSW<br>FAYWGQGTLVTVSS |
| 67 | VH_huCD3-H1L1-H101G_CDR3 HC_H101G CDR3 | VH_CDR3 | VRGGNFGNSYVSWFAY |
| 68 | VH_huCD3-H1L1-H101G HC_H101G | VH | EVKLVESGGGLVQPGGSLRLSCAASGFTFNTYAMNWV<br>RQAPGKGLEWVARIRSKYNNYATYYADSVKDRFTISRD<br>DSKSSLYLQMNNLKTEDTAMYYCVRGGNFGNSYVSW<br>FAYWGQGTLVTVSS |

-continued

| SEQ ID NO: | Name | Domain | Sequence |
|---|---|---|---|
| 69 | VH CDR3-H101N HC_H101N CDR3 | VH_CDR3 | VRNGNFGNSYVSWFAY |
| 70 | VH H101N full length sequence HC_H101N | VH | EVKLVESGGGLVQPGGSLRLSCAASGFTFNTYAMNWV RQAPGKGLEWVARIRSKYNNYATYYADSVKDRFTISRD DSKSSLYLQMNNLKTEDTAMYYCVRNGNFGNSYVSW FAYWGQGTLVTVSS |
| 71 | VH CDR3-G105P HC_G105P CDR3 | VH_CDR3 | VRHGNFPNSYVSWFAY |
| 72 | VH G105P full length sequence HC_G105P | VH | EVKLVESGGGLVQPGGSLRLSCAASGFTFNTYAMNWV RQAPGKGLEWVARIRSKYNNYATYYADSVKDRFTISRD DSKSSLYLQMNNLKTEDTAMYYCVRHGNFPNSYVSWF AYWGQGTLVTVSS |
| 73 | VH CDR3-S110A HC_S110A CDR3 | VH_CDR3 | VRHGNFGNSYVAWFAY |
| 74 | VH S110A full length sequence HC_S110A | VH | EVKLVESGGGLVQPGGSLRLSCAASGFTFNTYAMNWV RQAPGKGLEWVARIRSKYNNYATYYADSVKDRFTISRD DSKSSLYLQMNNLKTEDTAMYYCVRHGNFGNSYVAW FAYWGQGTLVTVSS |
| 75 | VH CDR3-S110G HC_S110G CDR3 | VH_CDR3 | VRHGNFGNSYVGWFAY |
| 76 | VH S110G full length sequence HC_S110G | VH | EVKLVESGGGLVQPGGSLRLSCAASGFTFNTYAMNWV RQAPGKGLEWVARIRSKYNNYATYYADSVKDRFTISRD DSKSSLYLQMNNLKTEDTAMYYCVRHGNFGNSYVGW FAYWGQGTLVTVSS |
| 77 | VH CDR3-Y114V HC_Y114V CDR3 | VH_CDR3 | VRHGNFGNSYVSWFAV |
| 78 | VH Y114V full length sequence HC_Y114V | VH | EVKLVESGGGLVQPGGSLRLSCAASGFTFNTYAMNWV RQAPGKGLEWVARIRSKYNNYATYYADSVKDRFTISRD DSKSSLYLQMNNLKTEDTAMYYCVRHGNFGNSYVSW FAVWGQGTLVTVSS |
| 79 | VH CDR3-Y114M HC_Y114M CDR3 | VH_CDR3 | VRHGNFGNSYVSWFAM |
| 80 | VH Y114M full length sequence HC_Y114M | VH | EVKLVESGGGLVQPGGSLRLSCAASGFTFNTYAMNWV RQAPGKGLEWVARIRSKYNNYATYYADSVKDRFTISRD DSKSSLYLQMNNLKTEDTAMYYCVRHGNFGNSYVSW FAMWGQGTLVTVSS |
| 81 | VH CDR3-Y114R HC_Y114R CDR3 | VH_CDR3 | VRHGNFGNSYVSWFAR |
| 82 | VH Y114R full length sequence HC Y114R | VH | EVKLVESGGGLVQPGGSLRLSCAASGFTFNTYAMNWV RQAPGKGLEWVARIRSKYNNYATYYADSVKDRFTISRD DSKSSLYLQMNNLKTEDTAMYYCVRHGNFGNSYVSW FARWGQGTLVTVSS |
| 83 | HC_5T4-A1 | VH | QIQLVQSGPELKKPGETVKISCKASGYTFTNFGMNWVK QGPGEGLKWMGWINTNTGEPRYAEEFKGRFAFSLETT ASTAYLQINNLKNEDTATYFCARDWDGAYFFDYWGQ GTTLTVSS |
| 84 | LC_5T4-A1 | VL | SIVMTQTPKFLLVSAGDRVTITCKASQSVSNDVAWYQ QKPGQSPKLLINFATNRYTGVPNRFTGSGYGTDFTFTIS TVQAEDLALYFCQQDYSSPWTFGGGTKLEIK |
| 85 | HC_5T4-A3 | VH | EVQLVESGGGLVQPKGSLKLSCAASGFTFNTYAMNWV RQAPGKGLEWVARIRSKSNNYATYYADSVKDRFTISRD DSQSMLYLQMNNLKTEDTAMYYCVRQWDYDVRAM NYWGQGTSVTVSS |
| 86 | LC_5T4-A3 | VL | DIVMTQSHIFMSTSVGDRVSITCKASQDVDTAVAWYQ QKPGQSPKLLIYWASTRLTGVPDRFTGSGSGTDFTLTIS NVQSEDLADYFCQQYSSYPYTFGGGTKLEIK |

-continued

| SEQ ID NO: | Name | Domain | Sequence |
|---|---|---|---|
| 87 | HC_5T4-H8 | VH | EVQLQQSGPDLVKPGASVKISCKASGYSFTGYYMHWV KQSHGKSLEWIGRINPNNGVTLYNQKFKDKAILTVDKS STTAYMELRSLTSEDSAVYYCARSTMITNYVMDYWGQ VTSVTVSS |
| 88 | LC_5T4-H8 | VL | SIVMTQTPTFLLVSAGDRVTITCKASQSVSNDVAWYQ QKPGQSPTLLISYTSSRYAGVPDRFIGSGYGTDFTFTISTL QAEDLAVYFCQQDYNSPPTFGGGTKLEIK |
| 89 | IgG1-Fc | Constant | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKRVEPKSCDKTHTCPPCPAPE LLGGPSVFLFPPKPKDTLMISRTPEVTCVVVDVSHEDPE VKFNWYVDGVEVHNAKTKPREEQYNSTYRVVSVLTVL HQDWLNGKEYKCKVSNKALPAPIEKTISKAKGQPREPQ VYTLPPSREEMTKNQVSLTCLVKGFYPSDIAVEWESNG QPENNYKTTPPVLDSDGSFFLYSKLTVDKSRWQQGNV FSCSVMHEALHNHYTQKSLSLSPGK |
| 90 | IgG1-Fc_F405L | Constant | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKRVEPKSCDKTHTCPPCPAPE LLGGPSVFLFPPKPKDTLMISRTPEVTCVVVDVSHEDPE VKFNWYVDGVEVHNAKTKPREEQYNSTYRVVSVLTVL HQDWLNGKEYKCKVSNKALPAPIEKTISKAKGQPREPQ VYTLPPSREEMTKNQVSLTCLVKGFYPSDIAVEWESNG QPENNYKTTPPVLDSDGSFLLYSKLTVDKSRWQQGNV FSCSVMHEALHNHYTQKSLSLSPGK |
| 91 | IgG1-Fc_FEA | Constant | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKRVEPKSCDKTHTCPPCPAPE FEGGPSVFLFPPKPKDTLMISRTPEVTCVVVAVSHEDPE VKFNWYVDGVEVHNAKTKPREEQYNSTYRVVSVLTVL HQDWLNGKEYKCKVSNKALPAPIEKTISKAKGQPREPQ VYTLPPSREEMTKNQVSLTCLVKGFYPSDIAVEWESNG QPENNYKTTPPVLDSDGSFLLYSKLTVDKSRWQQGNV FSCSVMHEALHNHYTQKSLSLSPGK |
| 92 | IgG1-Fc_FEAL | Constant | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKRVEPKSCDKTHTCPPCPAPE FEGGPSVFLFPPKPKDTLMISRTPEVTCVVVAVSHEDPE VKFNWYVDGVEVHNAKTKPREEQYNSTYRVVSVLTVL HQDWLNGKEYKCKVSNKALPAPIEKTISKAKGQPREPQ VYTLPPSREEMTKNQVSLTCLVKGFYPSDIAVEWESNG QPENNYKTTPPVLDSDGSFLLYSKLTVDKSRWQQGNV FSCSVMHEALHNHYTQKSLSLSPGK |
| 93 | IgG1-Fc_FEAR | Constant | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKRVEPKSCDKTHTCPPCPAPE FEGGPSVFLFPPKPKDTLMISRTPEVTCVVVAVSHEDPE VKFNWYVDGVEVHNAKTKPREEQYNSTYRVVSVLTVL HQDWLNGKEYKCKVSNKALPAPIEKTISKAKGQPREPQ VYTLPPSREEMTKNQVSLTCLVKGFYPSDIAVEWESNG QPENNYKTTPPVLDSDGSFFLYSRLTVDKSRWQQGNV FSCSVMHEALHNHYTQKSLSLSPGK |
| 94 | IgG1-Fc_K409R | Constant | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKRVEPKSCDKTHTCPPCPAPE LLGGPSVFLFPPKPKDTLMISRTPEVTCVVVDVSHEDPE VKFNWYVDGVEVHNAKTKPREEQYNSTYRVVSVLTVL HQDWLNGKEYKCKVSNKALPAPIEKTISKAKGQPREPQ VYTLPPSREEMTKNQVSLTCLVKGFYPSDIAVEWESNG QPENNYKTTPPVLDSDGSFFLYSRLTVDKSRWQQGNV FSCSVMHEALHNHYTQKSLSLSPGK |
| 95 | Kappa | Constant | RTVAAPSVFIFPPSDEQLKSGTASVVCLLNNFYPREAKV QWKVDNALQSGNSQESVTEQDSKDSTYSLSSTLTLSKA DYEKHKVYACEVTHQGLSSPVTKSFNRGEC |

-continued

| SEQ ID NO: | Name | Domain | Sequence |
|---|---|---|---|
| 96 | Lambda | Constant | GQPKAAPSVTLFPPSSEELQANKATLVCLISDFYPGAVT VAWKADSSPVKAGVETTTPSKQSNNKYAASSYLSLTPE QWKSHRSYSCQVTHEGSTVEKTVAPTECS |
| 97 | b12_VH | VH | QVQLVQSGAEVKKPGASVKVSCQASGYRFSNFVIHWV RQAPGQRFEWMGWINPYNGNKEFSAKFQDRVTFTA DTSANTAYMELRSLRSADTAVYYCARVGPYSWDDSPQ DNYYMDVWGKGTTVIVSS |
| 98 | b12_VL | VL | EIVLTQSPGTLSLSPGERATFSCRSSHSIRSRRVAWYQH KPGQAPRLVIHGVSNRASGISDRFSGSGSGTDFTLTITR VEPEDFALYYCQVYGASSYTFGQGTKLERK |
| 99 | 5T4ECDHis | ORF | MPGGCSRGPAAGDGRLRLARLALVLLGWVSSSSPTSS ASSFSSSAPFLASAVSAQPPLPDQCPALCECSEAARTVK CVNRNLTEVPTDLPAYVRNLFLTGNQLAVLPAGAFARR PPLAELAALNLSGSRLDEVRAGAFEHLPSLRQLDLSHNP LADLSPFAFSGSNASVSAPSPLVELILNHIVPPEDERQNR SFEGMVVAALLAGRALQGLRRLELASNHFLYLPRDVLA QLPSLRHLDLSNNSLVSLTYVSFRNLTHLESLHLEDNALK VLHNGTLAELQGLPHIRVFLDNNPWVCDCHMADMVT WLKETEVVQGKDRLTCAYPEKMRNRVLLELNSADLDC DPILPPSLQTSHHHHHHH |
| 100 | 5T4ECD91- FcRbHis | ORF | MPGGCSRGPAAGDGRLRLARLALVLLGWVSSSSPTSS ASSFSSSAPFLASAVSAQPPLPDQCPALCECSEAARTVK CVNRNLTEVPTDLPAAPSTCSKPTCPPPELLGGPSVFIFP PKPKDTLMISRTPEVTCVVVDVSQDDPEVQFTWYINN EQVRTARPPLREQQFNSTIRVVSTLPIAHQDWLRGKEF KCKVHNKALPAPIEKTISKARGQPLEPKVYTMGPPREEL SSRSVSLTCMINGFYPSDISVEWEKNGKAEDNYKTTPA VLDSDGSYFLYSKLSVPTSEWQRGDVFTCSVMHEALH NHYTQKSISRSPGKHHHHHHHH |
| 101 | CD3E27-GSKa | ORF | MWWRLWWLLLLLLLLWPMVWAQDGNEEMGGITQT PYKVSISGTTVILTGGGGSGGGGSGGGGSEIVLTQSPAT LSLSPGERATLSCRASQSVSSYLAWYQQKPGQAPRLLIY DASNRATGIPARFSGSGSGTDFTLTISSLEPEDFAVYYCQ QRSNWPITFGQGTRLEIKRTVAAPSVFIFPPSDEQLKSG TASVVCLLNNFYPREAKVQWKVDNALQSGNSQESVTE QDSKDSTYSLSSTLTLSKADYEKHKVYACEVTHQGLSSP VTKSFNRGE |
| 102 | HC_574-059 HC_5T4-207 HC_5T4-226 | VH-CDR3 C-term | YYGMDV |
| 103 | HC_5T4-207 HC_5T4-226 | VH-CDR-2 | IDHSX$_1$ST; X$_1$ is G or E |
| 104 | HC_5T4-207 HC_5T4-226 | VH-CDR-3 | AX$_2$WFGELX$_3$X$_4$YYYGMDV; X$_2$ is A or G, X$_3$ is W or Y, X$_4$ is D or H |
| 105 | HC_5T4-207 HC_5T4-226 | VL-CDR-1 | QSVSSX$_5$; X$_5$ is Y or F |
| 106 | HC-IgG1-huCD3- H101G | HC | EVKLVESGGGLVQPGGSLRLSCAASGFTFNTYAMNWV RQAPGKGLEWVARIRSKYNNYATYYADSVKDRFTISRD DSKSSLYLQMNNLKTEDTAMYYCVRGGNFGNSYVSW FAYWGQGTLVTVSSASTKGPSVFPLAPSSKSTSGGTAA LGCLVKDYFPEPVTVSWNSGALTSGVHTFPAVLQSSGL YSLSSVVTVPSSSLGTQTYICNVNHKPSNTKVDKRVEPK SCDKTHTCPPCPAPELLGGPSVFLFPPKPKDTLMISRTPE VTCVVVDVSHEDPEVKFNWYVDGVEVHNAKTKPREE QYNSTYRVVSVLTVLHQDWLNGKEYKCKVSNKALPAPI EKTISKAKGQPREPQVYTLPPSREEMTKNQVSLTCLVKG FYPSDIAVEWESNGQPENNYKTTPPVLDSDGSFFLYSKL TVDKSRWQQGNVFSCSVMHEALHNHYTQKSLSLSPG |
| 107 | LC-IgG1-huCD3- H101G | LC | QAVVTQEPSFSVSPGGTVTLTCRSSTGAVTTSNYANW VQQTPGQAFRGLIGGTNKRAPGVPARFSGSLIGDKAAL TITGAQADDESIYFCALWYSNLWVFGGGTKLTVLGQPK AAPSVTLFPPSSEELQANKATLVCLISDFYPGAVTVAWK ADSSPVKAGVETTTPSKQSNNKYAASSYLSLTPEQWKS HRSYSCQVTHEGSTVEKTVAPTECS |

| SEQ ID NO: | Name | Domain | Sequence |
|---|---|---|---|
| 108 | HC-IgG1-5T4-207 | HC | QVQLQQWGAGLLKPSETLSLTCAVYGGSFSGYYWTWI RQPPGKGLEWIGEIDHSESTNYNPSLKSRVTISVDTSKN QFSLKLSSVTAADTAVYYCAGWFGELYHYYYGMDVW GQGTTVTVSSASTKGPSVFPLAPSSKSTSGGTAALGCLV KDYFPEPVTVSWNSGALTSGVHTFPAVLQSSGLYSLSSV VTVPSSSLGTQTYICNVNHKPSNTKVDKRVEPKSCDKT HTCPPCPAPELLGGPSVFLFPPKPKDTLMISRTPEVTCV VVDVSHEDPEVKFNWYVDGVEVHNAKTKPREEQYNS TYRVVSVLTVLHQDWLNGKEYKCKVSNKALPAPIEKTIS KAKGQPREPQVYTLPPSREEMTKNQVSLTCLVKGFYPS DIAVEWESNGQPENNYKTTPPVLDSDGSFFLYSKLTVD KSRWQQGNVFSCSVMHEALHNHYTQKSLSLSPG |
| 109 | LC-IgG1-5T4-207 | LC | EIVLTQSPATLSLSPGERATLSCRASQSVSSYLAWYQQK PGQAPRLLIYDASNRATGIPARFSGSGSGTDFTLTISSLE PEDFAVYYCQQRSNWPLTFGGGTKVEIKRTVAAPSVFI FPPSDEQLKSGTASVVCLLNNFYPREAKVQWKVDNAL QSGNSQESVTEQDSKDSTYSLSSTLTLSKADYEKHKVYA CEVTHQGLSSPVTKSFNRGEC |
| 110 | HC-IgG1-huCD3-H101G-FEAL | HC | EVKLVESGGGLVQPGGSLRLSCAASGFTFNTYAMNWV RQAPGKGLEWVARIRSKYNNYATYYADSVKDRFTISRD DSKSSLYLQMNNLKTEDTAMYYCVRGGNFGNSYVSW FAYWGQGTLVTVSSASTKGPSVFPLAPSSKSTSGGTAA LGCLVKDYFPEPVTVSWNSGALTSGVHTFPAVLQSSGL YSLSSVVTVPSSSLGTQTYICNVNHKPSNTKVDKRVEPK SCDKTHTCPPCPAPEFEGGPSVFLFPPKPKDTLMISRTP EVTCVVVAVSHEDPEVKFNWYVDGVEVHNAKTKPREE QYNSTYRVVSVLTVLHQDWLNGKEYKCKVSNKALPAPI EKTISKAKGQPREPQVYTLPPSREEMTKNQVSLTCLVKG FYPSDIAVEWESNGQPENNYKTTPPVLDSDGSFLLYSKL TVDKSRWQQGNVFSCSVMHEALHNHYTQKSLS LSPG |
| 111 | HC-IgG1-5T4-207-FEAR | HC | QVQLQQWGAGLLKPSETLSLTCAVYGGSFSGYYWTWI RQPPGKGLEWIGEIDHSESTNYNPSLKSRVTISVDTSKN QFSLKLSSVTAADTAVYYCAGWFGELYHYYYGMDVW GQGTTVTVSSASTKGPSVFPLAPSSKSTSGGTAALGCLV KDYFPEPVTVSWNSGALTSGVHTFPAVLQSSGLYSLSSV VTVPSSSLGTQTYICNVNHKPSNTKVDKRVEPKSCDKT HTCPPCPAPEFEGGPSVFLFPPKPKDTLMISRTPEVTCV VVAVSHEDPEVKFNWYVDGVEVHNAKTKPREEQYNS TYRVVSVLTVLHQDWLNGKEYKCKVSNKALPAPIEKTIS KAKGQPREPQVYTLPPSREEMTKNQVSLTCLVKGFYPS DIAVEWESNGQPENNYKTTPPVLDSDGSFFLYSRLTVD KSRWQQGNVFSCSVMHEALHNHYTQKSLSLSPG |

The present invention is further illustrated by the following examples which should not be construed as further limiting.

EXAMPLES

Example 1—Generation of 5T4 Antibodies and Screenings Materials

Expression Constructs for 5T4

The following codon-optimized constructs for expression of various full length 5T4 variants were generated: human (*Homo sapiens*) 5T4 (Uniprot accession no. Q13641), cynomolgus monkey (*Macaca fascicularis*) 5T4 (Uniprot accession no. Q4R8Y9), and chicken (*Gallus gallus*) 5T4 (Uniprot accession no. R4GM46). In addition, the following codon-optimized constructs for various 5T4 extracellular domain (ECD) variants were generated: the ECD of human 5T4 (aa 1-355 from Uniprot accession no. Q13641) with a C-terminal His tag (5T4ECDHis)(SEQ ID NO: 99), and the ECD of human 5T4 (aa 1-91) fused to rabbit Fc domain and C-terminal His-tag (5T4ECD91-FcRbHis). In SEQ ID NO:

99, amino acid residues 1-31 are a signal peptide; hence the mature 5T4ECDHis protein corresponds to amino acid residues 32-363 of SEQ ID NO: 99. Likewise, amino acid residues 1-31 of SEQ ID NO: 100 are a signal peptide and the mature 5T4ECD91-FcRbHis protein corresponds to amino acid residues 32-327 of SEQ ID NO: 100.

The constructs contained suitable restriction sites for cloning and an optimal Kozak (GCCGCCACC) sequence (Kozak, M., Gene 1999; 234(2):187-208). The full length human 5T4 and cynomolgus monkey 5T4 codon-optimized constructs were cloned in the mammalian expression vector pcDNA3.3 (Invitrogen). The full length chicken 5T4 codon-optimized constructs was cloned in pSB, a mammalian expression vector containing Sleeping Beauty inverter terminal repeats flanking an expression cassette consisting of a CMV promoter and HSV-TK polyA signal.

Generation of HEK-293F cell lines transiently expressing full length human, cynomolgus or chicken 5T4 Freestyle™ 293-F (a HEK-293 subclone adapted to suspension growth and chemically defined Freestyle medium [HEK-293F]) cells were obtained from Invitrogen (cat. no. R790-07) and transfected with the codon-optimized constructs described supra, using 293fectin (Invitrogen, cat. no. 12347-019) according to the manufacturer's instructions.

Purification of His-Tagged 5T4

5T4ECDHis (mature protein of SEQ ID NO: 99) was expressed in HEK-293F cells as described supra. 5T4ECD91-FcRbHis was expressed using the Expi293F expression platform (Thermo Fisher Scientific, Waltham, MA, USA, cat. no. A14527) essentially as described by the manufacturer.

The His-tag enables purification with immobilized metal affinity chromatography. In this process, a chelator fixed onto the chromatographic resin is charged with $Co^{2+}$ cations. Supernatants containing the His-tagged protein were incubated with the resin in batch mode (i.e. solution). The His-tagged protein binds strongly to the resin beads, while other proteins present in the culture supernatant do not bind or bind weakly compared to the His-tagged proteins. After incubation, the beads were retrieved from the supernatant and packed into a column. The column was washed in order to remove weakly bound proteins. The strongly bound His-tagged proteins were then eluted with a buffer containing imidazole, which competes with the binding of His to CO2+. The eluent was removed by buffer exchange on a desalting column.

Immunization

For generation of antibodies IgG1-5T4-207 and IgG1-5T4-226, HCo17-BalbC transgenic mice (Bristol-Myers Squibb, New York, NY, USA) were immunized alternatingly intraperitoneally (IP) and subcutaneously (SC) with 20 μg of the 5T4ECDHis protein in Sigma adjuvant system (Sigma-Aldrich, St. Louis, MO, USA, cat. no. S6322) with an interval of 14 days. In total 8 immunizations were performed: 4 IP and 4 SC.

For generation of antibodies IgG1-5T4-076 and IgG1-5T4-059, HCo12-BalbC (IgG1-5T4-076) and HCo20-BalbC (IgG1-5T4-059) transgenic mice (Bristol-Myers Squibb) were immunized alternatingly IP and SC with 20 μg of the 5T4ECDHis protein in Sigma adjuvant system with an interval of 14 days. In total 8 immunizations were performed: 4 IP and 4 SC.

For generation of antibody IgG1-5T4-085, HCo17-BalbC transgenic mice were immunized alternatingly IP and SC with 20 μg of the 5T4ECDHis protein and 20 μg of the 5T4ECD91-FcRbHis mature protein in Sigma adjuvant system with an interval of 14 days. In total 8 immunizations were performed: 4 IP and 4 SC.

For generation of antibodies IgG1-5T4-106 and IgG1-5T4-127, HCo12-BalbC (IgG1-5T4-106) and HCo17-BalbC (IgG1-5T4-127) transgenic mice were immunized alternatingly IP and SC with 20 μg of the 5T4ECD91-FcRbHis mature protein in Sigma adjuvant system with an interval of 14 days. In total 8 immunizations were performed: 4 IP and 4 SC.

Mice with at least two sequential 5T4 specific antibody titers in the antigen specific screening Fluorometric Micro volume Assay Technology (FMAT) as described below, were boosted with 10 μg of 5T4ECDHis or 10 μg 5T4ECD91-FcRbHis (in PBS injected intravenously) and splenocytes and lymph node cells of these mice were fused 3-4 days later.

Homogeneous Antigen Specific Screening Assay

The presence of 5T4 antibodies in sera of immunized mice or HuMAb (human monoclonal antibody) hybridoma or transfectoma culture supernatant was determined by homogeneous antigen specific screening assays using FMAT (Applied Biosystems, Foster City, CA, USA). For this, a combination of 4 cell based assays was used.

Sera from immunized mice, or hybridoma or transfectoma culture supernatant samples were analyzed for binding of human antibodies to HEK-293F cells transiently expressing human 5T4, HEK-293F cells transiently expressing cynomolgus monkey 5T4, streptavidin-coated polystyrene particles (0.5% w/v; 6.7 μm; Spherotech, Lake Forest, IL, USA, cat. no. SVP-60-5) coated with 5T4ECD91-FcRBHis, and HEK-293 wild-type cells (negative control).

Samples were added to the cells to allow binding to 5T4. Subsequently, binding of HuMAb was detected using a fluorescent conjugate (AffiniPure Goat Anti-Human IgG Fc gamma-Alexa Fluor® 647; Jackson ImmunoResearch, cat no. 109-605-098). IgG1-5T4-H8-F405L was used as a positive control and ChromPure Human IgG, whole molecule (Jackson ImmunoResearch, cat no. 009-000-003) was used as negative control. The samples were scanned using an ImageXpress Velos (Molecular devices, LLC, Sunnyvale, CA, USA) and total fluorescence was used as read-out. Samples were stated positive when counts were higher than 50 and counts x fluorescence was at least three times higher than the negative control.

HuMAb Hybridoma Generation

HuMAb mice with sufficient antigen-specific titer development (described above) were sacrificed and the spleen and lymph nodes flanking the abdominal aorta and vena cava were collected. Fusion of splenocytes and lymph node cells to a mouse myeloma cell line (SP2.0 cells) was done by electrofusion using a CytoPulse CEEF 50 Electrofusion System (Cellectis, Paris, France), essentially according to the manufacturer's instructions. Next, the antigen-positive primary wells were sub-cloned using the ClonePix system (Genetix, Hampshire, UK). To this end, specific primary well hybridomas were seeded in semisolid medium made from 40% CloneMedia (Genetix, Hampshire, UK) and 60% HyQ 2x complete media (Hyclone, Waltham, USA). The subclones were retested for 5T4 binding according to the antigen-specific binding assay as described above and scanned using the IsoCyte system (Molecular Devices). IgG levels were measured using an Octet system (Fortebio, Menlo Park, USA) in order to select the best producing clone per primary well for further expansion. Further expansion and culturing of the resulting HuMAb hybridomas were done based upon standard protocols (e.g. as described in Coligan J. E., Bierer, B. E., Margulies, D. H., Shevach, E. M. and Strober, W., eds. Current Protocols in Immunology, John Wiley & Sons, Inc., 2006).

Sequence Analysis of the 5T4 Antibody Variable Domains and Cloning in Expression Vectors Total RNA was prepared from 2 to $5\times10^6$ hybridoma cells and 5'-RACE-complementary DNA (cDNA) was prepared from 100 ng total RNA, using the SMART RACE cDNA Amplification kit (Clontech), according to the manufacturer's instructions. VH and VL coding regions were amplified by PCR and cloned directly, in frame, in the p33G1f and p33Kappa expression vectors (pcDNA3.3 based vectors with codon optimized human IgG1m(f) and Kappa constant domains, respectively), by ligation independent cloning (Aslanidis, C. and P. J. de Jong, Nucleic Acids Res 1990; 18(20): 6069-74). The variable domains from these expression vectors were sequenced and CDRs were annotated according to IMGT definitions (Lefranc M P. et al., Nucleic Acids Research, 27, 209-212, 1999 and Brochet X. Nucl. Acids Res. 36, W503-508 (2008)). Clones with a correct Open Reading Frame (ORF) were expressed and tested for binding to the antigen. A lead panel was ordered as codon optimized sequences (GeneArt, Thermo Fisher Scientific) and produced with the Expi293 expression system according to manufacturer's instructions (Thermo Fisher Scientific). The antibodies in these supernatants were purified and used for functional characterization. The sequences of the resulting lead clones are shown in the table above.

5T4 Control Antibodies

In some of the Examples comparison antibodies against 5T4 were used (IgG1-5T4-H8, IgG1-5T4-A3 and IgG1-5T4-A1) that have been previously described in WO2007/106744. The codon optimized antibody encoding sequences were synthesized and cloned in pCDNA3.3 expression vectors (Thermo Fisher Scientific).

IgG1-b12 Antibody

In some of the Examples the antibody b12, an HIV-1 gp120 specific antibody (Barbas, CF. J Mol Biol. 1993 Apr. 5; 230(3):812-23) was used as a negative control. The codon optimized antibody encoding sequences for this control antibody were synthesized and cloned into pCDNA3.3 expression vectors (Thermo Fisher Scientific). The sequence of the variable heavy chain (VH) region and the sequence of the variable light chain (VL) region are included herein as SEQ ID NOs.: 97 and 98, respectively.

Example 2—Determination of the Binding Affinities of 5T4 Specific Antibodies Using Biolayer Interferometry Affinities of the 5T4 antibodies for recombinant 5T4 protein were determined using label-free biolayer interferometry on an Octet HTX instrument (ForteBio, Portsmouth, UK). 5T4 antibodies (1 μg/mL) were immobilized for 600 seconds on anti-human IgG Fc Capture biosensors (ForteBio). After a baseline measurement (100 s), the association (200 s) and dissociation (1000 s) of human 5T4ECDHis (mature protein of SEQ ID NO: 99) or recombinant cynomolgus monkey 5T4 protein (Cusabio; cat. no. CSB-MP024093MOV) in Sample Diluent (ForteBio) was determined using a 2-fold dilution series (ranging from 100 nM to 1.56 nM) starting at 3.58 μg/mL (100 nM) human 5T4ECDHis or 3.99 μg/mL (100 nM) cynomolgus 5T4, while shaking at 1000 rpm at 30° C. Data were analyzed with Data Analysis Software v9.0.0.12 (ForteBio). Values of reference wells containing only Sample Diluent during the association and dissociation steps were subtracted from values of wells containing antigen, for each antibody separately. The Y-axis was aligned to the last 10 s of the baseline and Interstep Correction alignment to dissociation as well as Savitzky-Golay filtering was applied. Responses <0.05 nm were excluded from analysis. The data were fitted using the 1:1 model and a global full fit with 200 s association time and 1000 s or 50 s dissociation time as Window of Interest. The fit with the full dissociation time (1000 s) as Window of Interest was used by default. Based on the $R^2$ value and visual inspection of the fit, a dissociation time of 50s was used as Window of Interest for IgG1-5T4-127-FEAR.

Table 1 shows the association rate constant $k_a$ (1/Ms), dissociation rate constant $k_d$ (1/s) and equilibrium dissociation constant $K_D$ (M) of the 5T4 antibodies for human 5T4ECDHis determined by biolayer interferometry. A range of affinities of the antibodies to human 5T4 was measured ranging from $1.3\times10^{-9}$-$2.7\times10^{-8}$ M. The response of IgG1-5T4-085-FEAR was lower than 0.05 nm, which prevented proper fitting of the data (low $R^2$ values for these fits). Furthermore, the response of IgG1-5T4-076-FEAR could not be fitted properly. These data are shown in italics.

Table 2 shows the association rate constant $k_a$ (1/Ms), dissociation rate constant $k_d$ (1/s) and equilibrium dissociation constant $K_D$ (M) for cynomolgus monkey 5T4 determined with biolayer interferometry. A range of affinities of the antibodies to cynomolgus monkey 5T4 was measured ranging from $1.1\times10^{-9}$-$4.1\times10^{-8}$ M. The responses of IgG1-5T4-085-FEAR, IgG1-5T4-106-FEAR and IgG1-5T4-H8-FEAR were lower than 0.05 nm, which prevented proper fitting of the data (low $R^2$ values for these fits). Furthermore, the response of IgG1-5T4-076-FEAR could not be fitted properly. These data are shown in italics.

TABLE 1

Binding affinities of monospecific, bivalent 5T4 antibodies to human 5T4 extracellular domain as determined by label-free biolayer interferometry.

| Antibody | On-rate $k_a$ (1/Ms) | Off-rate $k_d$ (1/s) | $K_D$ (M) |
|---|---|---|---|
| IgG1-5T4-059-FEAR | 2.1E+05 | 3.2E−04 | 1.5E−09 |
| IgG1-5T4-076-FEAR | | No fit | |
| IgG1-5T4-085-FEAR | | Response <0.05 nm | |
| IgG1-5T4-106-FEAR | 2.1E+05 | 1.2E−03 | 5.5E−09 |
| IgG1-5T4-127-FEAR | 5.8E+05 | 1.6E−02 | 2.7E−08 |
| IgG1-5T4-207-FEAR | 2.7E+05 | 6.8E−04 | 2.6E−09 |
| IgG1-5T4-226-FEAR | 3.3E+05 | 8.1E−04 | 2.5E−09 |
| IgG1-5T4-H8-FEAR | 2.2E+05 | 2.9E−04 | 1.3E−09 |

TABLE 2

Binding affinities of monospecific, bivalent 5T4 antibodies to cynomolgus monkey 5T4 extracellular domain as determined by label-free biolayer interferometry.

| Antibody | On-rate $k_a$ (1/Ms) | Off-rate $k_d$ (1/s) | $K_D$ (M) |
|---|---|---|---|
| IgG1-5T4-059-FEAR | 1.6E+05 | 2.8E−04 | 1.8E−09 |
| IgG1-5T4-076-FEAR | | No fit | |
| IgG1-5T4-085-FEAR | | Response <0.05 nm | |
| IgG1-5T4-106-FEAR | | Response <0.05 nm | |
| IgG1-5T4-127-FEAR | 3.7E+05 | 1.5E−02 | 4.1E−08 |
| IgG1-5T4-207-FEAR | 1.4E+05 | 8.7E−04 | 6.3E−09 |
| IgG1-5T4-226-FEAR | 1.4E+05 | 1.5E−03 | 1.1E−08 |
| IgG1-5T4-H8-FEAR | | Response <0.05 nm | |

Example 3—Cross-Block of 5T4 Antibodies Determined by Biolayer Interferometry Antibody cross-block analysis (epitope binning) was performed using biolayer interferometry on an Octet HTX instrument (ForteBio). 5T4 antibodies (20 μg/mL in 10 mM sodium acetate buffer pH 6.0, ForteBio) were immobilized on Amine-Reactive 2nd Generation (AR2G) biosensors (ForteBio) according to the manufacturer's instructions. After a baseline measurement (100 s) in Sample Diluent (ForteBio), biosensors containing immobilized antibodies were loaded for 500 s with human 5T4ECDHis (mature protein of SEQ ID NO: 99) 100 nM (3.6 μg/mL). Next, the association response of a second 5T4 antibody (10 μg/mL) was determined for 500 s. Biosensors were regenerated by 3 times 5 s exposure to 10 mM glycine pH 2.5 followed by Sample Diluent, and the measurement was repeated with a new set of second 5T4 antibodies starting from the baseline step. Each biosensor was used four times. Measurements were performed at 30° C. using a shaker speed of 1000 rpm. Data were analyzed using Data Analysis Software v9.0.0.12 (ForteBio). The Y-axis was aligned to the association step and Savitzky-Golay filtering was applied. The response of Sample Diluent during the association step was subtracted from the association response of the second antibody in order to correct for the dissociation of 5T4ECDHis from the immobilized antibody. The corrected association responses were plotted in a matrix format. In general, responses >0.1 nm were considered non-blocking antibody pairs (white), while responses between –0.1 and 0.1 nm were considered to be blocking antibody pairs (dark grey). For some antibody pairs the second antibody showed an initial positive response, followed by a decrease in signal. This was considered to be antibody displacement (light grey), i.e. the second antibody displacing the interaction between the first antibody and the antigen (Abdiche Y N, Yeung A Y, Ni I, Stone D, Miles A, Morishige W, et al. (2017) Antibodies Targeting Closely Adjacent or Minimally Overlapping Epitopes Can Displace One Another. PLoS ONE 12(1): e0169535. doi:10.1371/journal.pone.0169535). In some cases, the data curves needed visual inspection by an expert to assign blocking, non-blocking or displacement properties to antibody pairs.

Cross-block experiments were performed for antibodies IgG1-5T4-059-FEAR, IgG1-5T4-076-FEAR, IgG1-5T4-085-FEAR, IgG1-5T4-106-FEAR, IgG1-5T4-127-FEAR, IgG1-5T4-207-FEAR, IgG1-5T4-226-FEAR, and prior art antibodies IgG1-5T4-H8-FEAR, IgG1-5T4-A1-F405L and IgG1-5T4-A3-F405L. The results are summarized in Table 3.

None of the antibodies (except IgG1-5T4-A1-F405L itself) blocked binding of IgG1-5T4-A1-F405L to 5T4ECDHis. Antibodies IgG1-5T4-076-FEAR, IgG1-5T4-085-FEAR, IgG1-5T4-127-FEAR, IgG1-5T4-106-FEAR, IgG1-5T4-059-FEAR, IgG1-5T4-207-FEAR and IgG1-5T4-226-FEAR (as well as IgG1-5T4-H8-FEAR itself) blocked binding of IgG1-5T4-H8-FEAR to 5T4ECDHis. Antibodies IgG1-5T4-076-FEAR, IgG1-5T4-085-FEAR, and IgG1-5T4-127-FEAR (as well as IgG1-5T4-A3-F405L itself) also blocked binding of IgG1-5T4-A3-F405L to 5T4ECDHis, while antibodies IgG1-5T4-106-FEAR and IgG1-5T4-H8-FEAR did not block binding of IgG1-5T4-A3-F405L to 5T4ECDHis. Antibodies IgG1-5T4-059-FEAR, IgG1-5T4-207-FEAR and IgG1-5T4-226-FEAR showed antibody displacement in combination with IgG1-5T4-A3-F405L, which is described in more detail in Example 4.

Table 3: Antibody cross-block as determined by biolayer interferometry.

The first column shows the immobilized antibodies and the first row shows the antibodies in solution. Corrected association responses of the antibodies in solution are shown. Cross-block of antibodies is indicated by bolded and italicized font, displacing antibody combinations are indicated by an asterisk. Non-blocking antibody combinations are in normal font.

70

Example 4—Antibody Displacement of IgG1-5T4-059-FEAR, IgG1-5T4-207-FEAR and IgG1-5T4-226-FEAR in Combination with IgG1-5T4-A3-F405L Antibody displacement was demonstrated using biolayer interferometry on an Octet HTX instrument (ForteBio). IgG1-5T4-A3-F405L (20 µg/mL in 10 mM sodium acetate buffer pH 6.0, ForteBio) was immobilized on Amine-Reactive 2nd Generation (AR2G) biosensors (ForteBio) according to the manufacturer's instructions. After a baseline measurement (100 s) in Sample Diluent (ForteBio), biosensors containing immobilized IgG1-5T4-A3-F405L antibodies were loaded for 500 s with human 5T4ECDHis (mature protein of SEQ ID NO: 99) 100 nM (3.6 µg/mL). Next, the association response of a second 5T4 antibody (IgG1-5T4-059-FEAR, IgG1-5T4-207-FEAR or IgG1-5T4-226-FEAR; 10 µg/mL) or Sample Diluent (buffer control) was determined for 500 s. The experiment was performed at 30° C. using a shaker speed of 1000 rpm. Data was analyzed using Data Analysis Software v9.0.0.12 (ForteBio). The buffer control response was subtracted from the responses of the second antibodies to correct for the dissociation of human 5T4ECDHis from the immobilized IgG1-5T4-A3-F405L, the Y-axis was aligned to the association step and Savitzky-Golay filtering was applied.

Figure 1A:
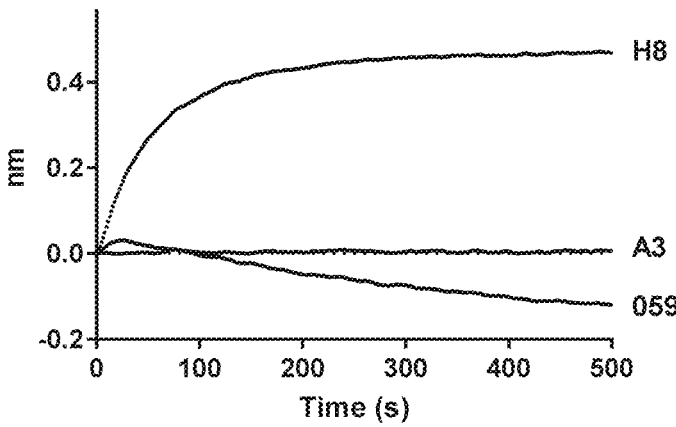
FIGS. 1A-1C: Antibody displacement of IgG1-5T4-059-FEAR, IgG1-5T4-207-FEAR and IgG1-5T4-226-FEAR in combination with IgG1-5T4-A3-F405L. Antibody displacement was determined by biolayer interferometry on an Octet HTX instrument (ForteBio). IgG1-5T4-A3-F405L was immobilized on the biosensor and loaded with human 5T4ECDHis (mature protein of SEQ ID NO. 99). Subsequently, the loaded biosensors were exposed to IgG1-5T4-A3-F405L, IgG1-5T4-H8-FEAR, IgG1-5T4-059-FEAR, IgG1-5T4-207-FEAR or IgG1-5T4-226-FEAR. The figure shows the association responses (500 s) upon exposure to the second antibodies.
Figure 1B:
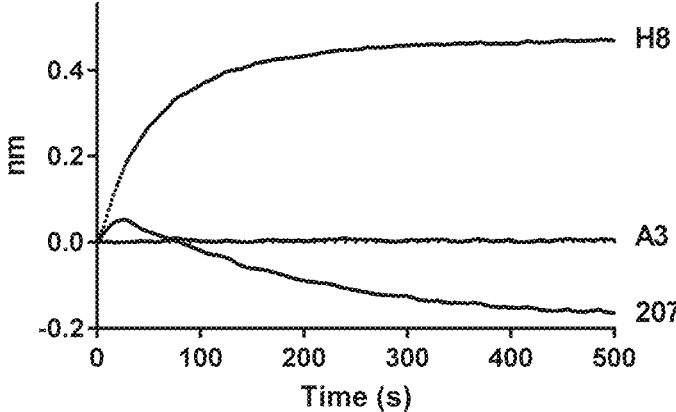
Figure 1C:
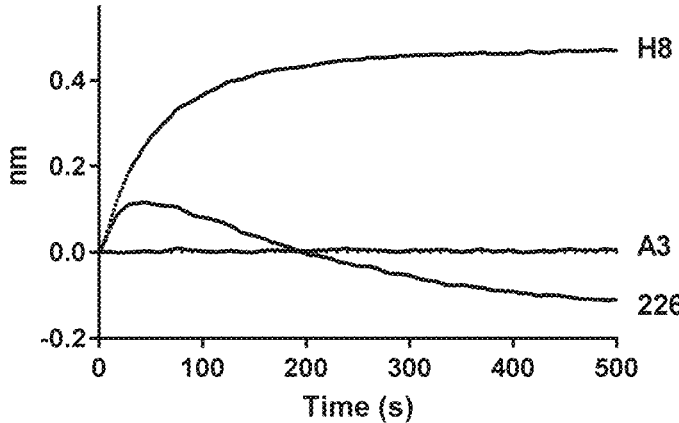

As shown in FIG. 1, IgG1-5T4-A3-F405L did not show binding, indicating cross-block (self-block) with IgG1-5T4-A3-F405L. IgG1-5T4-H8-FEAR showed binding to 5T4ECDHis and hence no cross-block with IgG1-5T4-A3-F405L. IgG1-5T4-059-FEAR, IgG1-5T4-207-FEAR and IgG1-5T4-226-FEAR initially showed a positive response (indicating binding to the IgG1-5T4-A3-F405L-5T4ECDHis complex instead of cross-blocking with IgG1-5T4-A3-F405L), followed by a decrease in response that dropped below the self-block response of IgG1-5T4-A3-F405L. This demonstrates loss of mass from the IgG1-5T4-A3-F405L-5T4ECDHis complex, indicating that IgG1-5T4-059-FEAR, IgG1-5T4-207-FEAR and IgG1-5T4-226-FEAR induce dissociation of human 5T4ECDHis from IgG1-5T4-A3-F405L upon binding to the complex. This phenomenon has been described as antibody displacement and indicates that the epitopes are closely adjacent or minimally overlapping (Abdiche Y N, Yeung A Y, Ni I, Stone D, Miles A, Morishige W, et al. (2017) Antibodies Targeting Closely Adjacent or Minimally Overlapping Epitopes Can Displace One Another. PLoS ONE 12(1): e0169535. doi:10.1371/journal.pone.0169535)). This indicates that antibodies IgG1-5T4-059-FEAR, IgG1-5T4-207-FEAR and IgG1-5T4-226-FEAR bind to a distinct epitope on 5T4 as compared to IgG1-5T4-A3-F405L.

| | A1 | A3 | 076 | 085 | 127 | 106 | H8 | 059 | 207 | 226 |
|---|---|---|---|---|---|---|---|---|---|---|
| A1 | −0.01 | 0.76 | 0.36 | 0.72 | 0.87 | 0.85 | 0.89 | 0.91 | 0.86 | 0.86 |
| A3 | 0.69 | 0.01 | 0.00 | 0.00 | 0.01 | 0.57 | 0.50 | * | * | * |
| 076 | 0.04 | 0.00 | −0.01 | −0.02 | −0.02 | −0.02 | 0.00 | −0.02 | 0.05 | 0.05 |
| 085 | 0.07 | −0.01 | −0.01 | −0.01 | 0.00 | −0.01 | −0.01 | −0.04 | 0.08 | 0.07 |
| 127 | 0.15 | −0.01 | −0.02 | −0.01 | −0.01 | −0.01 | −0.02 | −0.05 | 0.16 | 0.16 |
| 106 | 0.79 | 0.56 | −0.03 | −0.04 | −0.02 | −0.02 | −0.02 | −0.03 | −0.03 | −0.02 |
| H8 | 0.64 | 0.49 | −0.02 | −0.02 | −0.01 | −0.01 | 0.00 | −0.02 | −0.01 | −0.01 |
| 059 | 0.96 | * | 0.00 | −0.02 | −0.10 | 0.01 | 0.01 | 0.01 | 0.02 | 0.01 |
| 207 | 1.29 | * | 1.22 | 1.03 | 1.29 | −0.01 | −0.01 | −0.02 | −0.02 | −0.02 |
| 226 | 1.56 | * | 1.47 | 1.35 | 1.51 | −0.02 | −0.01 | −0.02 | −0.02 | −0.02 |

Example 5—Simultaneous Binding of 5T4
Antibodies to Membrane-Bound 5T4 Measured
with Flow Cytometry Binding of IgG1-5T4-207-FEAR and IgG1-5T4-226-FEAR antibodies to membrane-bound 5T4 in the presence of IgG1-5T4-A1-F405L and IgG1-5T4-A3-F405L was assessed by flow cytometry. IgG1-5T4-H8-FEAR, IgG1-5T4-207-FEAR and IgG1-5T4-226-FEAR were conjugated to fluorescein isothiocyanate (FITC, Thermo Fisher Scientific) according to manufacturer's instructions. SK-OV-3 cells (50,000 cells per condition), which express approximately 20,000 5T4 molecules/cell, were incubated with mixtures of 10 µg/mL unconjugated 5T4 antibodies (IgG1-5T4-H8-FEAR, IgG1-5T4-A1-F405L, IgG1-5T4-A3-F405L, IgG1-b12, IgG1-5T4-207-FEAR or IgG1-5T4-226-FEAR) and 2 µg/mL FITC-conjugated 5T4 antibodies (IgG1-5T4-H8-FEAR-FITC, IgG1-5T4-207-FEAR-FITC and IgG1-5T4-226-FEAR-FITC). Table 4 shows an overview of the tested combinations. After 30 min incubation at 4° C., cells were centrifuged at 1200 RPM for 5 min, and the supernatant was discarded. The cells were resuspended in 100 µL FACS-buffer supplemented with 1:4000 Topro-3-iodine (Molecular Probes). Mean fluorescence intensity (MFI) of the FITC signal was measured using a flow cytometer (FACS Fortessa, BD Biosciences). Percentage of binding was calculated using the following formula:

$$\frac{\{[MFI \text{ of cells } Ab - FITC \text{ and unconjugated } Ab - }{(MFI \text{ of cells with } Ab - FITC \text{ and isotype control} -}$$
$$\frac{MFI \text{ of cells without } Ab - FITC \text{ or unconjugated } Ab] * 100)}{MFI \text{ of cells without } Ab - FITC \text{ or unconjugated } Ab)}$$

Figure 2:
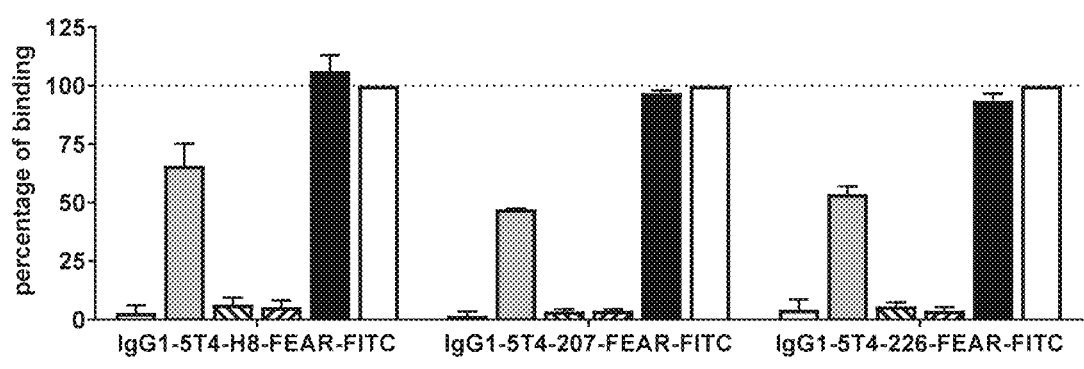
FIG. 2: Simultaneous binding of 5T4 antibodies to membrane-bound 5T4 measured with flow cytometry. 5T4 antibodies IgG1-5T4-H8-FEAR, IgG1-5T4-207-FEAR and IgG1-5T4-226-FEAR were conjugated to fluorescein isothiocyanate (FITC) and added at a concentration of 2 µg/mL to 5T4-expressing SK-OV-3 cells in presence of 10 µg/mL unconjugated IgG1-5T4-H8-FEAR, IgG1-5T4-A1-F405L, IgG1-5T4-A3-F405L, IgG1-b12, IgG1-5T4-207-FEAR or IgG1-5T4-226-FEAR. Percentage binding of FITC-labeled antibodies was calculated and depicted as mean percentage binding±standard deviation (SD).

FIG. 2 shows that binding of IgG1-5T4-H8-FEAR-FITC, IgG1-5T4-207-FEAR-FITC and IgG1-5T4-226-FEAR-FITC was blocked in presence of their unconjugated counterpart. However, binding of IgG1-5T4-207-FEAR-FITC and IgG1-5T4-226-FEAR-FITC to membrane-bound 5T4 was still observed in the presence of unconjugated IgG1-5T4-A1-F405L, IgG1-5T4-A3-F405L or IgG1-b12, and was comparable to binding of IgG1-5T4-H8-FEAR-FITC to membrane-bound 5T4 in the presence of unconjugated IgG1-5T4-A1-F405L, IgG1-5T4-A3-F405L or IgG1-b12. This demonstrates that antibodies IgG1-5T4-H8-FEAR, IgG1-5T4-207-FEAR and IgG1-5T4-226-FEAR bind to a distinct epitope on 5T4 as compared to antibodies IgG1-5T4-A1-F405L and IgG1-5T4-A3-F405L.

TABLE 4

Overview of antibody combinations used in flow cytometry experiment.

| | FITC-labeled antibody (2 µg/mL) | Unconjugated antibody (10 µg/mL) |
|---|---|---|
| 1 | IgG1-5T4-H8-FEAR-FITC | IgG1-5T4-H8-FEAR |
| 2 | IgG1-5T4-H8-FEAR-FITC | IgG1-5T4-A3-F405L |
| 3 | IgG1-5T4-H8-FEAR-FITC | IgG1-5T4-207-FEAR |
| 4 | IgG1-5T4-H8-FEAR-FITC | IgG1-5T4-226-FEAR |
| 5 | IgG1-5T4-H8-FEAR-FITC | IgG1-5T4-A1-F405L |
| 6 | IgG1-5T4-H8-FEAR-FITC | IgG1-b12 |
| 7 | IgG1-5T4-207-FEAR-FITC | IgG1-5T4-H8-FEAR |
| 8 | IgG1-5T4-207-FEAR-FITC | IgG1-5T4-A3-F405L |
| 9 | IgG1-5T4-207-FEAR-FITC | IgG1-5T4-207-FEAR |
| 10 | IgG1-5T4-207-FEAR-FITC | IgG1-5T4-226-FEAR |
| 11 | IgG1-5T4-207-FEAR-FITC | IgG1-5T4-A1-F405L |
| 12 | IgG1-5T4-207-FEAR-FITC | IgG1-b12 |
| 13 | IgG1-5T4-226-FEAR-FITC | IgG1-5T4-H8-FEAR |
| 14 | IgG1-5T4-226-FEAR-FITC | IgG1-5T4-A3-F405L |

TABLE 4-continued

Overview of antibody combinations used in flow cytometry experiment.

| | FITC-labeled antibody (2 µg/mL) | Unconjugated antibody (10 µg/mL) |
|---|---|---|
| 15 | IgG1-5T4-226-FEAR-FITC | IgG1-5T4-207-FEAR |
| 16 | IgG1-5T4-226-FEAR-FITC | IgG1-5T4-226-FEAR |
| 17 | IgG1-5T4-226-FEAR-FITC | IgG1-5T4-A1-F405L |
| 18 | IgG1-5T4-226-FEAR-FITC | IgG1-b12 |

Example 6—Binding of 5T4 Antibodies to
HEK-293 Cells Transfected with Human or
Chicken 5T4

Binding of 5T4 antibodies to HEK-293 cells transiently transfected with full length human or chicken 5T4 (generated as described in Example 1) was analyzed by flow cytometry. Cells ($5 \times 10^4$ cells/well) were incubated in polystyrene 96-well round-bottom plates (Greiner bio-one, cat. no. 650180) with serial dilutions of 5T4 antibodies (range 0.01 to 10 µg/mL in 3-fold dilution steps) in 50 µL PBS/0.1% BSA/0.02% azide (staining buffer) at 4° C. for 30 min. After washing twice in staining buffer, cells were incubated in 50 µL R-Phycoerythrin (PE)-conjugated goat-anti-human IgG F(ab')$_2$ (1:500 in staining buffer; Jackson ImmunoResearch Laboratories, Inc., West Grove, PA, cat. no. 109-116-098) at 4° C. for 30 min. Cells were washed twice in staining buffer, re-suspended in 20 µL staining buffer and analyzed on an iQue screener (Intellicyt Corporation, USA). Binding curves were analyzed by non-linear regression (sigmoidal dose-response with variable slope) using GraphPad Prism V7.02 software (GraphPad Software, San Diego, CA, USA).

Figure 3A:
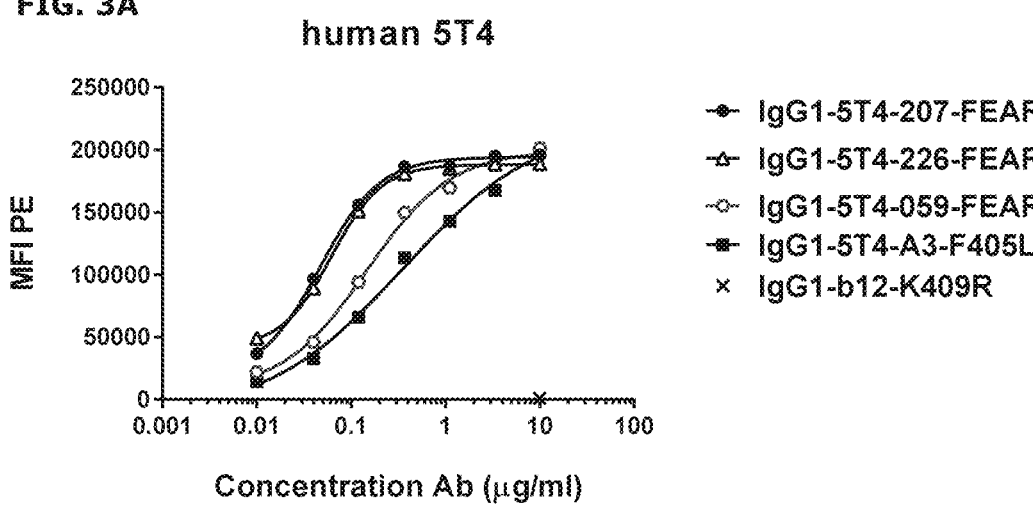
FIGS. 3A and 3B: Binding of 5T4 antibodies to HEK-293 cells transfected with full length human and chicken 5T4. HEK-293 cells transiently transfected with full length human 5T4 (SEQ ID NO: 1) (FIG. 3A) or chicken 5T4 (SEQ ID NO: 3) (FIG. 3B) were incubated with various concentrations of IgG1-5T4-A3-F405L, IgG1-5T4-059-FEAR, IgG1-5T4-207-FEAR or IgG1-5T4-226-FEAR antibodies. After incubation with R-Phycoerythrin (PE)-conjugated goat-anti-human IgG F(ab')2, the mean fluorescence intensity (MFI) was determined by flow cytometry. As negative control, IgG1-b12-K409R (10 μg/mL) was included.
Figure 3B:
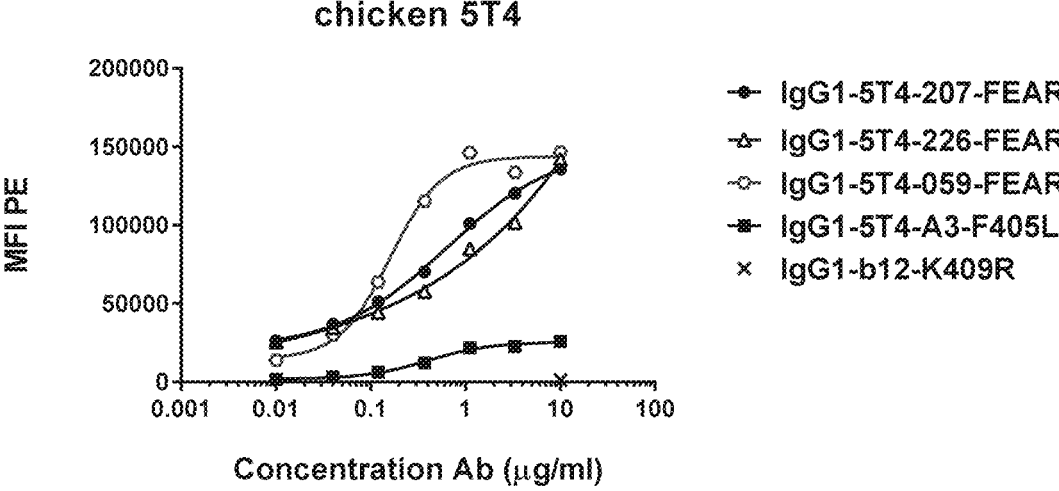

FIG. 3A shows dose-dependent binding of IgG1-5T4-207-FEAR, IgG1-5T4-226-FEAR, IgG1-5T4-059-FEAR and IgG1-5T4-A3-F405L to HEK-293 cells transfected with full length human 5T4. FIG. 3B shows that while dose-dependent binding of IgG1-5T4-207-FEAR, IgG1-5T4-226-FEAR and IgG1-5T4-059-FEAR to HEK-293 cells transfected with full length chicken 5T4 was observed, IgG1-5T4-A3-F405L showed minimal binding to HEK-293 cells transfected with full length chicken 5T4. The negative control antibody, IgG1-b12-K409R, did not show binding to HEK-293 cells transfected with full length human or chicken 5T4 at a concentration of 10 µg/mL.

Example 7—Internalization Capacity of 5T4
Antibodies in Tumor Cells

Experiments were performed to characterize the internalization capacity of monovalent 5T4 antibodies. Intracellular payload delivery and resulting cytotoxicity were used as a read out for internalization of the 5T4 antibodies upon target binding. Bispecific, toxin-conjugated antibodies that recognize 5T4 with one Fab-arm while recognizing an irrelevant antigen (HIV-1 gp120, which is not expressed on tumor cells) with the second Fab-arm, were generated by controlled Fab-arm exchange of unconjugated 5T4 antibodies with (HIV-1 gp120-specific) IgG1-b12 antibodies that had been conjugated with the microtubule-disrupting agent Duostatin-3. The resulting bispecific Duostatin-3 conjugated antibodies carry 1 toxin molecule per antibody (drug-antibody ratio 1). Serial dilutions (0.00152-10 µg/mL, 3-fold) of Duostatin-3 conjugated bispecific antibodies that monovalently bind 5T4, were added to MDA-MB-468 (mammary cancer cell line, ATCC, clone HTB-132) or HCC1954 (mammary cancer cell line, ATCC, clone CRL-2338) cells seeded in flat-bottom 96-well tissue culture plates (5,000 cells/well; Greiner-bio-one, The Netherlands, cat. no. 655180). The cells were incubated for 5 days at 37° C., after which cell viability was assessed using a CellTiter-Glo Luminescent Cell Viability Assay (Promega, USA, cat. no. G7570) according to manufacturer's instructions. Cytotoxicity curves were analyzed using non-linear regression (sigmoidal dose-response with variable slope) using GraphPad Prism V7.02 software (GraphPad Software, San Diego, CA, USA).

FIG. 4 shows the cytotoxic capacity of Duostatin-3 conjugated bispecific antibodies that monovalently bind 5T4 in MDA-MB-468 (A) or HCC1954 cells (B). BsIgG1-5T4-H8-FEARxb12-vcDuo3 was highly capable of inducing cytotoxicity, indicative of an effective internalization capacity of the antibody. In contrast, bsIgG1-5T4-076-FEARxb12-vcDuo3, bsIgG1-5T4-085-FEARxb12-vcDuo3 and bsIgG1-5T4-127-FEARxb12-vcDuo3 did not induce any cytotoxicity; dose response curves were similar to that of the non-binding IgG1-b12-vcDuo3 control antibody. This indicates poor internalization of those antibodies upon binding to membrane-bound 5T4. BsIgG1-5T4-059-FEARxb12-vcDuo3, bsIgG1-5T4-106-FEARxb12-vcDuo3, bsIgG1-5T4-207-FEARxb12-vcDuo3, and bsIgG1-5T4-226-FEARxb12-vcDuo3 induced intermediate cytotoxicity in both tested cell lines, indicating that these monovalent 5T4 antibodies induced internalization but to a lesser extent than bsIgG1-5T4-H8-FEARxb12-vcDuo3.

Example 8—Humanized CD3 Antibodies for the Generation of CD3x5T4 Bispecific Antibodies The generation of humanized antibody IgG1-huCD3-H1L1 is described in Example 1 of WO2015/001085. IgG1-huCD3-H1L1 is referred to herein as 'IgG1-huCD3'. Antibody IgG1-huCD3-H1L1-FEAL is a variant hereof with amino acid substitutions in the Fc domain that prevent interactions with IgG Fc receptors (Fc gamma receptors [FcγR]) and complement, in addition to a mutation that allows the generation of bispecific antibodies through controlled Fab-arm exchange: L234F, L235E, D265A and F405L, as described herein above. It has previously been demonstrated that these mutation have no effect on target binding of the antibodies in which they are introduced (see e.g. US 2015/0337049)

The generation of humanized antibody IgG1-huCD3-H1L1-H101G is described in Example 2 of WO2017/009442. IgG1-huCD3-H1L1-H101G will be referred to as 'IgG1-huCD3-H101G'. Antibody IgG1-huCD3-H101G-FEAL is a variant hereof with amino acid substitutions L234F, L235E, D265A and F405L, as described herein above.

Example 9—CD3 Binding Affinity Determination Using Biolayer Interferometry

Binding affinities of selected CD3 antibodies, including IgG1-huCD3 and IgG1-huCD3-H101G, were determined as described in Example 7 of WO2017/009442.

In short, binding affinities of selected CD3 antibodies in an IgG1-huCD3-FEAL format to for recombinant soluble CD3ε (CD3E27-GSKa) (mature protein of SEQ ID NO: 101) were determined using biolayer interferometry on a ForteBio Octet HTX (ForteBio). Anti-human Fc capture biosensors (ForteBio, cat. no. 18-5060) were loaded for 600 s with hIgG (1 mg/mL). After a baseline measurement (200 s), the association (1000 s) and dissociation (2000 s) of CD3E27-GSKa was determined, using a CD3E27-GSKa concentration range of 27.11 µg/mL-0.04 µg/mL (1000 nM-1.4 nM) with three-fold dilution steps (sample diluent, ForteBio, cat. no. 18-5028). For calculations, the theoretical molecular mass of CD3E27-GSKa based on the amino acid sequence was used, i.e. 27.11 kDa. Experiments were carried out while shaking at 1000 rpm and at 30° C. Each antibody was tested in at least two independent experiments. Data was analyzed with ForteBio Data Analysis Software v8.1, using the 1:1 model and a global full fit with 1000 s association time and 100 s dissociation time. Data traces were corrected by subtraction of a reference curve (antibody on biosensor, measurement with sample diluent only), the Y-axis was aligned to the last 10 s of the baseline, and interstep correction as well as Savitzky-Golay filtering was applied. Data traces with a response <0.05 nm were excluded from analysis.

Table 5 shows the association rate constant $k_a$ (1/Ms), dissociation rate constant $k_d$ (1/s) and equilibrium dissociation constant $K_D$ (M) for recombinant CD3ε determined by biolayer interferometry. IgG1-huCD3-FEAL showed a relatively high ($K_D$: 15 nM) binding affinity to recombinant CD3ε compared to IgG1-huCD3-H101G-FEAL ($K_D$: 638 nM).

TABLE 5

Binding affinities of monospecific, bivalent CD3 antibodies to recombinant CD3ε as determined by label-free biolayer interferometry

| Antibody | On-rate $k_a$ (1/Ms) | Off-rate $k_d$ (1/s) | $K_D$ (nM) |
|---|---|---|---|
| IgG1-huCD3-FEAL | 2.7E+05 | 4.0E−03 | 15 |
| IgG1-huCD3-H101G-FEAL | 3.0E+04 | 2.0E−02 | 683 |

Example 10—Generation of Bispecific Antibodies by 2-MEA-Induced Fab-Arm Exchange Bispecific antibodies were generated in vitro using the DuoBody® platform technology, i.e. 2-MEA-induced Fab-arm exchange as described in WO2011147986, WO2011131746 and WO2013060867 (Genmab) and Labrijn et al. (Labrijn et al., PNAS 2013, 110: 5145-50; Gramer et al., MAbs 2013, 5: 962-973). To enable the production of bispecific antibodies by this method, IgG1 molecules carrying a single mutation in the CH3 domain were generated: in one parental IgG1 antibody the F405L mutation (i.e. the CD3 antibodies), in the other parental IgG1 antibody the K409R mutation (i.e. the 5T4 or control, HIV-1 gp120-specific, antibodies). In addition to these mutations, the parental IgG1 antibodies included substitutions that result in a Fc domain that is unable to interact with IgG Fc receptors (Fc gamma receptors) and complement: L234F, L235E, D265A (FEA).

To generate bispecific antibodies, the two parental antibodies were mixed in equal mass amounts in PBS buffer (Phosphate Buffered Saline; 8.7 mM $HPO_4^{2-}$, 1.8 mM $H_2PO_4^-$, 163.9 mM $Na^+$, 140.3 mM $Cl^-$, pH 7.4). 2-mercaptoethylamine-HCl (2-MEA) was added to a final concentration of 75 mM and the reaction mixture was incubated at 31° C. for 5 h. The 2-MEA was removed by dialysis into PBS buffer using 10 kDa molecular-weight cutoff Slide-A-Lyzer carriages (Thermo Fisher Scientific) according to the manufacturer's protocol in order to allow re-oxidation of the inter-chain disulfide bonds and formation of intact bispecific antibodies.

The following antibodies were used in the examples:

CD3 Antibodies

IgG1-huCD3-FEAL (having the VH and VL sequences set forth in SEQ ID NO: 57 and SEQ ID NO: 60).

IgG1-huCD3-H101G-FEAL (having the VH and VL sequences set forth in SEQ ID NO: 68 and SEQ ID NO: 60)

5T4 Antibodies

IgG1-5T4-207-FEAR (having the VH and VL sequences set forth in SEQ ID NO: 40 and SEQ ID NO: 44)

IgG1-5T4-226-FEAR (having the VH and VL sequences set forth in SEQ ID NO: 47 and SEQ ID NO: 51)

IgG1-5T4-059-FEAR (having the VH and VL sequences set forth in SEQ ID NO: 5 and SEQ ID NO: 9)

IgG1-5T4-076-FEAR (having the VH and VL sequences set forth in SEQ ID NO: 12 and SEQ ID NO: 16)

IgG1-5T4-085-FEAR (having the VH and VL sequences set forth in SEQ ID NO: 19 and SEQ ID NO: 23)

IgG1-5T4-106-FEAR (having the VH and VL sequences set forth in SEQ ID NO: 26 and SEQ ID NO: 30)

IgG1-5T4-127-FEAR (having the VH and VL sequences set forth in SEQ ID NO: 33 and SEQ ID NO: 37)

IgG1-5T4-H8-FEAR (based on 5T4 antibody H8 from Wyeth (WO 2007/106744 and US2010/0173382); having the VH and VL sequences set forth in SEQ ID NO: 87 and SEQ ID NO: 88)

IgG1-5T4-A1-F405L (based on 5T4 antibody A1 from Wyeth (WO 2007/106744 and U.S. Pat. No. 8,044, 178); having the VH and VL sequences set forth in SEQ ID NO: 83 and SEQ ID NO: 84)

IgG1-5T4-A1-FEAR (based on 5T4 antibody A1 from Wyeth (WO 2007/106744 and U.S. Pat. No. 8,044, 178); having the VH and VL sequences set forth in SEQ ID NO: 83 and SEQ ID NO: 84)

IgG1-5T4-A3-F405L (based on 5T4 antibody A3 from Wyeth (WO 2007/106744 and U.S. Pat. No. 8,759, 495); having the VH and VL sequences set forth in SEQ ID NO: 85 and SEQ ID NO: 86)

IgG1-5T4-A3-FEAR (based on 5T4 antibody A3 from Wyeth (WO 2007/106744 and U.S. Pat. No. 8,759, 495); having the VH and VL sequences set forth in SEQ ID NO: 85 and SEQ ID NO: 86)

Bispecific Antibodies bsIgG1-huCD3-H101G-FEALx5T4-207-FEAR bsIgG1-huCD3-H101G-FEALx5T4-226-F EAR bsIgG1-huCD3-H101G-FEALx5T4-059-F EAR bsIgG1-huCD3-H101G-FEALx5T4-106-F EAR bsIgG1-huCD3-H101G-FEALx5T4-076-F EAR bsIgG1-huCD3-H101G-FEALx5T4-085-FEAR bsIgG1-huCD3-H101G-FEALx5T4-127-F EAR bsIgG1-huCD3-H101G-FEALx5T4-A1-F EAR bsIgG1-huCD3-H101G-FEALx5T4-A3-F EAR bsIgG1-huCD3-H101G-FEALx5T4-H8-FEAR bsIgG1-huCD3-H101G-FEALxb12-FEAR bsIgG1-huCD3-FEALx5T4-207-FEAR bsIgG1-huCD3-FEALx5T4-226-FEAR bsIgG1-huCD3-FEALx5T4-059-FEAR bsIgG1-huCD3-FEALx5T4-106-FEAR bsIgG1-huCD3-FEALx5T4-H8-FEAR bsIgG1-huCD3-FEALx5T4-A1-FEAR bsIgG1-huCD3-FEALx5T4-A3-FEAR bsIgG1-b12-FEALx5T4-207-FEAR Fluorescein Isothiocyanate (FITC)-Labeled Bispecific Antibodies bsIgG1-b12-FEALx5T4-059-FEAR-FITC bsIgG1-b12-FEALx5T4-207-FEAR-FITC bsIgG1-b12-FEALx5T4-226-FEAR-FITC bsIgG1-5T4-A1-F405Lxb12-FEAR-FITC bsIgG1-5T4-A3-F405Lxb12-FEAR-FITC Duostatin-3 Conjugated Bispecific Antibodies BsIgG1-5T4-H8-FEARxb12-vcDuo3 bsIgG1-5T4-076-FEARxb12-vcDuo3 bsIgG1-5T4-085-FEARxb12-vcDuo3 bsIgG1-5T4-127-FEARxb12-vcDuo3

BsIgG1-5T4-059-FEARxb12-vcDuo3 bsIgG1-5T4-106-FEARxb12-vcDuo3 bsIgG1-5T4-207-FEARxb12-vcDuo3 bsIgG1-5T4-226-FEARxb12-vcDuo3.

Non-Binding Control Antibodies

IgG-b12 is a HIV-1 gp120 specific antibody (Barbas, CF. J Mol Biol. 1993 Apr. 5; 230(3):812-23) that is used in some of the examples as negative, non-binding, control second arm for bispecific antibodies.

IgG1-b12-F405L is a variant hereof with the substitution F405L.

IgG1-b12-FEAL is a variant hereof with substitutions that result in a Fc domain that is unable to interact with IgG Fc receptors (Fc gamma receptors) and complement, in addition to a mutation that allows the generation of bispecific antibodies through controlled Fab-arm exchange: L234F, L235E, D265A and F405L.

IgG1-b12-K409R is a variant hereof with the substitution K409R.

IgG1-b12-FEAR is a variant hereof with substitutions that result in a Fc domain that is unable to interact with IgG Fc receptors (Fc gamma receptors) and complement, in addition to a mutation that allows the generation of bispecific antibodies through controlled Fab-arm exchange: L234F, L235E, D265A and K409R.

Example 11—Binding of CD3x5T4 Bispecific Antibodies to Cynomolgus Monkey and Human 5T4 Expressed in HEK-293 Cells Binding of bispecific, monovalent CD3x5T4 antibodies and monospecific, bivalent 5T4 antibodies to the plasma membrane of HEK-293 cells transiently transfected with human 5T4 or with cynomolgus monkey (*Macaca fascicularis*) 5T4 (generated as described in Example 1) was analyzed by flow cytometry.

Cells ($3 \times 10^4$ cells/well) were incubated in polystyrene 96-well round-bottom plates (Greiner bio-one, cat. no. 650180) with serial dilutions of antibodies (ranging from 0.0137 to 10 μg/mL in 3-fold dilution steps) in 100 μL PBS/0.1% BSA/0.02% azide (staining buffer) at 4° C. for 30 min. Experiments were performed in technical duplicate. After washing twice in staining buffer, cells were incubated in 50 μL secondary antibody at 4° C. for 30 min. As a secondary antibody, FITC-conjugated goat-anti-human IgG F(ab')$_2$ (Southern Biotech, USA, cat. no. 2043-02) diluted 1:200 in staining buffer, was used in all experiments. Cells were washed twice in staining buffer, re-suspended in 30 μL staining buffer and analyzed on an iQue Screener (Intellicyt Corporation, USA). Binding curves were analyzed using non-linear regression (sigmoidal dose-response with variable slope) using GraphPad Prism V7.02 software (GraphPad Software, San Diego, CA, USA).

FIG. 5(I) (left panels) shows that bispecific antibodies bsIgG1-huCD3-H101G-FEALx5T4-207-FEAR (A), bsIgG1-huCD3-H101G-FEALx5T4-226-FEAR (B), bsIgG1-huCD3-H101G-FEALx5T4-059-FEAR (C) and bsIgG1-huCD3-H101G-FEALx5T4-H8-FEAR (D), that monovalently bind 5T4, display dose-dependent binding to HEK-293 cells transfected with human 5T4, which was comparable to binding of monospecific, bivalent 5T4 antibodies IgG1-5T4-207-FEAR, IgG1-5T4-226-FEAR, IgG1-5T4-059-FEAR and IgG1-5T4-H8-FEAR, respectively.

FIG. 5(I) (right panels) shows the that bispecific antibodies bsIgG1-huCD3-H101G-FEALx5T4-207-FEAR (A), bsIgG1-huCD3-H101G-FEALx5T4-226-FEAR (B), and bsIgG1-huCD3-H101G-FEALx5T4-059-FEAR (C), that monovalently bind 5T4, display dose-dependent binding to HEK-293 cells transfected with cynomolgus monkey 5T4, which was comparable to binding of monospecific, bivalent 5T4 antibodies IgG1-5T4-207-FEAR, IgG1-5T4-226-FEAR and IgG1-5T4-059-FEAR, respectively. BsIgG1-huCD3-H101G-FEALx5T4-H8-FEAR and IgG1-5T4-H8-FEAR show poor binding to cynomolgus monkey 5T4, which is in line with Example 2 and experiments described in WO2007/106744. As negative control, IgG1-b12-K409R (3 µg/mL) was included in these experiments, which showed no binding to HEK-293 cells transfected with either human or cynomolgus monkey 5T4.

In a second experiment, the staining was performed as described above with minor adjustments. The cells were incubated with serial dilutions of antibodies ranging from 0.000128 to 10 µg/mL, in 5-fold dilution steps. As a secondary antibody, Phycoerythrin (PE)-conjugated goat-anti-human IgG F(ab')2 (Jackson Immunoresearch, UK, cat. no. 109-116-098) diluted 1:200 in staining buffer, was used.

FIG. 5(II) shows that antibodies bsIgG1-huCD3-H101G-FEALx5T4-207-FEAR and IgG1-5T4-207-FEAR (A), bsIgG1-huCD3-H101G-FEALx5T4-226-FEAR and IgG1-5T4-226-FEAR (B), bsIgG1-huCD3-H101G-FEALx5T4-059-FEAR and IgG1-5T4-059-FEAR (C), bsIgG1-huCD3-H101G-FEALx5T4-106-FEAR and IgG1-5T4-106-FEAR (D), bsIgG1-huCD3-H101G-FEALx5T4-076-FEAR and IgG1-5T4-076-FEAR (E), bsIgG1-huCD3-H101G-FEALx5T4-085-FEAR and IgG1-5T4-085-FEAR (F), bsIgG1-huCD3-H101G-FEALx5T4-127-FEAR and IgG1-5T4-127-FEAR (G), bsIgG1-huCD3-H101G-FEALx5T4-A1-FEAR and IgG1-5T4-A1-FEAR (H), bsIgG1-huCD3-H101G-FEALx5T4-A3-FEAR and IgG1-5T4-A3-FEAR (I) display dose-dependent binding to HEK-293 cells transfected with human 5T4 (left panels) as well as HEK-293 cells with cynomolgus monkey 5T4 (right panels). Again, the binding curves of the bivalent, monospecific and bispecific, monovalent antibodies display a similar trend between human and cynomolgus 5T4.

Example 12—Binding of CD3x5T4 Bispecific Antibodies to 5T4-Positive Human Tumor Cells Binding of CD3x5T4 bispecific antibodies to the 5T4-expressing human tumor cell lines HeLa (cervix adenocarcinoma; ATCC, cat. no. CCL-2) and MDA-MB-231 (breast adenocarcinoma; ATCC, cat. no. HTB-26) cell line was analyzed by flow cytometry. Neither HeLa nor MDA-MB-231 cells express CD3.

Cells ($3 \times 10^4$ cells/well) were incubated in polystyrene 96-well round-bottom plates (Greiner bio-one, cat. no. 650180) with serial dilutions of antibodies (range 0.000152 to 3 µg/mL in 3-fold dilution steps) in 100 µL PBS/0.1% BSA/0.02% azide (staining buffer) at 4° C. for 30 min. After washing twice in staining buffer, cells were incubated in 50 µL secondary antibody at 4° C. for 30 min. As a secondary antibody, Fluorescein isothiocyanate (FITC)-conjugated goat-anti-human IgG F(ab')₂ (Southern Biotech, USA, cat. no. 2043-02) diluted 1:400 in staining buffer, was used for the first experiment. Next, cells were washed twice in staining buffer, re-suspended in 120 µL staining buffer and analyzed on a BD LSRFortessa FACS (BD Biosciences, USA). Binding curves were analyzed using non-linear regression (sigmoidal dose-response with variable slope) using GraphPad Prism V7.02 software (GraphPad Software, San Diego, CA, USA).

FIG. 6(I) (left panels) shows that the CD3x5T4 bispecific antibodies bsIgG1-huCD3-H101G-FEALx5T4-207-FEAR (A) and bsIgG1-huCD3-H101G-FEALx5T4-059-FEAR (B) display dose-dependent binding to HeLa cells, with higher maximum binding than the monospecific, bivalent 5T4 antibodies IgG1-5T4-207-FEAR and IgG1-5T4-059-FEAR. For bsIgG1-huCD3-H101G-FEALx5T4-226-FEAR (C) the maximum binding was similar to that of the monospecific, bivalent 5T4 antibody IgG1-5T4-226-FEAR on HeLa cells.

FIG. 6(I) (right panels) shows that the CD3x5T4 bispecific antibodies bsIgG1-huCD3-H101G-FEALx5T4-207-FEAR (A), bsIgG1-huCD3-H101G-FEALx5T4-059-FEAR (B) and bsIgG1-huCD3-H101G-FEALx5T4-226-FEAR (C) display dose-dependent binding to MDA-MB-231 cells, with higher maximum binding than the monospecific, bivalent 5T4 antibodies IgG1-5T4-207-FEAR, IgG1-5T4-226-FEAR and IgG1-5T4-059-FEAR. The negative control antibody that was included in these experiments, IgG1-b12-K409R (3 µg/mL), did not show binding to HeLa and MDA-MB-231 cells.

In a second experiment, the staining was performed as described above with minor adjustments. The cells were incubated with serial dilutions of antibodies, ranging from 0.000128 to 10 µg/mL, in 5-fold dilution steps. As a secondary antibody, Phycoerythrin (PE)-conjugated goat-anti-human IgG F(ab')2 (Jackson Immunoresearch, UK, cat. no. 109-116-098) diluted 1:200 in staining buffer, was used.

FIGS. 6(II) and 6(III) show that antibodies bsIgG1-huCD3-H101G-FEALx5T4-207-FEAR and IgG1-5T4-207-FEAR, bsIgG1-huCD3-H101G-FEALx5T4-226-FEAR and IgG1-5T4-226-FEAR, bsIgG1-huCD3-H101G-FEALx5T4-059-FEAR and IgG1-5T4-059-FEAR, bsIgG1-huCD3-H101G-FEALx5T4-106-FEAR and IgG1-5T4-106-FEAR, bsIgG1-huCD3-H101G-FEALx5T4-085-FEAR and IgG1-5T4-085-FEAR, bsIgG1-huCD3-H101G-FEALx5T4-127-FEAR and IgG1-5T4-127-FEAR, bsIgG1-huCD3-H101G-FEALx5T4-A1-FEAR and IgG1-5T4-A1-FEAR, bsIgG1-huCD3-H101G-FEALx5T4-A3-FEAR and IgG1-5T4-A3-FEAR display dose-dependent binding to HeLa and MDA-MB-231 tumor cells. In general, bsIgG1-huCD3-H101G-FEALx5T4-207-FEAR, bsIgG1-huCD3-H101G-FEALx5T4-226-FEAR, bsIgG1-huCD3-H101G-FEALx5T4-059-FEAR, bsIgG1-huCD3-H101G-FEALx5T4-106-FEAR, IgG1-5T4-207-FEAR, IgG1-5T4-226-FEAR, IgG1-5T4-059-FEAR, IgG1-5T4-106-FEAR, IgG1-5T4-085-FEAR and IgG1-5T4-127-FEAR display binding at lower antibody concentrations compared to bsIgG1-huCD3-H101G-FEALx5T4-A1-FEAR, bsIgG1-huCD3-H101G-FEALx5T4-A3-FEAR, IgG1-5T4-A1-FEAR and IgG1-5T4-A3-FEAR.

Example 13—Induction of T-Cell Activation, Cytokine Release and Cytotoxicity In Vitro by CD3x5T4 Bispecific Antibodies Using Purified T Cells as Effector Cells CD3x5T4 bispecific antibodies were tested in an in vitro cytotoxicity assay using 5T4-positive tumor cell lines as target cells and purified T cells as effector cells. T cells were derived from healthy human donor buffy coats (Sanquin, Amsterdam, The Netherlands) and isolated using the RosetteSep human T cell enrichment cocktail (Stemcell Technologies, France, cat. no. 15061) according to the manufacturer's instructions. To determine the percentage of viable T cells after isolation (either total T cells, CD4$^+$ T cells or CD8$^+$ T cells), a sample of the isolated T cells (2.5×10$^5$ cells per condition) was stained for 30 min at 4° C. in a U-well 96-well plate (Cellstar, cat. no. 650180) using the following antibodies: Pacific Blue-anti-CD3 (eBiosciences, clone OKT3), APC-Cy-anti-CD4 (eBiosciences, clone OKT4), AF700-anti-CD8 (Biolegend, clone RPA-T8) and viability marker FVS 510 (BD Biosciences) in 100 μL PBS/0.1% BSA/0.02% azide (staining buffer). Next, cells were washed twice in staining buffer, re-suspended in 120 μL staining buffer and analyzed on a BD LSRFortessa FACS (BD Biosciences, USA). The percentages of CD3$^+$, CD3$^+$CD4$^+$ and CD3$^+$CD8$^+$ T cells for each of the donors used in the cytotoxicity experiment are described in Table 6.

TABLE 6

| Ratio CD3$^+$, CD4$^+$ and CD8$^+$ T cells per donor | | | |
| --- | --- | --- | --- |
| Donor | % CD3+ of viable cells | % CD4+ within CD3+ cells | % CD8+ within CD3+ cells |
| A | 91.2 | 84.2 | 11.8 |
| B | 77.8 | 78.3 | 18 |
| C | 97.6 | 78.1 | 19.6 |
| D | 92.6 | 77.3 | 15.5 |
| E | 99.2 | 78.4 | 20.3 |

MDA-MB-231 cells (16,000 cells/well) were seeded into flat bottom 96-well plates (Greiner-bio-one, The Netherlands, cat. no. 655180) and left to adhere for 4 hours at 37° C. T cells were added to tumor cells at an E:T ratio=8:1. Serial dilutions of bispecific CD3x5T4 antibodies or monospecific, bivalent 5T4 antibodies were added (final concentration ranging from 1000 to 0.0128 ng/mL; 5-fold dilutions) and plates were incubated for 72 hours at 37° C. Next, 110 μL supernatants containing T cells were transferred to U-bottom 96 Well culture plates (CellStar, cat. no. 650180). Plates were centrifuged (300×g) for 3 min at 4° C., after which 75 μL of supernatant was transferred to a new plate for cytokine production measurement, and T cells were kept to assess T cell activation markers (described below). Cytokine production induced by 0.2 μg/mL CD3x5T4 bispecific antibodies was analyzed by a multiplex U-plex assay (MeSo Scale Discovery, USA, cat. no. K15049K) according to manufacturer's instructions.

T cells were stained for T-cell markers CD3 (1:200; eBioscience, clone OKT3, conjugated to eFluor450), CD4 (1:50; eBioscience, clone OKT4, conjugated to APC-eFluor780), CD8 (1:100; Biolegend, clone RPA-T8, conjugated to AF700) and T-cell activation markers CD69 (1:50; BD Biosciences, clone AB2439, conjugated to APC), CD25 (1:50; eBioscience, clone BC96, conjugated to PE-Cy7) and CD279/PD1 (1:50; Biolegend, clone EH12.2H7, conjugated to BV605). Single stained samples with Ultracomp beads (5 μL; Invitrogen, cat. no. 01-2222-42) were used for compensation adjustments of the flow cytometer. After 30 min of incubation at 4° C., plates were washed three times with PBS/0.1% BSA/0.02% azide (staining buffer). Cells were resuspended in 120 μL staining buffer and analyzed using a FACS Fortessa (BD Biosciences). Data were processed using FlowJo (BD Biosciences).

In parallel, the viability of the tumor cells was assessed using Resazurin (7-Hydroxy-3H-phenoxazin-3-one 10-oxide). The adherent tumor cells were washed twice with PBS and incubated with 10% Resazurin (150 μL; Life Technologies, The Netherlands, cat. no. DAL1100) in RPMI-1640 (Lonza, Switzerland, cat. no. BE12-115F) medium containing 10% donor bovine serum with iron (Life Technologies, The Netherlands, cat. no. 10371-029) and pen/strep (Lonza, cat. no. DE17-603E) for 4 h at 37° C. The absorbance was measured with an Envision multilabel plate reader (PerkinElmer, US). The absorbance of staurosporine-treated (Sigma-Aldrich, US, cat. no. S6942) tumor cell samples was set as 0% viability and the absorbance of untreated tumor cell samples was set as 100% viability. The 'percentage viable cells' was calculated as follows:

% viable cells=([absorbance sample−absorbance staurosporine-treated target cells]/[absorbance untreated target cells−absorbance staurosporine treated target cells])×100.

Dose-response curves, EC50 and IC50 values were analyzed using non-linear regression (sigmoidal dose-response with variable slope) using GraphPad Prism V7.02 software (GraphPad Software, San Diego, CA, USA).

FIG. 7(I) shows that bsIgG1-huCD3-FEALx5T4-207-FEAR, bsIgG1-huCD3-H101G-FEALx5T4-207-FEAR, bsIgG1-huCD3-FEALx5T4-226-FEAR, bsIgG1-huCD3-H101G-FEALx5T4-226-FEAR, bsIgG1-huCD3-FEALx5T4-059-FEAR and bsIgG1-huCD3-H101G-FEALx5T4-059-FEAR induced dose-dependent cytotoxicity (shown as decrease in % viable cells) in the 5T4-positive tumor cell line MDA-MB-231. Donor-to-donor variation was observed, but T cells of both donors induced maximum kill in the presence of 1 μg/mL CD3x5T4 bispecific antibody. Monospecific, bivalent antibodies IgG1-5T4-207-FEAR, IgG1-5T4-226-FEAR and IgG1-5T4-059-FEAR did not induce cytotoxicity. IC$_{50}$ values calculated from the graphs are presented in FIG. 7(II). The IC$_{50}$ value of bsIgG1-huCD3-FEALx5T4-207-FEAR and bsIgG1-huCD3-FEALx5T4-059-FEAR were lower compared to bsIgG1-huCD3-H101G-FEALx5T4-207-FEAR and bsIgG1-huCD3-H101G-FEALx5T4-059-FEAR, respectively. In contrast, the IC$_{50}$ value of bsIgG1-huCD3-FEALx5T4-226-FEAR was comparable to bsIgG1-huCD3-H101G-FEALx5T4-226-FEAR.

FIG. 8(I) shows that bsIgG1-huCD3-FEALx5T4-207-FEAR, bsIgG1-huCD3-H101G-FEALx5T4-207-FEAR, bsIgG1-huCD3-FEALx5T4-226-FEAR, bsIgG1-huCD3-H101G-FEALx5T4-226-FEAR, bsIgG1-huCD3-FEALx5T4-059-FEAR, bsIgG1-huCD3-H101G-FEALx5T4-059-FEAR, bsIgG1-huCD3-FEALx5T4-106-FEAR, bsIgG1-huCD3-H101G-FEALx5T4-106-FEAR, bsIgG1-huCD3-FEALx5T4-A1-FEAR, bsIgG1-huCD3-H101G-FEALx5T4-A1-FEAR, bsIgG1-huCD3-FEALx5T4-A3-FEAR and bsIgG1-huCD3-H101G-FEALx5T4-A3-FEAR induced T-cell mediated cytotoxicity (shown as decrease in tumor cell survival) in MDA-MB-231 cell line. Bivalent, monospecific antibodies IgG1-5T4-207-FEAR, IgG1-5T4-226-FEAR, IgG1-5T4-059-FEAR, IgG1-5T4-106-FEAR, IgG1-5T4-A1-FEAR and IgG1-5T4-A3-FEAR did not induce T-cell-mediated cytotoxicity. IC50 values calculated from the graphs are presented in FIG. 8(II). IC50 values of the T-cell mediated cytotoxicity induced by bsIgG1-huCD3-FEALx5T4-207-FEAR, bsIgG1-huCD3-FEALx5T4-226-FEAR, bsIgG1-huCD3-FEALx5T4-059-FEAR and bsIgG1-huCD3-FEALx5T4-106-FEAR are lower than the IC50 values of bsIgG1-huCD3-FEALx5T4-A1-FEAR and bsIgG1-huCD3-FEALx5T4-A3-FEAR. Also, IC50 values of the T-cell mediated cytotoxicity induced by bsIgG1-huCD3-H101G-FEALx5T4-207-FEAR, bsIgG1-huCD3-H101G-

FEALx5T4-226-FEAR, bsIgG1-huCD3-H101G-FEALx5T4-059-FEAR and bsIgG1-huCD3-H101G-FEALx5T4-106-FEAR are lower than the IC50 values of bsIgG1-huCD3-H101G-FEALx5T4-A1-FEAR and bsIgG1-huCD3-H101G-FEALx5T4-A3-FEAR.

T-cell activation was determined by flow cytometry through staining for activation markers PD1, CD25 and CD69 (FIG. 9(I)). Monospecific, bivalent antibodies IgG1-5T4-207-FEAR, IgG1-5T4-226-FEAR and IgG1-5T4-059-FEAR did not induce upregulation of these T-cell activation markers, while bispecific antibodies bsIgG1-huCD3-FEALx5T4-207-FEAR, bsIgG1-huCD3-H101G-FEALx5T4-207-FEAR, bsIgG1-huCD3-FEALx5T4-226-FEAR, bsIgG1-huCD3-H101G-FEALx5T4-226-FEAR, bsIgG1-huCD3-FEALx5T4-059-FEAR and bsIgG1-huCD3-H101G-FEALx5T4-059-FEAR induced dose-dependent upregulation of PD1, CD25 and CD69. $EC_{50}$ values calculated from the graphs are represented in FIG. 9(II). The $EC_{50}$ values for upregulation of PD1, CD25 and CD69 by bsIgG1-huCD3-FEALx5T4-207-FEAR and bsIgG1-huCD3-FEALx5T4-059-FEAR were lower compared to bsIgG1-huCD3-H101G-FEALx5T4-207-FEAR and bsIgG1-huCD3-H101G-FEALx5T4-059-FEAR, respectively. The $EC_{50}$ values for upregulation of CD25 and CD69 by bsIgG1-huCD3-FEALx5T4-226-FEAR were lower compared to bsIgG1-huCD3-H101G-FEALx5T4-226-FEAR, while the $EC_{50}$ value for PD1 upregulation was comparable between bsIgG1-huCD3-FEALx5T4-226-FEAR and bsIgG1-huCD3-H101G-FEALx5T4-226-FEAR.

FIG. 10(I) shows that bsIgG1-huCD3-FEALx5T4-207-FEAR, bsIgG1-huCD3-H101G-FEALx5T4-207-FEAR, bsIgG1-huCD3-FEALx5T4-226-FEAR, bsIgG1-huCD3-H101G-FEALx5T4-226-FEAR, bsIgG1-huCD3-FEALx5T4-059-FEAR, bsIgG1-huCD3-H101G-FEALx5T4-059-FEAR, bsIgG1-huCD3-FEALx5T4-106-FEAR, bsIgG1-huCD3-H101G-FEALx5T4-106-FEAR, bsIgG1-huCD3-FEALx5T4-A1-FEAR, bsIgG1-huCD3-H101G-FEALx5T4-A1-FEAR, bsIgG1-huCD3-FEALx5T4-A3-FEAR and bsIgG1-huCD3-H101G-FEALx5T4-A3-FEAR induced T-cell activation (exemplified in FIG. 10(I) by increase in % CD69$^+$ T cells within the CD4$^+$ and CD8$^+$ T cell populations) when incubated with the MDA-MB-231 cell line, while the bivalent, monospecific antibodies IgG1-5T4-207-FEAR, IgG1-5T4-226-FEAR, IgG1-5T4-059-FEAR, IgG1-5T4-106-FEAR, IgG1-5T4-A1-FEAR and IgG1-5T4-A3-FEAR did not induce T-cell activation. EC50 values of three T-cell activation markers are shown in FIG. 10(II). In general, the EC50 values of the T-cell activation (increase in % CD69$^+$, CD25$^+$ and PD1$^+$ cells within the CD4$^+$ and CD8$^+$ T cell populations) induced by bsIgG1-huCD3-FEALx5T4-207-FEAR, bsIgG1-huCD3-FEALx5T4-226-FEAR, bsIgG1-huCD3-FEALx5T4-059-FEAR and bsIgG1-huCD3-FEALx5T4-106-FEAR are lower than the EC50 values of bsIgG1-huCD3-FEALx5T4-A1-FEAR and bsIgG1-huCD3-FEALx5T4-A3-FEAR. Also, EC50 values of T-cell activation (increase in % of CD69$^+$, CD25$^+$ and PD1$^+$ T cells within the CD4$^+$ and CD8$^+$ T cell populations) induced by bsIgG1-huCD3-H101G-FEALx5T4-207-FEAR, bsIgG1-huCD3-H101G-FEALx5T4-226-FEAR, bsIgG1-huCD3-H101G-FEALx5T4-059-FEAR and bsIgG1-huCD3-H101G-FEALx5T4-106-FEAR are lower than the EC50 values of bsIgG1-huCD3-H101G-FEALx5T4-A1-FEAR and bsIgG1-huCD3-H101G-FEALx5T4-A3-FEAR.

Production of the cytokines IL-10, IL-13 and TNF after exposure of co-cultures of T cells and MDA-MB-231 cells to 0.2 µg/mL CD3x5T4 bispecific antibodies was measured in culture supernatant, by multiplex U-plex assay. FIG. 11 shows the cytokine levels in the supernatant of T cell-tumor cell co-cultures, after incubation with bispecific antibodies. Experiments were performed using T cells from two different healthy donors; FIG. 11A shows the results from co-cultures with T cells derived from donor A, FIG. 11B shows the results from co-cultures with T cells derived donor B. Bispecific antibodies bsIgG1-huCD3-FEALx5T4-207-FEAR, bsIgG1-huCD3-H101G-FEALx5T4-207-FEAR, bsIgG1-huCD3-FEALx5T4-226-FEAR, bsIgG1-huCD3-H101G-FEALx5T4-226-FEAR, bsIgG1-huCD3-FEALx5T4-059-FEAR and bsIgG1-huCD3-H101G-FEALx5T4-059-FEAR all induced cytokine release, although the cytokine levels in T cell-tumor cell co-cultures incubated with CD3x5T4 bispecific antibodies containing a IgG1-huCD3-H101G-FEAL-derived CD3-specific Fab-arm were lower than cytokine levels in co-cultures that had been incubated with bispecific antibodies containing a IgG1-huCD3-FEAL-derived CD3-specific Fab-arm. The monospecific antibodies IgG1-5T4-207-FEAR, IgG1-5T4-226-FEAR and IgG1-5T4-059-FEAR did not induce any cytokine release.

Example 14—Induction of Cytotoxicity In Vitro by CD3x5T4 Bispecific Antibodies Using PBMCs or Purified T Cells as Effector Cells at Varying Effector to Target Ratios To determine the efficiency of the T-cell-mediated kill of bispecific antibodies bsIgG1-huCD3-H101G-FEALx5T4-207-FEAR and bsIgG1-huCD3-H101G-FEALx5T4-207-FEAR in more detail, a cytotoxicity assay was performed as described in Example 13, with varying effector to target cell (E:T) ratios. In addition, either peripheral blood mononuclear cells (PBMCs) or isolated T cells were used as effector cells. The ovarian cancer cell line SK-OV-3 (9,000 cells/well, ATCC, cat. no. HTB-77) was used as target cell line. PBMCs were isolated from 40 mL of buffy coat of human blood (Sanquin) using a Ficoll gradient (Lonza; lymphocyte separation medium, cat. no. 17-829E) according to the manufacturer's instructions. T cells were isolated as described in Example 13. For PBMCs, the following E:T ratios were used: 1:2, 1:1, 2:1, 4:1, 8:1 and 12:1. For isolated T cells, the following E:T ratios were used: 1:2, 1:1, 2:1, 4:1 and 8:1. In each experiment, effector cells from two separate donors were used. Table 7 provides an overview of the percentage of CD3$^+$, CD3$^+$CD4$^+$ and CD3$^+$CD8$^+$ T cells in the PMBC or T-cell isolates for each of the donors (determined as described in Example 13).

TABLE 7

| | Ratio CD3$^+$, CD4$^+$ and CD8$^+$ T cells per donor. | | |
| --- | --- | --- | --- |
| Donor | % CD3 with viable cell population | % CD4$^+$ within CD3$^+$ cells | % CD8$^+$ within CD3$^+$ cells |
| C (PBMCs) | 75 | 56.8 | 28.9 |
| D (PBMCs) | 60 | 63.2 | 32 |
| E (T cells) | 98.3 | 59.6 | 31.6 |
| F (T cells) | 97.2 | 70 | 26.4 |

As shown in FIG. 12, using effector cells from two different donors, E:T ratios from 4:1 to 12:1 resulted in efficient PBMC-mediated kill of the SK-OV-3 cells in the presence of bsIgG1-huCD3-FEALx5T4-207-FEAR or bsIgG1-huCD3-H101G-FEALx5T4-207-FEAR. At E:T ratios of 2:1 and lower, maximum kill of the SK-OV-3 cells was not achieved at the highest antibody concentration used (1000 ng/mL). A similar result was observed when isolated T cells were used as effector cells (FIG. 13). Using effector cells from two different donors, an E:T ratio of 4:1 and 8:1 resulted in maximum T-cell-mediated kill of the SK-OV-3 cells in the presence of bsIgG1-huCD3-FEALx5T4-207-FEAR or bsIgG1-huCD3-H101G-FEALx5T4-207-FEAR at the highest antibody concentration used (1000 ng/mL), whereas lower E:T ratios were not sufficient to induce maximum kill. The efficacy of the T-cell-mediated kill induced by bsIgG1-huCD3-FEALx5T4-207-FEAR and bsIgG1-huCD3-H101G-FEALx5T4-207-FEAR is thus dependent on a sufficiently high E:T ratio.

Example 15—Anti-Tumor Activity of CD3x5T4 Bispecific Antibodies in a Humanized Immune System Mouse Xenograft Model The in vivo anti-tumor efficacy of the CD3x5T4 bispecific antibodies bsIgG1-huCD3-FEALx5T4-207-FEAR and bsIgG1-huCD3-H101G-FEALx5T4-207-FEAR was evaluated in humanized (tail vein injected CD34+ hematopoietic stem cells [HSC] at an age of 3-4 weeks) NOD.Cg-Prkdc$^{scid}$ Il2rg$^{tm1Wjl}$/SzJ (NSG-HIS) mice (obtained from The Jackson Laboratory) that were inoculated subcutaneously with human MDA-MB-231 tumor cells. Humanization of the immune system of NSG-HIS mice was confirmed 16 weeks post-engraftment by flow cytometry. Subsequently, NSG-HIS mice were randomized in three groups (8 mice per group), based on HSC donor (#5239 or #2328) and the percentage of human CD3$^+$ T cells within the human CD45$^+$ population in peripheral blood (mean % hCD45$^+$ and % hCD3$^+$ cells respectively; 42% hCD45$^+$ and 39% hCD3$^+$ for the PBS group, 34% hCD45$^+$ and 25% hCD3$^+$ for the bsIgG1-huCD3-FEALx5T4-207-FEAR group, and 36% hCD45$^+$ and 29% hCD3$^+$ for the bsIgG1-huCD3-H101G-FEALx5T4-207-FEAR). 5×10$^6$ MDA-MB-231 cells (in 100 µL PBS) were injected subcutaneously (SC) in the flank of the mice; this was indicated as day 0 in the study. At day 14, 18, 21 and 25, the mice were injected intravenously (IV) with either 0.5 mg/kg antibody or PBS. Treatment groups are shown in Table 8. Tumor growth was evaluated twice per week (starting at day 14) using a caliper. Tumor volumes (mm$^3$) were calculated from caliper measurements as 0.52× (length)×(width)$^2$.

The results are shown in FIG. 14. FIG. 14A shows that both bsIgG1-huCD3-FEALx5T4-207-FEAR (p<0.01) and bsIgG1-huCD3-H101G-FEALx5T4-207-FEAR (p<0.05) efficiently inhibited tumor growth based on Mann-Whitney statistical analysis at day 43 compared to the control group. Furthermore, statistical analysis of the tumor-free survival curves (Kaplan Meier plot, using a tumor size <500 mm$^3$ as a cut-off) using a Mantel Cox test demonstrated that the difference in tumor-free survival was statistically different, showing increased tumor-free survival in animals treated with bsIgG1-huCD3-FEALx5T4-207-FEAR (p<0.001) or bsIgG1-huCD3-H101G-FEALx5T4-207-FEAR (p<0.001) compared to the untreated animals (FIG. 14B).

TABLE 8

Treatment groups.

| Antibody | Dose | Treatment days | Animals per group |
|---|---|---|---|
| PBS | — | 14, 18, 21, 25 | 8 |
| bsIgG1-huCD3-FEALx5T4-207-FEAR | 0.5 mg/kg | 14, 18, 21, 25 | 8 |
| bsIgG1-huCD3-H101G-FEALx5T4-207-FEAR | 0.5 mg/kg | 14, 18, 21, 25 | 8 |

Example 16. Determination of the Contribution of 5T4 Amino Acid Residues to Antibody Binding Using Alanine Scanning Library Design A human 5T4 (Uniprot ID Q13641) single residue alanine library was synthesized (GeneArt, Thermo Fisher Scientific), in which all amino acid residues in the extracellular domain of human 5T4 were individually mutated to alanine, except for positions already containing an alanine or cysteine. To minimize the chance of structural disruption of the antigen, cysteines were not mutated. The library was cloned in the pMAC expression vector containing a CMV/TK-polyA expression cassette, an Ampicillin resistance gene and a pBR322 replication origin.

Library Production and Screening

The wild type 5T4 and alanine mutants were expressed individually in FreeStyle HEK293 cells according to the manufacturer's instructions (Thermo Fisher Scientific, cat. no. 12347-019). One day post transfection, the cells were harvested. Approximately 80,000 cells were incubated with 20 µL FITC-conjugated antibody (3 µg/mL; in FACS buffer (PBS [Lonza, cat. no. BE17-517]+0.1% [w/v] BSA [Roche, cat. no. 10735086001]+0.02% [w/v] sodium azide [NaN$_3$; EMELCA Bioscience, cat. no. 41920044-3]); Table 9) at room temperature for 40 min. Subsequently, cells were washed twice by centrifugation using 150-180 µL FACS buffer. Cells were resuspended in 30 µL FACS buffer and stored at 4° C. until analysis by flow cytometry using an iQue screener (Intellicyt Corporation).

The entire experiment was performed twice yielding duplicate measurements.

Table 9: Antibodies used in determination of the contribution of 5T4 amino acid residues in antibody binding using alanine scanning. Antibodies monovalently binding to 5T4 were labeled with FITC (Thermo Fisher Scientific, cat. no. 46425), prior to performing the experiment. IgG1-5T4-A1-F405L and IgG1-5T4-A3-F405L are surrogate A1 and A3 antibodies, respectively, that were cloned into the human IgG1 backbone containing the F405L mutations. Hence, the surrogate A1 antibody has a variable region identical to that of the A1 antibody disclosed in WO2007106744. Likewise, the A3 surrogate antibody has a variable region identical to that of the A3 antibody disclosed in WO2007106744. In both antibodies, the Fc domain carries the F405L substitution.

| Antibody | Test or control antibody |
|---|---|
| bsIgG1-b12-FEALx5T4-059-FEAR-FITC | Test antibody |
| bsIgG1-b12-FEALx5T4-207-FEAR-FITC | Test antibody |
| bsIgG1-b12-FEALx5T4-226-FEAR-FITC | Test antibody |
| bsIgG1-5T4-A3-F405Lxb12-FEAR-FITC | Test antibody |

-continued

| Antibody | Test or control antibody |
|---|---|
| bsIgG1-5T4-A1-F405Lxb12-FEAR-FITC | Control antibody used for normalization |

Data Analysis

For every sample, the average amount of antibody bound per cell was determined as the geometric mean of the fluorescence intensity (gMFI) for the viable, single cell population. The gMFI is influenced by the affinity of the antibody for the 5T4 mutant and the expression level of the 5T4 mutant per cell. Since specific alanine mutations can impact the surface expression level of the mutant 5T4, and to correct for expression differences for each 5T4 mutant in general, data for each test antibody were normalized against the binding intensity of a non-cross blocking 5T4-specific control antibody, using the following equation:

$$\text{Normalized } gMFI_{aa\,position} = \text{Log}_{10}\left(\frac{gMFI_{Test\,Ab}}{gMFI_{Control\,Ab}}\right)$$

In which 'aa position' refers to the position that was mutated into an alanine; and the Z-score was calculated to express loss or gain of binding of the antibodies, according to the following calculation:

$$Z-\text{score(fold change)} = \frac{\text{Normalized } gMFI_{aa\,position} - \mu}{\sigma}$$

Where $\mu$ and $\alpha$ are the mean and standard deviation of the Normalized gMFI calculated from all mutants.

If the gMFI of the control antibody for a particular 5T4 mutant was lower than the mean gMFIControl Ab—2.5×SD of the mean gMFIControl Ab (from all mutants), data were excluded from analysis (it was assumed that expression levels for those 5T4 mutants were not sufficient to draw conclusions). This was the case for amino acid W at position 296 (SEQ ID NO: 1).

Results

FIG. 15 shows the binding results of the tested antibodies to human 5T4 variants with single alanine mutations in the ECD: positions 32 to 355 (according to SEQ ID NO: 1). The results indicate that antibody bsIgG1-b12-FEALx5T4-059-FEAR-FITC showed loss of binding when aa R at position 73, T at position 74, Y at position 92, R at position 94, N at position 95 or F at position 138 of human 5T4 were mutated to an alanine. This suggests that binding of antibody IgG1-5T4-059-04-FEAR is at least dependent on aa R73, T74, Y92, R94, N95, F138 of human 5T4 (SEQ ID NO: 1), antibody bsIgG1-b12-FEALx5T4-207-FEAR-FITC showed loss of binding when aa S at position 69, R at position 73, Y at position 92, R at position 94, F at position 111, F at position 138, D at position 148 of human 5T4 were mutated to an alanine. This suggests that binding of antibody IgG1-5T4-207-FEAR is at least dependent on aa S69, R73, Y92, R94, F111, F138 and D148 of human 5T4 (SEQ ID NO: 1),antibody bsIgG1-b12-FEALx5T4-226-FEAR-FITC showed loss of binding when aa R at position 73, Y at position 92, R at position 94, F at position 111, F at position 138, L at position 144 or D at position 148 of human 5T4 were mutated to an alanine. This suggests that binding of antibody IgG1-5T4-226-FEAR is at least dependent on aa R73, Y92, R94, F111, F138, L144 and D148 of human 5T4 (SEQ ID NO: 1), antibody bsIgG1-5T4-A3-F405Lxb12-FEAR-FITC showed loss of binding when aa D at position 60, Q at position 61, D at position 88, L at position 89, Y at position 92, F at position 111, P at position 115, L at position 117, F at position 138, D at position 148 or N at position 152 of human 5T4 were mutated to an alanine. This suggests that binding of antibody IgG1-5T4-A3-FEAR is at least dependent on aa D60, Q61, D88, L89, Y92, F111, P115, L117, F138, D148 and N152 of human 5T4 (SEQ ID NO: 1).

Some amino acids might be indirectly involved in binding. For example, mutating a hydrophobic residue to alanine might impact the local folding and affect the positioning of directly interacting residues (Zhao et al., 2014 Structure 22, 612-620). Based on structural data (human 5T4 crystal structure 4 cnm; RCSB protein databank) the following residues are buried and therefore expected to indirectly contribute to binding to:

antibody bsIgG1-b12-FEALx5T4-059-04-FEAR-FITC: F138, antibody bsIgG1-b12-FEALx5T4-207-FEAR-FITC: F111, F138, D148, antibody bsIgG1-b12-FEALx5T4-226-FEAR-FITC: F111, F138, L144, D148, antibody bsIgG1-5T4-A3-F405Lxb12-FEAR-FITC: L89, F111, L117, F138, D148, N152.

Since only surface-exposed residues can directly interact with the antibody, the following residues are expected to directly interact with:

antibody bsIgG1-b12-FEALx5T4-059-FEAR-FITC: R73, T74, Y92, R94 and N95, antibody bsIgG1-b12-FEALx5T4-207-FEAR-FITC: S69, R73, Y92 and R94, antibody bsIgG1-b12-FEALx5T4-226-FEAR-FITC: R73, Y92 and R94, antibody bsIgG1-5T4-A3-F405Lxb12-FEAR-FITC: D60, Q61, D88, Y92 and P115.

Together, these results propose that antibodies IgG1-5T4-059, IgG1-5T4-207 and IgG1-5T4-226 all bind by direct interaction with amino acid residues R73, Y92 and R94. The results also indicate that antibodies IgG1-5T4-059, IgG1-5T4-207 and IgG1-5T4-226 each bind to a epitope which is different from but partially overlapping with the epitope bound by IgG1-5T4-A3. This is in line with the displacement behavior described in Example 3 and 4.

Example 17: Induction of T-Cell Activation and Cytotoxicity by CD3x5T4 Bispecific Antibodies in Cell Lines of Different Indications In Vitro CD3x5T4 bispecific antibodies were tested in an in vitro cytotoxicity assay using tumor cell lines of pancreas and cervical cancer as target cells and purified T cells as effector cells. For each indication (pancreas cancer and cervical cancer) two representative cell lines were selected. The tumor cell lines used in the in vitro cytotoxicity assay are summarized in Table 10. T cells were derived from human donor buffy coats (Sanquin, Amsterdam, The Netherlands) and isolated using the RosetteSep human T cell enrichment cocktail (Stemcell Technologies, France, cat. no. 15061) according to manufacturer's instructions. For each cell line, at least three different donors were tested in the in vitro cytotoxicity assay and T-cell activation analysis, as summarized in Table 10.

TABLE 10

| Tumor cell lines used for in vitro cytotoxicity assay | | | | |
|---|---|---|---|---|
| Tumor cell line | Indication | ATCC clone no. | cytotox (n) | T-cell activation (n) |
| BxPC-3 | Pancreas | CRL-1687 | 3 | 3 |
| PANC-1 | Pancreas | CRL-1469 | 9 | 4 |
| Ca Ski | Cervical | CRL-1550 | 5 | 3 |
| SiHa | Cervical | HTB-35 | 3 | 3 |

Tumor cells (16,000 cells/well) were seeded into flat-bottom 96-well plates (Greiner Bio-One, The Netherlands, cat. no. 655180) and left to adhere at 37° C. for 4 h. T cells were added to tumor cells at an E:T ratio=4:1. Serial dilutions of bsIgG1-huCD3-H101G-FEALx5T4-207-FEAR or control antibodies (bsIgG1-huCD3-H101G-FEALxb12-FEAR, bsIgG1-b12-FEALx5T4-207-FEAR) were added (final concentration ranging from 5000 to 0.0128 ng/mL; 5-fold dilutions) and plates were incubated at 37° C. for 72 h. Next, 110 µL supernatants containing T cells were transferred to round-bottom 96-well culture plates (CellStar, cat. no. 650180) and centrifuged (300×g) at 4° C. for 3 min. T cells were stained for T-cell markers by incubation with CD3-eFluor450 (1:200; eBioscience, clone OKT3), CD4-APC-eFluor780 (1:50; eBioscience, clone OKT4), CD8-AF700 (1:100; Biolegend, clone RPA-T8) and T-cell activation markers CD69-APC (1:50; BD Biosciences, clone AB2439), CD25-PE-Cy7 (1:50; eBioscience, clone BC96) and CD279/PD1-BV605 (1:50; Biolegend, clone EH12.2H7) diluted in 50 µL PBS/0.1% BSA/0.02% azide (staining buffer). Single stained samples with Ultracomp beads (5 µL; Invitrogen, cat. no. 01-2222-42) were used for compensation adjustments of the flow cytometer. After 30 min of incubation at 4° C., plates were washed three times with staining buffer. Cells were resuspended in 120 µL staining buffer and analyzed using a FACS Fortessa (BD Biosciences). Data were processed using FlowJo (version 10, BD Biosciences).

In parallel, the viability of the tumor cells was assessed using Resazurin (7-Hydroxy-3H-phenoxazin-3-one 10-oxide). The adherent tumor cells were washed twice with PBS and incubated with 10% Resazurin (150 µL; Life Technologies, The Netherlands, cat. no. DAL1100) in RPMI-1640 medium (Lonza, Switzerland, cat. no. BE12-115F) supplemented with 10% donor bovine serum with iron (Life Technologies, The Netherlands, cat. no. 10371-029) and pen/strep (Lonza, cat. no. DE17-603E) at 37° C. for 4 h. The absorbance was measured with an Envision multilabel plate reader (PerkinElmer, US). The absorbance of staurosporine-treated (Sigma-Aldrich, US, cat. no. S6942) cells were set as 0% viability and the absorbance of untreated cells were set as 100% viability. The 'percentage viable cells' was calculated as follows:

% viable cells=([absorbance sample−absorbance staurosporine-treated target cells]/[absorbance untreated target cells−absorbance staurosporine treated target cells])×100.

Cytotoxicity curves, T-cell activation curves, IC50 (cytotoxicity) and EC50 (T-cell activation) values were analyzed using non-linear regression (sigmoidal dose-response with variable slope) using GraphPad Prism V7.02 software (GraphPad Software, San Diego, CA, USA).

FIG. 16(I) shows that bsIgG1-huCD3-H101G-FEALx5T4-207-FEAR induced cytotoxicity in a range of cell lines of different indications, while the control bispecific antibodies (bsIgG1-huCD3-H101G-FEALxb12-FEAR, bsIgG1-b12-FEALx5T4-207-FEAR) targeting only the tumor cells or the T cells did not show any cytotoxicity. FIG. 16(II) shows the mean IC$_{50}$ values for each of the cell lines tested with different donors (at least n=3). FIG. 17(I) shows the T-cell activation induced by bsIgG1-huCD3-H101G-FEALx5T4-207-FEAR in a range of cell lines of different indications as measured by the upregulation of CD69 on CD4$^+$ and CD8$^+$ T cells (% of CD69$^+$ cells within the CD4$^+$ or CD8$^+$ population).

The control bispecific antibodies (bsIgG1-huCD3-H101G-FEALxb12-FEAR, bsIgG1-b12-FEALx5T4-207-FEAR) targeting only the tumor cells or the T cells, did not induce any T-cell activation. FIG. 17(II) shows the mean EC$_{50}$ values for each of the cell lines tested with different donors (at least n=3).

These data indicate that bsIgG1-huCD3-H101G-FEALx5T4-207-FEAR can specifically induce T-cell mediated cytotoxicity and T-cell activation in pancreas and cervical cancer, while control bispecific antibodies bsIgG1-huCD3-H101G-FEALxb12-FEAR and bsIgG1-b12-FEALx5T4-207-FEAR do not induce T-cell activation and T-cell mediated cytotoxicity.

Example 18: Binding of a CD3x5T4 Bispecific Antibody to Esophageal, Squamous Non-Small Cell Lung and Squamous Head and Neck Tumor Cells Binding of a CD3x5T4 bispecific antibody to the esophageal, squamous non-small cell lung (NSCL) and squamous head and neck tumor cells (see Table 11) was analyzed by flow cytometry. These cell lines were confirmed to express 5T4, but are negative for CD3 expression.

TABLE 11

| Tumor cell lines | | | |
|---|---|---|---|
| Tumor cell line | Indication | Vendor | clone no. |
| Fadu | head and neck, squamous | ATCC | HTB-43 |
| SCC-9 | head and neck, squamous | ATCC | CRL-1629 |
| EPLC-272H | NSCLC, squamous | DSMZ | ACC 383 |
| NCI-H292 | NSCLC, squamous | ATCC | CRL-1848 |
| OE33 | Esophageal cancer | Sigma-Aldrich | 96070808 |
| SK-GT-4 | Esophageal cancer | Sigma-Aldrich | 11012007 |

Adherent tumor cells were harvested by trypsinization (Trypsin-ethylendiaminetetraacetic acid [EDTA, 0.5%], Gibco, cat. no. 15400-054) at 37° C. for 3-10 min. Cells were washed and resuspended in assay medium (RPMI-1640 medium [Lonza] containing 10% DBSI [Life Technologies] and Pen/Strep) at 1×10$^6$ cells/mL, seeded (50 µL; 30,000-50,000 cells/well) in round-bottom 96-well plates (Greiner Bio-One, cat. no. 650180) and centrifuged at 300× g, 4° C. for 3 min. After removal of supernatant, the cells were washed once in FACS buffer and incubated with 50 µL bsIgG1-huCD3-H101G-FEALx5T4-207-FEAR or bsIgG1-huCD3-H101G-FEALxb12-FEAR (final concentrations of 1.28 x10$^{-4}$-10 µg/mL, in 5-fold dilution steps) and incubated at 4° C. for 30 min. Cells were washed twice in FACS buffer and incubated with 50 µL secondary antibody R-PE-conjugated goat-anti-human IgG F(ab')$^2$ (diluted 1:500 in FACS buffer; Jackson ImmunoResearch) at 4° C. protected from light for 30 min. Cells were washed in FACS buffer, resuspended in 20 µL FACS buffer and measured on an iQue screener (Intellicyt Corporation, ForeCyt® Enterprise Client Edition 6.2 (R3), Version 6.2.652). Binding curves were analyzed using non-linear regression analysis (sigmoidal dose-response with variable slope) using GraphPad Prism software.

FIG. 18 shows that bispecific antibody bsIgG1-huCD3-H101G-FEALx5T4-207-FEAR displays dose-dependent binding to squamous head and neck FaDu (A) and SCC-9 (B) tumor cells. FIG. 19 shows that bispecific antibody bsIgG1-huCD3-H101G-FEALx5T4-207-FEAR displays dose-dependent binding to squamous NSCL EPLC-272H (A) and NCI-H292 (B) tumor cells. FIG. 20 shows that bispecific antibody bsIgG1-huCD3-H101G-FEALx5T4-207-FEAR displays dose-dependent binding to esophageal OE33 (A) and SK-GT-4 (B) tumor cells. Control antibody bsIgG1-huCD3-H101G-FEALxb12-FEAR that recognizes CD3 but not 5T4, does not bind to any of these cell lines, indicating that binding of bsIgG1-huCD3-H101G-FEALx5T4-207-FEAR was driven by monovalent binding of the 5T4-specific Fab-arm.

Example 19: Induction of T-Cell Activation and Cytotoxicity by a CD3x5T4 Bispecific Antibody in an Esophageal Cancer Cell Line In Vitro A CD3x5T4 bispecific antibody was tested in an in vitro cytotoxicity assay using SK-GT-4 (Sigma-Aldrich, cat. no. 11012007) esophageal cancer cells as 5T4-expressing target cells and purified T cells as effector cells (effector: target cell ratio=4:1). T cells were derived from human healthy donor buffy coats (Sanquin, Amsterdam, The Netherlands) and isolated using the RosetteSep human T cell enrichment cocktail (Stemcell Technologies, France, cat. no. 15061) according to manufacturer's instructions. T cells from three different donors were tested in the in vitro T-cell-mediated cytotoxicity assay, T-cell activation analysis, cytokine release and production of granzyme B and perforin Tumor cells (16,000 cells/well) were seeded into flat-bottom 96-well plates (Greiner Bio-One, The Netherlands, cat. no. 655180) and left to adhere at 37° C. for 4 h. T cells were added to tumor cells at an effector: target cell (E:T) ratio=4:1. Serial dilutions of bsIgG1-huCD3-H101G-FEALx5T4-207-FEAR or control antibodies (bsIgG1-huCD3-H101G-FEALxb12-FEAR [that recognize CD3 but not 5T4], bsIgG1-b12-FEALx5T4-207-FEAR [that recognize 5T4 but not CD3]) were added (final concentration ranging from 5000 to 0.0128 ng/mL; 5-fold dilutions) and plates were incubated at 37° C. for 72 h. As a positive control for cytotoxicity, cells were incubated with 16 µg/mL phenylarsine oxide (PAO; Sigma-Aldrich, cat. no. P3075; dissolved in dimethylsulfoxide [DMSO; Sigma-Adrich, cat. no. D2438]). After 72 h, 110 µL supernatants containing T cells were transferred to round-bottom 96-well culture plates (CellStar, cat. no. 650180) and centrifuged (300×g) at 4° C. for 3 min. Adherent cells were kept for quantification of tumor cell viability, as described below. T cells in the pellet were stained for T-cell markers by incubation with CD3-eFluor450 (1:200; eBioscience, clone OKT3), CD4-APC-eFluor780 (1:50; eBioscience, clone OKT4), CD8-AF700 (1:100; Biolegend, clone RPA-T8) and T-cell activation markers CD69-APC (1:50; BD Biosciences, clone AB2439), CD25-PE-Cy7 (1:50; eBioscience, clone BC96) and CD279/PD1-BV605 (1:50; Biolegend, clone EH12.2H7) diluted in 50 µL PBS/0.1% BSA/0.02% azide (staining buffer). Single stained samples with Ultracomp beads (5 µL; Invitrogen, cat. no. 01-2222-42) were used for compensation adjustments of the flow cytometer. After 30 min of incubation at 4° C., plates were washed three times with staining buffer. Cells were resuspended in 120 µL staining buffer and analyzed using a FACS Fortessa (BD Biosciences). Data were processed using FlowJo (version 10, BD Biosciences).

The supernatants derived from the T-cell mediated cytotoxicity assay were used for the measurement of cytokine, granzyme B and perforin production by activated T cells. The cytokine production was analyzed by a multiplex U-plex assay (MeSo Scale Discovery, cat. no. K15049K), measuring IFN-γ, TNF-α, IL-1β, IL-2, IL-4, IL-6, IL-8, IL-10, IL-12p70 and IL-13, essentially according to manufacturer's instructions, with the small adaptation that the initially dissolved calibrator standards were not pre-diluted five times before generation of the standard curve (as recommended by the manufacturer).

Perforin release in cell culture supernatant was analyzed using the human Perforin ELISA development kit (MabTech, cat. No. 3465-1H-6), according to manufacturer's instructions. In short, a 96-well flat bottom MICRO-LON® 600 ELISA plate (Greiner BioOne, cat no. 655092) was coated with capture antibody (50 µL/well, 4 µg/mL mAb Pf-80/164, diluted in PBS [Hyclone GE Healthcare, cat no. SH3A3830.03]) at 4-8° C., while shaking (300 RPM), O/N. After washing twice with PBS (200 µL/well), the wells were blocked with 100 µL incubation buffer (PBS supplemented with 0.1% BSA [Roche, cat. no. 10735086001] and 0.05% Tween 20 [Sigma Aldrich, cat no. P1379-1L]) at RT, while shaking (300 RPM), for 1 h. After washing three times with washing buffer (PBS supplemented with 0.05% Tween 20), 50 µL of standard (0-2500 µg/mL diluted in incubation buffer, using two-fold dilution steps) or samples (supernatant, diluted 1:2 or 1:10 in incubation buffer, see Table 12) were added to the wells and incubated at RT, while shaking (300 RPM), for 2 h. After washing three times with washing buffer, the wells were incubated with 50 µL detection antibody (1 µg/mL Ab Pf-344-biotin, diluted in incubation buffer) incubated at RT, while shaking (300 RPM), for 1 h. Again, the plates were washed three times with washing buffer, and the wells were incubated with 50 µL streptavidin-HRP solution (1:1000 dilution in incubation buffer; MabTech, cat no. 3310-9) at RT while shaking (300 RPM) for 1 h, followed by washing as described above. Next, 50 µL of 1-Step Ultra TMB-ELISA (Thermo Scientific, cat no. 34028) substrate solution was added to the wells and incubated at RT, while shaking (300 RPM), protected from light, for 30 min. The reaction was stopped by adding 25 µL of 1 M sulfuric acid (H$_2$SO$_4$; VWR Chemicals, cat no. 30149.291) and absorbance was measured at 450 nm at an ELISA plate reader (Biotel EL808 ELISA Reader, Biotek Instruments).

Granzyme B release in the cell culture supernatants was analyzed using the human Granzyme B DuoSet ELISA kit (R&D Systems, cat. no. DY2906-5), according to manufacturer's instructions. In short, the protocol was similar as described above for the perforin ELISA, but with minor adaptations. The capture antibody (800 ng/mL) was diluted in PBS, while the samples (diluted 1:10 or 1:500 in incubation buffer, see Table 12) and standards (0-2500 µg/mL, 2-step dilutions) were diluted in incubation buffer. Streptavidin-HRP solution (diluted 1:40; R&D Systems, cat no. 893975) and the detection antibody (50 ng/mL) were diluted in reagent diluent (PBS supplemented with 1% BSA and filter-sterilized through a 0.2 m filter). In addition, the wells were blocked in 150 µL reagent diluent

TABLE 12

Supernatant dilutions used for granzyme B and perforin ELISAs

| Cell line | Donor | Selected dilution supernatant used for analysis of granzyme B ELISA (tested 1:10 or 1:500) | Selected dilution supernatant used for analysis of perforin ELISA (tested 1:2 or 1:10) |
|---|---|---|---|
| SK-GT-4 | 1 | *Combined | 1:2 |
| | 2 | *Combined | *Combined |
| | 3 | *Combined | 1:2 |

*Combined = a combination of the data of two dilutions was used for calculating the concentration of granzyme B or perforin.

In parallel, the viability of the adherent tumor cells was assessed using Resazurin (7-Hydroxy-3H-phenoxazin-3-one 10-oxide). The adherent tumor cells were washed twice with PBS and incubated with 10% Resazurin (150 μL; Life Technologies, The Netherlands, cat. no. DAL1100) in RPMI-1640 medium (Lonza, Switzerland, cat. no. BE12-115F) supplemented with 10% donor bovine serum with iron (Life Technologies, The Netherlands, cat. no. 10371-029) and pen/strep (Lonza, cat. no. DE17-603E) at 37° C. for 4 h. The absorbance was measured with an Envision multilabel plate reader (PerkinElmer, US). The absorbance of PAO-treated (Sigma-Aldrich, US, cat. no. S6942) cells were set as 0% viability and the absorbance of untreated cells were set as 100% viability. The 'percentage viable cells' was calculated as follows:

Percentage tumor cell viability=([absorbance sample–absorbance PAO-treated target cells]/ [absorbance untreated target cells–absorbance PAO-treated target cells])×100.

Dose-response curves for tumor cell viability (cytotoxicity), T-cell activation, cytokine production, granzyme B and perforin release and were generated using non-linear regression (sigmoidal dose-response with variable slope) using GraphPad Prism V7.02 software (GraphPad Software, San Diego, CA, USA).

FIG. 21 shows that bsIgG1-huCD3-H101G-FEALx5T4-207-FEAR induced T-cell mediated cytotoxicity and T-cell activation in SK-GT-4 esophageal cancer cells, while the control bispecific antibodies (bsIgG1-huCD3-H101G-FE-ALxb12-FEAR, bsIgG1-b12-FEALx5T4-207-FEAR) targeting only the tumor cells or the T cells did not induce any cytotoxicity or T-cell activation. T-cell activation is measured by the upregulation of CD69 on CD4+ and CD8+ T cells (% of CD69+ cells within the CD4+ or CD8+ population). FIG. 22 shows the cytokine production induced by incubating SK-GT-4 esophageal cancer cells and bsIgG1-huCD3-H101G-FEALx5T4-207-FEAR with T cells derived from three different donors. FIG. 23 shows the granzyme B and perforin released by T cells induced by incubating SK-GT-4 esophageal cancer cells and bsIgG1-huCD3-H101G-FEALx5T4-207-FEAR with T cells derived from three different donors.

These data indicate that bsIgG1-huCD3-H101G-FEALx5T4-207-FEAR can specifically and dose-dependently induce T-cell mediated cytotoxicity, T-cell activation, cytokine production, granzyme B and perforin release in an esophageal cancer cell line.

Example 20: Induction of T-Cell Activation and Cytotoxicity by a CD3x5T4 Bispecific Antibody in Squamous Non-Small Cell Lung Cancer Cell Lines In Vitro A CD3x5T4 bispecific antibody was tested in an in vitro cytotoxicity assay using EPLC-272H (DSMZ, cat. no. ACC 383) and NCI-H292 (ATCC, cat. no. CRL-1848) squamous non-small cell lung (NSCL) cancer cells as 5T4-expressing target cells and purified T cells as effector cells (effector: target cell ratio=4:1). T cells were derived from human healthy donor buffy coats (Sanquin, Amsterdam, The Netherlands) and isolated using the RosetteSep human T cell enrichment cocktail (Stemcell Technologies, France, cat. no. 15061) according to manufacturer's instructions. T cells from three different donors were tested in the in vitro T-cell-mediated cytotoxicity assay, T-cell activation analysis, cytokine release and production of granzyme B and perforin Tumor cells (16,000 cells/well) were seeded into flat-bottom 96-well plates (Greiner Bio-One, The Netherlands, cat. no. 655180) and left to adhere at 37° C. for 4 h. T cells were added to tumor cells at an effector: target cell (E:T) ratio=4:1. Serial dilutions of bsIgG1-huCD3-H101G-FEALx5T4-207-FEAR or control antibodies (bsIgG1-huCD3-H101G-FEALxb12-FEAR [that recognize CD3 but not 5T4], bsIgG1-b12-FEALx5T4-207-FEAR [that recognize 5T4 but not CD3]) were added (final concentration ranging from 5000 to 0.0128 ng/mL; 5-fold dilutions) and plates were incubated at 37° C. for 72 h. As a positive control for cytotoxicity, cells were incubated with 16 μg/mL phenylarsine oxide (PAO; Sigma-Aldrich, cat. no. P3075; dissolved in dimethylsulfoxide [DMSO; Sigma-Adrich, cat. no. D2438]). After 72 h, 110 μL supernatants containing T cells were transferred to round-bottom 96-well culture plates (CellStar, cat. no. 650180) and centrifuged (300×g) at 4° C. for 3 min. Adherent cells were kept for quantification of tumor cell viability, as described below. T cells in the pellet were stained for T-cell markers by incubation with CD3-eFluor450 (1:200; eBioscience, clone OKT3), CD4-APC-eFluor780 (1:50; eBioscience, clone OKT4), CD8-AF700 (1:100; Biolegend, clone RPA-T8) and T-cell activation markers CD69-APC (1:50; BD Biosciences, clone AB2439), CD25-PE-Cy7 (1:50; eBioscience, clone BC96) and CD279/PD1-BV605 (1:50; Biolegend, clone EH12.2H7) diluted in 50 μL PBS/0.1% BSA/0.02% azide (staining buffer). Single stained samples with Ultracomp beads (5 μL; Invitrogen, cat. no. 01-2222-42) were used for compensation adjustments of the flow cytometer. After 30 min of incubation at 4° C., plates were washed three times with staining buffer. Cells were resuspended in 120 μL staining buffer and analyzed using a FACS Fortessa (BD Biosciences). Data were processed using FlowJo (version 10, BD Biosciences).

The supernatants derived from the T-cell mediated cytotoxicity assay were used for the measurement of cytokine, granzyme B and perforin production by activated T cells. The cytokine production was analyzed by a multiplex U-plex assay (MeSo Scale Discovery, cat. no. K15049K), measuring IFN-γ, TNF-α, IL-1β, IL-2, IL-4, IL-6, IL-8, IL-10, IL-12p70 and IL-13, essentially according to manufacturer's instructions, with the small adaptation that the initially dissolved calibrator standards were not pre-diluted five times before generation of the standard curve (as recommended by the manufacturer).

Perforin release in cell culture supernatant was analyzed using the human Perforin ELISA development kit (MabTech, cat. No. 3465-1H-6), according to manufacturer's instructions. In short, a 96-well flat bottom MICRO-LON® 600 ELISA plate (Greiner BioOne, cat no. 655092) was coated with capture antibody (50 μL/well, 4 μg/mL mAb Pf-80/164, diluted in PBS [Hyclone GE Healthcare, cat no. SH3A3830.03]) at 4-8° C., while shaking (300 RPM), 0/N. After washing twice with PBS (200 μL/well), the wells were blocked with 100 μL incubation buffer (PBS supplemented with 0.1% BSA [Roche, cat. no. 10735086001] and 0.05%

Tween 20 [Sigma Aldrich, cat no. P1379-1L]) at RT, while shaking (300 RPM), for 1 h. After washing three times with washing buffer (PBS supplemented with 0.05% Tween 20), 50 μL of standard (0-2500 μg/mL diluted in incubation buffer, using two-fold dilution steps) or samples (supernatant, diluted 1:2 or 1:10 in incubation buffer, see Table 13) were added to the wells and incubated at RT, while shaking (300 RPM), for 2 h. After washing three times with washing buffer, the wells were incubated with 50 μL detection antibody (1 μg/mL Ab Pf-344-biotin, diluted in incubation buffer) incubated at RT, while shaking (300 RPM), for 1 h. Again, the plates were washed three times with washing buffer, and the wells were incubated with 50 μL streptavidin-HRP solution (1:1000 dilution in incubation buffer; MabTech, cat no. 3310-9) at RT while shaking (300 RPM) for 1 h, followed by washing as described above. Next, 50 μL of 1-Step Ultra TMB-ELISA (Thermo Scientific, cat no. 34028) substrate solution was added to the wells and incubated at RT, while shaking (300 RPM), protected from light, for 30 min. The reaction was stopped by adding 25 μL of 1 M sulfuric acid ($H_2SO_4$; VWR Chemicals, cat no. 30149.291) and absorbance was measured at 450 nm at an ELISA plate reader (Biotel EL808 ELISA Reader, Biotek Instruments).

Granzyme B release in the cell culture supernatants was analyzed using the human Granzyme B DuoSet ELISA kit (R&D Systems, cat. no. DY2906-5), according to manufacturer's instructions. In short, the protocol was similar as described above for the perforin ELISA, but with minor adaptations. The capture antibody (800 ng/mL) was diluted in PBS, while the samples (diluted 1:10 or 1:500 in incubation buffer, see Table 13) and standards (0-2500 μg/mL, 2-step dilutions) were diluted in incubation buffer. Streptavidin-HRP solution (diluted 1:40; R&D Systems, cat no. 893975) and the detection antibody (50 ng/mL) were diluted in reagent diluent (PBS supplemented with 1% BSA and filter-sterilized through a 0.2 μm filter). In addition, the wells were blocked in 150 μL reagent diluent

TABLE 13

Supernatant dilutions used for granzyme B and perforin ELISAs

| Cell line | Donor | Selected dilution supernatant used for analysis of granzyme B ELISA (tested 1:10 or 1:500) | Selected dilution supernatant used for analysis of perforin ELISA (tested 1:2 or 1:10) |
|---|---|---|---|
| EPLC-272H | 1 | 1:10 | 1:2 |
| | 2 | *Combined | 1:2 |
| | 3 | 1:10 | 1:2 |
| NCI-H292 | 1 | 1:10 | 1:2 |
| | 2 | 1:10 | 1:2 |
| | 3 | 1:10 | 1:2 |

*Combined = a combination of the data of two dilutions was used for calculating the concentration of granzyme B or perforin.

In parallel, the viability of the adherent tumor cells was assessed using Resazurin (7-Hydroxy-3H-phenoxazin-3-one 10-oxide). The adherent tumor cells were washed twice with PBS and incubated with 10% Resazurin (150 μL; Life Technologies, The Netherlands, cat. no. DAL1100) in RPMI-1640 medium (Lonza, Switzerland, cat. no. BE12-115F) supplemented with 10% donor bovine serum with iron (Life Technologies, The Netherlands, cat. no. 10371-029) and pen/strep (Lonza, cat. no. DE17-603E) at 37° C. for 4 h. The absorbance was measured with an Envision multilabel plate reader (PerkinElmer, US). The absorbance of PAO-treated (Sigma-Aldrich, US, cat. no. S6942) cells were set as 0% viability and the absorbance of untreated cells were set as 100% viability. The 'percentage viable cells' was calculated as follows:

Percentage tumor cell viability=([absorbance sample–absorbance PAO-treated target cells]/[absorbance untreated target cells–absorbance PAO-treated target cells])×100.

Dose-response curves for tumor cell viability (cytotoxicity), T-cell activation, cytokine production, granzyme B and perforin release and were generated using non-linear regression (sigmoidal dose-response with variable slope) using GraphPad Prism V7.02 software (GraphPad Software, San Diego, CA, USA).

FIG. 24 shows that bsIgG1-huCD3-H101G-FEALx5T4-207-FEAR induced T-cell mediated cytotoxicity and T-cell activation in EPLC-272H and NCI-H292 squamous NSCL cancer cells, while the control bispecific antibodies (bsIgG1-huCD3-H101G-FEALxb12-FEAR, bsIgG1-b12-FEALx5T4-207-FEAR) targeting only the tumor cells or the T cells did not induce any cytotoxicity or T-cell activation. T-cell activation is measured by the upregulation of CD69 on $CD4^+$ and $CD8^+$ T cells (% of $CD69^+$ cells within the $CD4^+$ or $CD8^+$ population). FIG. 25 shows the cytokine production induced by incubating EPLC-272H squamous NSCL cancer cells and bsIgG1-huCD3-H101G-FEALx5T4-207-FEAR with T cells derived from three different donors. FIG. 26 shows the cytokine production induced by incubating NCI-H292 squamous NSCL cancer cells and bsIgG1-huCD3-H101G-FEALx5T4-207-FEAR with T cells derived from three different donors. FIG. 27 shows the granzyme B and perforin released by T cells induced by incubating EPLC-272H and NCI-H292 squamous NSCL cells and bsIgG1-huCD3-H101G-FEALx5T4-207-FEAR with T cells derived from three different donors.

These data indicate that bsIgG1-huCD3-H101G-FEALx5T4-207-FEAR can specifically and dose-dependently induce T-cell mediated cytotoxicity, T-cell activation, cytokine production, granzyme B and perforin release in squamous NSCL cancer cell lines.

Example 21: Induction of T-Cell Activation and Cytotoxicity by a CD3x5T4 Bispecific Antibody in Squamous Head and Neck Cancer Cell Lines In Vitro A CD3x5T4 bispecific antibody was tested in an in vitro cytotoxicity assay using FaDu (ATCC, cat. no. HTB-43) and SCC-9 (ATCC, cat no. CRL-1629) squamous head and neck cancer cells as 5T4-expressing target cells and purified T cells as effector cells (effector: target cell ratio=4:1). T cells were derived from human healthy donor buffy coats (Sanquin, Amsterdam, The Netherlands) and isolated using the RosetteSep human T cell enrichment cocktail (Stemcell Technologies, France, cat. no. 15061) according to manufacturer's instructions. T cells from three different donors were tested in the in vitro T-cell-mediated cytotoxicity assay, T-cell activation analysis, cytokine release and production of granzyme B and perforin Tumor cells (16,000 cells/well) were seeded into flat-bottom 96-well plates (Greiner Bio-One, The Netherlands, cat. no. 655180) and left to adhere at 37° C. for 4 h. T cells were added to tumor cells at an effector: target cell (E:T) ratio=4:1. Serial dilutions of bsIgG1-huCD3-H101G-FEALx5T4-207-FEAR or control antibodies (bsIgG1-huCD3-H101G-FEALxb12-FEAR [that recognize CD3 but not 5T4], bsIgG1-b12-FEALx5T4-207-FEAR [that recognize 5T4 but not CD3]) were added (final concentration ranging from 5000 to 0.0128 ng/mL; 5-fold dilutions) and plates were incubated at 37° C. for 72 h. As a positive control for cytotoxicity, cells were incubated with 16 µg/mL phenylarsine oxide (PAO; Sigma-Aldrich, cat. no. P3075; dissolved in dimethylsulfoxide [DMSO; Sigma-Adrich, cat. no. D2438]). After 72 h, 110 µL supernatants containing T cells were transferred to round-bottom 96-well culture plates (CellStar, cat. no. 650180) and centrifuged (300×g) at 4° C. for 3 min. Adherent cells were kept for quantification of tumor cell viability, as described below. T cells in the pellet were stained for T-cell markers by incubation with CD3-eFluor450 (1:200; eBioscience, clone OKT3), CD4-APC-eFluor780 (1:50; eBioscience, clone OKT4), CD8-AF700 (1:100; Biolegend, clone RPA-T8) and T-cell activation markers CD69-APC (1:50; BD Biosciences, clone AB2439), CD25-PE-Cy7 (1:50; eBioscience, clone BC96) and CD279/PD1-BV605 (1:50; Biolegend, clone EH12.2H7) diluted in 50 µL PBS/0.1% BSA/0.02% azide (staining buffer). Single stained samples with Ultracomp beads (5 µL; Invitrogen, cat. no. 01-2222-42) were used for compensation adjustments of the flow cytometer. After 30 min of incubation at 4° C., plates were washed three times with staining buffer. Cells were resuspended in 120 µL staining buffer and analyzed using a FACS Fortessa (BD Biosciences). Data were processed using FlowJo (version 10, BD Biosciences).

The supernatants derived from the T-cell mediated cytotoxicity assay were used for the measurement of cytokine, granzyme B and perforin production by activated T cells. The cytokine production was analyzed by a multiplex U-plex assay (MeSo Scale Discovery, cat. no. K15049K), measuring IFN-γ, TNF-α, IL-1β, IL-2, IL-4, IL-6, IL-8, IL-10, IL-12p70 and IL-13, essentially according to manufacturer's instructions, with the small adaptation that the initially dissolved calibrator standards were not pre-diluted five times before generation of the standard curve (as recommended by the manufacturer).

Perforin release in cell culture supernatant was analyzed using the human Perforin ELISA development kit (MabTech, cat. No. 3465-1H-6), according to manufacturer's instructions. In short, a 96-well flat bottom MICRO-LON® 600 ELISA plate (Greiner BioOne, cat no. 655092) was coated with capture antibody (50 µL/well, 4 µg/mL mAb Pf-80/164, diluted in PBS [Hyclone GE Healthcare, cat no. SH3A3830.03]) at 4-8° C., while shaking (300 RPM), O/N. After washing twice with PBS (200 µL/well), the wells were blocked with 100 µL incubation buffer (PBS supplemented with 0.1% BSA [Roche, cat. no. 10735086001] and 0.05% Tween 20 [Sigma Aldrich, cat no. P1379-1L]) at RT, while shaking (300 RPM), for 1 h. After washing three times with washing buffer (PBS supplemented with 0.05% Tween 20), 50 µL of standard (0-2500 µg/mL diluted in incubation buffer, using two-fold dilution steps) or samples (supernatant, diluted 1:2 or 1:10 in incubation buffer, see Table 14) were added to the wells and incubated at RT, while shaking (300 RPM), for 2 h. After washing three times with washing buffer, the wells were incubated with 50 µL detection antibody (1 µg/mL Ab Pf-344-biotin, diluted in incubation buffer) incubated at RT, while shaking (300 RPM), for 1 h. Again, the plates were washed three times with washing buffer, and the wells were incubated with 50 µL streptavidin-HRP solution (1:1000 dilution in incubation buffer; MabTech, cat no. 3310-9) at RT while shaking (300 RPM) for 1 h, followed by washing as described above. Next, 50 µL of 1-Step Ultra TMB-ELISA (Thermo Scientific, cat no. 34028) substrate solution was added to the wells and incubated at RT, while shaking (300 RPM), protected from light, for 30 min. The reaction was stopped by adding 25 µL of 1

M sulfuric acid ($H_2SO_4$; VWR Chemicals, cat no. 30149.291) and absorbance was measured at 450 nm at an ELISA plate reader (Biotel EL808 ELISA Reader, Biotek Instruments).

Granzyme B release in the cell culture supernatants was analyzed using the human Granzyme B DuoSet ELISA kit (R&D Systems, cat. no. DY2906-5), according to manufacturer's instructions. In short, the protocol was similar as described above for the perforin ELISA, but with minor adaptations. The capture antibody (800 ng/mL) was diluted in PBS, while the samples (diluted 1:10 or 1:500 in incubation buffer, see Table 14) and standards (0-2500 µg/mL, 2-step dilutions) were diluted in incubation buffer. Streptavidin-HRP solution (diluted 1:40; R&D Systems, cat no. 893975) and the detection antibody (50 ng/mL) were diluted in reagent diluent (PBS supplemented with 1% BSA and filter-sterilized through a 0.2 m filter). In addition, the wells were blocked in 150 µL reagent diluent.

TABLE 14

| Supernatant dilutions used for granzyme B and perforin ELISAs | | | |
|---|---|---|---|
| Cell line | Donor | Selected dilution supernatant used for analysis of granzyme B ELISA (tested 1:10 or 1:500) | Selected dilution supernatant used for analysis of perforin ELISA (tested 1:2 or 1:10) |
| Fadu | 1 | 1:500 | 1:2 |
| | 2 | 1:500 | 1:2 |
| | 3 | 1:10 | 1:2 |
| SCC-9 | 1 | 1:500 | 1:2 |
| | 2 | 1:10 | 1:2 |
| | 3 | 1:10 | 1:2 |

*Combined = a combination of the data of two dilutions was used for calculating the concentration of granzyme B or perforin.

In parallel, the viability of the adherent tumor cells was assessed using Resazurin (7-Hydroxy-3H-phenoxazin-3-one 10-oxide). The adherent tumor cells were washed twice with PBS and incubated with 10% Resazurin (150 µL; Life Technologies, The Netherlands, cat. no. DAL1100) in RPMI-1640 medium (Lonza, Switzerland, cat. no. BE12-115F) supplemented with 10% donor bovine serum with iron (Life Technologies, The Netherlands, cat. no. 10371-029) and pen/strep (Lonza, cat. no. DE17-603E) at 37° C. for 4 h. The absorbance was measured with an Envision multilabel plate reader (PerkinElmer, US). The absorbance of PAO-treated (Sigma-Aldrich, US, cat. no. S6942) cells were set as 0% viability and the absorbance of untreated cells were set as 100% viability. The 'percentage viable cells' was calculated as follows:

Percentage tumor cell viability=([absorbance sample−absorbance PAO-treated target cells]/ [absorbance untreated target cells−absorbance PAO-treated target cells])×100.

Dose-response curves for tumor cell viability (cytotoxicity), T-cell activation, cytokine production, granzyme B and perforin release and were generated using non-linear regression (sigmoidal dose-response with variable slope) using GraphPad Prism V7.02 software (GraphPad Software, San Diego, CA, USA).

FIG. 28 shows that bsIgG1-huCD3-H101G-FEALx5T4-207-FEAR induced T-cell mediated cytotoxicity and T-cell activation in FaDu and SCC-9 squamous head and neck cancer cells, while the control bispecific antibodies (bsIgG1-huCD3-H101G-FEALxb12-FEAR, bsIgG1-b12-FEALx5T4-207-FEAR) targeting only the tumor cells or the T cells did not induce any cytotoxicity or T-cell activation.

T-cell activation is measured by the upregulation of CD69 on $CD4^+$ and $CD8^+$ T cells (% of $CD69^+$ cells within the $CD4^+$ or $CD8^+$ population). FIG. 29 shows the cytokine production induced by incubating FaDu squamous head and neck cancer cells and bsIgG1-huCD3-H101G-FEALx5T4-207-FEAR with T cells derived from three different donors. FIG. 30 shows the cytokine production induced by incubating SCC-9 squamous head and neck cancer cells and bsIgG1-huCD3-H101G-FEALx5T4-207-FEAR with T cells derived from three different donors. FIG. 31 shows the granzyme B and perforin released by T cells induced by incubating FaDu and SCC-9 squamous head and neck cancer cells and bsIgG1-huCD3-H101G-FEALx5T4-207-FEAR with T cells derived from three different donors.

These data indicate that bsIgG1-huCD3-H101G-FEALx5T4-207-FEAR can specifically and dose-dependently induce T-cell mediated cytotoxicity, T-cell activation, cytokine production, granzyme B and perforin release in squamous head and neck cancer cell lines.

Example 22: Induction of Cytotoxicity by a CD3x5T4 Bispecific Antibody in Human Papillomavirus Positive and Negative SCCHN Cell Lines In Vitro A CD3x5T4 bispecific antibody was tested in an in vitro cytotoxicity assay using four human papillomavirus (HPV)-negative (VU-SCC-017, UM-SCC-22A, UM-SCC-22B, and VU-SCC-080, see Table 14) and two HPV-positive (UM-SCC-47 and UPCI-SCC-154, see Table 14) squamous cell carcinoma of the head and neck (SCCHN) cell lines as 5T4-expressing target cells, and purified T cells as effector cells at varying effector:target (E:T) cell ratios.

The SCCHN cell lines were cultured in culture medium (Dulbecco's Modified Eagle Medium [DMEM; Lonza, cat. no. 12-709F], supplemented with 1% L-glutamine [Lonza, cat. no. BE-17-605E] and 5% heat-inactivated fetal bovine serum [FBS; Biological Industries, cat. no. 04-007-1A]). 5T4 expression was quantified using quantitative flow cytometry. Tumor cells were harvested by trypsinization followed by resuspension in culture medium and added at 100,000 cells/well to round-bottom 96-well plates (Greiner CELLSTAR, cat. no. 650180). The cells were centrifuged at 300×g for 5 min and washed in PBS (Lonza, cat. no. 17-516F). After removal of supernatant, cells were incubated with 50 µL of 0.4 µg/mL bsIgG1-huCD3-H101G-FEALx5T4-207-FEAR or bsIgG1-huCD3-H101G-FEALxb12-FEAR diluted in fluorescence-activated cell sorting (FACS) buffer (0.5% bovine serum albumin [Sigma, cat. no. 05479-250G] in PBS) at 4° C. for 30 min. In parallel, a standard curve was generated using a Human IgG Calibrator Kit (Biocytex, cat. no. CP010), essentially according to the manufacturer's instructions. Cells and beads were washed twice with PBS and incubated with 50 µL secondary antibody R-PE-conjugated goat-anti-human IgG $F(ab')_2$ (diluted 1:200 in FACS buffer; Jackson ImmunoResearch, cat. no. 109-116-098) at 4° C., protected from light, for 30 min. Next, cells and beads were washed in PBS three times, resuspended in 100 µL FACS buffer and measured on a BD LSRFortessa (Becton-Dickinson, New Jersey, USA). The mean fluorescence intensity (MFI) of the bsIgG1-huCD3-H101G-FEALxb12-FEAR, that does not bind to tumor cells and was used as a negative control antibody, was subtracted from the MFI of the corresponding bsIgG1-huCD3-H101G-FEALx5T4-207-FEAR sample. The standard curve obtained using the Human IgG Calibrator Kit was used to interpolate the number of bsIgG1-huCD3-H101G-FEALx5T4-207-FEAR molecules bound per cell, representing the estimated number of 5T4 molecules expressed per cell.

To determine the T-cell mediated cytotoxicity induced by the CD3x5T4 bispecific antibody, T cells were isolated from human healthy donor buffy coats (Sanquin, Amsterdam, The Netherlands) using the RosetteSep human T cell enrichment cocktail (Stemcell Technologies, France, cat. no. 15061) according to manufacturer's instructions. Tumor cells were cultured and harvested as described supra, and seeded (1,000-8,000 cells/well, see Table 14) in 100 µL culture medium in flat-bottom 96-well plates (Greiner CELLSTAR, cat. no. 655180) and left to adhere at 37° C. for 24 h.

TABLE 14

| | | SCCHN cell lines used for T-cell mediated cytotoxicity assays | | |
|---|---|---|---|---|
| Cell line | HPV status | Origin of cell line | Research Resource Identifier (RRID) or Reference | Seeding density (cells/well) |
| UM-SCC-22A | HPV-negative | Floor of mouth, primary (T1N0) | CVCL_7731 | 4,000 |
| UM-SCC-22B | | Floor of mouth, local recurrence (T2N0) | CVCL_7732 | 4,000 |
| VU-SCC-017 (also described as VU-SCC-9917) | | Oral cavity (T2N2b) | (Martens-de Kemp et al., 2013, PLoS One 8, e61555) | 1,000 |
| VU-SCC-080 | | Base of tongue, recurrence | (Hermsen et al., 1996 (1996) Genes Chromosomes Cancer 15, 1-9) | 3,000 |
| UM-SCC-47 | HPV-positive | Oral cavity (T3N1) | CVCL_7759 | 5,000 |
| UPCI-SCC-154 | | Oral SSC | CVCL_2230 | 8,000 |

(trypsin-EDTA 1× in solution without calcium or magnesium, with phenol red [Biowest, cat. no. L0930-100]) at 37° C. for 2-10 min.

To quantify 5T4 expression on the SCCHN cell lines, cells were washed in culture medium (300×g for 5 min), T cells were added to tumor cells in 25 µL culture medium at E:T ratios of 4:1, 10:1, or 25:1. Serial dilutions of bsIgG1-huCD3-H101G-FEALx5T4-207-FEAR or control antibodies (bsIgG1-huCD3-H101G-FEALxb12-FEAR [which recognizes CD3 but not 5T4], or bsIgG1-b12-

FEALx5T4-207-FEAR [which recognizes 5T4 but not CD3]) were added (final concentration ranging from 5000 to 0.0128 ng/mL; 5-fold dilutions) and plates were incubated at 37° C. for 72 h. As a positive control for cytotoxicity, cells were incubated with 16.7 µg/mL PAO (Acros Organics, cat. no. 180350010; dissolved in DMSO (Santa Cruz Biotechnology, cat. no. SC-358801). After 72 h, supernatants were removed and the adherent cells in the wells were washed twice with PBS. To quantify tumor cell viability, 110 µL DMEM and 10 µL CellTiter-Blue (Promega, cat. no. G8081) were mixed and added to each well, after which the plate was incubated at 37° C. for 2 h. Fluorescence was measured with GloMax Explorer Multimode Microplate Reader (Promega; excitation: 520 nm, emission: 580-640 nm). The fluorescence of PAO-treated cells was set as 0% viability and the fluorescence of cells treated with T cells only was set as 100% viability. The 'percentage viable cells' was calculated as follows:

Percentage tumor cell viability=([fluorescence sample−fluorescence PAO-treated target cells]/ [fluorescence tumor cells with T cells only− fluorescence PAO-treated target cells])×100.

Dose-response curves were generated using non-linear regression (log(inhibitor) versus response, variable slope with four parameters) in the GraphPad Prism V8.1.1 software (GraphPad Software, San Diego, CA, USA).

Table 15 shows that the HPV-negative VU-SCC-017, UM-SCC-22A, UM-SCC-22B, and VU-SCC-080 SCCHN cell lines and the HPV-positive UM-SCC-47 and UPCI-SCC-154 SCCHN cell lines all express 5T4, with average expression ranging from approximately 12,00 (VU-SCC- 017) to approximately 60,000 (UM-SCC-22B) 5T4 molecules/cell. FIG. 32 shows that bsIgG1-huCD3-H101G-FEALx5T4-207-FEAR induced T-cell mediated cytotoxicity in all tested HPV-negative (VU-SCC-017, UM-SCC-22A, UM-SCC-22B, and VU-SCC-080) and HPV-positive (UM-SCC-47 and UPCI-SCC-154) SCCHN cell lines at E:T ratios higher than 4:1. Control bispecific antibodies (bsIgG1-huCD3-H101G-FEALxb12-FEAR, bsIgG1-b12-FEALx5T4-207-FEAR) targeting only the tumor cells or the T cells did not induce cytotoxicity in any of the tested SCCHN cell lines at the highest E:T ratio tested (25:1).

These data indicate that bsIgG1-huCD3-H101G-FEALx5T4-207-FEAR can specifically and dose-dependently induce T-cell mediated cytotoxicity in both HPV-negative and HPV-positive SCCHN cancer cell lines.

TABLE 15

| | 5T4 expression per cell line as determined by quantitative flow cytometry | | |
|---|---|---|---|
| Cell line | Average number of 5T4 molecules/cell | Range | Number of measurements performed |
| VU-SCC-017 | 11,902 | 11,154-12,649 | 2 |
| UM-SCC-22A | 36,434 | 33,666-39,202 | 2 |
| UM-SCC-22B | 62,745 | 59,345-66,145 | 2 |
| VU-SCC-080 | 56,504 | 56,237-56,772 | 2 |
| UM-SCC-47 | 49,866 | 48,674-51,058 | 2 |
| UPCI-SCC-154 | 22,776 | 20,702-24,850 | 2 |

The invention claimed is:

1. A method of treating esophageal cancer, Non-small Cell Lung Cancer (NSCLC) or Squamous Cell Carcinoma of the Head and Neck (SCCHN), the method comprising administering to a subject in need thereof an antibody which binds to 5T4, wherein the antibody comprises a heavy chain and a light chain, and wherein the antibody comprises:

a) a heavy chain variable region (VH) comprising the CDR1, CDR2, and CDR3 sequences of SEQ ID NOs: 6, 7 and 8, respectively, and a light chain variable region (VL) comprising the CDR1, CDR2, and CDR3 sequences of SEQ ID NO: 10, the sequence AAS, and SEQ ID NO: 11, respectively, b) a VH comprising the CDR1, CDR2, and CDR3 sequences of SEQ ID NOs: 13, 14 and 15, respectively; and a VL comprising the CDR1, CDR2, and CDR3 sequences of SEQ ID NO: 17, the sequence DAS, and SEQ ID NO:18, respectively, c) a VH comprising the CDR1, CDR2, and CDR3 sequences of SEQ ID NOs: 20, 21 and 22, respectively; and a VL comprising the CDR1, CDR2, and CDR3 sequences of SEQ ID NO: 24, the sequence DAS, and SEQ ID NO: 25, respectively, d) a VH comprising the CDR1, CDR2, and CDR3 sequences of SEQ ID NOs: 27, 28 and 29, respectively; and a VL comprising the CDR1, CDR2, and CDR3 sequences of SEQ ID NO: 31, the sequence DVS, and SEQ ID NO: 32, respectively, e) a VH comprising the CDR1, CDR2, and CDR3 sequences of SEQ ID NOs: 34, 35 and 36, respectively; and a VL comprising the CDR1, CDR2, and CDR3 sequences of SEQ ID NO: 38, the sequence DAS, and SEQ ID NO: 39, respectively, f) a VH comprising the CDR1, CDR2, and CDR3 sequences of SEQ ID NOs: 41, 42 and 43, respectively, and a VL comprising the CDR1, CDR2, and CDR3 sequences of SEQ ID NO: 45, the sequence DAS, and SEQ ID NO: 46, respectively, or g) a VH comprising the CDR1, CDR2, and CDR3 sequences of SEQ ID NOs: 48, 49 and 50, respectively, and a VL comprising the CDR1, CDR2, and CDR3 sequences of SEQ ID NO: 52, the sequence DAS, and SEQ ID NO: 53, respectively.

2. The method of claim 1, wherein:

(a) the esophageal cancer is an adenocarcinoma, a squamous cell carcinoma, an adenosquamous carcinoma, a Siewert type I adenocarcinoma of the esophagogastric junction (EGJ) or a HER2/neu-positive cancer;

(b) the NSCLC is an adenocarcinoma, a squamous cell carcinoma or an adenosquamous carcinoma; or (c) the SCCHN is human papillomavirus (HPV)-positive SCCHN or HPV-associated SCCHN, HPV-negative SCCHN, squamous cell carcinoma of the oral cavity, squamous cell carcinoma of the oropharynx, squamous cell carcinoma of the paranasal sinuses, squamous cell carcinoma of the nasal cavity, squamous cell carcinoma of the hypopharynx or squamous cell carcinoma of the larynx.

3. The method of claim 1, wherein the esophageal cancer or NSCLC is advanced, locally advanced or metastatic.

4. The method of claim 1, wherein the subject with esophageal cancer:

(a) has received at least one prior line of systemic treatment for advanced esophageal cancer;

(b) has progressed on or after at least one prior line of systemic treatment for advanced esophageal cancer; or (c) has received prior treatment with HER2/neu targeted therapy.

5. The method of claim 1, wherein the subject with NSCLC:

(a) has received at least one prior line of systemic treatment for locally advanced, advanced or metastatic NSCLC;

(b) has experienced progression of the NSCLC on or after prior systemic treatment for locally advanced or metastatic NSCLC; or (c) has received prior therapy with a platinum-based regimen, a tyrosine kinase inhibitor or anti-PD-1/PD-L1 therapy.

6. The method of claim 5, wherein:

(a) the platinum-based regimen comprises tubulin inhibition in combination with platin and 5-fluorouracil (5-FU) or irinotecan; or (b) the tyrosine kinase inhibitor is selected from the group consisting of an inhibitor of Anaplastic lymphoma kinase, an inhibitor of proto-oncogene tyrosine-protein kinase ROS1 and an inhibitor of the epidermal growth factor receptor (EGFR).

7. The method of claim 1, wherein the subject with SCCHN has received prior therapy selected from the group consisting of therapy with a platinum-based regimen, an anti-PD-1/PD-L1 therapy, anti-EGFR therapy and 5-fluorouracil.

8. The method of claim 7, wherein:

(a) the platinum-based regimen comprises cisplatin or carboplatin;

(b) the anti-PD-1/PD-L1 PD-1 therapy is selected from the group consisting of nivolumab, genolimzumab, atezolizumab, durvalumab, avelumab, pembrolizumab, genolimzumab, nivolumab, cemiplimab and tislelizumab; or (c) the anti-EGFR therapy is selected from the group consisting of erlotinib, osimertinib, gefintinib, olmutinib, nazartinib, avitinib, cetuximab and panitumumab.

9. The method of claim 1, wherein the antibody binds to the same epitope as, or competes for binding to 5T4 with, a reference antibody selected from the group consisting of:

a) an antibody comprising a VH region comprising the sequence set forth in SEQ ID NO: 5 and a VL region comprising the sequence set forth in SEQ ID NO: 9, b) an antibody comprising a VH region comprising the sequence set forth in SEQ ID NO: 12 and a VL region comprising the sequence set forth in SEQ ID NO: 16, c) an antibody comprising a VH region comprising the sequence set forth in SEQ ID NO: 19 and a VL region comprising the sequence set forth in SEQ ID NO: 23, d) an antibody comprising a VH region comprising the sequence set forth in SEQ ID NO: 26 and a VL region comprising the sequence set forth in SEQ ID NO: 30, e) an antibody comprising a VH region comprising the sequence set forth in SEQ ID NO: 33 and a VL region comprising the sequence set forth in SEQ ID NO: 37, f) an antibody comprising a VH region comprising the sequence set forth in SEQ ID NO: 40 and a VL region comprising the sequence set forth in SEQ ID NO: 44; and g) an antibody comprising a VH region comprising the sequence set forth in SEQ ID NO: 47 and a VL region comprising the sequence set forth in SEQ ID NO: 51.

10. The method of claim 1, wherein the antibody binds to an epitope on human 5T4 comprising:

(a) the amino acid residues R73, Y92 and R94;

(b) the amino acid residues S69, R73, Y92 and R94; or (c) the amino acid residues R73, T74, Y92, R94 and N95;

wherein the numbering of each amino acid residue refers to its position in SEQ ID NO: 1.

11. The method of claim 1, wherein:

(a) one or more of the following additional amino acid residues of 5T4 is/are involved binding of the antigen binding region capable of binding to 5T4: L89, F111, L117, F138, L144, D148 and N152;

(b) the antibody binds to an epitope on human 5T4 within which amino acid residues R73, Y92 and R94 are directly involved in binding the antibody, and wherein one or more of amino acid residues F111, F138, L144 and D148 are indirectly involved in said binding;

(c) the antibody binds to an epitope on human 5T4 within which amino acid residues S69, R73, Y92 and R94 are directly involved in binding the antibody, and wherein one or more of amino acid residues F111, F138 and D148 are indirectly involved in said binding; or (d) the antibody binds to an epitope on human 5T4 within which amino acid residues R73, T74, Y92, R94 and N95 are directly involved in binding the antibody, and wherein amino acid residue F138 is indirectly involved in said binding;

wherein the numbering of each amino acid residue refers to its position in SEQ ID NO: 1.

12. The method of claim 1, wherein:

(a) there is loss of binding or binding is reduced by the antibody if any one or more of the amino acid residues R73, Y92 and R94 is/are substituted with alanine;

(b) there is loss of binding or binding is reduced if any one or more of the amino acid residues S69, R73, Y92 and R94 is/are substituted with alanine;

(c) there is loss of binding or binding is reduced if any one or more of the amino acid residues R73, T74, Y92, R94 and N95 is/are substituted with alanine; the numbering of each amino acid residue referring to its position in SEQ ID NO: 1;

(d) there is loss of binding or binding is reduced if any one or more of the amino acid residues: L89, F111, L117, F138, L144, D148 and N152 is/are substituted with alanine; the numbering of each amino acid residue referring to its position in SEQ ID NO: 1;

(e) there is loss of binding or binding is reduced if any one or more of the amino acid residues R73, Y92, R94, F111, F138, L144 and D148 is/are substituted with alanine; the numbering of each amino acid residue referring to its position in SEQ ID NO: 1;

(f) there is loss of binding or binding is reduced if any one or more of the amino acid residues S69, R73, Y92, R94, F111, F138 and D148 is/are substituted with alanine; or (g) there is loss of binding or binding is reduced if any one or more of the amino acid residues R73, T74, Y92, R94, N95 and F138 is/are substituted with alanine;

wherein the numbering of each amino acid residue referring to its position in SEQ ID NO: 1.

13. The method of claim 1, wherein the antibody comprises:

a) a heavy chain variable region (VH) comprising the sequence of SEQ ID NO: 5, and a light chain variable region (VL) comprising the sequence of SEQ ID NO: 9, b) a VH comprising the sequence of SEQ ID NO: 12, and a VL comprising the sequence of SEQ ID NO: 16, c) a VH comprising the sequence of SEQ ID NO: 19, and a VL comprising the sequence of SEQ ID NO: 23, d) a VH comprising the sequence of SEQ ID NO: 26, and a VL comprising the sequence of SEQ ID NO: 30, e) a VH comprising the sequence of SEQ ID NO: 33, and a VL comprising the sequence of SEQ ID NO: 37, f) a VH comprising the sequence of SEQ ID NO: 40, and a VL comprising the sequence of SEQ ID NO: 44; or g) a VH comprising the sequence of SEQ ID NO: 47, and a VL comprising the sequence of SEQ ID NO: 51.

14. The method of claim 1, wherein the antibody comprises a first and a second heavy chain, each of said first heavy chain and second heavy chain comprises at least a hinge region, a CH2 and CH3 region, wherein in said first heavy chain at least one of the amino acids in the positions corresponding to positions selected from the group consisting of T366, L368, K370, D399, F405, Y407 and K409 in a human IgG1 heavy chain has been substituted, and in said second heavy chain at least one of the amino acids in the positions corresponding to a position selected from the group consisting of T366, L368, K370, D399, F405, Y407, and K409 in a human IgG1 heavy chain has been substituted, wherein said substitutions of said first heavy chain and said second heavy chain are not in the same positions, and wherein the amino acid positions are numbered according to EU numbering.

15. The method of claim 1, wherein the antibody comprises a first and a second heavy chain, and wherein in both the first heavy chain and the second heavy chain, the amino acid residues at the positions corresponding to positions L234 and L235 in a human IgG1 heavy chain according to EU numbering are F and E, respectively, and/or the amino acid residue at the position corresponding to position D265 in a human IgG1 heavy chain according to EU numbering is A.

16. The method of claim 1, wherein the antibody comprises a first and a second heavy chain, and the constant region of said first heavy chain or second heavy chain comprises an amino acid sequence selected from the group consisting of:

a) the sequence set forth in SEQ ID NO: 89, b) a subsequence of the sequence in a), wherein 1, 2, 3, 4, 5, 6, 7, 8, 9 or 10 consecutive amino acids has/have deleted, starting from the N-terminus or C-terminus of the sequence defined in a); and c) a sequence having at the most 5 substitutions compared to the amino acid sequence defined in a) or b).

17. The method of claim 1, wherein said antibody comprises a first heavy chain and a second heavy chain, and wherein the first heavy chain and the second heavy chain are modified so that the antibody induces Fc-mediated effector function to a lesser extent relative to an identical non-modified antibody.

18. The method of claim 1, wherein said antibody comprises a kappa ($\kappa$) light chain or a lambda ($\lambda$) light chain.

19. The method of claim 18, wherein:

(I) the kappa ($\kappa$) light chain comprises an amino acid sequence selected from the group consisting of:

a) the sequence set forth in SEQ ID NO: 95, b) a subsequence of the sequence in a), wherein 1, 2, 3, 4, 5, 6, 7, 8, 9 or 10 consecutive amino acids has/have deleted, starting from the N-terminus or C-terminus of the sequence defined in a); and c) a sequence having at the most 5 substitutions compared to the amino acid sequence defined in a) or b); or (II) the lambda ($\lambda$) light chain comprises an amino acid sequence selected from the group consisting of:

a) the sequence set forth in SEQ ID NO: 96, b) a subsequence of the sequence in a), wherein 1, 2, 3, 4, 5, 6, 7, 8, 9 or 10 consecutive amino acids has/have deleted, starting from the N-terminus or C-terminus of the sequence defined in a); and c) a sequence having at the most 5 substitutions compared to the amino acid sequence defined in a) or b).

20. The method of claim 1, wherein the antibody comprises a VH comprising the CDR1, CDR2, and CDR3 sequences of SEQ ID NOs: 6, 7 and 8 , respectively, and a VL comprising the CDR1, CDR2, and CDR3 sequences of SEQ ID NO: 10, the sequence AAS, and SEQ ID NO: 11, respectively.

21. The method of claim 1, wherein the antibody comprises a VH comprising the CDR1, CDR2, and CDR3 sequences of SEQ ID NOs: 41, 42 and 43, respectively, and a VL comprising the CDR1, CDR2, and CDR3 sequences of SEQ ID NO: 45, the sequence DAS, and SEQ ID NO: 46, respectively.

22. The method of claim 1, wherein the antibody comprises a VH comprising the CDR1, CDR2, and CDR3 sequences of SEQ ID NOs: 48, 49 and 50, respectively, and a VL comprising the CDR1, CDR2, and CDR3 sequences of SEQ ID NO: 52, the sequence DAS, and SEQ ID NO: 53, respectively.

23. The method of claim 13, wherein the antibody comprises a VH comprising the sequence of SEQ ID NO: 5, and a VL comprising the sequence of SEQ ID NO: 9.

24. The method of claim 13, wherein the antibody comprises a VH comprising the sequence of SEQ ID NO: 40, and a VL comprising the sequence of SEQ ID NO: 44.

25. The method of claim 13, wherein the antibody comprises a VH comprising the sequence of SEQ ID NO: 47, and a VL comprising the sequence of SEQ ID NO: 51.

\* \* \* \* \*

SEQUENCE LISTING

```
<160> NUMBER OF SEQ ID NOS: 111

<210> SEQ ID NO 1
<211> LENGTH: 420
<212> TYPE: PRT
<213> ORGANISM: Homo Sapiens

<400> SEQUENCE: 1

Met Pro Gly Gly Cys Ser Arg Gly Pro Ala Ala Gly Asp Gly Arg Leu
1               5                   10                  15

Arg Leu Ala Arg Leu Ala Leu Val Leu Leu Gly Trp Val Ser Ser Ser
            20                  25                  30

Ser Pro Thr Ser Ser Ala Ser Ser Phe Ser Ser Ser Ala Pro Phe Leu
        35                  40                  45

Ala Ser Ala Val Ser Ala Gln Pro Pro Leu Pro Asp Gln Cys Pro Ala
    50                  55                  60

Leu Cys Glu Cys Ser Glu Ala Ala Arg Thr Val Lys Cys Val Asn Arg
65                  70                  75                  80

Asn Leu Thr Glu Val Pro Thr Asp Leu Pro Ala Tyr Val Arg Asn Leu
                85                  90                  95

Phe Leu Thr Gly Asn Gln Leu Ala Val Leu Pro Ala Gly Ala Phe Ala
                100                 105                 110

Arg Arg Pro Pro Leu Ala Glu Leu Ala Ala Leu Asn Leu Ser Gly Ser
            115                 120                 125

Arg Leu Asp Glu Val Arg Ala Gly Ala Phe Glu His Leu Pro Ser Leu
    130                 135                 140

Arg Gln Leu Asp Leu Ser His Asn Pro Leu Ala Asp Leu Ser Pro Phe
145                 150                 155                 160
```

```
Ala Phe Ser Gly Ser Asn Ala Ser Val Ser Ala Pro Ser Pro Leu Val
            165             170             175

Glu Leu Ile Leu Asn His Ile Val Pro Pro Glu Asp Glu Arg Gln Asn
            180             185             190

Arg Ser Phe Glu Gly Met Val Val Ala Ala Leu Leu Ala Gly Arg Ala
            195             200             205

Leu Gln Gly Leu Arg Arg Leu Glu Leu Ala Ser Asn His Phe Leu Tyr
    210             215             220

Leu Pro Arg Asp Val Leu Ala Gln Leu Pro Ser Leu Arg His Leu Asp
225             230             235             240

Leu Ser Asn Asn Ser Leu Val Ser Leu Thr Tyr Val Ser Phe Arg Asn
            245             250             255

Leu Thr His Leu Glu Ser Leu His Leu Glu Asp Asn Ala Leu Lys Val
            260             265             270

Leu His Asn Gly Thr Leu Ala Glu Leu Gln Gly Leu Pro His Ile Arg
            275             280             285

Val Phe Leu Asp Asn Asn Pro Trp Val Cys Asp Cys His Met Ala Asp
    290             295             300

Met Val Thr Trp Leu Lys Glu Thr Glu Val Val Gln Gly Lys Asp Arg
305             310             315             320

Leu Thr Cys Ala Tyr Pro Glu Lys Met Arg Asn Arg Val Leu Leu Glu
            325             330             335

Leu Asn Ser Ala Asp Leu Asp Cys Asp Pro Ile Leu Pro Pro Ser Leu
            340             345             350

Gln Thr Ser Tyr Val Phe Leu Gly Ile Val Leu Ala Leu Ile Gly Ala
            355             360             365

Ile Phe Leu Leu Val Leu Tyr Leu Asn Arg Lys Gly Ile Lys Lys Trp
    370             375             380

Met His Asn Ile Arg Asp Ala Cys Arg Asp His Met Glu Gly Tyr His
385             390             395             400

Tyr Arg Tyr Glu Ile Asn Ala Asp Pro Arg Leu Thr Asn Leu Ser Ser
            405             410             415

Asn Ser Asp Val
            420

<210> SEQ ID NO 2
<211> LENGTH: 420
<212> TYPE: PRT
<213> ORGANISM: Macaca Fascicularis

<400> SEQUENCE: 2

Met Pro Gly Gly Cys Ser Arg Gly Pro Ala Ala Gly Asp Gly Arg Leu
1               5               10              15

Arg Leu Ala Arg Leu Ala Leu Val Leu Leu Gly Trp Val Ser Ser Ser
            20              25              30

Ser Ser Thr Ser Ser Ala Ser Ser Ser Ser Ser Ala Pro Phe Leu
            35              40              45

Ala Ser Ala Ala Ser Ala Gln Pro Pro Leu Pro Asp Gln Cys Pro Ala
    50              55              60

Leu Cys Glu Cys Ser Glu Ala Ala Arg Thr Val Lys Cys Val Asn Arg
65              70              75              80

Asn Leu Thr Glu Val Pro Thr Asp Leu Pro Leu Tyr Val Arg Asn Leu
            85              90              95

Phe Leu Thr Gly Asn Gln Leu Ala Val Leu Pro Ala Gly Ala Phe Ala
```

-continued

```
              100              105              110

Arg Arg Pro Pro Leu Ala Glu Leu Ala Ala Leu Asn Leu Ser Gly Ser
        115              120              125

Arg Leu Asp Glu Val Arg Gly Gly Ala Phe Glu His Leu Pro Ser Leu
    130              135              140

Arg Gln Leu Asp Leu Ser His Asn Pro Leu Ala Tyr Leu Ser Pro Phe
145              150              155              160

Ala Phe Ser Gly Ser Asn Ala Ser Ile Ser Ala Pro Ser Pro Leu Val
            165              170              175

Glu Leu Ile Leu Asn His Ile Val Pro Pro Asp Asp Lys Arg Gln Asn
            180              185              190

Arg Ser Phe Glu Gly Met Val Ala Ala Ala Leu Val Ala Gly Arg Ala
        195              200              205

Leu Gln Gly Leu His Leu Leu Glu Leu Ala Ser Asn His Phe Leu Tyr
    210              215              220

Leu Pro Arg Asp Val Leu Ala Gln Leu Pro Ser Leu Arg Tyr Leu Asp
225              230              235              240

Leu Ser Asn Asn Ser Leu Val Ser Leu Thr Tyr Val Ser Phe Arg Asn
            245              250              255

Leu Thr His Leu Glu Ser Leu His Leu Glu Asp Asn Ala Leu Lys Val
            260              265              270

Leu His Asn Gly Thr Leu Ala Glu Leu Gln Gly Leu Pro His Val Arg
        275              280              285

Val Phe Leu Asp Asn Asn Pro Trp Val Cys Asp Cys His Met Ala Asp
    290              295              300

Met Val Thr Trp Leu Lys Gln Thr Gly Val Val Gln Gly Lys Asp Arg
305              310              315              320

Leu Thr Cys Ala Phe Pro Glu Lys Met Arg Asn Arg Val Leu Leu Glu
            325              330              335

Leu Asn Ser Ala Asp Leu Asp Cys Asp Pro Ile Leu Pro Pro Ser Leu
            340              345              350

Gln Thr Ser Tyr Val Phe Leu Gly Ile Val Leu Ala Leu Ile Gly Ala
        355              360              365

Ile Phe Leu Leu Val Leu Tyr Leu Asn Arg Lys Gly Ile Lys Lys Trp
    370              375              380

Met His Asn Ile Arg Asp Ala Cys Arg Asp His Met Glu Gly Tyr His
385              390              395              400

Tyr Arg Tyr Glu Ile Asn Ala Asp Pro Arg Leu Thr Asn Leu Ser Ser
            405              410              415

Asn Ser Asp Val
            420

<210> SEQ ID NO 3
<211> LENGTH: 379
<212> TYPE: PRT
<213> ORGANISM: Gallus Gallus

<400> SEQUENCE: 3

Met Pro Gly Arg Glu Ala Glu Arg Arg Gly Ala Leu Cys Leu Gly Leu
1               5               10              15

Leu Leu His Ala Leu Leu Gly Cys Gly Ser Ala Gln Pro Pro Ala Ala
            20              25              30

Cys Pro Ala Pro Cys Glu Cys Ser Glu Ala Ala Lys Thr Val Lys Cys
        35              40              45
```

-continued

```
Val Asn Lys Asn Leu Thr Glu Val Pro Pro Asp Leu Pro Pro Tyr Val
    50                  55                  60

Arg Asn Leu Phe Ile Thr Gly Asn Arg Leu Gly Arg Leu Pro Ala Gly
65                  70                  75                  80

Ala Leu Ser Ala Pro Arg Leu Ala Glu Leu Gly Ser Leu Asn Leu Ser
                85                  90                  95

Gly Asn His Leu Arg Ala Val Glu Ala Gly Ala Leu Ala Ala Leu Pro
            100                 105                 110

Ala Leu Arg Gln Leu Asp Leu Gly Gly Asn Pro Leu Ala Glu Leu Ser
            115                 120                 125

Pro Leu Ala Phe Gly Arg Ala Ser Pro Leu Glu Glu Leu Ala Leu Arg
    130                 135                 140

Gly Ala Leu Arg Glu Gln Gly Ala Leu Leu Gly Leu Ala Asp Leu Leu
145                 150                 155                 160

Gln Ala Gly Ala Leu Arg Asn Leu Ser Arg Leu Glu Leu Ala Asp Asn
                165                 170                 175

Gly Leu Leu Leu Leu Pro Thr Gly Met Leu Gly Ala Leu Pro Ala Leu
            180                 185                 190

Arg His Leu Asp Leu Ser Asn Asn Ser Leu Val Gly Leu Arg Asn Val
            195                 200                 205

Ser Phe Gln Gly Leu Val Arg Leu Gln Ser Leu Asn Leu Ser Asp Asn
    210                 215                 220

Ser Leu Gly Val Leu Arg Asn Gly Thr Leu Ala Gln Trp Arg Gly Leu
225                 230                 235                 240

Pro Ala Leu Arg Arg Ile Ser Leu Ser His Asn Thr Trp Val Cys Asp
                245                 250                 255

Cys Ala Ile Glu Asp Met Val Ala Trp Leu Lys Glu Ser Asp Gln Val
            260                 265                 270

Glu Gly Lys Glu Ala Leu Ser Cys Ala Phe Pro Glu Lys Met Ala Gly
            275                 280                 285

Arg Ala Leu Leu Lys Leu Asn Thr Ser Glu Leu Asn Cys Ser Ala Pro
    290                 295                 300

Val Asp Val Pro Ser Gln Leu Gln Thr Ser Tyr Val Phe Leu Gly Ile
305                 310                 315                 320

Val Leu Ala Leu Ile Gly Ala Ile Phe Leu Leu Val Leu Tyr Leu Asn
                325                 330                 335

Arg Lys Gly Ile Lys Lys Trp Met His Asn Ile Arg Asp Ala Cys Arg
            340                 345                 350

Asp His Met Glu Gly Tyr His Tyr Arg Tyr Glu Ile Asn Ala Asp Pro
            355                 360                 365

Arg Leu Thr Asn Leu Ser Ser Asn Ser Asp Val
    370                 375
```

```
<210> SEQ ID NO 4
<211> LENGTH: 186
<212> TYPE: PRT
<213> ORGANISM: Homo Sapiens

<400> SEQUENCE: 4
```

```
Gln Asp Gly Asn Glu Glu Met Gly Gly Ile Thr Gln Thr Pro Tyr Lys
1                   5                   10                  15

Val Ser Ile Ser Gly Thr Thr Val Ile Leu Thr Cys Pro Gln Tyr Pro
                20                  25                  30

Gly Ser Glu Ile Leu Trp Gln His Asn Asp Lys Asn Ile Gly Gly Asp
            35                  40                  45
```

-continued

```
Glu Asp Asp Lys Asn Ile Gly Ser Asp Glu Asp His Leu Ser Leu Lys
    50              55              60

Glu Phe Ser Glu Leu Glu Gln Ser Gly Tyr Tyr Val Cys Tyr Pro Arg
65              70              75              80

Gly Ser Lys Pro Glu Asp Ala Asn Phe Tyr Leu Tyr Leu Arg Ala Arg
                85              90              95

Val Cys Glu Asn Cys Met Glu Met Asp Val Met Ser Val Ala Thr Ile
            100             105             110

Val Ile Val Asp Ile Cys Ile Thr Gly Gly Leu Leu Leu Leu Val Tyr
        115             120             125

Tyr Trp Ser Lys Asn Arg Lys Ala Lys Ala Lys Pro Val Thr Arg Gly
    130             135             140

Ala Gly Ala Gly Gly Arg Gln Arg Gly Gln Asn Lys Glu Arg Pro Pro
145             150             155             160

Pro Val Pro Asn Pro Asp Tyr Glu Pro Ile Arg Lys Gly Gln Arg Asp
                165             170             175

Leu Tyr Ser Gly Leu Asn Gln Arg Arg Ile
            180             185
```

```
<210> SEQ ID NO 5
<211> LENGTH: 125
<212> TYPE: PRT
<213> ORGANISM: Artificial sequence
<220> FEATURE:
<223> OTHER INFORMATION: Antibody variable region

<400> SEQUENCE: 5
```

```
Gln Val Gln Leu Val Glu Ser Gly Gly Gly Val Val Gln Pro Gly Arg
1               5               10              15

Ser Leu Arg Leu Ser Cys Ala Val Ser Gly Phe Thr Phe Ser Ser Tyr
            20              25              30

Asp Met Asn Trp Val Arg Gln Ala Pro Gly Lys Gly Leu Glu Trp Val
        35              40              45

Thr Phe Ile Ser Tyr Asp Gly Ser Asn Lys Tyr Asn Ala Asp Ser Val
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
                85              90              95

Ala Arg Asp Ser Tyr Ser Arg Ser Trp Tyr Gly Asp Tyr Tyr Gly Met
            100             105             110

Asp Val Trp Gly Gln Gly Thr Thr Val Thr Val Ser Ser
        115             120             125
```

```
<210> SEQ ID NO 6
<211> LENGTH: 8
<212> TYPE: PRT
<213> ORGANISM: Artificial sequence
<220> FEATURE:
<223> OTHER INFORMATION: CDR sequence

<400> SEQUENCE: 6
```

```
Gly Phe Thr Phe Ser Ser Tyr Asp
1               5
```

```
<210> SEQ ID NO 7
<211> LENGTH: 8
<212> TYPE: PRT
```

<213> ORGANISM: Artificial sequence
<220> FEATURE:
<223> OTHER INFORMATION: CDR sequence

<400> SEQUENCE: 7

Ile Ser Tyr Asp Gly Ser Asn Lys
1               5

<210> SEQ ID NO 8
<211> LENGTH: 18
<212> TYPE: PRT
<213> ORGANISM: Artificial sequence
<220> FEATURE:
<223> OTHER INFORMATION: CDR sequence

<400> SEQUENCE: 8

Ala Arg Asp Ser Tyr Ser Arg Ser Trp Tyr Gly Asp Tyr Tyr Gly Met
1               5                   10                  15

Asp Val

<210> SEQ ID NO 9
<211> LENGTH: 107
<212> TYPE: PRT
<213> ORGANISM: Artificial sequence
<220> FEATURE:
<223> OTHER INFORMATION: Antibody variable region

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 10
<211> LENGTH: 6
<212> TYPE: PRT
<213> ORGANISM: Artificial sequence
<220> FEATURE:
<223> OTHER INFORMATION: CDR sequence

<400> SEQUENCE: 10

Gln Gly Ile Ser Ser Trp
1               5

<210> SEQ ID NO 11
<211> LENGTH: 9
<212> TYPE: PRT
<213> ORGANISM: Artificial sequence
<220> FEATURE:
<223> OTHER INFORMATION: CDR sequence

<400> SEQUENCE: 11

Gln Gln Tyr Asn Ser Tyr Pro Leu Thr

-continued

```
1               5

<210> SEQ ID NO 12
<211> LENGTH: 121
<212> TYPE: PRT
<213> ORGANISM: Artificial sequence
<220> FEATURE:
<223> OTHER INFORMATION: Antibody variable region

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Arg Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Pro Gly Tyr Phe Asp Trp Leu Tyr Gly Asp Tyr Trp Gly
            100                 105                 110

Gln Gly Thr Leu Val Thr Val Ser Ser
        115                 120

<210> SEQ ID NO 13
<211> LENGTH: 8
<212> TYPE: PRT
<213> ORGANISM: Artificial sequence
<220> FEATURE:
<223> OTHER INFORMATION: CDR sequence

<400> SEQUENCE: 13

Gly Tyr Thr Phe Thr Ser Tyr Gly
1               5

<210> SEQ ID NO 14
<211> LENGTH: 8
<212> TYPE: PRT
<213> ORGANISM: Artificial sequence
<220> FEATURE:
<223> OTHER INFORMATION: CDR sequence

<400> SEQUENCE: 14

Ile Ser Ala Tyr Asn Gly Asn Thr
1               5

<210> SEQ ID NO 15
<211> LENGTH: 14
<212> TYPE: PRT
<213> ORGANISM: Artificial sequence
<220> FEATURE:
<223> OTHER INFORMATION: CDR sequence

<400> SEQUENCE: 15

Ala Arg Asp Pro Gly Tyr Phe Asp Trp Leu Tyr Gly Asp Tyr
1               5                   10

<210> SEQ ID NO 16
<211> LENGTH: 107
<212> TYPE: PRT
```

```
<213> ORGANISM: Artificial sequence
<220> FEATURE:
<223> OTHER INFORMATION: Antibody variable region

<400> SEQUENCE: 16

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Arg
                85                  90                  95

Thr Phe Gly Gln Gly Thr Lys Val Glu Ile Lys
            100                 105

<210> SEQ ID NO 17
<211> LENGTH: 6
<212> TYPE: PRT
<213> ORGANISM: Artificial sequence
<220> FEATURE:
<223> OTHER INFORMATION: CDR sequence

<400> SEQUENCE: 17

Gln Gly Ile Ser Ser Ala
1               5

<210> SEQ ID NO 18
<211> LENGTH: 9
<212> TYPE: PRT
<213> ORGANISM: Artificial sequence
<220> FEATURE:
<223> OTHER INFORMATION: CDR sequence

<400> SEQUENCE: 18

Gln Gln Phe Asn Ser Tyr Pro Arg Thr
1               5

<210> SEQ ID NO 19
<211> LENGTH: 121
<212> TYPE: PRT
<213> ORGANISM: Artificial sequence
<220> FEATURE:
<223> OTHER INFORMATION: Antibody variable region

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Asn Ala Asp Ser Val
    50                  55                  60

Lys Gly Arg Phe Thr Ile Phe Arg Asp Asn Ser Lys Asn Thr Leu Tyr
65                  70                  75                  80

Leu His Met Asn Ser Leu Arg Ala Glu Asp Thr Ala Val Tyr Tyr Cys
```

-continued

```
                    85                 90                 95

Ala Arg Asp Pro Gly Tyr Asn Asn Val Glu Tyr Leu Asp His Trp Gly
            100                 105                 110

Gln Gly Thr Leu Val Thr Val Ser Ser
        115                 120

<210> SEQ ID NO 20
<211> LENGTH: 8
<212> TYPE: PRT
<213> ORGANISM: Artificial sequence
<220> FEATURE:
<223> OTHER INFORMATION: CDR sequence

<400> SEQUENCE: 20

Gly Phe Thr Phe Ser Ser Tyr Ala
1               5

<210> SEQ ID NO 21
<211> LENGTH: 8
<212> TYPE: PRT
<213> ORGANISM: Artificial sequence
<220> FEATURE:
<223> OTHER INFORMATION: CDR sequence

<400> SEQUENCE: 21

Ile Ser Gly Ser Gly Gly Ser Thr
1               5

<210> SEQ ID NO 22
<211> LENGTH: 14
<212> TYPE: PRT
<213> ORGANISM: Artificial sequence
<220> FEATURE:
<223> OTHER INFORMATION: CDR sequence

<400> SEQUENCE: 22

Ala Arg Asp Pro Gly Tyr Asn Asn Val Glu Tyr Leu Asp His
1               5                   10

<210> SEQ ID NO 23
<211> LENGTH: 107
<212> TYPE: PRT
<213> ORGANISM: Artificial sequence
<220> FEATURE:
<223> OTHER INFORMATION: Antibody variable region

<400> SEQUENCE: 23

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105
```

```
<210> SEQ ID NO 24
<211> LENGTH: 6
<212> TYPE: PRT
<213> ORGANISM: Artificial sequence
<220> FEATURE:
<223> OTHER INFORMATION: CDR sequence

<400> SEQUENCE: 24

Gln Gly Ile Ser Ser Ala
1               5

<210> SEQ ID NO 25
<211> LENGTH: 9
<212> TYPE: PRT
<213> ORGANISM: Artificial sequence
<220> FEATURE:
<223> OTHER INFORMATION: CDR sequence

<400> SEQUENCE: 25

Gln Gln Phe Asn Ser Tyr Pro Leu Thr
1               5

<210> SEQ ID NO 26
<211> LENGTH: 115
<212> TYPE: PRT
<213> ORGANISM: Artificial sequence
<220> FEATURE:
<223> OTHER INFORMATION: Antibody variable region

<400> SEQUENCE: 26

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Arg Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Ala Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Gly Met Tyr Tyr Cys
                85                  90                  95

Ala Arg Ser Val Leu Phe Asp Tyr Trp Gly Gln Gly Thr Leu Val Thr
            100                 105                 110

Val Ser Ser
        115

<210> SEQ ID NO 27
<211> LENGTH: 8
<212> TYPE: PRT
<213> ORGANISM: Artificial sequence
<220> FEATURE:
<223> OTHER INFORMATION: CDR sequence

<400> SEQUENCE: 27

Gly Tyr Arg Phe Thr Ser Tyr Trp
1               5

<210> SEQ ID NO 28
<211> LENGTH: 8
<212> TYPE: PRT
<213> ORGANISM: Artificial sequence
<220> FEATURE:
<223> OTHER INFORMATION: CDR sequence
```

-continued

<400> SEQUENCE: 28

Ile Tyr Pro Gly Asp Ser Asp Ala
1               5

<210> SEQ ID NO 29
<211> LENGTH: 8
<212> TYPE: PRT
<213> ORGANISM: Artificial sequence
<220> FEATURE:
<223> OTHER INFORMATION: CDR sequence

<400> SEQUENCE: 29

Ala Arg Ser Val Leu Phe Asp Tyr
1               5

<210> SEQ ID NO 30
<211> LENGTH: 107
<212> TYPE: PRT
<213> ORGANISM: Artificial sequence
<220> FEATURE:
<223> OTHER INFORMATION: Antibody variable region

<400> SEQUENCE: 30

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
                20                  25                  30

Leu Ala Trp Tyr Gln Gln Lys Pro Gly Lys Ala Pro Lys Leu Leu Ile
            35                  40                  45

Tyr Asp Val Ser Asn Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro His
                85                  90                  95

Thr Phe Gly Gln Gly Thr Lys Leu Glu Ile Lys
            100                 105

<210> SEQ ID NO 31
<211> LENGTH: 6
<212> TYPE: PRT
<213> ORGANISM: Artificial sequence
<220> FEATURE:
<223> OTHER INFORMATION: CDR sequence

<400> SEQUENCE: 31

Gln Gly Ile Ser Ser Ala
1               5

<210> SEQ ID NO 32
<211> LENGTH: 9
<212> TYPE: PRT
<213> ORGANISM: Artificial sequence
<220> FEATURE:
<223> OTHER INFORMATION: CDR sequence

<400> SEQUENCE: 32

Gln Gln Phe Asn Ser Tyr Pro His Thr
1               5

<210> SEQ ID NO 33
<211> LENGTH: 123

```
<212> TYPE: PRT
<213> ORGANISM: Artificial sequence
<220> FEATURE:
<223> OTHER INFORMATION: Antibody variable region

<400> SEQUENCE: 33

Glu Val Gln Leu Leu Glu Ser Arg Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Thr Ile Ser Gly Ser Gly Gly Ser Thr Tyr Tyr Ala Asp Ser Val
            50                  55                  60

Lys Gly Arg Phe Thr Ile Ser Arg Asp Asn Ser Lys Lys Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Trp Gly Ser Gly Ser Tyr Pro Ala Glu Tyr Phe Gln His
            100                 105                 110

Trp Gly Gln Gly Thr Leu Val Thr Val Ser Ser
        115                 120

<210> SEQ ID NO 34
<211> LENGTH: 8
<212> TYPE: PRT
<213> ORGANISM: Artificial sequence
<220> FEATURE:
<223> OTHER INFORMATION: CDR sequence

<400> SEQUENCE: 34

Gly Phe Thr Phe Ser Ser Tyr Ala
1               5

<210> SEQ ID NO 35
<211> LENGTH: 8
<212> TYPE: PRT
<213> ORGANISM: Artificial sequence
<220> FEATURE:
<223> OTHER INFORMATION: CDR sequence

<400> SEQUENCE: 35

Ile Ser Gly Ser Gly Gly Ser Thr
1               5

<210> SEQ ID NO 36
<211> LENGTH: 16
<212> TYPE: PRT
<213> ORGANISM: Artificial sequence
<220> FEATURE:
<223> OTHER INFORMATION: CDR sequence

<400> SEQUENCE: 36

Ala Lys Asp Trp Gly Ser Gly Ser Tyr Pro Ala Glu Tyr Phe Gln His
1               5                   10                  15

<210> SEQ ID NO 37
<211> LENGTH: 108
<212> TYPE: PRT
<213> ORGANISM: Artificial sequence
<220> FEATURE:
<223> OTHER INFORMATION: Antibody variable region

<400> SEQUENCE: 37
```

-continued

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Leu Met
                85                  90                  95

Tyr Thr Phe Gly Gln Gly Thr Lys Leu Glu Ile Lys
            100                 105
```

```
<210> SEQ ID NO 38
<211> LENGTH: 6
<212> TYPE: PRT
<213> ORGANISM: Artificial sequence
<220> FEATURE:
<223> OTHER INFORMATION: CDR sequence

<400> SEQUENCE: 38

Gln Ser Val Ser Ser Tyr
1               5
```

```
<210> SEQ ID NO 39
<211> LENGTH: 10
<212> TYPE: PRT
<213> ORGANISM: Artificial sequence
<220> FEATURE:
<223> OTHER INFORMATION: CDR sequence

<400> SEQUENCE: 39

Gln Gln Arg Ser Asn Trp Leu Met Tyr Thr
1               5                   10
```

```
<210> SEQ ID NO 40
<211> LENGTH: 122
<212> TYPE: PRT
<213> ORGANISM: Artificial sequence
<220> FEATURE:
<223> OTHER INFORMATION: Antibody variable region

<400> SEQUENCE: 40

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Thr Trp Ile Arg Gln Pro Pro Gly Lys Gly Leu Glu Trp Ile
        35                  40                  45

Gly Glu Ile Asp His Ser Glu Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Gly Trp Phe Gly Glu Leu Tyr His Tyr Tyr Tyr Gly Met Asp Val Trp
            100                 105                 110
```

Gly Gln Gly Thr Thr Val Thr Val Ser Ser
        115                 120

<210> SEQ ID NO 41
<211> LENGTH: 8
<212> TYPE: PRT
<213> ORGANISM: Artificial sequence
<220> FEATURE:
<223> OTHER INFORMATION: CDR sequence

<400> SEQUENCE: 41

Gly Gly Ser Phe Ser Gly Tyr Tyr
1               5

<210> SEQ ID NO 42
<211> LENGTH: 7
<212> TYPE: PRT
<213> ORGANISM: Artificial sequence
<220> FEATURE:
<223> OTHER INFORMATION: CDR sequence

<400> SEQUENCE: 42

Ile Asp His Ser Glu Ser Thr
1               5

<210> SEQ ID NO 43
<211> LENGTH: 16
<212> TYPE: PRT
<213> ORGANISM: Artificial sequence
<220> FEATURE:
<223> OTHER INFORMATION: CDR sequence

<400> SEQUENCE: 43

Ala Gly Trp Phe Gly Glu Leu Tyr His Tyr Tyr Tyr Gly Met Asp Val
1               5                   10                  15

<210> SEQ ID NO 44
<211> LENGTH: 107
<212> TYPE: PRT
<213> ORGANISM: Artificial sequence
<220> FEATURE:
<223> OTHER INFORMATION: Antibody variable region

<400> SEQUENCE: 44

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 45
<211> LENGTH: 6
<212> TYPE: PRT
<213> ORGANISM: Artificial sequence
<220> FEATURE:

<223> OTHER INFORMATION: CDR sequence

<400> SEQUENCE: 45

Gln Ser Val Ser Ser Tyr
1               5

<210> SEQ ID NO 46
<211> LENGTH: 9
<212> TYPE: PRT
<213> ORGANISM: Artificial sequence
<220> FEATURE:
<223> OTHER INFORMATION: CDR sequence

<400> SEQUENCE: 46

Gln Gln Arg Ser Asn Trp Pro Leu Thr
1               5

<210> SEQ ID NO 47
<211> LENGTH: 122
<212> TYPE: PRT
<213> ORGANISM: Artificial sequence
<220> FEATURE:
<223> OTHER INFORMATION: Antibody variable region

<400> SEQUENCE: 47

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Ala Trp Phe Gly Glu Leu Trp Asp Tyr Tyr Tyr Gly Met Asp Val Trp
            100                 105                 110

Gly Gln Gly Thr Thr Val Thr Val Ser Ser
        115                 120

<210> SEQ ID NO 48
<211> LENGTH: 8
<212> TYPE: PRT
<213> ORGANISM: Artificial sequence
<220> FEATURE:
<223> OTHER INFORMATION: CDR sequence

<400> SEQUENCE: 48

Gly Gly Ser Phe Ser Gly Tyr Tyr
1               5

<210> SEQ ID NO 49
<211> LENGTH: 7
<212> TYPE: PRT
<213> ORGANISM: Artificial sequence
<220> FEATURE:
<223> OTHER INFORMATION: CDR sequence

<400> SEQUENCE: 49

Ile Asp His Ser Gly Ser Thr
1               5

```
<210> SEQ ID NO 50
<211> LENGTH: 16
<212> TYPE: PRT
<213> ORGANISM: Artificial sequence
<220> FEATURE:
<223> OTHER INFORMATION: CDR sequence

<400> SEQUENCE: 50

Ala Ala Trp Phe Gly Glu Leu Trp Asp Tyr Tyr Tyr Gly Met Asp Val
1               5                   10                  15

<210> SEQ ID NO 51
<211> LENGTH: 107
<212> TYPE: PRT
<213> ORGANISM: Artificial sequence
<220> FEATURE:
<223> OTHER INFORMATION: Antibody variable region

<400> SEQUENCE: 51

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Phe
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Arg Leu Glu Ile Lys
            100                 105

<210> SEQ ID NO 52
<211> LENGTH: 6
<212> TYPE: PRT
<213> ORGANISM: Artificial sequence
<220> FEATURE:
<223> OTHER INFORMATION: CDR sequence

<400> SEQUENCE: 52

Gln Ser Val Ser Ser Phe
1               5

<210> SEQ ID NO 53
<211> LENGTH: 9
<212> TYPE: PRT
<213> ORGANISM: Artificial sequence
<220> FEATURE:
<223> OTHER INFORMATION: CDR sequence

<400> SEQUENCE: 53

Gln Gln Arg Ser Asn Trp Pro Leu Thr
1               5

<210> SEQ ID NO 54
<211> LENGTH: 8
<212> TYPE: PRT
<213> ORGANISM: Artificial sequence
<220> FEATURE:
<223> OTHER INFORMATION: CDR sequence
```

<400> SEQUENCE: 54

Gly Phe Thr Phe Asn Thr Tyr Ala
1               5

<210> SEQ ID NO 55
<211> LENGTH: 10
<212> TYPE: PRT
<213> ORGANISM: Artificial sequence
<220> FEATURE:
<223> OTHER INFORMATION: CDR sequence

<400> SEQUENCE: 55

Ile Arg Ser Lys Tyr Asn Asn Tyr Ala Thr
1               5                   10

<210> SEQ ID NO 56
<211> LENGTH: 16
<212> TYPE: PRT
<213> ORGANISM: Artificial sequence
<220> FEATURE:
<223> OTHER INFORMATION: CDR sequence

<400> SEQUENCE: 56

Val Arg His Gly Asn Phe Gly Asn Ser Tyr Val Ser Trp Phe Ala Tyr
1               5                   10                  15

<210> SEQ ID NO 57
<211> LENGTH: 125
<212> TYPE: PRT
<213> ORGANISM: Artificial sequence
<220> FEATURE:
<223> OTHER INFORMATION: Antibody variable region

<400> SEQUENCE: 57

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 58
<211> LENGTH: 9
<212> TYPE: PRT
<213> ORGANISM: Artificial sequence
<220> FEATURE:
<223> OTHER INFORMATION: CDR sequence

<400> SEQUENCE: 58

Thr Gly Ala Val Thr Thr Ser Asn Tyr
1               5

-continued

```
<210> SEQ ID NO 59
<211> LENGTH: 9
<212> TYPE: PRT
<213> ORGANISM: Artificial sequence
<220> FEATURE:
<223> OTHER INFORMATION: CDR sequence

<400> SEQUENCE: 59

Ala Leu Trp Tyr Ser Asn Leu Trp Val
1               5

<210> SEQ ID NO 60
<211> LENGTH: 109
<212> TYPE: PRT
<213> ORGANISM: Artificial sequence
<220> FEATURE:
<223> OTHER INFORMATION: Antibody variable region

<400> SEQUENCE: 60

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 61
<211> LENGTH: 8
<212> TYPE: PRT
<213> ORGANISM: Artificial sequence
<220> FEATURE:
<223> OTHER INFORMATION: CDR sequence

<400> SEQUENCE: 61

Gly Phe Thr Phe Asn Pro Tyr Ala
1               5

<210> SEQ ID NO 62
<211> LENGTH: 125
<212> TYPE: PRT
<213> ORGANISM: Artificial sequence
<220> FEATURE:
<223> OTHER INFORMATION: Antibody variable region

<400> SEQUENCE: 62

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Pro Tyr
                20                  25                  30

Ala Met Asn Trp Val Arg Gln Ala Pro Gly Lys Gly Leu Glu Trp Val
                35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
```

```
65                    70                    75                    80

Leu Tyr Leu Gln Met Asn Asn Leu Lys Thr Glu Asp Thr Ala Met Tyr
                85                    90                    95

Tyr Cys Val Arg His Gly Asn Phe Gly Asn Ser Tyr Val Ser Trp Phe
                100                   105                   110

Ala Tyr Trp Gly Gln Gly Thr Leu Val Thr Val Ser Ser
        115                   120                   125

<210> SEQ ID NO 63
<211> LENGTH: 8
<212> TYPE: PRT
<213> ORGANISM: Artificial sequence
<220> FEATURE:
<223> OTHER INFORMATION: CDR sequence

<400> SEQUENCE: 63

Gly Phe Thr Phe Asn Met Tyr Ala
1               5

<210> SEQ ID NO 64
<211> LENGTH: 125
<212> TYPE: PRT
<213> ORGANISM: Artificial sequence
<220> FEATURE:
<223> OTHER INFORMATION: Antibody variable region

<400> SEQUENCE: 64

Glu Val Lys Leu Val Glu Ser Gly Gly Gly Leu Val Gln Pro Gly Gly
1               5                     10                    15

Ser Leu Arg Leu Ser Cys Ala Ala Ser Gly Phe Thr Phe Asn Met Tyr
                20                    25                    30

Ala Met Asn Trp Val Arg Gln Ala Pro Gly Lys Gly Leu Glu Trp Val
            35                    40                    45

Ala Arg Ile Arg Ser Lys Tyr Asn Asn Tyr Ala Thr Tyr Tyr Ala Asp
        50                    55                    60

Ser Val Lys Asp Arg Phe Thr Ile Ser Arg Asp Asp Ser Lys Ser Ser
65                    70                    75                    80

Leu Tyr Leu Gln Met Asn Asn Leu Lys Thr Glu Asp Thr Ala Met Tyr
                85                    90                    95

Tyr Cys Val Arg His Gly Asn Phe Gly Asn Ser Tyr Val Ser Trp Phe
                100                   105                   110

Ala Tyr Trp Gly Gln Gly Thr Leu Val Thr Val Ser Ser
        115                   120                   125

<210> SEQ ID NO 65
<211> LENGTH: 10
<212> TYPE: PRT
<213> ORGANISM: Artificial sequence
<220> FEATURE:
<223> OTHER INFORMATION: CDR sequence

<400> SEQUENCE: 65

Ile Arg Ser Lys Tyr Asn Glu Tyr Ala Thr
1               5                     10

<210> SEQ ID NO 66
<211> LENGTH: 125
<212> TYPE: PRT
<213> ORGANISM: Artificial sequence
<220> FEATURE:
<223> OTHER INFORMATION: Antibody variable region
```

<400> SEQUENCE: 66

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Glu Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
            85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 67
<211> LENGTH: 16
<212> TYPE: PRT
<213> ORGANISM: Artificial sequence
<220> FEATURE:
<223> OTHER INFORMATION: CDR sequence

<400> SEQUENCE: 67

Val Arg Gly Gly Asn Phe Gly Asn Ser Tyr Val Ser Trp Phe Ala Tyr
1               5                   10                  15

<210> SEQ ID NO 68
<211> LENGTH: 125
<212> TYPE: PRT
<213> ORGANISM: Artificial sequence
<220> FEATURE:
<223> OTHER INFORMATION: Antibody variable region

<400> SEQUENCE: 68

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
            85                  90                  95

Tyr Cys Val Arg Gly Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 69
<211> LENGTH: 16
<212> TYPE: PRT
<213> ORGANISM: Artificial sequence
<220> FEATURE:

```
<223> OTHER INFORMATION: CDR sequence

<400> SEQUENCE: 69

Val Arg Asn Gly Asn Phe Gly Asn Ser Tyr Val Ser Trp Phe Ala Tyr
1               5                   10                  15

<210> SEQ ID NO 70
<211> LENGTH: 125
<212> TYPE: PRT
<213> ORGANISM: Artificial sequence
<220> FEATURE:
<223> OTHER INFORMATION: Antibody variabl region

<400> SEQUENCE: 70

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg Asn Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 71
<211> LENGTH: 16
<212> TYPE: PRT
<213> ORGANISM: Artificial sequence
<220> FEATURE:
<223> OTHER INFORMATION: CDR sequence

<400> SEQUENCE: 71

Val Arg His Gly Asn Phe Pro Asn Ser Tyr Val Ser Trp Phe Ala Tyr
1               5                   10                  15

<210> SEQ ID NO 72
<211> LENGTH: 125
<212> TYPE: PRT
<213> ORGANISM: Artificial sequence
<220> FEATURE:
<223> OTHER INFORMATION: Antibody variable region

<400> SEQUENCE: 72

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80
```

-continued

```
Leu Tyr Leu Gln Met Asn Asn Leu Lys Thr Glu Asp Thr Ala Met Tyr
            85              90                  95

Tyr Cys Val Arg His Gly Asn Phe Pro Asn Ser Tyr Val Ser Trp Phe
        100             105             110

Ala Tyr Trp Gly Gln Gly Thr Leu Val Thr Val Ser Ser
        115             120             125
```

<210> SEQ ID NO 73
<211> LENGTH: 16
<212> TYPE: PRT
<213> ORGANISM: Artificial sequence
<220> FEATURE:
<223> OTHER INFORMATION: CDR sequence

<400> SEQUENCE: 73

```
Val Arg His Gly Asn Phe Gly Asn Ser Tyr Val Ala Trp Phe Ala Tyr
1               5               10              15
```

<210> SEQ ID NO 74
<211> LENGTH: 125
<212> TYPE: PRT
<213> ORGANISM: Artificial sequence
<220> FEATURE:
<223> OTHER INFORMATION: Antibody variable region

<400> SEQUENCE: 74

```
Glu Val Lys Leu Val Glu Ser Gly Gly Gly Leu Val Gln Pro Gly Gly
1               5               10                  15

Ser Leu Arg Leu Ser Cys Ala Ala Ser Gly Phe Thr Phe Asn Thr Tyr
            20              25                  30

Ala Met Asn Trp Val Arg Gln Ala Pro Gly Lys Gly Leu Glu Trp Val
            35              40                  45

Ala Arg Ile Arg Ser Lys Tyr Asn Asn Tyr Ala Thr Tyr Tyr Ala Asp
    50              55                  60

Ser Val Lys Asp Arg Phe Thr Ile Ser Arg Asp Asp Ser Lys Ser Ser
65              70                  75                  80

Leu Tyr Leu Gln Met Asn Asn Leu Lys Thr Glu Asp Thr Ala Met Tyr
            85              90                  95

Tyr Cys Val Arg His Gly Asn Phe Gly Asn Ser Tyr Val Ala Trp Phe
        100             105             110

Ala Tyr Trp Gly Gln Gly Thr Leu Val Thr Val Ser Ser
        115             120             125
```

<210> SEQ ID NO 75
<211> LENGTH: 16
<212> TYPE: PRT
<213> ORGANISM: Artificial sequence
<220> FEATURE:
<223> OTHER INFORMATION: CDR sequence

<400> SEQUENCE: 75

```
Val Arg His Gly Asn Phe Gly Asn Ser Tyr Val Gly Trp Phe Ala Tyr
1               5               10              15
```

<210> SEQ ID NO 76
<211> LENGTH: 125
<212> TYPE: PRT
<213> ORGANISM: Artificial sequence
<220> FEATURE:
<223> OTHER INFORMATION: Antibody variable region

<400> SEQUENCE: 76

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Gly Trp Phe
                100                 105                 110

Ala Tyr Trp Gly Gln Gly Thr Leu Val Thr Val Ser Ser
            115                 120                 125
```

<210> SEQ ID NO 77
<211> LENGTH: 16
<212> TYPE: PRT
<213> ORGANISM: Artificial sequence
<220> FEATURE:
<223> OTHER INFORMATION: CDR sequence

<400> SEQUENCE: 77

```
Val Arg His Gly Asn Phe Gly Asn Ser Tyr Val Ser Trp Phe Ala Val
1               5                   10                  15
```

<210> SEQ ID NO 78
<211> LENGTH: 125
<212> TYPE: PRT
<213> ORGANISM: Artificial sequence
<220> FEATURE:
<223> OTHER INFORMATION: CDR sequence

<400> SEQUENCE: 78

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
                100                 105                 110

Ala Val Trp Gly Gln Gly Thr Leu Val Thr Val Ser Ser
            115                 120                 125
```

<210> SEQ ID NO 79
<211> LENGTH: 16
<212> TYPE: PRT
<213> ORGANISM: Artificial sequence
<220> FEATURE:
<223> OTHER INFORMATION: CDR sequence -continued

<400> SEQUENCE: 79

Val Arg His Gly Asn Phe Gly Asn Ser Tyr Val Ser Trp Phe Ala Met
1               5                   10                  15

<210> SEQ ID NO 80
<211> LENGTH: 125
<212> TYPE: PRT
<213> ORGANISM: Artificial sequence
<220> FEATURE:
<223> OTHER INFORMATION: Antibody variable region

<400> SEQUENCE: 80

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Met Trp Gly Gln Gly Thr Leu Val Thr Val Ser Ser
        115                 120                 125

<210> SEQ ID NO 81
<211> LENGTH: 16
<212> TYPE: PRT
<213> ORGANISM: Artificial sequence
<220> FEATURE:
<223> OTHER INFORMATION: CDR sequence

<400> SEQUENCE: 81

Val Arg His Gly Asn Phe Gly Asn Ser Tyr Val Ser Trp Phe Ala Arg
1               5                   10                  15

<210> SEQ ID NO 82
<211> LENGTH: 125
<212> TYPE: PRT
<213> ORGANISM: Artificial sequence
<220> FEATURE:
<223> OTHER INFORMATION: Antibody variable region

<400> SEQUENCE: 82

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

-continued

```
Tyr Cys Val Arg His Gly Asn Phe Gly Asn Ser Tyr Val Ser Trp Phe
            100                 105                 110

Ala Arg Trp Gly Gln Gly Thr Leu Val Thr Val Ser Ser
        115                 120                 125

<210> SEQ ID NO 83
<211> LENGTH: 119
<212> TYPE: PRT
<213> ORGANISM: Artificial sequence
<220> FEATURE:
<223> OTHER INFORMATION: Antibody variable region

<400> SEQUENCE: 83

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Phe
            20                  25                  30

Gly Met Asn Trp Val Lys Gln Gly Pro Gly Glu Gly Leu Lys Trp Met
        35                  40                  45

Gly Trp Ile Asn Thr Asn Thr Gly Glu Pro Arg Tyr Ala Glu Glu Phe
    50                  55                  60

Lys Gly Arg Phe Ala Phe Ser Leu Glu Thr Thr Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Asp Trp Asp Gly Ala Tyr Phe Phe Asp Tyr Trp Gly Gln Gly
            100                 105                 110

Thr Thr Leu Thr Val Ser Ser
        115

<210> SEQ ID NO 84
<211> LENGTH: 107
<212> TYPE: PRT
<213> ORGANISM: Artificial sequence
<220> FEATURE:
<223> OTHER INFORMATION: Antibody variable region

<400> SEQUENCE: 84

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Asn Phe Ala Thr Asn Arg Tyr Thr Gly Val Pro Asn Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Leu Tyr Phe Cys Gln Gln Asp Tyr Ser Ser Pro Trp
                85                  90                  95

Thr Phe Gly Gly Gly Thr Lys Leu Glu Ile Lys
            100                 105

<210> SEQ ID NO 85
<211> LENGTH: 122
<212> TYPE: PRT
<213> ORGANISM: Artificial sequence
<220> FEATURE:
<223> OTHER INFORMATION: Antibody variable region
```

<400> SEQUENCE: 85

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
        50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gln Trp Asp Tyr Asp Val Arg Ala Met Asn Tyr Trp
            100                 105                 110

Gly Gln Gly Thr Ser Val Thr Val Ser Ser
        115                 120

<210> SEQ ID NO 86
<211> LENGTH: 107
<212> TYPE: PRT
<213> ORGANISM: Artificial sequence
<220> FEATURE:
<223> OTHER INFORMATION: Antibody variable region

<400> SEQUENCE: 86

Asp Ile Val Met Thr Gln Ser His Ile Phe Met Ser Thr Ser Val Gly
1               5                   10                  15

Asp Arg Val Ser Ile Thr Cys Lys Ala Ser Gln Asp Val Asp Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg Leu Thr Gly Val Pro Asp Arg Phe Thr Gly
        50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Tyr
                85                  90                  95

Thr Phe Gly Gly Gly Thr Lys Leu Glu Ile Lys
            100                 105

<210> SEQ ID NO 87
<211> LENGTH: 120
<212> TYPE: PRT
<213> ORGANISM: Artificial sequence
<220> FEATURE:
<223> OTHER INFORMATION: Antibody variable region

<400> SEQUENCE: 87

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Met His Trp Val Lys Gln Ser His Gly Lys Ser Leu Glu Trp Ile
        35                  40                  45

Gly Arg Ile Asn Pro Asn Asn Gly Val Thr Leu Tyr Asn Gln Lys Phe
        50                  55                  60

```
Lys Asp Lys Ala Ile Leu Thr Val Asp Lys Ser Ser Thr Thr Ala Tyr
65              70                  75                  80

Met Glu Leu Arg Ser Leu Thr Ser Glu Asp Ser Ala Val Tyr Tyr Cys
                85                  90                  95

Ala Arg Ser Thr Met Ile Thr Asn Tyr Val Met Asp Tyr Trp Gly Gln
                100                 105                 110

Val Thr Ser Val Thr Val Ser Ser
        115                 120

<210> SEQ ID NO 88
<211> LENGTH: 107
<212> TYPE: PRT
<213> ORGANISM: Homo Sapiens

<400> SEQUENCE: 88

Ser Ile Val Met Thr Gln Thr Pro Thr Phe Leu Leu Val Ser Ala Gly
1               5                   10                  15

Asp Arg Val Thr Ile Thr Cys Lys Ala Ser Gln Ser Val Ser Asn Asp
                20                  25                  30

Val Ala Trp Tyr Gln Gln Lys Pro Gly Gln Ser Pro Thr Leu Leu Ile
        35                  40                  45

Ser Tyr Thr Ser Ser Arg Tyr Ala Gly Val Pro Asp Arg Phe Ile Gly
    50                  55                  60

Ser Gly Tyr Gly Thr Asp Phe Thr Phe Thr Ile Ser Thr Leu Gln Ala
65                  70                  75                  80

Glu Asp Leu Ala Val Tyr Phe Cys Gln Gln Asp Tyr Asn Ser Pro Pro
                85                  90                  95

Thr Phe Gly Gly Gly Thr Lys Leu Glu Ile Lys
            100                 105

<210> SEQ ID NO 89
<211> LENGTH: 330
<212> TYPE: PRT
<213> ORGANISM: Artificial sequence
<220> FEATURE:
<223> OTHER INFORMATION: Antibody variable region

<400> SEQUENCE: 89

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140
```

-continued

```
Val Val Val Asp Val Ser His Glu Asp Pro Glu Val Lys Phe Asn Trp
145             150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 90
<211> LENGTH: 330
<212> TYPE: PRT
<213> ORGANISM: Artificial sequence
<220> FEATURE:
<223> OTHER INFORMATION: Antibody constant region

<400> SEQUENCE: 90

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Leu
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 91
<211> LENGTH: 330
<212> TYPE: PRT
<213> ORGANISM: Artificial sequence
<220> FEATURE:
<223> OTHER INFORMATION: Antibody constant region

<400> SEQUENCE: 91

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205
```

-continued

```
Lys Ala Leu Pro Ala Pro Ile Glu Lys Thr Ile Ser Lys Ala Lys Gly
    210             215             220

Gln Pro Arg Glu Pro Gln Val Tyr Thr Leu Pro Pro Ser Arg Glu Glu
225             230             235             240

Met Thr Lys Asn Gln Val Ser Leu Thr Cys Leu Val Lys Gly Phe Tyr
            245             250             255

Pro Ser Asp Ile Ala Val Glu Trp Glu Ser Asn Gly Gln Pro Glu Asn
            260             265             270

Asn Tyr Lys Thr Thr Pro Pro Val Leu Asp Ser Asp Gly Ser Phe Phe
            275             280             285

Leu Tyr Ser Lys Leu Thr Val Asp Lys Ser Arg Trp Gln Gln Gly Asn
    290             295             300

Val Phe Ser Cys Ser Val Met His Glu Ala Leu His Asn His Tyr Thr
305             310             315             320

Gln Lys Ser Leu Ser Leu Ser Pro Gly Lys
            325             330
```

```
<210> SEQ ID NO 92
<211> LENGTH: 330
<212> TYPE: PRT
<213> ORGANISM: Artificial sequence
<220> FEATURE:
<223> OTHER INFORMATION: Antibody constant region

<400> SEQUENCE: 92
```

```
Ala Ser Thr Lys Gly Pro Ser Val Phe Pro Leu Ala Pro Ser Ser Lys
1               5               10              15

Ser Thr Ser Gly Gly Thr Ala Ala Leu Gly Cys Leu Val Lys Asp Tyr
            20              25              30

Phe Pro Glu Pro Val Thr Val Ser Trp Asn Ser Gly Ala Leu Thr Ser
            35              40              45

Gly Val His Thr Phe Pro Ala Val Leu Gln Ser Ser Gly Leu Tyr Ser
    50              55              60

Leu Ser Ser Val Val Thr Val Pro Ser Ser Ser Leu Gly Thr Gln Thr
65              70              75              80

Tyr Ile Cys Asn Val Asn His Lys Pro Ser Asn Thr Lys Val Asp Lys
            85              90              95

Arg Val Glu Pro Lys Ser Cys Asp Lys Thr His Thr Cys Pro Pro Cys
            100             105             110

Pro Ala Pro Glu Phe Glu Gly Gly Pro Ser Val Phe Leu Phe Pro Pro
            115             120             125

Lys Pro Lys Asp Thr Leu Met Ile Ser Arg Thr Pro Glu Val Thr Cys
    130             135             140

Val Val Val Ala Val Ser His Glu Asp Pro Glu Val Lys Phe Asn Trp
145             150             155             160

Tyr Val Asp Gly Val Glu Val His Asn Ala Lys Thr Lys Pro Arg Glu
            165             170             175

Glu Gln Tyr Asn Ser Thr Tyr Arg Val Val Ser Val Leu Thr Val Leu
            180             185             190

His Gln Asp Trp Leu Asn Gly Lys Glu Tyr Lys Cys Lys Val Ser Asn
            195             200             205

Lys Ala Leu Pro Ala Pro Ile Glu Lys Thr Ile Ser Lys Ala Lys Gly
    210             215             220

Gln Pro Arg Glu Pro Gln Val Tyr Thr Leu Pro Pro Ser Arg Glu Glu
225             230             235             240
```

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Leu
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 93
<211> LENGTH: 330
<212> TYPE: PRT
<213> ORGANISM: Artificial Sequence
<220> FEATURE:
<223> OTHER INFORMATION: N/A

<400> SEQUENCE: 93

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

-continued

```
Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 94
<211> LENGTH: 330
<212> TYPE: PRT
<213> ORGANISM: Artificial sequence
<220> FEATURE:
<223> OTHER INFORMATION: Antibody constant region

<400> SEQUENCE: 94

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
        20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
        100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Gln Gly Asn
        290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 95
<211> LENGTH: 107
<212> TYPE: PRT
<213> ORGANISM: Homo Sapiens

<400> SEQUENCE: 95

Arg Thr Val Ala Ala Pro Ser Val Phe Ile Phe Pro Pro Ser Asp Glu
1                   5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 96
<211> LENGTH: 106
<212> TYPE: PRT
<213> ORGANISM: Homo Sapiens

<400> SEQUENCE: 96

Gly Gln Pro Lys Ala Ala Pro Ser Val Thr Leu Phe Pro Pro Ser Ser
1                   5                   10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
        50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 97
<211> LENGTH: 127
<212> TYPE: PRT
<213> ORGANISM: Artificial sequence
<220> FEATURE:
<223> OTHER INFORMATION: Antibody variable region

<400> SEQUENCE: 97

Gln Val Gln Leu Val Gln Ser Gly Ala Glu Val Lys Lys Pro Gly Ala
1                   5                   10                  15

Ser Val Lys Val Ser Cys Gln Ala Ser Gly Tyr Arg Phe Ser Asn Phe
                20                  25                  30
```

```
Val Ile His Trp Val Arg Gln Ala Pro Gly Gln Arg Phe Glu Trp Met
    35                  40                  45

Gly Trp Ile Asn Pro Tyr Asn Gly Asn Lys Glu Phe Ser Ala Lys Phe
    50                  55                  60

Gln Asp Arg Val Thr Phe Thr Ala Asp Thr Ser Ala Asn Thr Ala Tyr
65                  70                  75                  80

Met Glu Leu Arg Ser Leu Arg Ser Ala Asp Thr Ala Val Tyr Tyr Cys
                85                  90                  95

Ala Arg Val Gly Pro Tyr Ser Trp Asp Asp Ser Pro Gln Asp Asn Tyr
                100                 105                 110

Tyr Met Asp Val Trp Gly Lys Gly Thr Thr Val Ile Val Ser Ser
    115                 120                 125

<210> SEQ ID NO 98
<211> LENGTH: 108
<212> TYPE: PRT
<213> ORGANISM: Artificial sequence
<220> FEATURE:
<223> OTHER INFORMATION: Antibody variable region

<400> SEQUENCE: 98

Glu Ile Val Leu Thr Gln Ser Pro Gly Thr Leu Ser Leu Ser Pro Gly
1               5                   10                  15

Glu Arg Ala Thr Phe Ser Cys Arg Ser Ser His Ser Ile Arg Ser Arg
                20                  25                  30

Arg Val Ala Trp Tyr Gln His Lys Pro Gly Gln Ala Pro Arg Leu Val
            35                  40                  45

Ile His Gly Val Ser Asn Arg Ala Ser Gly Ile Ser Asp Arg Phe Ser
    50                  55                  60

Gly Ser Gly Ser Gly Thr Asp Phe Thr Leu Thr Ile Thr Arg Val Glu
65                  70                  75                  80

Pro Glu Asp Phe Ala Leu Tyr Tyr Cys Gln Val Tyr Gly Ala Ser Ser
                85                  90                  95

Tyr Thr Phe Gly Gln Gly Thr Lys Leu Glu Arg Lys
            100                 105

<210> SEQ ID NO 99
<211> LENGTH: 363
<212> TYPE: PRT
<213> ORGANISM: Artificial sequence
<220> FEATURE:
<223> OTHER INFORMATION: His tagged protein

<400> SEQUENCE: 99

Met Pro Gly Gly Cys Ser Arg Gly Pro Ala Ala Gly Asp Gly Arg Leu
1               5                   10                  15

Arg Leu Ala Arg Leu Ala Leu Val Leu Leu Gly Trp Val Ser Ser Ser
                20                  25                  30

Ser Pro Thr Ser Ser Ala Ser Ser Phe Ser Ser Ser Ala Pro Phe Leu
            35                  40                  45

Ala Ser Ala Val Ser Ala Gln Pro Pro Leu Pro Asp Gln Cys Pro Ala
    50                  55                  60

Leu Cys Glu Cys Ser Glu Ala Ala Arg Thr Val Lys Cys Val Asn Arg
65                  70                  75                  80

Asn Leu Thr Glu Val Pro Thr Asp Leu Pro Ala Tyr Val Arg Asn Leu
                85                  90                  95

Phe Leu Thr Gly Asn Gln Leu Ala Val Leu Pro Ala Gly Ala Phe Ala
```

```
               100                105                 110

Arg Arg Pro Pro Leu Ala Glu Leu Ala Ala Leu Asn Leu Ser Gly Ser
        115                120                125

Arg Leu Asp Glu Val Arg Ala Gly Ala Phe Glu His Leu Pro Ser Leu
    130                135                140

Arg Gln Leu Asp Leu Ser His Asn Pro Leu Ala Asp Leu Ser Pro Phe
145                150                155                160

Ala Phe Ser Gly Ser Asn Ala Ser Val Ser Ala Pro Ser Pro Leu Val
            165                170                175

Glu Leu Ile Leu Asn His Ile Val Pro Pro Glu Asp Glu Arg Gln Asn
            180                185                190

Arg Ser Phe Glu Gly Met Val Val Ala Ala Leu Leu Ala Gly Arg Ala
        195                200                205

Leu Gln Gly Leu Arg Arg Leu Glu Leu Ala Ser Asn His Phe Leu Tyr
    210                215                220

Leu Pro Arg Asp Val Leu Ala Gln Leu Pro Ser Leu Arg His Leu Asp
225                230                235                240

Leu Ser Asn Asn Ser Leu Val Ser Leu Thr Tyr Val Ser Phe Arg Asn
            245                250                255

Leu Thr His Leu Glu Ser Leu His Leu Glu Asp Asn Ala Leu Lys Val
            260                265                270

Leu His Asn Gly Thr Leu Ala Glu Leu Gln Gly Leu Pro His Ile Arg
        275                280                285

Val Phe Leu Asp Asn Asn Pro Trp Val Cys Asp Cys His Met Ala Asp
    290                295                300

Met Val Thr Trp Leu Lys Glu Thr Glu Val Val Gln Gly Lys Asp Arg
305                310                315                320

Leu Thr Cys Ala Tyr Pro Glu Lys Met Arg Asn Arg Val Leu Leu Glu
            325                330                335

Leu Asn Ser Ala Asp Leu Asp Cys Asp Pro Ile Leu Pro Pro Ser Leu
        340                345                350

Gln Thr Ser His His His His His His His
        355                360
```

<210> SEQ ID NO 100
<211> LENGTH: 327
<212> TYPE: PRT
<213> ORGANISM: Artificial sequence
<220> FEATURE:
<223> OTHER INFORMATION: His tagged protein

<400> SEQUENCE: 100

```
Met Pro Gly Gly Cys Ser Arg Gly Pro Ala Ala Gly Asp Gly Arg Leu
1               5                  10                 15

Arg Leu Ala Arg Leu Ala Leu Val Leu Leu Gly Trp Val Ser Ser Ser
            20                25                30

Ser Pro Thr Ser Ser Ala Ser Ser Phe Ser Ser Ser Ala Pro Phe Leu
        35                40                45

Ala Ser Ala Val Ser Ala Gln Pro Pro Leu Pro Asp Gln Cys Pro Ala
    50                55                60

Leu Cys Glu Cys Ser Glu Ala Ala Arg Thr Val Lys Cys Val Asn Arg
65                70                75                80

Asn Leu Thr Glu Val Pro Thr Asp Leu Pro Ala Ala Pro Ser Thr Cys
            85                90                95

Ser Lys Pro Thr Cys Pro Pro Pro Glu Leu Leu Gly Gly Pro Ser Val
```

```
                100                 105                 110

Phe Ile Phe Pro Pro Lys Pro Lys Asp Thr Leu Met Ile Ser Arg Thr
            115                 120                 125

Pro Glu Val Thr Cys Val Val Val Asp Val Ser Gln Asp Asp Pro Glu
        130                 135                 140

Val Gln Phe Thr Trp Tyr Ile Asn Asn Glu Gln Val Arg Thr Ala Arg
145                 150                 155                 160

Pro Pro Leu Arg Glu Gln Gln Phe Asn Ser Thr Ile Arg Val Val Ser
                165                 170                 175

Thr Leu Pro Ile Ala His Gln Asp Trp Leu Arg Gly Lys Glu Phe Lys
            180                 185                 190

Cys Lys Val His Asn Lys Ala Leu Pro Ala Pro Ile Glu Lys Thr Ile
            195                 200                 205

Ser Lys Ala Arg Gly Gln Pro Leu Glu Pro Lys Val Tyr Thr Met Gly
        210                 215                 220

Pro Pro Arg Glu Glu Leu Ser Ser Arg Ser Val Ser Leu Thr Cys Met
225                 230                 235                 240

Ile Asn Gly Phe Tyr Pro Ser Asp Ile Ser Val Glu Trp Glu Lys Asn
                245                 250                 255

Gly Lys Ala Glu Asp Asn Tyr Lys Thr Thr Pro Ala Val Leu Asp Ser
                260                 265                 270

Asp Gly Ser Tyr Phe Leu Tyr Ser Lys Leu Ser Val Pro Thr Ser Glu
                275                 280                 285

Trp Gln Arg Gly Asp Val Phe Thr Cys Ser Val Met His Glu Ala Leu
            290                 295                 300

His Asn His Tyr Thr Gln Lys Ser Ile Ser Arg Ser Pro Gly Lys His
305                 310                 315                 320

His His His His His His
                325
```

```
<210> SEQ ID NO 101
<211> LENGTH: 276
<212> TYPE: PRT
<213> ORGANISM: Artificial sequence
<220> FEATURE:
<223> OTHER INFORMATION: His tagged protein

<400> SEQUENCE: 101

Met Trp Trp Arg Leu Trp Trp Leu Leu Leu Leu Leu Leu Leu Leu Trp
1               5                   10                  15

Pro Met Val Trp Ala Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
            35                  40                  45

Gly Gly Gly Gly Ser Gly Gly Gly Gly Ser Gly Gly Gly Gly Ser Glu
        50                  55                  60

Ile Val Leu Thr Gln Ser Pro Ala Thr Leu Ser Leu Ser Pro Gly Glu
65                  70                  75                  80

Arg Ala Thr Leu Ser Cys Arg Ala Ser Gln Ser Val Ser Ser Tyr Leu
                85                  90                  95

Ala Trp Tyr Gln Gln Lys Pro Gly Gln Ala Pro Arg Leu Leu Ile Tyr
            100                 105                 110

Asp Ala Ser Asn Arg Ala Thr Gly Ile Pro Ala Arg Phe Ser Gly Ser
        115                 120                 125

Gly Ser Gly Thr Asp Phe Thr Leu Thr Ile Ser Ser Leu Glu Pro Glu
```

-continued

```
            130                 135                 140

Asp Phe Ala Val Tyr Tyr Cys Gln Gln Arg Ser Asn Trp Pro Ile Thr
145                 150                 155                 160

Phe Gly Gln Gly Thr Arg Leu Glu Ile Lys Arg Thr Val Ala Ala Pro
                165                 170                 175

Ser Val Phe Ile Phe Pro Pro Ser Asp Glu Gln Leu Lys Ser Gly Thr
                180                 185                 190

Ala Ser Val Val Cys Leu Leu Asn Asn Phe Tyr Pro Arg Glu Ala Lys
            195                 200                 205

Val Gln Trp Lys Val Asp Asn Ala Leu Gln Ser Gly Asn Ser Gln Glu
        210                 215                 220

Ser Val Thr Glu Gln Asp Ser Lys Asp Ser Thr Tyr Ser Leu Ser Ser
225                 230                 235                 240

Thr Leu Thr Leu Ser Lys Ala Asp Tyr Glu Lys His Lys Val Tyr Ala
                245                 250                 255

Cys Glu Val Thr His Gln Gly Leu Ser Ser Pro Val Thr Lys Ser Phe
                260                 265                 270

Asn Arg Gly Glu
        275
```

<210> SEQ ID NO 102
<211> LENGTH: 6
<212> TYPE: PRT
<213> ORGANISM: Artificial sequence
<220> FEATURE:
<223> OTHER INFORMATION: CDR sequence

<400> SEQUENCE: 102

```
Tyr Tyr Gly Met Asp Val
1               5
```

<210> SEQ ID NO 103
<211> LENGTH: 7
<212> TYPE: PRT
<213> ORGANISM: Artificial sequence
<220> FEATURE:
<223> OTHER INFORMATION: CDR consensus sequence
<220> FEATURE:
<221> NAME/KEY: Xaa
<222> LOCATION: (5)..(5)
<223> OTHER INFORMATION: Xaa is G or E

<400> SEQUENCE: 103

```
Ile Asp His Ser Xaa Ser Thr
1               5
```

<210> SEQ ID NO 104
<211> LENGTH: 16
<212> TYPE: PRT
<213> ORGANISM: Artificial sequence
<220> FEATURE:
<223> OTHER INFORMATION: CDR consensus sequence
<220> FEATURE:
<221> NAME/KEY: Xaa
<222> LOCATION: (2)..(2)
<223> OTHER INFORMATION: Xaa is A or G
<220> FEATURE:
<221> NAME/KEY: Xaa
<222> LOCATION: (8)..(8)
<223> OTHER INFORMATION: Xaa is W or Y
<220> FEATURE:
<221> NAME/KEY: Xaa
<222> LOCATION: (9)..(9)
<223> OTHER INFORMATION: Xaa is D or H

<400> SEQUENCE: 104

Ala Xaa Trp Phe Gly Glu Leu Xaa Xaa Tyr Tyr Tyr Gly Met Asp Val
1               5                   10                  15

<210> SEQ ID NO 105
<211> LENGTH: 6
<212> TYPE: PRT
<213> ORGANISM: Artificial sequence
<220> FEATURE:
<223> OTHER INFORMATION: CDR consensus sequence
<220> FEATURE:
<221> NAME/KEY: Xaa
<222> LOCATION: (6)..(6)
<223> OTHER INFORMATION: Xaa is Y or F

<400> SEQUENCE: 105

Gln Ser Val Ser Ser Xaa
1               5

<210> SEQ ID NO 106
<211> LENGTH: 454
<212> TYPE: PRT
<213> ORGANISM: Artificial sequence
<220> FEATURE:
<223> OTHER INFORMATION: Antibody heavy chain

<400> SEQUENCE: 106

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg Gly Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
            290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
            325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
            355                 360                 365

Asn Gln Val Ser Leu Thr Cys Leu Val Lys Gly Phe Tyr Pro Ser Asp
            370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly
    450

<210> SEQ ID NO 107
<211> LENGTH: 215
<212> TYPE: PRT
<213> ORGANISM: Artificial seequence
<220> FEATURE:
<223> OTHER INFORMATION: Antibody light chain

<400> SEQUENCE: 107

Gln Ala Val Val Thr Gln Glu Pro Ser Phe Ser Val Ser Pro Gly Gly
1                   5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
            35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
            85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
            130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
            165             170             175

Ala Ser Ser Tyr Leu Ser Leu Thr Pro Glu Gln Trp Lys Ser His Arg
            180             185             190

Ser Tyr Ser Cys Gln Val Thr His Glu Gly Ser Thr Val Glu Lys Thr
        195             200             205

Val Ala Pro Thr Glu Cys Ser
    210             215

<210> SEQ ID NO 108
<211> LENGTH: 451
<212> TYPE: PRT
<213> ORGANISM: Artificial sequence
<220> FEATURE:
<223> OTHER INFORMATION: Antibody heavy chain

<400> SEQUENCE: 108

Gln Val Gln Leu Gln Gln Trp Gly Ala Gly Leu Leu Lys Pro Ser Glu
1               5               10              15

Thr Leu Ser Leu Thr Cys Ala Val Tyr Gly Gly Ser Phe Ser Gly Tyr
            20              25              30

Tyr Trp Thr Trp Ile Arg Gln Pro Pro Gly Lys Gly Leu Glu Trp Ile
        35              40              45

Gly Glu Ile Asp His Ser Glu Ser Thr Asn Tyr Asn Pro Ser Leu Lys
    50              55              60

Ser Arg Val Thr Ile Ser Val Asp Thr Ser Lys Asn Gln Phe Ser Leu
65              70              75              80

Lys Leu Ser Ser Val Thr Ala Ala Asp Thr Ala Val Tyr Tyr Cys Ala
            85              90              95

Gly Trp Phe Gly Glu Leu Tyr His Tyr Tyr Tyr Gly Met Asp Val Trp
            100             105             110

Gly Gln Gly Thr Thr Val Thr Val Ser Ser Ala Ser Thr Lys Gly Pro
        115             120             125

Ser Val Phe Pro Leu Ala Pro Ser Ser Lys Ser Thr Ser Gly Gly Thr
    130             135             140

Ala Ala Leu Gly Cys Leu Val Lys Asp Tyr Phe Pro Glu Pro Val Thr
145             150             155             160

Val Ser Trp Asn Ser Gly Ala Leu Thr Ser Gly Val His Thr Phe Pro
            165             170             175

Ala Val Leu Gln Ser Ser Gly Leu Tyr Ser Leu Ser Ser Val Val Thr
            180             185             190

Val Pro Ser Ser Ser Leu Gly Thr Gln Thr Tyr Ile Cys Asn Val Asn
        195             200             205

His Lys Pro Ser Asn Thr Lys Val Asp Lys Arg Val Glu Pro Lys Ser
    210             215             220

Cys Asp Lys Thr His Thr Cys Pro Pro Cys Pro Ala Pro Glu Leu Leu
225             230             235             240

Gly Gly Pro Ser Val Phe Leu Phe Pro Pro Lys Pro Lys Asp Thr Leu
            245             250             255

Met Ile Ser Arg Thr Pro Glu Val Thr Cys Val Val Val Asp Val Ser
            260             265             270

His Glu Asp Pro Glu Val Lys Phe Asn Trp Tyr Val Asp Gly Val Glu
        275             280             285

Val His Asn Ala Lys Thr Lys Pro Arg Glu Glu Gln Tyr Asn Ser Thr
    290             295             300

```
Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 109
<211> LENGTH: 214
<212> TYPE: PRT
<213> ORGANISM: Artificial sequence
<220> FEATURE:
<223> OTHER INFORMATION: Antibody light chain

<400> SEQUENCE: 109

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205
```

-continued

Phe Asn Arg Gly Glu Cys
    210

<210> SEQ ID NO 110
<211> LENGTH: 454
<212> TYPE: PRT
<213> ORGANISM: Artificial sequence
<220> FEATURE:
<223> OTHER INFORMATION: Antibody heavy chain

<400> SEQUENCE: 110

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg Gly Gly Asn Phe Gly Asn Ser Tyr Val Ser Trp Phe
                100                 105                 110

Ala Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
        130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Gln Thr Tyr Ile Cys
                195                 200                 205

Asn Val Asn His Lys Pro Ser Asn Thr Lys Val Asp Lys Arg Val Glu
        210                 215                 220

Pro Lys Ser Cys Asp Lys Thr His Thr Cys Pro Pro Cys Pro Ala Pro
225                 230                 235                 240

Glu Phe Glu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
                260                 265                 270

Ala Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
                340                 345                 350

Glu Pro Gln Val Tyr Thr Leu Pro Pro Ser Arg Glu Glu Met Thr Lys
        355              360              365

Asn Gln Val Ser Leu Thr Cys Leu Val Lys Gly Phe Tyr Pro Ser Asp
    370              375              380

Ile Ala Val Glu Trp Glu Ser Asn Gly Gln Pro Glu Asn Asn Tyr Lys
385              390              395              400

Thr Thr Pro Pro Val Leu Asp Ser Asp Gly Ser Phe Leu Leu Tyr Ser
            405              410              415

Lys Leu Thr Val Asp Lys Ser Arg Trp Gln Gln Gly Asn Val Phe Ser
            420              425              430

Cys Ser Val Met His Glu Ala Leu His Asn His Tyr Thr Gln Lys Ser
            435              440              445

Leu Ser Leu Ser Pro Gly
    450

<210> SEQ ID NO 111
<211> LENGTH: 451
<212> TYPE: PRT
<213> ORGANISM: Artificial sequence
<220> FEATURE:
<223> OTHER INFORMATION: Antibody heavy chain

<400> SEQUENCE: 111

Gln Val Gln Leu Gln Gln Trp Gly Ala Gly Leu Leu Lys Pro Ser Glu
1                5                10              15

Thr Leu Ser Leu Thr Cys Ala Val Tyr Gly Gly Ser Phe Ser Gly Tyr
            20              25              30

Tyr Trp Thr Trp Ile Arg Gln Pro Pro Gly Lys Gly Leu Glu Trp Ile
        35              40              45

Gly Glu Ile Asp His Ser Glu Ser Thr Asn Tyr Asn Pro Ser Leu Lys
    50              55              60

Ser Arg Val Thr Ile Ser Val Asp Thr Ser Lys Asn Gln Phe Ser Leu
65              70              75              80

Lys Leu Ser Ser Val Thr Ala Ala Asp Thr Ala Val Tyr Tyr Cys Ala
            85              90              95

Gly Trp Phe Gly Glu Leu Tyr His Tyr Tyr Tyr Gly Met Asp Val Trp
        100              105              110

Gly Gln Gly Thr Thr Val Thr Val Ser Ser Ala Ser Thr Lys Gly Pro
        115              120              125

Ser Val Phe Pro Leu Ala Pro Ser Ser Lys Ser Thr Ser Gly Gly Thr
    130              135              140

Ala Ala Leu Gly Cys Leu Val Lys Asp Tyr Phe Pro Glu Pro Val Thr
145              150              155              160

Val Ser Trp Asn Ser Gly Ala Leu Thr Ser Gly Val His Thr Phe Pro
            165              170              175

Ala Val Leu Gln Ser Ser Gly Leu Tyr Ser Leu Ser Ser Val Val Thr
        180              185              190

Val Pro Ser Ser Ser Leu Gly Thr Gln Thr Tyr Ile Cys Asn Val Asn
        195              200              205

His Lys Pro Ser Asn Thr Lys Val Asp Lys Arg Val Glu Pro Lys Ser
    210              215              220

Cys Asp Lys Thr His Thr Cys Pro Pro Cys Pro Ala Pro Glu Phe Glu
225              230              235              240

Gly Gly Pro Ser Val Phe Leu Phe Pro Pro Lys Pro Lys Asp Thr Leu
            245              250              255

-continued

```
Met Ile Ser Arg Thr Pro Glu Val Thr Cys Val Val Val Ala Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
            435                 440                 445

Ser Pro Gly
    450
```